(12) United States Patent
Glinka et al.

(10) Patent No.: US 8,268,865 B2
(45) Date of Patent: Sep. 18, 2012

(54) QUATERNARY ALKYL AMMONIUM BACTERIAL EFFLUX PUMP INHIBITORS AND THERAPEUTIC USES THEREOF

(75) Inventors: Tomasz Glinka, Cupertino, CA (US); Olga Lomovskaya, Mountain View, CA (US); Keith Bostian, Atherton, CA (US); David M. Wallace, San Diego, CA (US)

(73) Assignee: Rempex Pharmaceuticals, Inc., San Diego, CA (US)

( * ) Notice: Subject to any disclaimer, the term of this patent is extended or adjusted under 35 U.S.C. 154(b) by 1141 days.

(21) Appl. No.: 12/116,164

(22) Filed: May 6, 2008

(65) Prior Publication Data

US 2012/0165276 A1 Jun. 28, 2012

Related U.S. Application Data

(60) Provisional application No. 60/917,599, filed on May 11, 2007.

(51) Int. Cl.
*C07D 215/38* (2006.01)
*A61K 31/04* (2006.01)

(52) U.S. Cl. .......... 514/311; 514/313; 546/159

(58) Field of Classification Search .......... None
See application file for complete search history.

*Primary Examiner* — Shengjun Wang
*Assistant Examiner* — Svetlana M Ivanova
(74) *Attorney, Agent, or Firm* — Knobbe, Martens, Olson & Bear LLP

(57) ABSTRACT

Disclosed are compounds having at least one quaternary alkyl ammonium functionality. The compounds inhibit bacterial efflux pump inhibitors and are used in combination with an anti-bacterial agent to treat or prevent bacterial infections. These combinations can be effective against bacterial infections that have developed resistance to anti-bacterial agents through an efflux pump mechanism.

58 Claims, No Drawings

QUATERNARY ALKYL AMMONIUM BACTERIAL EFFLUX PUMP INHIBITORS AND THERAPEUTIC USES THEREOF

RELATED APPLICATIONS

This application claims the benefit of U.S. Provisional Application No. 60/917,599, filed May 11, 2007, which is incorporated herein by reference in its entirety.

BACKGROUND OF THE INVENTION

1. Field of the Invention

This invention relates to the field of antimicrobial agents and more specifically it relates to Efflux Pump Inhibitor (EPI) compounds to be co-administered with antimicrobial agents for the treatment of infections caused by drug resistant pathogens. The invention includes novel compounds useful as efflux pump inhibitors, compositions and devices comprising such efflux pump inhibitors, and therapeutic use of such compounds.

2. Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of antibacterial therapy. The increase in antibiotic resistant strains has been particularly common in major hospitals and care centers. The consequences of the increase in resistant strains include higher morbidity and mortality, longer patient hospitalization, and an increase in treatment costs.

Bacteria have developed several different mechanisms to overcome the action of antibiotics. These mechanisms of resistance can be specific for a molecule or a family of antibiotics, or can be non-specific and be involved in resistance to unrelated antibiotics. Several mechanisms of resistance can exist in a single bacterial strain, and those mechanisms may act independently or they may act synergistically to overcome the action of an antibiotic or a combination of antibiotics. Specific mechanisms include degradation of the drug, inactivation of the drug by enzymatic modification, and alteration of the drug target. There are, however, more general mechanisms of drug resistance, in which access of the antibiotic to the target is prevented or reduced by decreasing the transport of the antibiotic into the cell or by increasing the efflux of the drug from the cell to the outside medium. Both mechanisms can lower the concentration of drug at the target site and allow bacterial survival in the presence of one or more antibiotics that would otherwise inhibit or kill the bacterial cells. Some bacteria utilize both mechanisms, combining a low permeability of the cell wall (including membranes) with an active efflux of antibiotics.

In recent years interest in efflux-mediated resistance in bacteria has been triggered by the growing amount of data implicating efflux pumps in clinical isolates. The phenomenon of antibiotic efflux was first discovered in 1980, in the context of the mechanism of tetracycline resistance in enterobacteria. Since then, it has been shown that efflux of antibiotics can be mediated by more than one pump in a single organism and that almost all antibiotics are subject to resistance by this mechanism.

Some efflux pumps selectively extrude specific antibiotics. Examples of such pumps include the Tet or CmlA transporters, which can extrude tetracycline or chloramphenicol, respectively. Other efflux pumps, so-called multi-drug resistance (MDR) pumps, extrude a variety of structurally diverse compounds. In the latter case, a single efflux system may confer resistance to multiple antibiotics with different modes of action. In this respect, bacterial MDR pumps are similar to mammalian MDR transporters. In fact, one such pump, P-glycoprotein, the first discovered MDR pump, confers multiple drug resistance on cancer cells and is considered to be one of the major reasons tumor resistance to anti-cancer therapy. A typical example of bacterial MDR pump is MexAB-OprM from *Pseudomonas aeruginosa*. This pump has been shown to affect the susceptibility of the organism to almost all antibiotic classes which fluoroquinolones, β-lactams, macrolides, phenicols, tetracyclines, and oxazolidinones.

Efflux pumps in gram-positive bacteria excrete their substrates across a single cytoplasmic membrane. This is also the case for some pumps in gram-negative bacteria, and as a result their substrates are effluxed into the periplasmic space. Other efflux pumps from gram-negative bacteria efflux their substrates directly into the external medium, bypassing the periplasm and the outer membrane. These pumps are organized in complex three component structures, which traverse both inner and outer membranes. They consist of a transporter located in the cytoplasmic membrane, an outer membrane channel and a periplasmic 'linker' protein, which brings the other two components into contact. It is clearly advantageous for gram-negative bacteria to efflux drugs by bypassing the periplasm and outer membrane. In gram-negative bacteria the outer membrane significantly slows down the entry of both lipophilic and hydrophilic agents. The former, such as erythromycin and fusidic acid, are hindered by the lipopolysaccharide components of the outer leaflet of the outer membrane bilayer. Hydrophilic agents cross the outer membrane through water-filled porins whose size prevents rapid diffusion, even for small compounds such as fluoroquinolones and some β-lactams. Thus, direct efflux creates the possibility for two different mechanisms to work synergistically to provide the cell with a potent defense mechanism. Furthermore, direct efflux into the medium leads to decreased amounts of drugs not only in the cytoplasmic but also in the periplasmic space. This could explain the apparently paradoxical finding that efflux pumps protect gram-negative bacteria from β-lactam antibiotics whose target penicillin-binding proteins are found in the periplasm.

Many MDR pumps are encoded by the genes, which are normal constituents of bacterial chromosomes. In this case increased antibiotic resistance is a consequence of over-expression of these genes. Thus bacteria have the potential to develop multi-drug resistance without the acquisition of multiple specific resistance determinants. In some cases, the simultaneous operation of efflux pumps and other resistance mechanisms in the same cell results in synergistic effects.

While some genes encoding efflux pumps are not expressed in wild type cells and require induction or regulatory mutations for expression to occur, other efflux genes are expressed constitutively. As a result wild type cells have basal level of efflux activity. This basal activity of multi-drug efflux pumps in wild type cells contribute to intrinsic antibiotic resistance, or more properly, decreased antibiotic susceptibility. This intrinsic resistance may be low enough for the bacteria to still be clinically susceptible to therapy. However, the bacteria might be even more susceptible if efflux pumps were rendered non-functional, allowing lower doses of antibiotics to be effective. To illustrate, *P. aeruginosa* laboratory-derived mutant strain PAM1626, which does not produce any measurable amounts of efflux pump is 8 to 10 fold more susceptible to levofloxacin and meropenem than the parent strain *P. aeruginosa* PAM1020, which produces the basal level of MexAB-OprM efflux pump. Were it not for efflux pumps, the spectrum of activity of many so-called 'gram-positive' antibiotics could be expanded to previously non-susceptible gram-negative species. This can be applied to 'narrow-spectrum' β-lactams, macrolides, lincosamides, streptogramins, rifamycins, fusidic acid, and oxazolidinones—all of which have a potent antibacterial effect against engineered mutants lacking efflux pumps.

It is clear that in many cases, a dramatic effect on the susceptibility of problematic pathogens would be greatly enhanced if efflux-mediated resistance were to be nullified. Two approaches to combat the adverse effects of efflux on the efficacy of antimicrobial agents can be envisioned: identification of derivatives of known antibiotics that are not effluxed and development of therapeutic agents that inhibit transport activity of efflux pumps and could be used in combination with existing antibiotics to increase their potency.

There are several examples when the first approach has been successfully reduced to practice. These examples include new fluoroquinolones, which are not affected by multidrug resistance pumps in *Staphylococcus aureus* or *Streptococcus pneumoniae* or new tetracycline and macrolide derivatives, which are not recognized by the corresponding antibiotic-specific pumps. However, this approach appears to be much less successful in the case of multidrug resistance pumps from gram-negative bacteria. In gram-negative bacteria, particular restrictions are imposed on the structure of successful drugs: they must be amphiphilic in order to cross both membranes. It is this very property that makes antibiotics good substrates of multi-drug resistance efflux pumps from gram-negative bacteria. In the case of these bacteria the efflux pump inhibitory approach becomes the major strategy in improving the clinical effectiveness of existing antibacterial therapy.

The efflux pump inhibitory approach was first validated in the case of mammalian P-glycoprotein. And the first inhibitors have been found among compounds with previously described and quite variable pharmacological activities. For example, P-glycoprotein-mediated resistance, can be reversed by calcium channel blockers such as verpamyl and azidopine, immunosuppressive agents cyclosporin A and FK506 as well as antifungal agents such as rapamycin and FK520 (Raymond et al, 1994). It is important that efflux pump inhibitory activity was by no means connected to other activities of these compounds. In fact, the most advanced inhibitor of P-glycoprotein is a structural derivative of cyclosporin A and is devoid if immunosuppressive activity.

SUMMARY OF THE INVENTION

Some embodiments disclosed herein include bacterial efflux pump inhibitors having at least one quaternary alkyl ammonium functionality. Other embodiments disclosed herein include pharmaceutical compositions and methods of treatment using these compounds.

Some embodiments disclosed herein include a compound having the structure of formula I, II, III, IV or V:

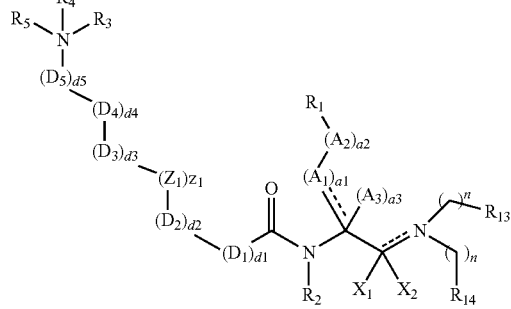

I

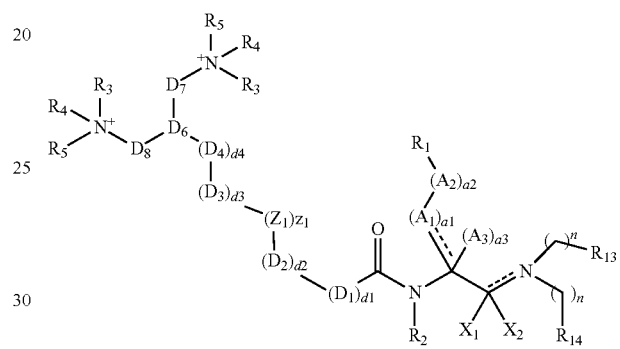

II

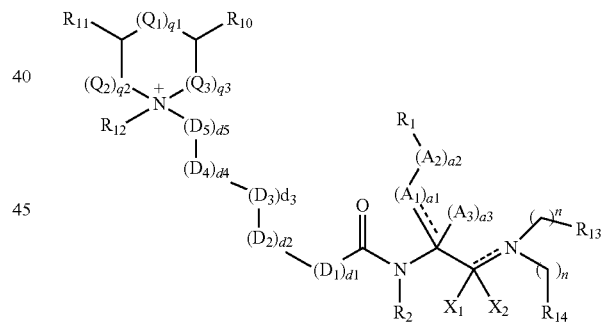

III

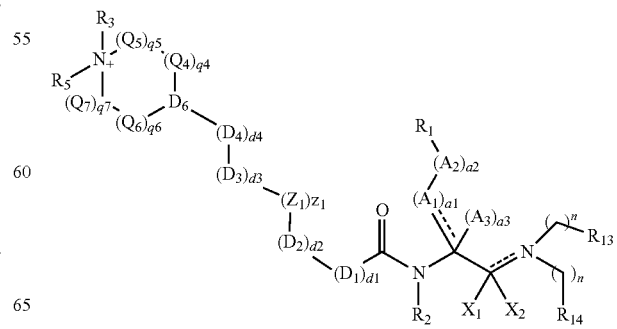

IV

-continued

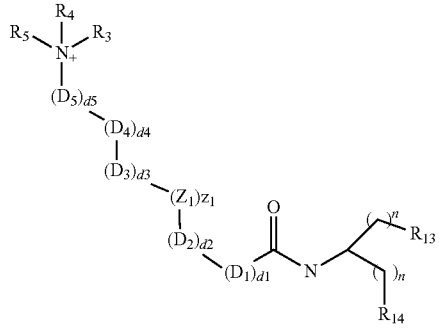

V or a pharmaceutically acceptable salt or pro-drug thereof wherein;

each bond represented by a dashed and solid line represents a bond selected from the group consisting of a single bond and a double bond;

each $R_1$ is independently selected from $C_1$-$C_6$ alkyl, $C_3$-$C_6$ carbocyclyl, heterocyclyl, aryl and heteroaryl, each optionally substituted with up to 3 substituents independently selected from the group consisting of halo, $C_1$-$C_6$ alkyl, carbocyclyl, $-(CH_2)_n$aryl, $-OR_2$, $-OR_{14}$, $-S(R_2)_2$, $-SO_2NHR_{14}$, $-(CH_2)_n SH$, $-CF_3$, $-OCF_3$, $-N(R_2)_2$, $-NO_2$, $-CN$, $-CO_2$alkyl, and $-CO_2$aryl;

each $R_2$ is independently selected from H and $C_1$-$C_6$ alkyl; $R_3$ is $-(CH_2)_n CHR_6 R_7$ each $R_4$ is independently selected from $-(CH_2)_m R_9$, allyl, $-(CH_2)_n CO_2H-$, $-(CH_2)_n CONH_2$ and $-(CH_2)_n CHR_6R_7$;

each $R_5$ is independently selected from $-(CH_2)_m R_9$, $-NHR_2$, and $-(CH_2)_n CHR_6R_7$;

each $R_6$ is independently selected from H and $-(CH_2)_m NH_2$;

each $R_7$ is independently selected from $-(CH_2)_m NHR_8$, $-(CH_2)_m NHC(=NH)NH_2$, $-(CH_2)_m NHC(R_2)=NH$, and $-(CH_2)_m C(=NH)NH_2$;

each $R_8$ is independently selected from H, $C_1$-$C_6$ alkyl, $-C(O)CH(R_{15})(NH_2)$, $-C(O)A_2CH_2NH_2$, Alanine, Arginine, Asparagine, Aspartic acid, Glutamic acid, Glutamine, Cysteine, Glycine, Histidine, Isoleucine, Leucine, Lysine, Methionine, Phenylalanine, Proline, Serine, Threonine, Tryptophan, Tyrosine, and Valine;

each $R_9$ is independently selected from H, $C_1$-$C_6$ alkyl, SH and OH;

$R_{10}$ and $R_{11}$ are independently selected from the group consisting of $-(CH_2)_n NHR_2$ and $-(CH_2)_n CHR_6R_7$;

$R_{12}$ is selected from $C_1$-$C_4$ alkyl, $-NHR_2$, $-(CH_2)_m R_9$, allyl, $-(CH_2)_n CO_2H-$, $-(CH_2)_n CONH_2$ and $-(CH_2)_n CHR_6R_7$;

$R_{13}$ is selected from H, $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, $-(CH_2)_n R_1$, $-(CH=CH)_n R_1$, $-OR_2$, $-OR_1$, $=O$, $-S(R_2)_2$, $-SO_2NHR_1$, $-(CH_2)_n SH$, $-CF_3$, $-OCF_3$, $-N(R_2)_2$, $-NO_2$, $-CN$, $-(C=X)R_1$, $-(C=X)R_2$, $-CO_2$alkyl, and $-CO_2$aryl;

$R_{14}$ is selected from $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, $-(CH_2)_n R_1$, $-OR_2$, $-OR_1$, $=O$, $-S(R_2)_2$, $-SO_2NHR_1$, $-(CH_2)_n SH$, $-CF_3$, $-OCF_3$, $-N(R_2)_2$, $-NO_2$, $-CN$, $-(C=X)R_1$, $-(C=X)R_2$, $-CO_2$alkyl, and $-CO_2$aryl;

$R_{13}$ and $R_{14}$ are optionally linked to form a ring;

$R_{15}$ is selected from $-(CH_2)_n CHR_6(CH_2)_n NH_2$, $-(CH_2)_m NR_6(CH_2)_n NH_2$ and $-(CH_2)_m C(=O)NR_6(CH_2)_n NH_2$;

$A_1$ is $-(CH_2)_m-$, $-[C(R_2R_9)]_m-$, or $=CR_2[C(R_2R_8)]_m-$, wherein if $A_1$ is $=CR_2[C(R_2R_8)]_m-$, then a3 is 0;

$A_2$ is $-(CH_2)_m-$, $-NR_2-C(=X)-$, $-O(CH_2)_n-$, $-S(CH_2)_n-$, $-CH=CH-$, or $-C(=N-OR_2)-$;

$A_3$ is H or $C_1$-$C_4$ alkyl, or $A_3$ is $-CH_2-$ bonded to $A_1$, $A_2$ or $R_1$ to form a ring;

a1, a2, and a3 are independently equal to 0 or 1;

$D_1$ is selected from $-CH_2-$, $-CH(NHR_8)-$, $-CH(R_2)-$, and $-CH(CH_2SH)-$;

$D_2$, $D_3$, and $D_4$ are independently selected from the group consisting of $-(CH_2)_m-$, $-CH(R_2)-$, $-CH(NHR_8)-$, $-N(R_6)-$, $-O-$, $-S-$, $-C(=O)-$, $-S(=O)-$ and $-SO_2-$;

$D_5$ is selected from $-(CH_2)_m-$, $-CH(R_2)-$ and $-NH-$, or any two atoms of $D_2$, $D_3$, $D_4$ and $D_5$ are bonded to form a four, five or six membered saturated ring optionally comprising a nitrogen within the ring;

$D_6$ is selected from $-CH-$ and $-N-$;

$D_7$ and $D_8$ are independently selected from the group consisting of $-[CH(R_2)]_m-$, $-(CH_2)_m C(=O)-$, $-C(=O)(CH_2)_m-$, $-(CH_2)_m NH-$ and $-NH(CH_2)_m-$;

d1, d2, d3, d4 and d5 are independently equal to 0 or 1;

$Q_1$ is selected from $-CH_2-$, $-NH-$, $-N(Me)-$, and $-N^+(Me_2)-$;

$Q_2$ and $Q_3$ are independently selected from the group consisting of $-CH_2-$ and N;

with the proviso that no more than one of $Q_1$, $Q_2$, and $Q_3$ comprises a nitrogen;

q1, q2, and q3 are independently equal to 0 or 1;

$Q_4$, $Q_5$, $Q_6$ and $Q_7$ are each $-CH_2-$;

q4, q5, q6 and q7 are independently equal to 0 or 1;

with the proviso that at least two of q4, q5, q6 and q7 are equal to 1;

$Z_1$ is an aryl, heteroaryl, carbocyclyl, or heterocyclyl;

z1 is 0 or 1;

if z1 is 0 then at least two of d1, d2, d3, d4 and d5 are equal to 1;

if z1 is 1 then at least one of d1, d2, d3, d4 and d5 is equal to 1;

$X_1$ and $X_2$ are each hydrogen or taken together are $=O$ or $=S$, or $X_1$ is hydrogen and $X_2$ is $-O-$ or $-S-$ bonded to $R_{14}$ to form a 5- or 6-membered heterocyclyl, or $X_1$ is absent and $X_2$ is $-O-$, $-OCH_2-$, $-S-$, or $-SCH_2-$ bonded to $R_{14}$ to form a 5- or 6-membered heterocyclyl or heteroaryl, wherein when $X_1$ is absent, the bond to nitrogen represented by a dashed and solid line is a double bond;

each X is independently O or S;

each n is independently an integer from 0 to 4; and each m is independently an integer from 1 to 3.

Another embodiment disclosed herein includes a compound having the structure of formula (VI) or (VII):

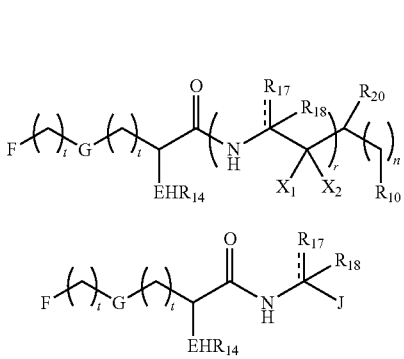

(VI)

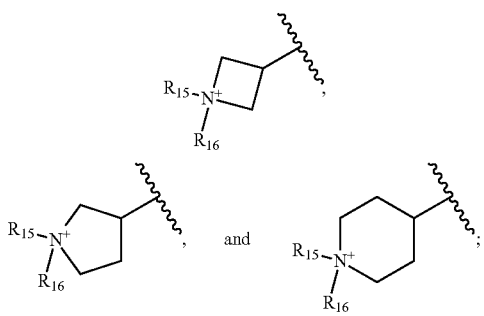

(VII)

or a pharmaceutically acceptable salt or prodrug thereof, wherein:

each E is independently CH or N;

F is selected from the group consisting of $-N^+R_{15}R_{16}R_{21}$, $-N[(CH_2)_tN^+R_{15}R_{16}R_{21}]_2$, $-CH[(CH_2)_tN^+R_{15}R_{16}R_{21}]_2$,

[three cyclic structures shown: azetidinium with $R_{15}$, $R_{16}$; pyrrolidinium with $R_{15}$, $R_{16}$; and piperidinium with $R_{15}$, $R_{16}$]

G is selected from $-CH_2-$, $-CH(alkyl)-$, $-S(O)_2-$, $-NHC(O)CH(NH_2)-$, $-NHC(O)-$, $-C(O)NH-$, $-C(O)N(CH_2CH_2NH)-$, $-NH-$, $-C(O)-$, carbocyclyl, aryl, $-S-$:

J is a heterocyclyl or heteroaryl, each optionally substituted with up to 3 substituents independently selected from the group consisting of a halide, alkyl optionally substituted with $-SH$, $-CF_3$, $-OCF_3$, $-NO_2$, $-CN$, $-OH$, $=O$, carbocyclyl, heterocyclyl, aryl optionally substituted with halide or $-OH$, heteroaryl optionally substituted with alkyl, aralkyl optionally substituted with halide or $-CF_3$, $-O$-aryl, $-O$-heteroaryl, $-O$-heterocyclyl, $-SO_2NH$-heteroaryl, $-O-C_1-C_6$ alkyl, and di($C_1$-$C_6$)alkylamino;

$X_1$ and $X_2$ are each hydrogen or together are $=O$ or $=S$;

$R_{10}$ is selected from carbocyclyl, heterocyclyl, aryl, and heteroaryl, each optionally substituted with up to 3 substituents independently selected from the group consisting of a halide, alkyl optionally substituted with $-SH$, $-CF_3$, $-OCF_3$, $-NO_2$, $-CN$, $-OH$, $=O$, carbocyclyl, heterocyclyl, aryl optionally substituted with halide or $-OH$, heteroaryl optionally substituted with alkyl, aralkyl optionally substituted with halide or $-CF_3$, $-O$-aryl, $-O$-heteroaryl, $-O$-heterocyclyl, $-SO_2NH$-heteroaryl, $-O-C_1-C_6$ alkyl, and di($C_1$-$C_6$)alkylamino;

$R_{14}$ is selected from H, $-C(O)CH(NH_2)(CH_2SH)$, $-C(O)CH(NH_2)(CH_2CH_2CH_2NHC(NH_2)(=NH))$, $-C(O)CH(NH_2)(CH_2COOH)$, $-C(O)-CH(Me)(NH_2)$, and $-SH$;

$R_{15}$ is selected from $-(CH_2)_sNH_2$, $-(CH_2)_sNHC(=NH)NH_2$, $-(CH_2)_sCH(CH_2NH_2)_2$, $-(CH_2)_sNHC(O)CH(NH_2)CH_2COOH$, $-(CH_2)_sNHCH(=NH)$, $-(CH_2)_sNHC(O)CH(NH_2)(CH_2SH)$, $-(CH_2)_sNHCH_3$, and $-(CH_2)_sC(O)NH_2$;

$R_{16}$ is selected from alkyl, $-(CH_2)_sCOOH$, allyl, $-(CH_2)_sSH$, $-(CH_2)_sNH_2$, $-(CH_2)_sNHC(=NH)NH_2$, $-(CH_2)_sCH(CH_2NH_2)_2$, $-(CH_2)_sNHC(O)CH(NH_2)CH_2COOH$, $-(CH_2)_sNHCH(=NH)$, $-(CH_2)_sNHC(O)CH(NH_2)(CH_2SH)$, $-(CH_2)_sNHCH_3$, and $-(CH_2)_sC(O)NH_2$;

or $R_{15}$ and $R_{16}$ together form a heterocyclyl substituted with at least two substituents independently selected from $-(CH_2)_sNH_2$, $-(CH_2)_sNHC(=NH)NH_2$, $-(CH_2)_sN^+(CH_3)_3$, $-(CH_2)_sNHCH_2CH_2NH_2$, $-(CH_2)_sN(CH_2CH_2NH_2)_2$, $-(CH_2)_sC(O)N(CH_2CH_2NH_2)_2$, and $-(CH_2)_sCH(CH_2NH_2)_2$;

$R_{17}$ is selected from alkyl, aralkyl, heteroaralkyl, carbocyclyl-alkyl, heterocyclyl-alkyl, aryl, and carbocyclyl, each optionally substituted with up to 3 substituents independently selected from the group consisting of $-CF_3$, $-OH$, $-SH$, $-CH_2SH$, $-OCF_3$, halide, $-CN$, alkyl, $-O$-aralkyl, $-CH_2-O$-aryl, aryl, $-S(CH_3)_2$, $-C(O)$aryl, $-S$-aralkyl optionally substituted with $-OMe$, $=O$, and $=N-OH$;

$R_{18}$ is H, alkyl, or absent, or $R_{17}$ together with $R_{18}$ form a carbocyclyl optionally substituted with aryl or heteroaryl;

$R_{20}$ is H or alkyl;

$R_{21}$ is selected from alkyl, $-(CH_2)_sCOOH$, allyl, $-(CH_2)_sSH$, $-(CH_2)_sNH_2$, $-(CH_2)_sNHC(=NH)NH_2$, $-(CH_2)_sCH(CH_2NH_2)_2$, $-(CH_2)_sNHC(O)CH(NH_2)CH_2COOH$, $-(CH_2)_sNHCH(=NH)$, $-(CH_2)_sNHCH_2C(O)CH(NH_2)(CH_2SH)$, $-(CH_2)_sNHCH_3$, and $-(CH_2)_sC(O)NH_2$;

each t is independently an integer from 0 to 4;
each s is independently an integer from 0 to 3;
r is 0 or 1; and
n is an integer from 0 to 4.

Other embodiments disclosed herein include methods of inhibiting a bacterial efflux pump by administering to a subject infected with a bacteria a compound according to any of the above formulas.

Another embodiment disclosed herein includes a method of treating or preventing a bacterial infection by co-administering to a subject infected with a bacteria or subject to infection with a bacteria, a compound according to any of the above formulas and another anti-bacterial agent.

Another embodiment disclosed herein includes a pharmaceutical composition that has a compound according to any of the above formulas and a pharmaceutically acceptable carrier, diluent, or excipient.

It is to be understood that both the foregoing general description and the following detailed description are exemplary and explanatory only and are not restrictive of the invention, as claimed.

DETAILED DESCRIPTION OF THE PREFERRED EMBODIMENT

Improved compositions and methods for inhibiting intrinsic drug resistance and/or preventing acquired drug resistance in microbes would be of tremendous benefit. Certain embodiments described herein provide such compositions and methods.

Some embodiments relate to a method for treating a microbial infection whose causative microbe employs an efflux pump resistance mechanism, comprising contacting the microbial cell with an efflux pump inhibitor in combination with an antimicrobial agent. The efflux pump inhibitors of preferred embodiments can comprise polybasic structures, as disclosed herein.

Some embodiments include a method for prophylactic treatment of a mammal. In this method, an efflux pump inhibitor is administered to a mammal at risk of a microbial infection, e.g., a bacterial infection. In some embodiments, an antimicrobial agent is administered in combination with or coadministered with the efflux pump inhibitor.

Some embodiments also feature a method of enhancing the antimicrobial activity of an antimicrobial agent against a microbe, in which such a microbe is contacted with a efflux pump inhibitor, and an antibacterial agent.

In some embodiments, pharmaceutical compositions are provided that are effective for treatment of an infection of an animal, e.g., a mammal, by a microbe, such as a bacterium or a fungus. The composition includes a pharmaceutically acceptable carrier and an efflux pump inhibitor as described herein. Some embodiments provide antimicrobial formulations that include an antimicrobial agent, an efflux pump inhibitor, and a carrier. In some embodiments, the antimicrobial agent is an antibacterial agent.

In some embodiments, the efflux pump inhibitor is administered to the lungs as an aerosol. In some such embodiments, a co-adminsitered antimicrobial agent may be administered in conjunction with the efflux pump inhibitor by any known means.

DEFINITIONS

In this specification and in the claims, the following terms have the meanings as defined. As used herein, "alkyl" means a branched or straight chain chemical group containing only carbon and hydrogen, such as methyl, isopropyl, isobutyl, sec-butyl, pentyl, and adamantyl. Alkyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Alkyl groups can be saturated or unsaturated (e.g., containing —C=C— or —C≡C— subunits), at one or several positions. Typically, alkyl groups will comprise 1 to 8 carbon atoms, preferably 1 to 6, and more preferably 1 to 4 carbon atoms.

As used herein, "lower alkyl" means a subset of alkyl, and thus is a hydrocarbon substituent, which is linear or branched. Preferred lower alkyls are of 1 to about 4 carbons, and may be branched or linear, and may include cyclic substituents, either as part or all of their structure. Examples of lower alkyl include butyl, propyl, isopropyl, ethyl, and methyl. Likewise, radicals using the terminology "lower" refer to radicals preferably with 1 to about 4 carbons in the alkyl portion of the radical.

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Typically, carbocyclyl groups will comprise 3 to 8 carbon atoms, preferably 3 to 6.

As used herein, "amido" means a H—CON— or alkyl-CON—, aryl-CON— or heterocyclyl-CON group wherein the alkyl, aryl or heterocyclyl group is as herein described.

As used herein, "aryl" means an aromatic radical having a single-ring (e.g., phenyl) or multiple condensed rings (e.g., naphthyl or anthryl) with only carbon atoms present in the ring backbone. Aryl groups can either be unsubstituted or substituted with one or more substitutents, e.g., amino, cyano, hydroxyl, lower alkyl, haloalkyl, alkoxy, nitro, halo, mercapto, and other substituents. A preferred carbocyclic aryl is phenyl.

As used herein, the term "heteroaryl" means an aromatic radical having one or more heteroatom(s) (e.g., N, O, or S) in the ring backbone and may include a single ring (e.g., pyridine) or multiple condensed rings (e.g., quinoline). Heteroaryl groups can either be unsubstituted or substituted with one or more substituents, e.g., amino, cyano, nitro, hydroxyl, alkyl, cycloalkyl, haloalkyl, alkoxy, aryl, halo, and mercapto. Examples of heteroaryl include thienyl, pyrridyl, furyl, oxazolyl, oxadiazolyl, pyrollyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl and others.

In these definitions it is clearly contemplated that substitution on the aryl and heteraryl rings is within the scope of certain embodiments. Where substitution occurs, the radical is called substituted aryl or substituted heteroaryl. Preferably one to three, more preferably one or two, and most preferably one substituent occur on the aryl ring. Preferred substitution patterns in five membered rings are substituted in the 2 position relative to the connection to the claimed molecule. Though many substituents will be useful, preferred substituents include those commonly found in aryl compounds, such as alkyl, hydroxy, alkoxy, cyano, halo, haloalkyl, mercapto and the like.

As used herein, "amide" includes both RNR' CO— (in the case of R=alkyl, alkaminocarbonyl-) and RCONR'— (in the case of R=alkyl, alkyl carbonylamino-).

As used herein, the term "ester" includes both ROCO— (in the case of R=alkyl, alkoxycarbonyl-) and RCOO— (in the case of R=alkyl, alkylcarbonyloxy-).

As used herein, "acyl" means an H—CO— or alkyl-CO—, aryl-CO— or heterocyclyl-CO— group wherein the alkyl, aryl or heterocycicyl group is as herein described. Preferred acyls contain a lower alkyl. Exemplary alkyl acyl groups include formyl, acetyl, propanoyl, 2-methylpropanoyl, t-butylacetyl, butanoyl and palmitoyl.

As used herein, "halo or halide" is a chloro, bromo, fluoro or iodo atom radical. Chloro, bromo and fluoro are preferred halides. The term "halo" also contemplates terms sometimes referred to as "halogen", or "halide".

As used herein, "haloalkyl" means a hydrocarbon substituent, which is linear or branched or cyclic alkyl, alkenyl or alkynyl substiuted with chloro, bromo, fluoro or iodo atom(s). Most preferred of these are fluoroalkyls, wherein one or more of the hydrogen atoms have been substituted by fluoro. Preferred haloalkyls are of 1 to about 3 carbons in length, More preferred haloalkyls are 1 to about 2 carbons, and most preferred are 1 carbon in length. The skilled artisan will recognize then that as used herein, "haloalkylene" means a diradical variant of haloalkyl, such diradicals may act as spacers between radicals, other atoms, or between the parent ring and another functional group.

As used herein, "heterocyclyl" means a cyclic ring system comprising at least one heteroatom in the ring system backbone. Heterocyclyls may include multiple fused rings. Heterocyclyls may have any degree of saturation provided that at least one ring in the ring system is not aromatic. Heterocyclyls may be substituted or unsubstituted, and are attached to other groups via any available valence, preferably any available carbon or nitrogen. More preferred heterocycles are of 5 or 6 members. In six membered monocyclic heterocycles, the heteroatom(s) are selected from one up to three of O, N or S, and wherein when the heterocycle is five membered, preferably it has one or two heteroatoms selected from O, N, or S.

As used herein quaternary ammonium refers to a positively charged nitrogen atom linked to four aliphatic carbon atoms or a positively charged nitrogen of the heteroaryl ring linked to an aliphatic carbon as in N-pridinium, N-thiazolium, N-imidazolium, N-triazolium and like.

As used herein, "substituted amino" means an amino radical which is substituted by one or two alkyl, aryl, or heterocyclyl groups, wherein the alkyl, aryl or heterocyclyl are defined as above.

As used herein, "substituted thiol" means RS— group wherein R is an alkyl, an aryl, or a heterocyclyl group, wherein the alkyl, aryl or heterocyclyl are defined as above.

As used herein, "sulfonyl" means an alkyl$SO_2$, aryl$SO_2$ or heterocyclyl-$SO_2$ group wherein the alkyl, aryl or heterocyclyl are defined as above.

As used herein, "sulfamido" means an alkyl-N—S(O)$_2$N—, aryl-NS(O)$_2$N— or heterocyclyl-NS(O)$_2$N— group wherein the alkyl, aryl or heterocycicyl group is as herein described.

As used herein, "sulfonamido" means an alkyl-S(O)$_2$N—, aryl-S(O)$_2$N— or heterocyclyl-S(O)$_2$N— group wherein the alkyl, aryl or heterocycicyl group is as herein described.

As used herein, "ureido" means an alkyl-NCON—, aryl-NCON— or heterocyclyl-NCON— group wherein the alkyl, aryl or heterocycicyl group is as herein described As used herein, when two groups are indicated to be "linked" or "bonded" to form a "ring," it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions, and it is within the purview of the skilled artisan to both envision such rings and the methods of their formations. Preferred are rings having from 3-7 members, more preferably 5 or 6 members. As used herein the term "ring" or "rings" when formed by the combination of two radicals refers to heterocyclic, carbocyclic, aryl, or heteroaryl rings.

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this invention, though such resonance forms or tautomers are not represented herein.

The term "administration" or "administering" refers to a method of giving a dosage of an antimicrobial pharmaceutical composition to a vertebrate or invertebrate, including a mammal, a bird, a fish, or an amphibian, where the method is, e.g., intrarespiratory, topical, oral, intravenous, intraperitoneal, or intramuscular. The preferred method of administration can vary depending on various factors, e.g., the components of the pharmaceutical composition, the site of the potential or actual bacterial infection, the microbe involved, and the severity of an actual microbial infection.

A "diagnostic" as used herein is a compound, method, system, or device that assists in the identification and characterization of a health or disease state. The diagnostic can be used in standard assays as is known in the art.

The term "efflux pump" refers to a protein assembly that exports substrate molecules from the cytoplasm or periplasm of a cell, in an energy dependent fashion. Thus an efflux pump will typically be located in the cytoplasmic membrane of the cell (spanning the cytoplasmic membrane). In Gram-negative bacteria the pump may span the periplasmic space and there may also be portion of the efflux pump, which spans the outer membrane.

An "efflux pump inhibitor" ("EPI") is a compound that specifically interferes with the ability of an efflux pump to export its normal substrate, or other compounds such as an antibiotic. The inhibitor may have intrinsic antimicrobial (e.g., antibacterial) activity of its own, but at least a significant portion of the relevant activity is due to the efflux pump inhibiting activity.

The term "mammal" is used in its usual biological sense. Thus, it specifically includes humans, cattle, horses, dogs, and cats, but also includes many other species.

The term "microbial infection" refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term "multidrug resistance pump" refers to an efflux pump that is not highly specific to a particular antibiotic. The term thus includes broad substrate pumps (efflux a number of compounds with varying structural characteristics). These pumps are different from pumps, which are highly specific for tetracyclines. Tetracycline efflux pumps are involved in specific resistance to tetracycline in bacteria. However, they do not confer resistance to other antibiotics. The genes for the tetracycline pump components are found in plasmids in Gram-negative as well as in Gram-positive bacteria.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); *Goodman and Gilman's: The Pharmacological Basis of Therapeutics*, 8*th Ed., Pergamon Press.*

The term "pharmaceutically acceptable salt" refers to salts that retain the biological effectiveness and properties of the compounds of the preferred embodiments and, which are not biologically or otherwise undesirable. In many cases, the compounds of the preferred embodiments are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in World Patent Publication 87/05297, Johnston et al., published Sep. 11, 1987 (incorporated by reference herein).

"Solvate" refers to the compound formed by the interaction of a solvent and an EPI, a metabolite, or salt thereof. Suitable solvates are pharmaceutically acceptable solvates including hydrates.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

In the context of the response of a microbe, such as a bacterium, to an antimicrobial agent, the term "susceptibility" refers to the sensitivity of the microbe for the presence of the antimicrobial agent. So, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced.

By "therapeutically effective amount" or "pharmaceutically effective amount" is meant an amount of an efflux pump inhibitor, or amounts individually of an efflux pump inhibitor and an antimicrobial agent, as disclosed in the preferred embodiments, which have a therapeutic effect, which generally refers to the inhibition to some extent of the normal metabolism of microbial cells causing or contributing to a microbial infection. The doses of efflux pump inhibitor and antimicrobial agent, which are useful in combination as a treatment, are therapeutically effective amounts. Thus, as used herein, a therapeutically effective amount means those amounts of efflux pump inhibitor and antimicrobial agent which, when used in combination, produce the desired therapeutic effect as judged by clinical trial results and/or model animal infection studies. In particular embodiments, the efflux pump inhibitor and antimicrobial agent are combined in pre-determined proportions and thus a therapeutically effective amount would be an amount of the combination. This amount and the amount of the efflux pump inhibitor and antimicrobial agent individually can be routinely determined by one of skill in the art, and will vary, depending on several factors, such as the particular microbial strain involved and the particular efflux pump inhibitor and antimicrobial agent used. This amount can further depend upon the patient's height, weight, sex, age and medical history. For prophylactic treatments, a therapeutically effective amount is that amount which would be effective if a microbial infection existed.

A therapeutic effect relieves, to some extent, one or more of the symptoms of the infection, and includes curing an infection. "Curing" means that the symptoms of active infection are eliminated, including the elimination of excessive members of viable microbe of those involved in the infection. However, certain long-term or permanent effects of the infection may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a patient who is not yet infected, but who is susceptible to, or otherwise at risk of, a particular infection. The term "therapeutic treatment" refers to administering treatment to a patient already suffering from an infection. Thus, in preferred embodiments, treating is the administration to a mammal (either for therapeutic or prophylactic purposes) of therapeutically effective amounts of an efflux pump inhibitor and an antibacterial (or antimicrobial) agent in combination (either simultaneously or serially).

Compounds

One class of efflux pump inhibitors include diamine efflux pump inhibitors, which in general contain within the Box A fragment of their structures at least two basic nitrogen functionalities. Some diamine efflux pump inhibitors comprise aliphatic or aromatic groups of considerable lipophilicity. This lipophilicity results in a high level of binding to serum proteins, which often represents a serious limitation with regard to achieving high efflux pump inhibitory activity. Increasing lipophilicity of some fragments of the molecules, while beneficial from the standpoint of their EPI inhibitory activity, often produces molecules with unacceptably high affinity to serum proteins. Attempts to balance out the increased lipophilicity with introduction of hydrophilic functionalities into various parts of their molecules are usually unsuccessful due to concomitant loss of EPI activity. Accordingly, some embodiments include efflux pump inhibitors comprising at least one quaternary ammonium functionality within the Box A fragment. These compounds achieve high EPI inhibitory activity while keeping their affinity to serum proteins at an acceptably low level.

Some embodiments include compounds containing within the Box A fragment at least two basic nitrogen functionalities basic enough to be protonated to an appreciable degree at physiological pH of 7.4, and additionally comprise at least one quaternary alkyl ammonium functionality, also located within the Box A fragment. One embodiment includes a compound having the structure of formula (I):

Formula (I)

$$\text{Formula (I)}$$

or a pharmaceutically acceptable salt or pro-drug thereof wherein;

each bond represented by a dashed and solid line represents a bond selected from the group consisting of a single bond and a double bond;

each $R_1$ is independently selected from $C_1$-$C_6$ alkyl, $C_3$-$C_6$ carbocyclyl, heterocyclyl, aryl and heteroaryl, each optionally substituted with up to 3 substituents independently selected from the group consisting of halo, $C_1$-$C_6$ alkyl, carbocyclyl, —$(CH_2)_n$aryl, —$OR_2$, —$OR_{14}$, —$S(R_2)_2$, —$SO_2NHR_{14}$, —$(CH_2)_n SH$, —$CF_3$, —$OCF_3$, —$N(R^2)_2$, —$NO_2$, —$CN$, —$CO_2$alkyl, and —$CO_2$aryl;

each $R_2$ is independently selected from H and $C_1$-$C_6$ alkyl;

$R_3$ is —$(CH_2)_n CHR_6 R_7$;

each $R_4$ is independently selected from —$(CH_2)_m R_9$, allyl, —$(CH_2)_n CO_2 H$—, —$(CH_2)_n CONH_2$ and —$(CH_2)_n CHR_6 R_7$;

each $R_5$ is independently selected from —$(CH_2)_m R_9$, —$NHR_2$, and —$(CH_2)_n CHR_6 R_7$;

each $R_6$ is independently selected from H and —$(CH_2)_m NH_2$;

each $R_7$ is independently selected from —$(CH_2)_m NHR_8$, —$(CH_2)_m NHC(=NH)NH_2$, —$(CH_2)_m NHC(R_2)=NH$, and —$(CH_2)_m C(=NH)NH_2$;

each $R_8$ is independently selected from H, $C_1$-$C_6$ alkyl, —$C(O)CH(R_{15})(NH_2)$, —$C(O)A_2CH_2NH_2$, Alanine, Arginine, Asparagine, Aspartic acid, Glutamic acid, Glutamine, Cysteine, Glycine, Histidine, Isoleucine, Leucine, Lysine, Methionine, Phenylalanine, Proline, Serine, Threonine, Tryptophan, Tyrosine, and Valine;

each $R_9$ is independently selected from H, $C_1$-$C_6$ alkyl, SH and OH;

$R_{13}$ is selected from H, $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, —$(CH_2)_n R_1$, —$(CH=CH)_n R_1$, —$OR_2$, —$OR_1$, =O, —$S(R_2)_2$, —$SO_2NHR_1$, —$(CH_2)_n SH$, —$CF_3$, —$OCF_3$, —$N(R_2)_2$, —$NO_2$, —$CN$, —$(C=X)R_1$, —$(C=X)R_2$, —$CO_2$alkyl, and —$CO_2$aryl;

$R_{14}$ is selected from $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, —$(CH_2)_n R_1$, —$OR_2$, —$OR_1$, =O, —$S(R_2)_2$, —$SO_2NHR_1$, —$(CH_2)_n SH$, —$CF_3$, —$OCF_3$, —$N(R_2)_2$, —$NO_2$, —$CN$, —$(C=X)R_1$, —$(C=X)R_2$, —$CO_2$alkyl, and —$CO_2$aryl;

$R_{13}$ and $R_{14}$ are optionally linked to form a ring;

$R_{15}$ is selected from —$(CH_2)_n CHR_6(CH_2)_n NH_2$, —$(CH_2)_m NR_6(CH_2)_n NH_2$ and —$(CH_2)_m C(=O)NR_6(CH_2)_n NH_2$;

$A_1$ is —$(CH_2)_m$—, —$[C(R_2 R_9)]_m$—, or =$CR_2[C(R_2 R_8)]_m$—, wherein if $A_1$ is =$CR_2[C(R_2 R_8)]_m$—, then a3 is 0;

$A_2$ is —$(CH_2)_m$—, —$NR_2$—$C(=X)$—, —$O(CH_2)_n$—, —$S(CH_2)_n$—, —$CH=CH$—, or —$C(=N-OR_2)$—;

$A_3$ is H or $C_1$-$C_4$ alkyl, or $A_3$ is —$CH_2$— bonded to $A_1$, $A_2$ or $R_1$ to form a ring;

a1, a2, and a3 are independently equal to 0 or 1;

$D_1$ is selected from —$CH_2$—, —$CH(NHR_8)$—, —$CH(R_2)$—, and —$CH(CH_2SH)$—;

$D_2$, $D_3$, and $D_4$ are independently selected from the group consisting of —$(CH_2)_m$—, —$CH(R_2)$—, —$CH(NHR_8)$—, —$N(R_6)$—, —$O$—, —$S$—, —$C(=O)$—, —$S(=O)$— and —$SO_2$—;

$D_5$ is selected from —$(CH_2)_m$—, —$CH(R_2)$— and —$NH$—, or any two atoms of $D_2$, $D_3$, $D_4$ and $D_5$ are bonded to form a four, five or six membered saturated ring optionally comprising a nitrogen within the ring;

d1, d2, d3, d4 and d5 are independently equal to 0 or 1;

$Z_1$ is an aryl, heteroaryl, carbocyclyl, or heterocyclyl;

z1 is 0 or 1;

if z1 is 0 then at least two of d1, d2, d3, d4 and d5 are equal to 1;

if z1 is 1 then at least one of d1, d2, d3, d4 and d5 is equal to 1;

$X_1$ and $X_2$ are each hydrogen or taken together are =O or =S, or $X_1$ is hydrogen and $X_2$ is —O— or —S— bonded to $R_{14}$ to form a 5- or 6-membered heterocyclyl, or $X_1$ is absent and $X_2$ is —O—, —$OCH_2$—, —S—, or —$SCH_2$— bonded to $R_{14}$ to form a 5- or 6-membered heterocyclyl or heteroaryl, wherein when $X_1$ is absent, the bond to nitrogen represented by a dashed and solid line is a double bond;

each X is independently O or S;

each n is independently an integer from 0 to 4; and each m is independently an integer from 1 to 3.

In another embodiment, the compounds have the structure of formula (II)

Formula (II)

$$\text{Formula (II)}$$

or a pharmaceutically acceptable salt or pro-drug thereof wherein;

each bond represented by a dashed and solid line represents a bond selected from the group consisting of a single bond and a double bond;

each $R_1$ is independently selected from $C_1$-$C_6$ alkyl, $C_3$-$C_6$ carbocyclyl, heterocyclyl, aryl and heteroaryl, each optionally substituted with up to 3 substituents independently selected from the group consisting of halo, $C_1$-$C_6$ alkyl, carbocyclyl, —(CH$_2$)$_n$aryl, —OR$_2$, —OR$_{14}$, —S(R$_2$)$_2$, —SO$_2$NHR$_{14}$, —(CH$_2$)$_n$SH, —CF$_3$, —OCF$_3$, —N(R$_2$)$_2$, —NO$_2$, —CN, —CO$_2$alkyl, and —CO$_2$aryl;

each $R_2$ is independently selected from H and $C_1$-$C_6$ alkyl;

$R_3$ is —(CH$_2$)$_n$CHR$_6$R$_7$;

each $R_4$ is independently selected from —(CH$_2$)$_m$R$_9$, allyl, —(CH$_2$)$_n$CO$_2$H—, —(CH$_2$)$_n$CONH$_2$ and —(CH$_2$)$_6$CHR$_6$R$_7$;

each $R_5$ is independently selected from —(CH$_2$)$_m$R$_9$, —NHR$_2$, and —(CH$_2$)$_n$CHR$_6$R$_7$;

each $R_6$ is independently selected from H and —(CH$_2$)$_m$NH$_2$;

each $R_7$ is independently selected from —(CH$_2$)$_m$NHR$_8$, (CH$_2$)$_m$NHC(=NH)NH$_2$, —(CH$_2$)$_m$NHC(R$_2$)=NH, and —(CH$_2$)$_m$C(=NH)NH$_2$;

each $R_8$ is independently selected from H, $C_1$-$C_6$ alkyl, —C(O)CH(R$_{15}$)(NH$_2$), —C(O)A$_2$CH$_2$NH$_2$, Alanine, Arginine, Asparagine, Aspartic acid, Glutamic acid, Glutamine, Cysteine, Glycine, Histidine, Isoleucine, Leucine, Lysine, Methionine, Phenylalanine, Proline, Serine, Threonine, Tryptophan, Tyrosine, and Valine;

each $R_9$ is independently selected from H, $C_1$-$C_6$ alkyl, SH and OH;

$R_{13}$ is selected from H, $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, —(CH$_2$)$_n$R$_1$, —(CH=CH)$_n$R$_1$, —OR$_2$, —OR$_1$, =O, —S(R$_2$)$_2$, —SO$_2$NHR$_1$, —(CH$_2$)$_n$SH, —CF$_3$, —OCF$_3$, —N(R$_2$)$_2$, —NO$_2$, —CN, —(C=X)R$_1$, —(C=X)R$_2$, —CO$_2$alkyl, and —CO$_2$aryl;

$R_{14}$ is selected from $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, —(CH$_2$)$_n$R$_1$, —OR$_2$, —OR$_1$, =O, —S(R$_2$)$_2$, —SO$_2$NHR$_1$, —(CH$_2$)$_n$SH, —CF$_3$, —OCF$_3$, —N(R$_2$)$_2$, —NO$_2$, —CN, —(C=X)R$_1$, —(C=X)R$_2$, —CO$_2$alkyl, and —CO$_2$aryl;

$R_{13}$ and $R_{14}$ are optionally linked to form a ring;

$R_{15}$ is selected from —(CH$_2$)$_n$CHR$_6$(CH$_2$)$_n$NH$_2$, —(CH$_2$)$_m$NR$_6$(CH$_2$)$_n$NH$_2$ and —(CH$_2$)$_m$C(=O)NR$_6$(CH$_2$)$_n$NH$_2$;

$A_1$ is —(CH$_2$)$_m$—, —[C(R$_2$R$_9$)]$_m$—, or =CR$_2$[C(R$_2$R$_8$)]$_m$—, wherein if $A_1$ is =CR$_2$[C(R$_2$R$_8$)]$_m$—, then a3 is 0;

$A_2$ is —(CH$_2$)$_m$—, —NR$_2$—C(=X)—, —O(CH$_2$)$_n$—, —S(CH$_2$)$_n$—, —CH=CH—, or —C(=N—OR$_2$)—;

$A_3$ is H or $C_1$-$C_4$ alkyl, or $A_3$ is —CH$_2$— bonded to $A_1$, $A_2$ or $R_1$ to form a ring;

a1, a2, and a3 are independently equal to 0 or 1;

$D_1$ is selected from —CH$_2$—, —CH(NHR$_8$)—, —CH(R$_2$)—, and —CH(CH$_2$SH)—;

$D_2$, $D_3$, and $D_4$ are independently selected from the group consisting of —(CH$_2$)$_m$—, —CH(R$_2$)—, —CH(NHR$_8$)—, —N(R$_6$)— —O—, —S—, —C(=O)—, —S(=O)— and —SO$_2$—, $D_5$ is selected from —(CH$_2$)$_m$—, —CH(R$_2$)— and —NH—, or any two atoms of $D_2$, $D_3$, $D_4$ and $D_5$ are bonded to form a four, five or six membered saturated ring optionally comprising a nitrogen within the ring;

$D_6$ is selected from —CH— and —N—;

$D_7$ and $D_8$ are independently selected from the group consisting of —[CH(R$_2$)]$_m$—, —(CH$_2$)$_m$C(=O)—, —C(=O)(CH$_2$)$_m$—, —(CH$_2$)$_m$NH— and —NH(CH$_2$)$_m$—;

d1, d2, d3, d4 and d5 are independently equal to 0 or 1;

$Z_1$ is an aryl, heteroaryl, carbocyclyl, or heterocyclyl;

z1 is 0 or 1;

if z1 is 0 then at least two of d1, d2, d3, d4 and d5 are equal to 1;

if z1 is 1 then at least one of d1, d2, d3, d4 and d5 is equal to 1;

$X_1$ and $X_2$ are each hydrogen or taken together are =O or =S, or $X_1$ is hydrogen and $X_2$ is —O— or —S— bonded to $R_{14}$ to form a 5- or 6-membered heterocyclyl, or $X_1$ is absent and $X_2$ is —O—, —OCH$_2$—, —S—, or —SCH$_2$— bonded to $R_{14}$ to form a 5- or 6-membered heterocyclyl or heteroaryl, wherein when $X_1$ is absent, the bond to nitrogen represented by a dashed and solid line is a double bond;

each X is independently O or S;

each n is independently an integer from 0 to 4; and each m is independently an integer from 1 to 3.

In another embodiment, the compounds have the structure of formula (III)

Formula (III)

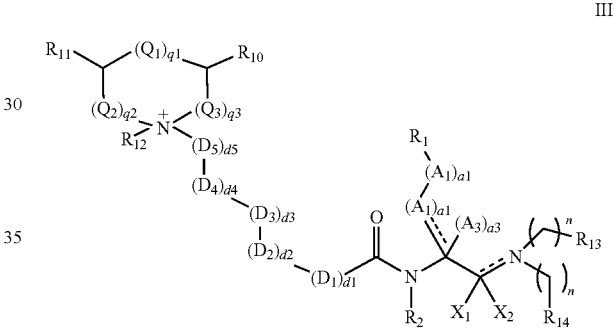

III or a pharmaceutically acceptable salt or pro-drug thereof wherein;

each bond represented by a dashed and solid line represents a bond selected from the group consisting of a single bond and a double bond;

each $R_1$ is independently selected from $C_1$-$C_6$ alkyl, $C_3$-$C_6$ carbocyclyl, heterocyclyl, aryl and heteroaryl, each optionally substituted with up to 3 substituents independently selected from the group consisting of halo, $C_1$-$C_6$ alkyl, carbocyclyl, —(CH$_2$)$_n$aryl, —OR$_2$, —OR$_{14}$, —S(R$_2$)$_2$, —SO$_2$NHR$_{14}$, —(CH$_2$)$_n$SH, —CF$_3$, —OCF$_3$, —N(R$^2$)$_2$, —NO$_2$, —CN, —CO$_2$alkyl, and —CO$_2$aryl;

each $R_2$ is independently selected from H and $C_1$-$C_6$ alkyl;

each $R_4$ is independently selected from —(CH$_2$)$_m$R$_9$, allyl, —(CH$_2$)$_n$CO$_2$H—, —(CH$_2$)$_n$CONH$_2$ and —(CH$_2$)$_n$CHR$_6$R$_7$;

each $R_5$ is independently selected from —(CH$_2$)$_m$R$_9$, —NHR$_2$, and —(CH$_2$)$_n$CHR$_6$R$_7$;

each $R_6$ is independently selected from H and —(CH$_2$)$_m$NH$_2$;

each $R_7$ is independently selected from —(CH$_2$)$_m$NHR$_8$, (CH$_2$)$_m$NHC(=NH)NH$_2$, —(CH$_2$)$_m$NHC(R$_2$)=NH, and —(CH$_2$)$_m$C(=NH)NH$_2$;

each $R_8$ is independently selected from H, $C_1$-$C_6$ alkyl, —C(O)CH(R$_{15}$)(NH$_2$), —C(O)A$_2$CH$_2$NH$_2$, Alanine, Arginine, Asparagine, Aspartic acid, Glutamic acid, Glutamine, Cysteine, Glycine, Histidine, Isoleucine, Leucine, Lysine, Methionine, Phenylalanine, Proline, Serine, Threonine, Tryptophan, Tyrosine, and Valine;

each $R_9$ is independently selected from H, $C_1$-$C_6$ alkyl, SH and OH;

$R_{10}$ and $R_{11}$ are independently selected from the group consisting of —$(CH_2)_n NHR_2$ and —$(CH_2)_n CHR_6 R_7$;

$R_{12}$ is selected from $C_1$-$C_4$ alkyl, —$NHR_2$, —$(CH_2)_m R_9$, allyl, —$(CH_2)_n CO_2 H$—, —$(CH_2)_n CONH_2$ and —$(CH_2)_n CHR_6 R_7$;

$R_{13}$ is selected from H, $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, —$(CH_2)$—$R_1$, —$(CH=CH)_n R_1$, —$OR_2$, —$OR_1$, =O, —$S(R_2)_2$, —$SO_2 NHR_1$, —$(CH_2)$—SH, —$CF_3$, —$OCF_3$, —$N(R_2)_2$, —$NO_2$, —CN, —$(C=X)R_1$, —$(C=X)R_2$, —$CO_2$alkyl, and —$CO_2$aryl;

$R_{14}$ is selected from $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, —$(CH_2)_n R_1$, —$OR_2$, —$OR_1$, =O, —$S(R_2)_2$, —$SO_2 NHR_1$, —$(CH_2)$—SH, —$CF_3$, —$OCF_3$, —$N(R_2)_2$, —$NO_2$, —CN, —$(C=X)R_1$, —$(C=X)R_2$, —$CO_2$alkyl, and —$CO_2$aryl;

$R_{13}$ and $R_{14}$ are optionally linked to form a ring;

$R_{15}$ is selected from —$(CH_2)_n CHR_6 (CH_2)_n NH_2$, —$(CH_2)_m NR_6 (CH_2)_n NH_2$ and —$(CH_2)_m C(=O)NR_6 (CH_2)_n NH_2$;

$A_1$ is —$(CH_2)_m$—, —$[C(R_2 R_9)]_m$—, or =$CR_2 [C(R_2 R_8)]_m$—, wherein if $A_1$ is =$CR_2 [C(R_2 R_8)]_m$—, then a3 is 0;

$A_2$ is —$(CH_2)_m$—, —$NR_2$—$C(=X)$—, —$O(CH_2)_n$—, —$S(CH_2)_n$—, —CH=CH—, or —$C(=N$—$OR_2)$—;

$A_3$ is H or $C_1$-$C_4$ alkyl, or $A_3$ is —$CH_2$— bonded to $A_1$, $A_2$ or $R_1$ to form a ring;

a1, a2, and a3 are independently equal to 0 or 1;

$D_1$ is selected from —$CH_2$—, —$CH(NHR_8)$—, —$CH(R_2)$—, and —$CH(CH_2 SH)$—;

$D_2$, $D_3$, and $D_4$ are independently selected from the group consisting of —$(CH_2)_m$—, —$CH(R_2)$—, —$CH(NHR_8)$—, —$N(R_6)$—, —O—, —S—, —$C(=O)$—, —$S(=O)$— and —$SO_2$—, $D_5$ is selected from —$(CH_2)_m$—, —$CH(R_2)$— and —NH—, or any two atoms of $D_2$, $D_3$, $D_4$ and $D_5$ are bonded to form a four, five or six membered saturated ring optionally comprising a nitrogen within the ring;

d1, d2, d3, d4 and d5 are independently equal to 0 or 1;

$Q_1$ is selected from —$CH_2$—, —NH—, —N(Me)—, and —$N^+(Me_2)$—;

$Q_2$ and $Q_3$ are independently selected from the group consisting of —$CH_2$— and N;

with the proviso that no more than one of $Q_1$, $Q_2$, and $Q_3$ comprises a nitrogen;

q1, q2, and q3 are independently equal to 0 or 1;

$X_1$ and $X_2$ are each hydrogen or taken together are =O or =S, or $X_1$ is hydrogen and $X_2$ is —O— or —S— bonded to $R_{14}$ to form a 5- or 6-membered heterocyclyl, or $X_1$ is absent and $X_2$ is —O—, —$OCH_2$—, —S—, or —$SCH_2$— bonded to $R_{14}$ to form a 5- or 6-membered heterocyclyl or heteroaryl, wherein when $X_1$ is absent, the bond to nitrogen represented by a dashed and solid line is a double bond;

each X is independently O or S;

each n is independently an integer from 0 to 4; and each m is independently an integer from 1 to 3.

In another embodiment, the compounds have the structure of formula (IV)

Formula (IV)

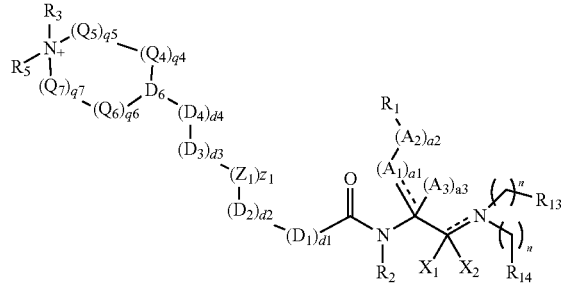

or a pharmaceutically acceptable salt or pro-drug thereof wherein;

each bond represented by a dashed and solid line represents a bond selected from the group consisting of a single bond and a double bond;

each $R_1$ is independently selected from $C_1$-$C_6$ alkyl, $C_3$-$C_6$ carbocyclyl, heterocyclyl, aryl and heteroaryl, each optionally substituted with up to 3 substituents independently selected from the group consisting of halo, $C_1$-$C_6$ alkyl, carbocyclyl, —$(CH_2)_n$aryl, —$OR_2$, —$OR_{14}$, —$S(R_2)_2$, —$SO_2 NHR_{14}$, —$(CH_2)_n SH$, —$CF_3$, —$OCF_3$, —$N(R_2)_2$, —$NO_2$, —CN, —$CO_2$alkyl, and —$CO_2$aryl;

each $R_2$ is independently selected from H and $C_1$-$C_6$ alkyl;

$R_3$ is —$(CH_2)_n CHR_6 R_7$;

each $R_4$ is independently selected from —$(CH_2)_m R_9$, allyl, —$(CH_2)_n CO_2 H$—, —$(CH_2)_n CONH_2$ and —$(CH_2)_n CHR_6 R_7$;

each $R_5$ is independently selected from —$(CH_2)_m R_9$, —$NHR_2$, and —$(CH_2)_n CHR_6 R_7$;

each $R_6$ is independently selected from H and —$(CH_2)_m NH_2$;

each $R_7$ is independently selected from —$(CH_2)_m NHR_8$, —$(CH_2)_m NHC(=NH)NH_2$, —$(CH_2)_m NHC(R_2)=NH$, and —$(CH_2)_m C(=NH)NH_2$;

each $R_8$ is independently selected from H, $C_1$-$C_6$ alkyl, —$C(O)CH(R_{15})(NH_2)$, —$C(O)A_2 CH_2 NH_2$, Alanine, Arginine, Asparagine, Aspartic acid, Glutamic acid, Glutamine, Cysteine, Glycine, Histidine, Isoleucine, Leucine, Lysine, Methionine, Phenylalanine, Proline, Serine, Threonine, Tryptophan, Tyrosine, and Valine;

each $R_9$ is independently selected from H, $C_1$-$C_6$ alkyl, SH and OH;

$R_{13}$ is selected from H, $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, —$(CH_2)_n R_1$, —$(CH=CH)_n R_1$, —$OR_2$, —$OR_1$, =O, —$S(R_2)_2$, —$SO_2 NHR_1$, —$(CH_2)_n SH$, —$CF_3$, —$OCF_3$, —$N(R_2)_2$, —$NO_2$, —CN, —$(C=X)R_1$, —$(C=X)R_2$, —$CO_2$alkyl, and —$CO_2$aryl;

$R_{14}$ is selected from $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, —$(CH_2)_n R_1$, —$OR_2$, —$OR_1$, =O, —$S(R_2)_2$, —$SO_2 NHR_1$, —$(CH_2)_n SH$, —$CF_3$, —$OCF_3$, —$N(R_2)_2$, —$NO_2$, —CN, —$(C=X)R_1$, —$(C=X)R_2$, —$CO_2$alkyl, and —$CO_2$aryl;

$R_{13}$ and $R_{14}$ are optionally linked to form a ring;

$R_{15}$ is selected from —$(CH_2)_n CHR_6 (CH_2)_n NH_2$, —$(CH_2)_m NR_6 (CH_2)_n NH_2$ and —$(CH_2)_m C(=O)NR_6 (CH_2)_n NH_2$;

$A_1$ is —$(CH_2)_m$—, —$[C(R_2R_9)]_m$—, or =$CR_2[C(R_2R_8)]_m$—, wherein if $A_1$ is =$CR_2[C(R_2R_8)]_m$—, then a3 is 0;

$A_2$ is —$(CH_2)_m$—, —$NR_2$—$C(=X)$—, —$O(CH_2)_6$—, —$S(CH_2)_n$—, —$CH=CH$—, or —$C(=N-OR_2)$—;

$A_3$ is H or $C_1$-$C_4$ alkyl, or $A_3$ is —$CH_2$— bonded to $A_1$, $A_2$ or $R_1$ to form a ring;

a1, a2, and a3 are independently equal to 0 or 1;

$D_1$ is selected from —$CH_2$—, —$CH(NHR_8)$—, —$CH(R_2)$—, and —$CH(CH_2SH)$—;

$D_2$, $D_3$, and $D_4$ are independently selected from the group consisting of —$(CH_2)_m$—, —$CH(R_2)$—, —$CH(NHR_8)$—, —$N(R_6)$—, —O—, —S—, —C(=O)—, —S(=O)— and —$SO_2$—, or any two atoms of $D_2$, $D_3$, and $D_4$ are bonded to form a four, five or six membered saturated ring optionally comprising a nitrogen within the ring;

$D_6$ is selected from —CH— and —N—;

d1, d2, d3, d4 and d5 are independently equal to 0 or 1;

$Q_4$, $Q_5$, $Q_6$ and $Q_7$ are each —$CH_2$—;

q4, q5, q6 and q7 are independently equal to 0 or 1;

with the proviso that at least two of q4, q5, q6 and q7 are equal to 1;

$Z_1$ is an aryl, heteroaryl, carbocyclyl, or heterocyclyl;

z1 is 0 or 1;

if z1 is 0 then at least two of d1, d2, d3, d4 and d5 are equal to 1;

if z1 is 1 then at least one of d1, d2, d3, d4 and d5 is equal to 1;

$X_1$ and $X_2$ are each hydrogen or taken together are =O or =S, or $X_1$ is hydrogen and $X_2$ is —O— or —S— bonded to $R_{14}$ to form a 5- or 6-membered heterocyclyl, or $X_1$ is absent and $X_2$ is —O—, —$OCH_2$—, —S—, or —$SCH_2$— bonded to $R_{14}$ to form a 5- or 6-membered heterocyclyl or heteroaryl, wherein when $X_1$ is absent, the bond to nitrogen represented by a dashed and solid line is a double bond;

each X is independently O or S;

each n is independently an integer from 0 to 4; and each m is independently an integer from 1 to 3.

In another embodiment, the compounds have the structure of formula (V)

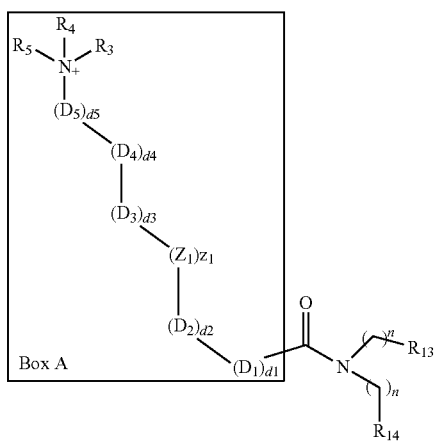

Formula (V)

or a pharmaceutically acceptable salt or pro-drug thereof wherein;

each bond represented by a dashed and solid line represents a bond selected from the group consisting of a single bond and a double bond;

each $R_1$ is independently selected from $C_1$-$C_6$ alkyl, $C_3$-$C_6$ carbocyclyl, heterocyclyl, aryl and heteroaryl, each optionally substituted with up to 3 substituents independently selected from the group consisting of halo, $C_1$-$C_6$ alkyl, carbocyclyl, —$(CH_2)_n$aryl, —$OR_2$, —$OR_{14}$, —$S(R_2)_2$, —$SO_2NHR_{14}$, —$(CH_2)_n$SH, —$CF_3$, —$OCF_3$, —$N(R_2)_2$, —$NO_2$, —CN, —$CO_2$alkyl, and —$CO_2$aryl;

each $R_2$ is independently selected from H and $C_1$-$C_6$ alkyl;

$R_3$ is —$(CH_2)_n CHR_6R_7$ each $R_4$ is independently selected from —$(CH_2)_m R_9$, allyl, —$(CH_2)_n CO_2H$—, —$(CH_2)_n CONH_2$ and —$(CH_2)_n CHR_6R_7$;

each $R_5$ is independently selected from —$(CH_2)_m R_9$, —$NHR_2$, and —$(CH_2)_n CHR_6R_7$;

each $R_6$ is independently selected from H and —$(CH_2)_m NH_2$;

each $R_7$ is independently selected from —$(CH_2)_m NHR_8$, $(CH_2)_m NHC(=NH)NH_2$, —$(CH_2)_m NHC(R_2)=NH$, and —$(CH_2)_m C(=NH)NH_2$;

each $R_8$ is independently selected from H, $C_1$-$C_6$ alkyl, —$C(O)CH(R_{15})(NH_2)$, —$C(O)A_2CH_2NH_2$, Alanine, Arginine, Asparagine, Aspartic acid, Glutamic acid, Glutamine, Cysteine, Glycine, Histidine, Isoleucine, Leucine, Lysine, Methionine, Phenylalanine, Proline, Serine, Threonine, Tryptophan, Tyrosine, and Valine;

each $R_9$ is independently selected from H, $C_1$-$C_6$ alkyl, SH and OH;

$R_{13}$ is selected from H, $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, —$(CH_2)$—$R_1$, —$(CH=CH)_n R_1$, —$OR_2$, —$OR_1$, =O, —$S(R_2)_2$, —$SO_2NHR_1$, —$(CH_2)$—SH, —$CF_3$, —$OCF_3$, —$N(R_2)_2$, —$NO_2$, —CN, —$(C=X)R_1$, —$(C=X)R_2$, —$CO_2$alkyl, and —$CO_2$aryl;

$R_{14}$ is selected from $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, —$(CH_2)_n R_1$, —$OR_2$, —$OR_1$, =O, —$S(R_2)_2$, —$SO_2NHR_1$, —$(CH_2)$—SH, —$CF_3$, —$OCF_3$, —$N(R_2)_2$, —$NO_2$, —CN, —$(C=X)R_1$, —$(C=X)R_2$, —$CO_2$alkyl, and —$CO_2$aryl;

$R_{13}$ and $R_{14}$ are optionally linked to form a ring;

$R_{15}$ is selected from —$(CH_2)$—$CHR_6(CH_2)_n NH_2$, —$(CH_2)_m NR_6(CH_2)_n NH_2$ and —$(CH_2)_m C(=O)NR_6(CH_2)_n NH_2$;

$A_1$ is —$(CH_2)_m$—, —$[C(R_2R_9)]_m$—, or =$CR_2[C(R_2R_8)]_m$—, wherein if $A_1$ is =$CR_2[C(R_2R_8)]_m$—, then a3 is 0;

$A_2$ is —$(CH_2)_m$—, —$NR_2$—$C(=X)$—, —$O(CH_2)_n$—, —$S(CH_2)_n$—, —$CH=CH$—, or —$C(=N-OR_2)$—;

$A_3$ is H or $C_1$-$C_4$ alkyl, or $A_3$ is —$CH_2$— bonded to $A_1$, $A_2$ or $R_1$ to form a ring;

a1, a2, and a3 are independently equal to 0 or 1;

$D_1$ is selected from —$CH_2$—, —$CH(NHR_8)$—, —$CH(R_2)$—, and —$CH(CH_2SH)$—;

$D_2$, $D_3$, and $D_4$ are independently selected from the group consisting of —$(CH_2)_m$—, —$CH(R_2)$—, —$CH(NHR_8)$—, —$N(R_6)$—O—, —S—, —C(=O)—, —S(=O)— and —$SO_2$—;

$D_5$ is selected from —$(CH_2)_m$—, —$CH(R_2)$— and —NH—, or any two atoms of $D_2$, $D_3$, $D_4$ and $D_5$ are bonded to form a four, five or six membered saturated ring optionally comprising a nitrogen within the ring;

d1, d2, d3, d4 and d5 are independently equal to 0 or 1;

$Z_1$ is an aryl, heteroaryl, carbocyclyl, or heterocyclyl;

z1 is 0 or 1;

if z1 is 0 then at least two of d1, d2, d3, d4 and d5 are equal to 1;

if z1 is 1 then at least one of d1, d2, d3, d4 and d5 is equal to 1;

$X_1$ and $X_2$ are each hydrogen or taken together are =O or =S, or $X_1$ is hydrogen and $X_2$ is —O— or —S— bonded to $R_{14}$ to form a 5- or 6-membered heterocyclyl, or $X_1$ is absent and $X_2$ is —O—, —OCH$_2$—, —S—, or —SCH$_2$— bonded to $R_{14}$ to form a 5- or 6-membered heterocyclyl or heteroaryl, wherein when $X_1$ is absent, the bond to nitrogen represented by a dashed and solid line is a double bond;

each X is independently O or S;

each n is independently an integer from 0 to 4; and each m is independently an integer from 1 to 3.

In another embodiment, the compounds have the structure of formula (VI):

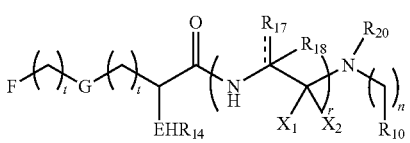

(VI)

or a pharmaceutically acceptable salt or prodrug thereof, wherein:

each E is independently CH or N;

F is selected from the group consisting of —N$^+$R$_{15}$R$_{16}$R$_{21}$, —N[(CH$_2$)$_r$N$^+$R$_{15}$R$_{16}$R$_{21}$]$_2$, —CH[(CH$_2$)$_r$N$^+$R$_{15}$R$_{16}$R$_{21}$]$_2$,

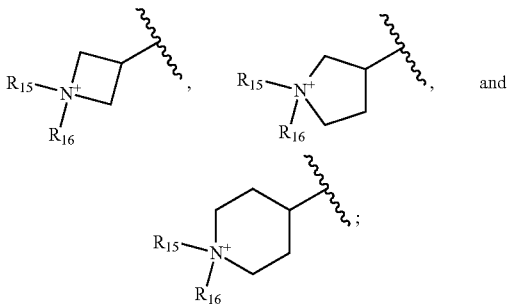

G is selected from —CH$_2$—, —CH(alkyl)—, —S(O)$_2$—, —NHC(O)CH(NH$_2$)—, —NHC(O)—, —C(O)NH—, —C(O)N(CH$_2$CH$_2$NH)—, —NH—, —C(O)—, carbocyclyl, aryl, —S—:

$X_1$ and $X_2$ are each hydrogen or together are =O or =S;

$R_{10}$ is selected from carbocyclyl, heterocyclyl, aryl, and heteroaryl, each optionally substituted with up to 3 substituents independently selected from the group consisting of a halide, alkyl optionally substituted with —SH, —CF$_3$, —OCF$_3$, —NO$_2$, —CN, —OH, =O, carbocyclyl, heterocyclyl, aryl optionally substituted with halide or —OH, heteroaryl optionally substituted with alkyl, aralkyl optionally substituted with halide or —CF$_3$, —O-aryl, —O-heteroaryl, —O-heterocyclyl, —SO$_2$NH-heteroaryl, —O—C$_1$-C$_6$ alkyl, and di(C$_1$-C$_6$)alkylamino;

$R_{14}$ is selected from H, —C(O)CH(NH$_2$)(CH$_2$SH), —C(O)CH(NH$_2$)(CH$_2$CH$_2$CH$_2$NHC(NH$_2$)(=NH)), —C(O)CH(NH$_2$)(CH$_2$COOH), —C(O)—CH(Me)(NH$_2$), and —SH;

$R_{15}$ is selected from —(CH$_2$)$_s$NH$_2$, —(CH$_2$)$_s$NHC(=NH) NH$_2$, —(CH$_2$)$_s$CH(CH$_2$NH$_2$)$_2$, —(CH$_2$)$_s$NHC(O)CH(NH$_2$) CH$_2$COOH, —(CH$_2$)$_s$NHCH(=NH), —(CH$_2$)$_n$NHC(O)CH (NH$_2$)(CH$_2$SH), —(CH$_2$)$_s$NHCH$_3$, and —(CH$_2$)$_n$C(O)NH$_2$;

$R_{16}$ is selected from alkyl, —(CH$_2$)$_s$COOH, allyl, —(CH$_2$)$_s$SH, —(CH$_2$)$_s$NH$_2$, —(CH$_2$)$_s$NHC(=NH)NH$_2$, —(CH$_2$)$_s$CH(CH$_2$NH$_2$)$_2$, (CH$_2$)$_s$NHC(O)CH(NH$_2$) CH$_2$COOH, —(CH$_2$)$_s$NHCH(=NH), (CH$_2$)$_s$NHC(O)CH (NH$_2$)(CH$_2$SH), —(CH$_2$)$_s$NHCH$_3$, and —(CH$_2$)$_s$C(O)NH$_2$;

or $R_{15}$ and $R_{16}$ together form a heterocyclyl substituted with at least two substituents independently selected from —(CH$_2$)$_s$NH$_2$, —(CH$_2$)$_s$NHC(=NH)NH$_2$, —(CH$_2$)$_s$N$^+$(CH$_3$)$_3$, —(CH$_2$)$_s$NHCH$_2$CH$_2$NH$_2$, —(CH$_2$)$_s$N(CH$_2$CH$_2$NH$_2$)$_2$, —(CH$_2$)$_s$C(O)N(CH$_2$CH$_2$NH$_2$)$_2$, and —(CH$_2$)$_s$CH(CH$_2$NH$_2$)$_2$;

$R_{17}$ is selected from alkyl, aralkyl, heteroaralkyl, carbocyclyl-alkyl, heterocyclyl-alkyl, aryl, and carbocyclyl, each optionally substituted with up to 3 substituents independently selected from the group consisting of —CF$_3$, —OH, —SH, —CH$_2$SH, —OCF$_3$, halide, —CN, alkyl, —O-aralkyl, —CH$_2$—O-aryl, aryl, —S(CH$_3$)$_2$, —C(O)aryl, —S-aralkyl optionally substituted with —OMe, =O, and =N—OH;

$R_{18}$ is H, alkyl, or absent, or $R_{17}$ together with $R_{18}$ form a carbocyclyl optionally substituted with aryl or heteroaryl;

$R_{20}$ is H or alkyl;

$R_{21}$ is selected from alkyl, —(CH$_2$)$_s$COOH, allyl, —(CH$_2$)$_s$SH, —(CH$_2$)$_s$NH$_2$, —(CH$_2$)$_s$NHC(=NH)NH$_2$, —(CH$_2$)$_s$CH(CH$_2$NH$_2$)$_2$, (CH$_2$)$_s$NHC(O)CH(NH$_2$) CH$_2$COOH, —(CH$_2$)$_s$NHCH(=NH), (CH$_2$)$_s$NHCH$_2$C(O) CH(NH$_2$)(CH$_2$SH), —(CH$_2$)$_s$NHCH$_3$, and —(CH$_2$)$_s$C(O) NH$_2$;

each t is independently an integer from 0 to 4;

each s is independently an integer from 0 to 3;

r is 0 or 1; and n is an integer from 0 to 4.

In another embodiment, the compounds have the structure of formula (VII):

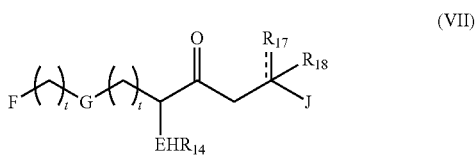

(VII)

or a pharmaceutically acceptable salt or prodrug thereof, wherein:

each E is independently CH or N;

F is selected from the group consisting of —N$^+$R$_{15}$R$_{16}$R$_{21}$, —N[(CH$_2$)$_r$N$^+$R$_{15}$R$_{16}$R$_{21}$]$_2$, —CH[(CH$_2$)$_r$N$^+$R$_{15}$R$_{16}$R$_{21}$]$_2$,

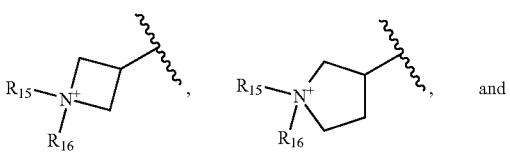

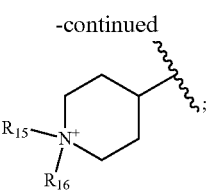

G is selected from —CH$_2$—, —CH(alkyl)—, —S(O)$_2$—, —NHC(O)CH(NH$_2$)—, —NHC(O)—, —C(O)NH—, —C(O)N(CH$_2$CH$_2$NH)—, —NH—, —C(O)—, carbocyclyl, aryl, —S—:

J is a heterocyclyl or heteroaryl, each optionally substituted with up to 3 substituents independently selected from the group consisting of a halide, alkyl optionally substituted with —SH, —CF$_3$, —OCF$_3$, —NO$_2$, —CN, —OH, =O, carbocyclyl, heterocyclyl, aryl optionally substituted with halide or —OH, heteroaryl optionally substituted with alkyl, aralkyl optionally substituted with halide or —CF$_3$, —O-aryl, —O-heteroaryl, —O-heterocyclyl, —SO$_2$NH-heteroaryl, —O—C$_1$-C$_6$ alkyl, and di(C$_1$-C$_6$)alkylamino;

R$_{14}$ is selected from H, —C(O)CH(NH$_2$)(CH$_2$SH), —C(O)CH(NH$_2$)(CH$_2$CH$_2$CH$_2$NHC(NH$_2$)(=NH)), —C(O)CH(NH$_2$)(CH$_2$COOH), —C(O)—CH(Me)(NH$_2$), and —SH;

R$_{15}$ is selected from —(CH$_2$)$_s$NH$_2$, —(CH$_2$)$_s$NHC(=NH)NH$_2$, —(CH$_2$)$_s$CH(CH$_2$NH$_2$)$_2$, —(CH$_2$)$_s$NHC(O)CH(NH$_2$)CH$_2$COOH, —(CH$_2$)$_s$NHCH(=NH), —(CH$_2$)$_s$NHC(O)CH(NH$_2$)(CH$_2$SH), —(CH$_2$)$_s$NHCH$_3$, and —(CH$_2$)$_s$C(O)NH$_2$;

R$_{16}$ is selected from alkyl, —(CH$_2$)$_s$COOH, allyl, —(CH$_2$)$_s$SH, —(CH$_2$)$_s$NH$_2$, —(CH$_2$)$_s$NHC(=NH)NH$_2$, —(CH$_2$)$_s$CH(CH$_2$NH$_2$)$_2$, —(CH$_2$)$_s$NHC(O)CH(NH$_2$)CH$_2$COOH, —(CH$_2$)$_s$NHCH(=NH), —(CH$_2$)$_s$NHC(O)CH(NH$_2$)(CH$_2$SH), —(CH$_2$)$_s$NHCH$_3$, and —(CH$_2$)$_s$C(O)NH$_2$;

or R$_{15}$ and R$_{16}$ together form a heterocyclyl substituted with at least two substituents independently selected from —(CH$_2$)$_s$NH$_2$, —(CH$_2$)$_s$NHC(=NH)NH$_2$, —(CH$_2$)$_s$N$^+$(CH$_3$)$_3$, —(CH$_2$)$_s$NHCH$_2$CH$_2$NH$_2$, —(CH$_2$)$_s$N(CH$_2$CH$_2$NH$_2$)$_2$, —(CH$_2$)$_s$C(O)N(CH$_2$CH$_2$NH$_2$)$_2$, and —(CH$_2$)$_s$CH(CH$_2$NH$_2$)$_2$;

R$_{17}$ is selected from alkyl, aralkyl, heteroaralkyl, carbocyclyl-alkyl, heterocyclyl-alkyl, aryl, and carbocyclyl, each optionally substituted with up to 3 substituents independently selected from the group consisting of —CF$_3$, —OH, —SH, —CH$_2$SH, —OCF$_3$, halide, —CN, alkyl, —O-aralkyl, —CH$_2$—O-aryl, aryl, —S(CH$_3$)$_2$, —C(O)aryl, —S-aralkyl optionally substituted with —OMe, =O, and =N—OH;

R$_{18}$ is H, alkyl, or absent, or R$_{17}$ together with R$_{18}$ form a carbocyclyl optionally substituted with aryl or heteroaryl;

R$_{21}$ is selected from alkyl, —(CH$_2$)$_s$COOH, allyl, —(CH$_2$)$_s$SH, —(CH$_2$)$_s$NH$_2$, —(CH$_2$)$_s$NHC(=NH)NH$_2$, —(CH$_2$)$_s$CH(CH$_2$NH$_2$)$_2$, —(CH$_2$)$_s$NHC(O)CH(NH$_2$)CH$_2$COOH, —(CH$_2$)$_s$NHCH(=NH), —(CH$_2$)$_s$NHCH$_2$C(O)CH(NH$_2$)(CH$_2$SH), —(CH$_2$)$_s$NHCH$_3$, and —(CH$_2$)$_s$C(O)NH$_2$;

each t is independently an integer from 0 to 4;

each s is independently an integer from 0 to 3;

r is 0 or 1; and n is an integer from 0 to 4.

Some embodiments of the compounds of formulas (I)-(VII) are shown below. Although the structures are shown with defined configurations at selected stereocenters, the shown stereochemistries are not meant to be limiting and all possible stereoisomers of the shown structures are contemplated. Compounds of any absolute and relative configurations at the stereocenters as well as mixtures of enantiomers and diastereoisomers of any given structure are also contemplated.

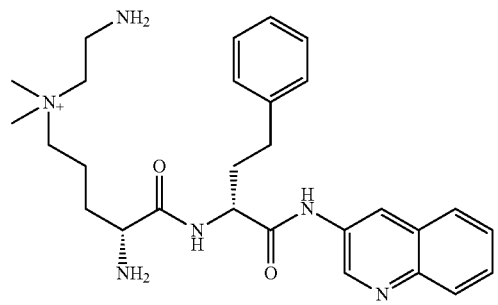

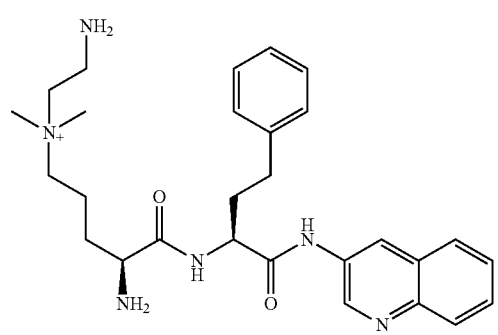

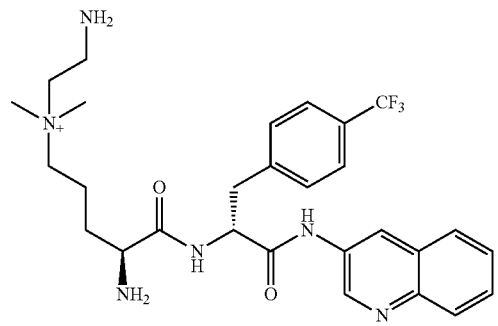

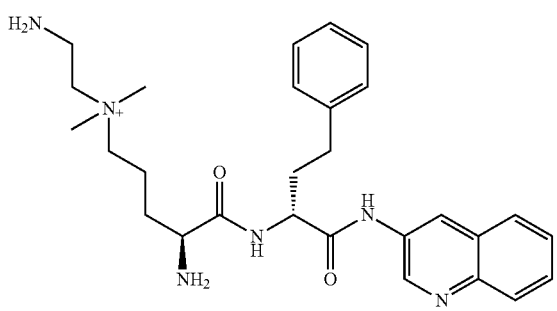

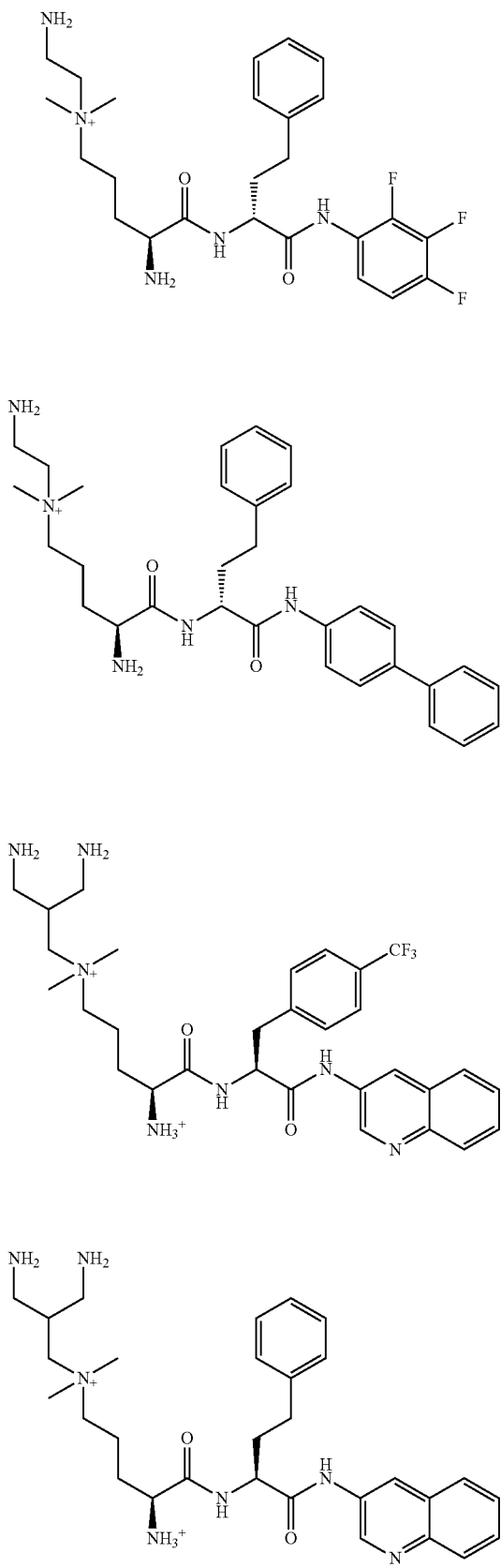
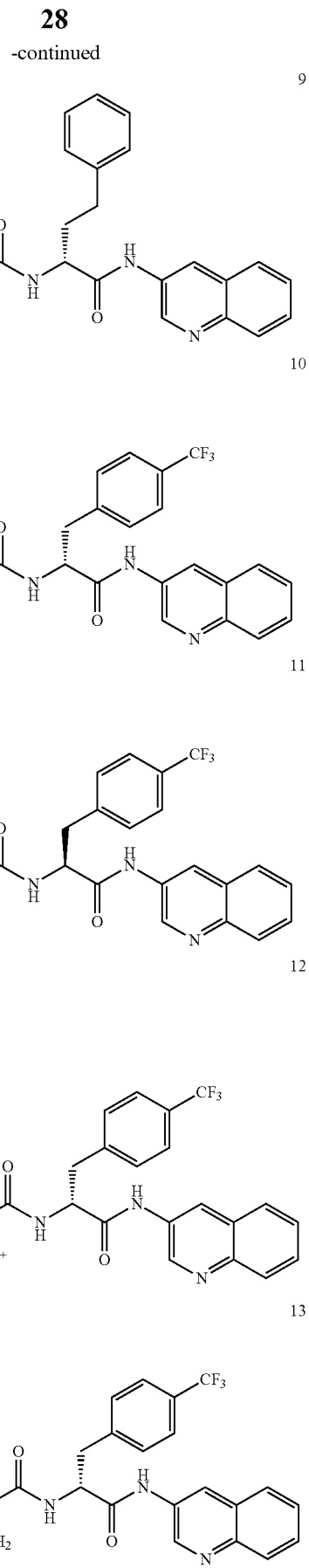

14
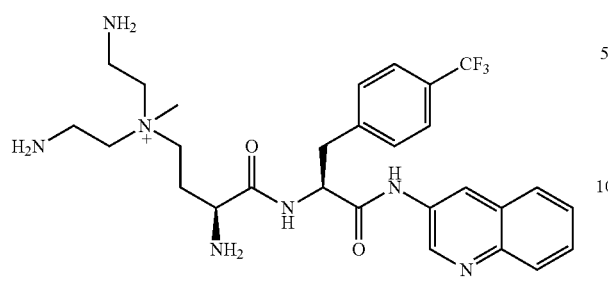
15
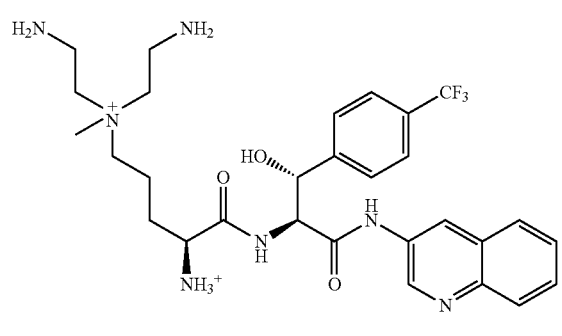
16
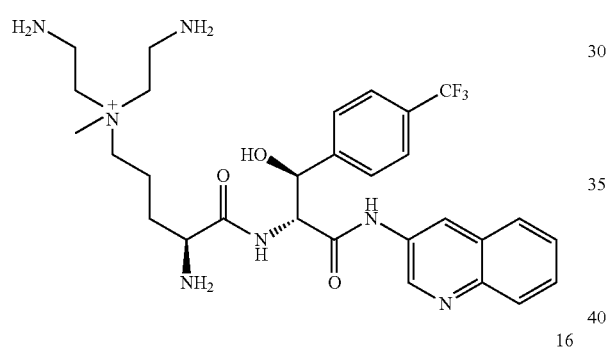
17
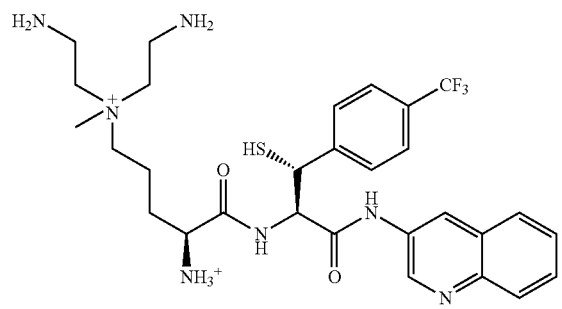
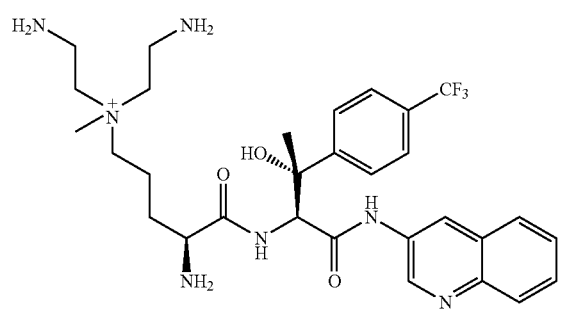
18
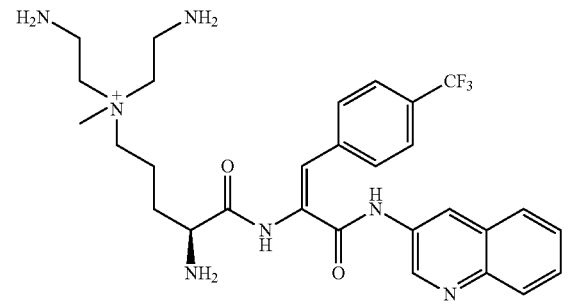
19
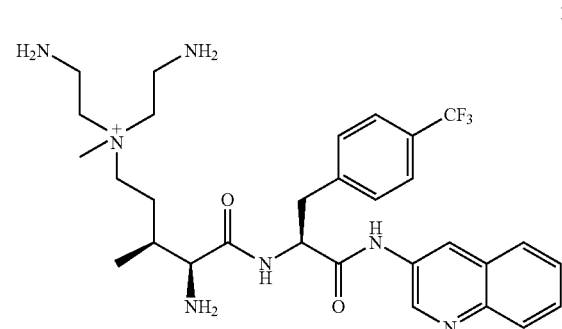
20
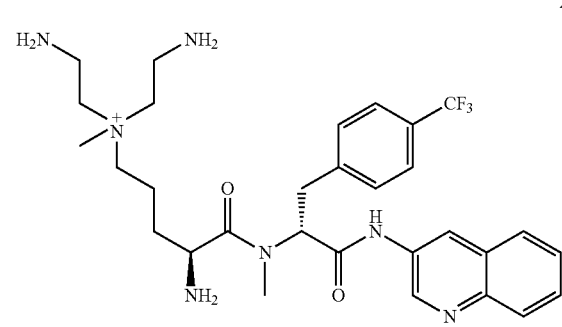
21
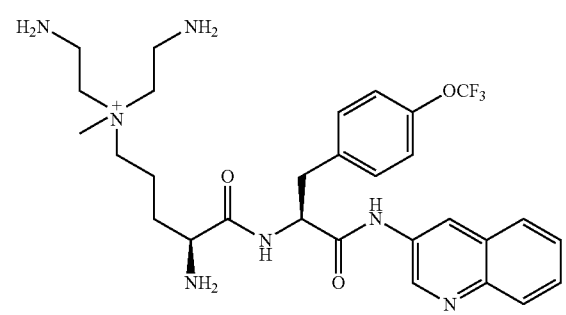
22
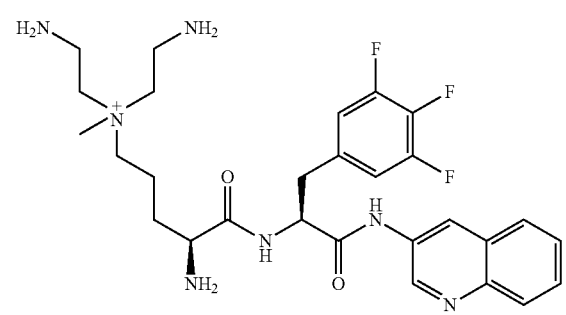

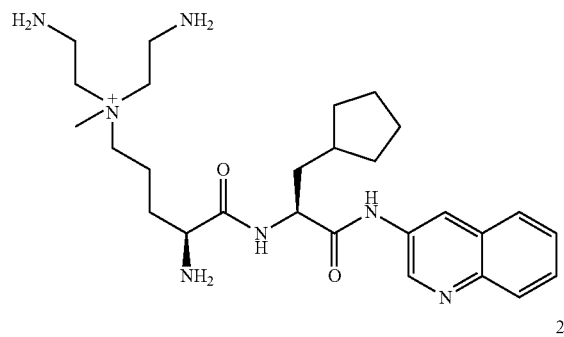
23
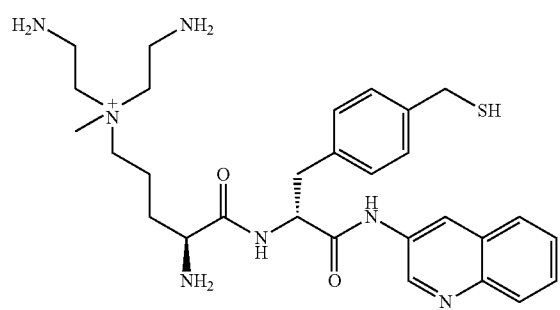
24
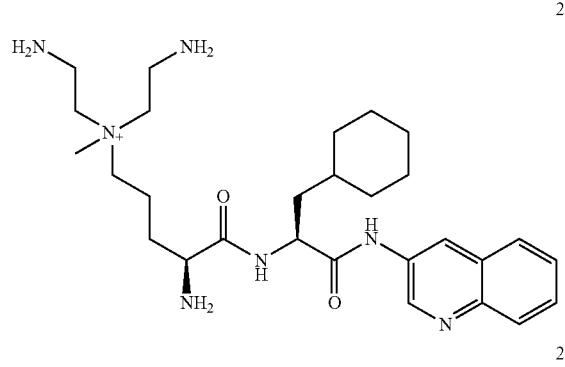
25
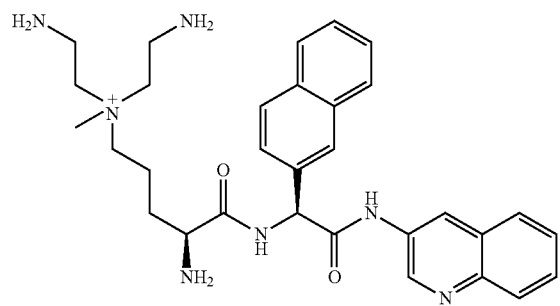
26
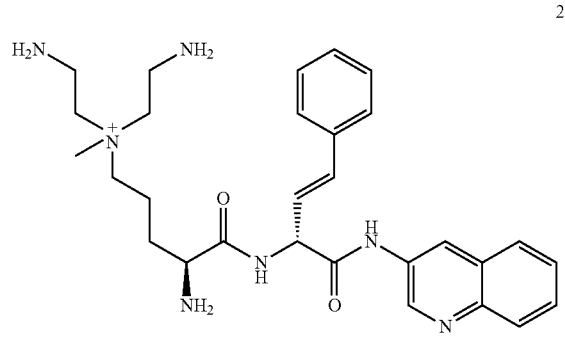
27
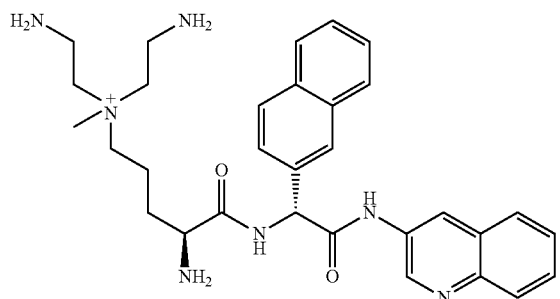
28
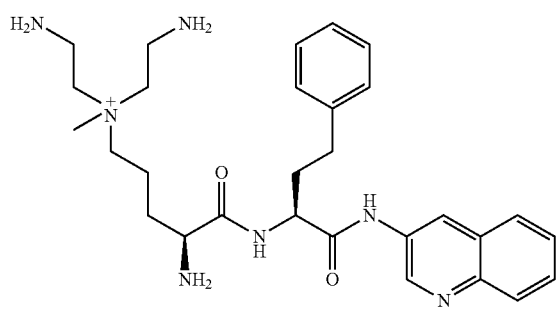
29
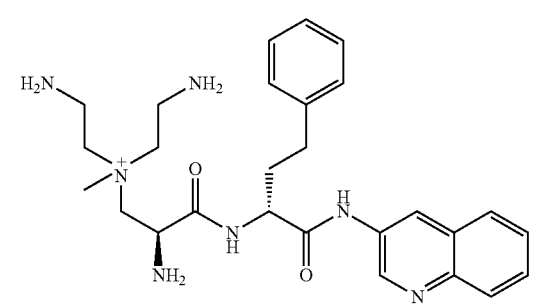
30
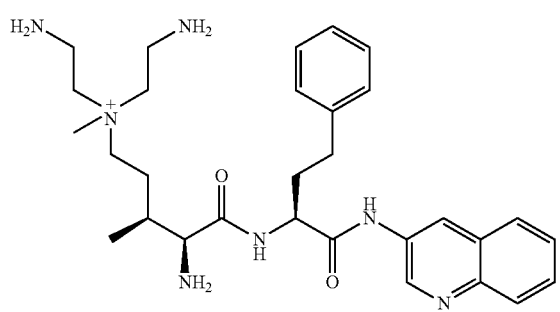
31
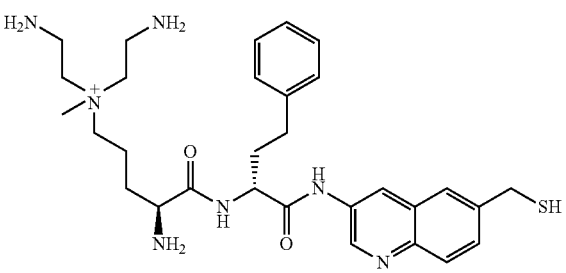
32

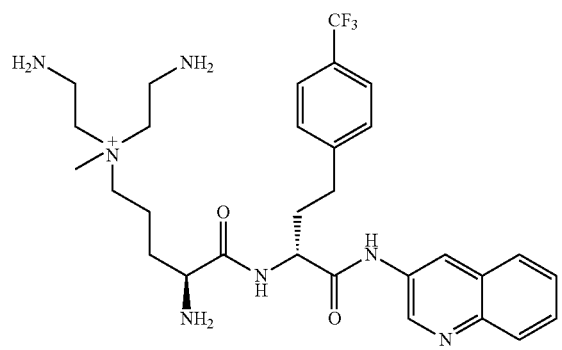
33
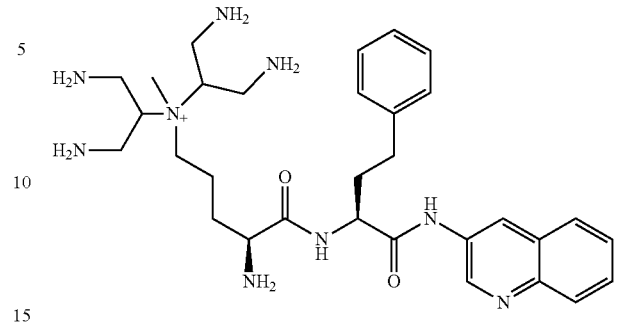
37
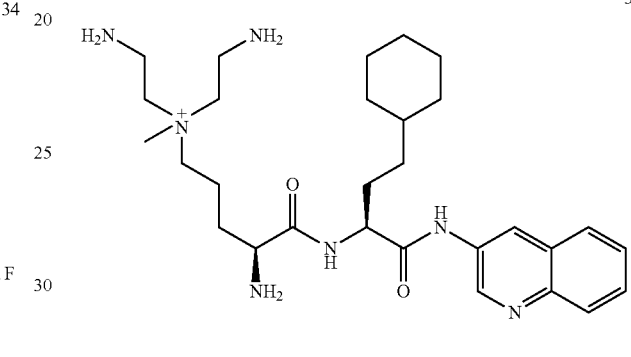
38
34
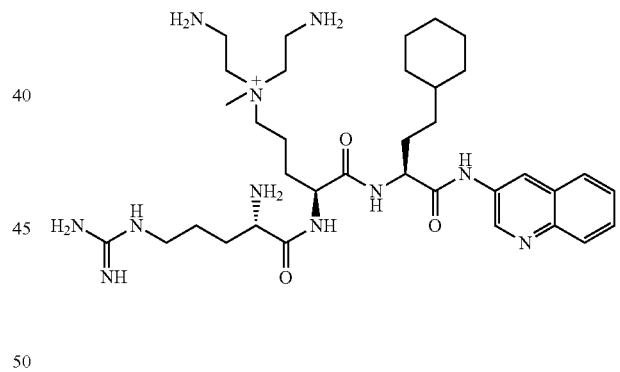
39
35
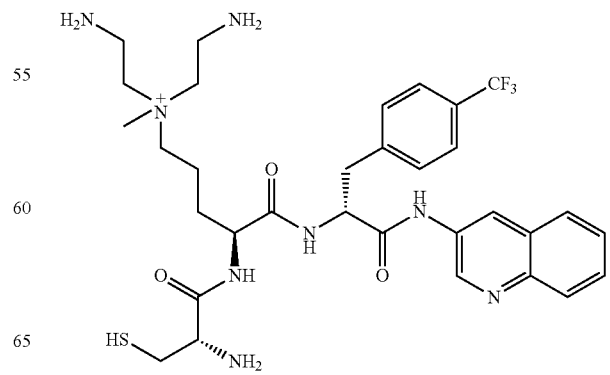
40
36

35
-continued
36
-continued

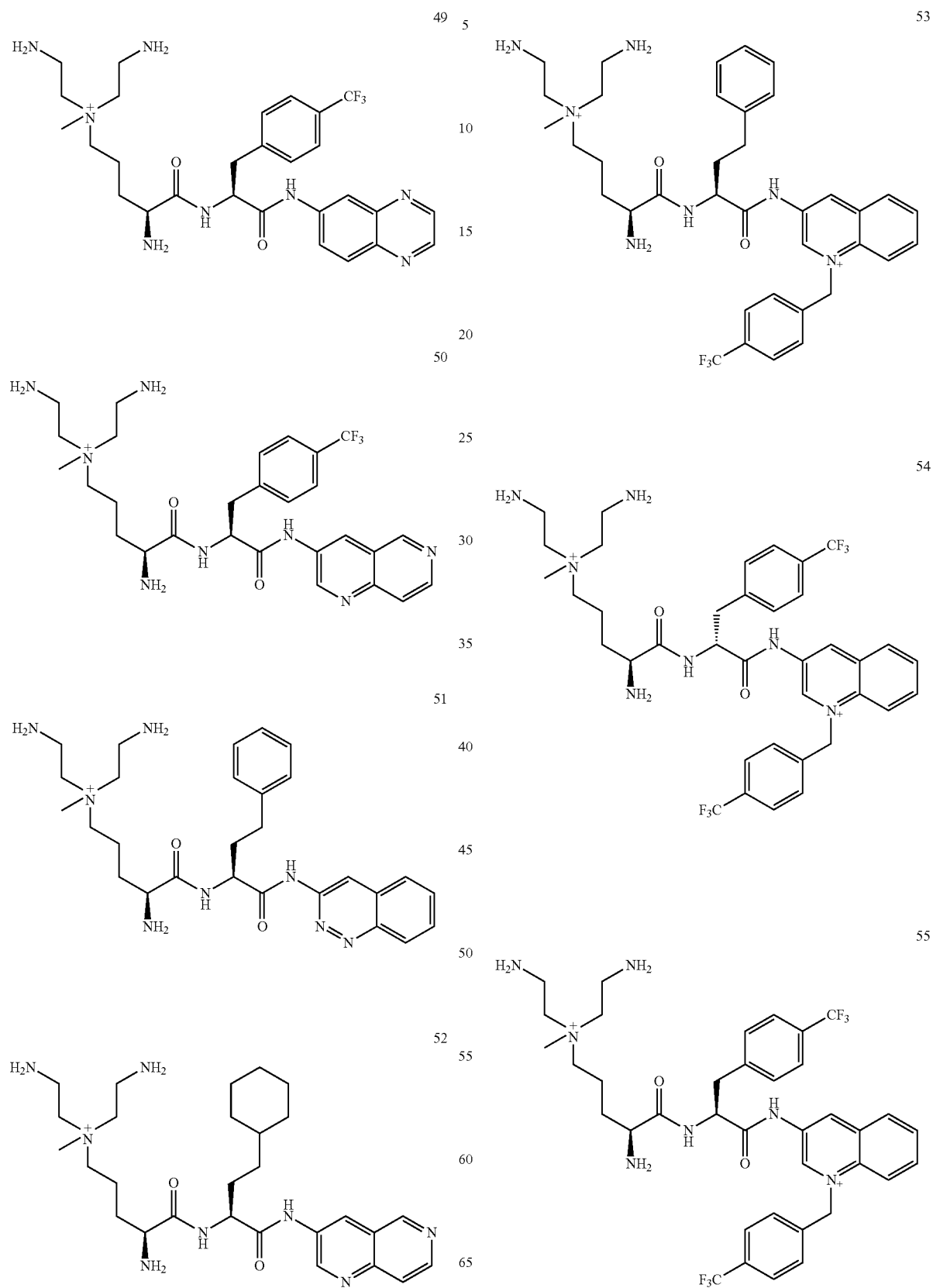

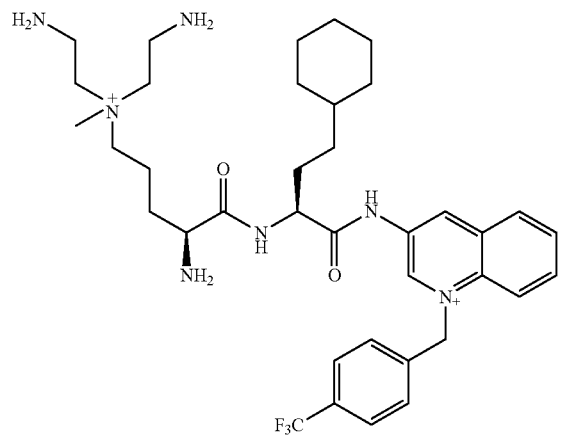
56
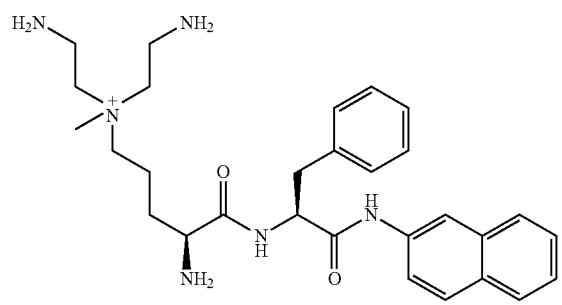
57
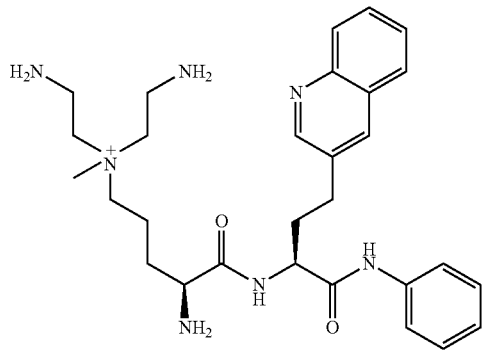
58
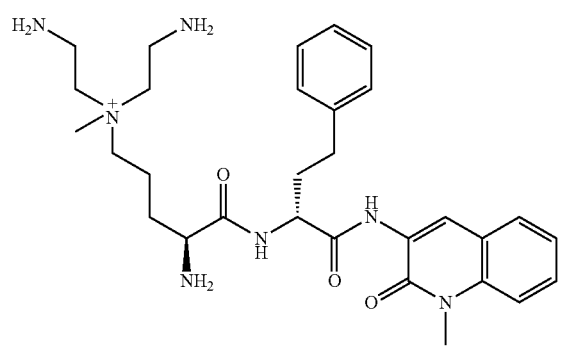
59
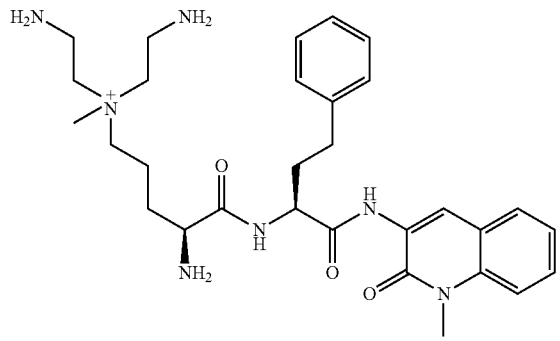
60
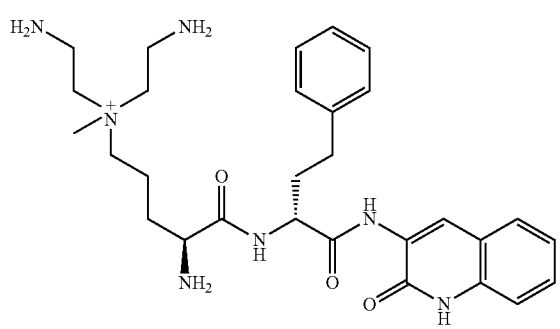
61
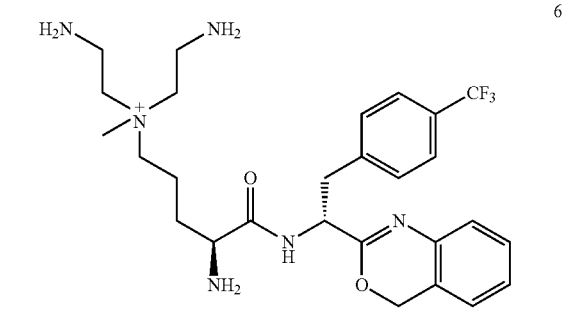
62
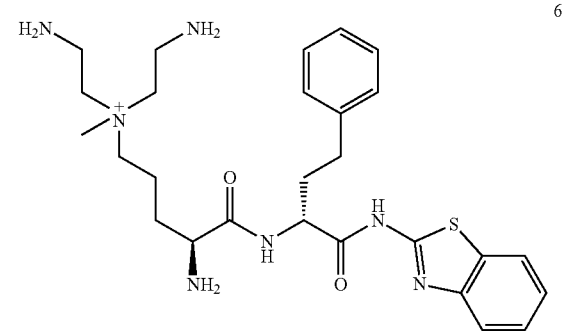
63
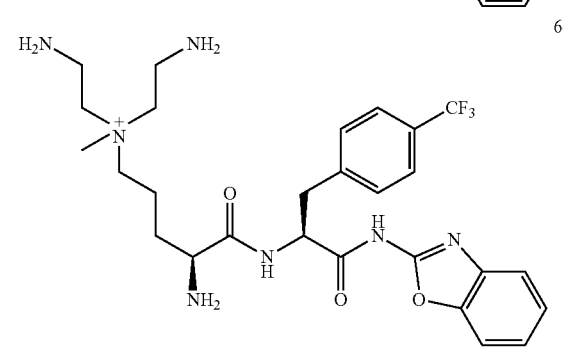
64

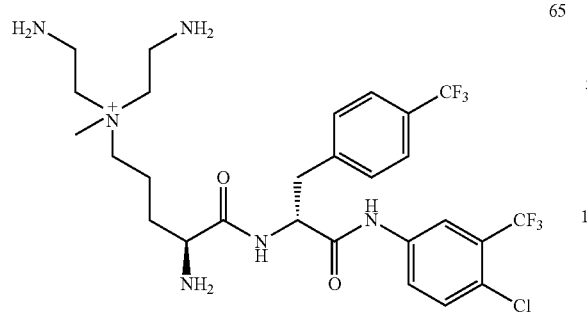
65
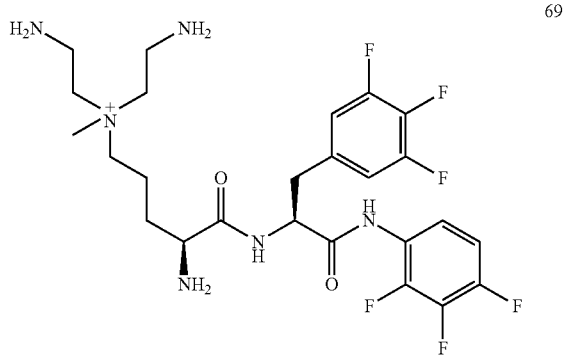
69
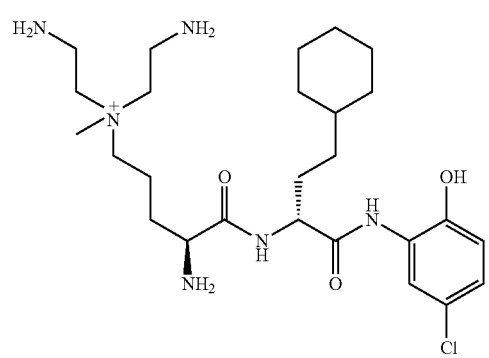
66
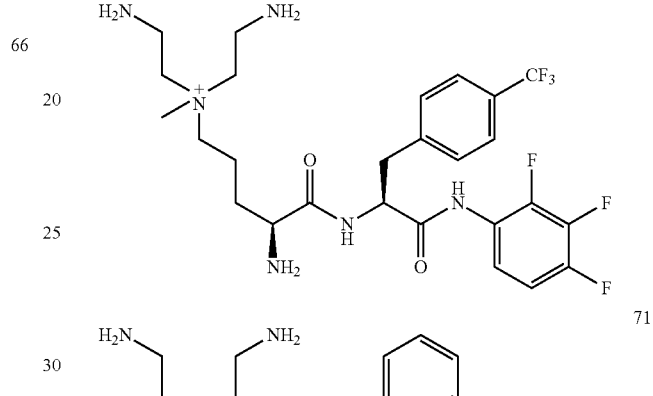
70
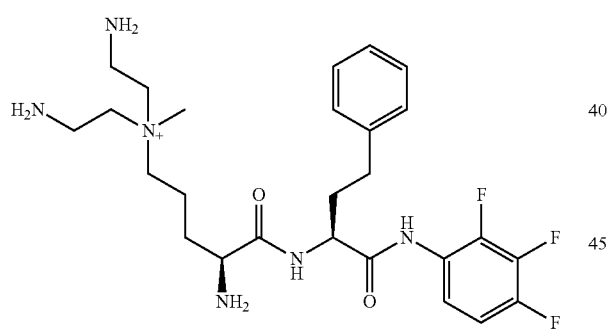
67
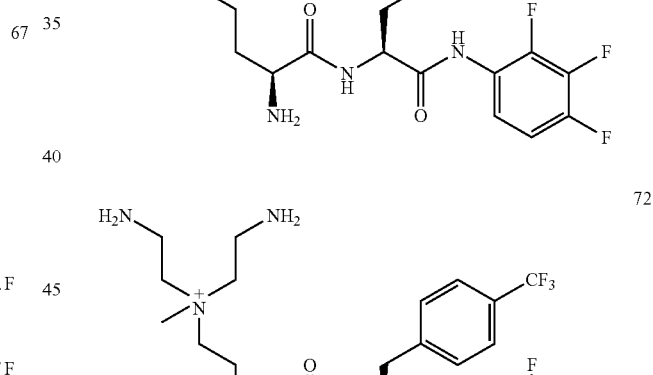
71
72
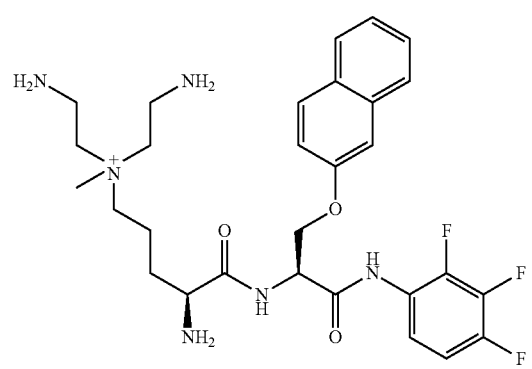
68
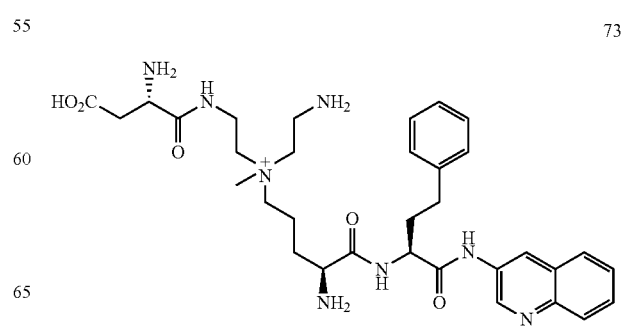
73

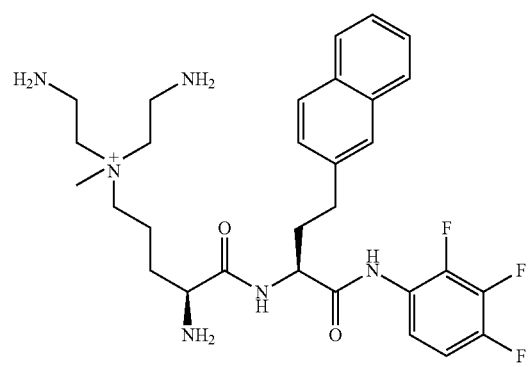
74
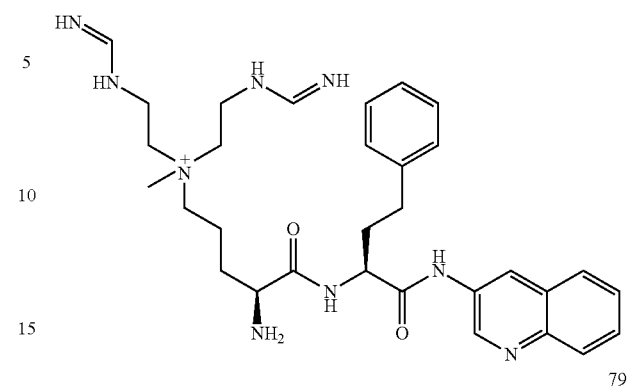
78
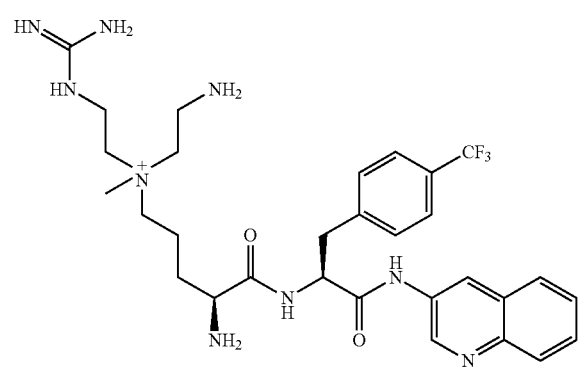
75
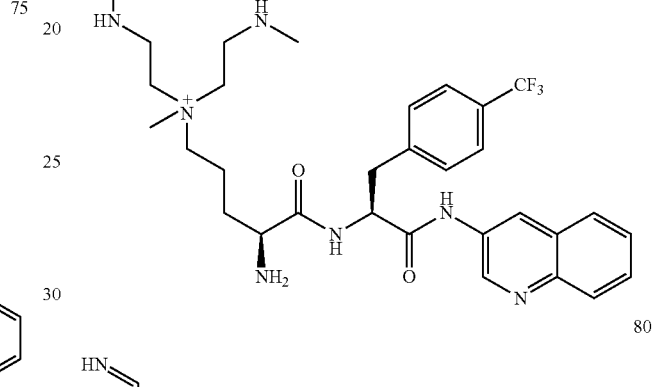
79
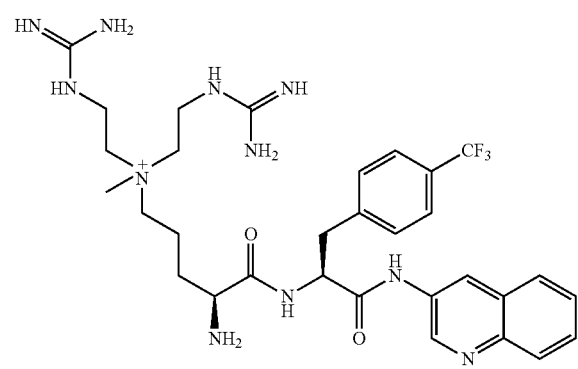
76
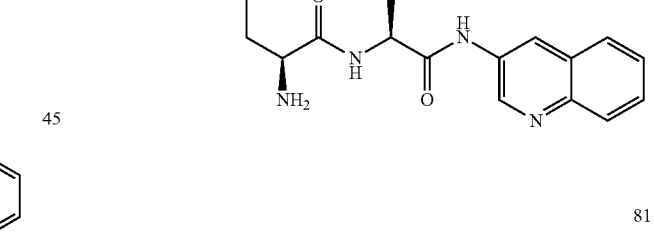
80
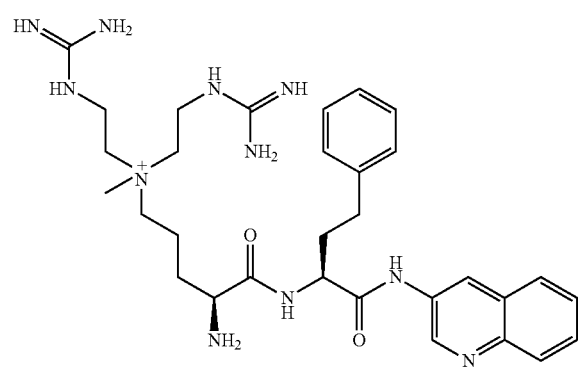
77
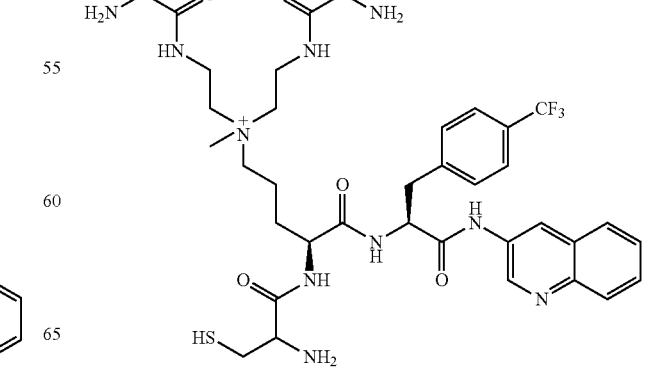
81

82
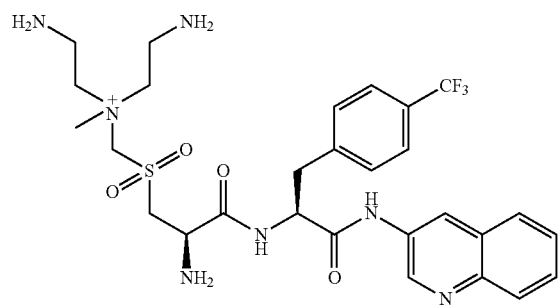
86
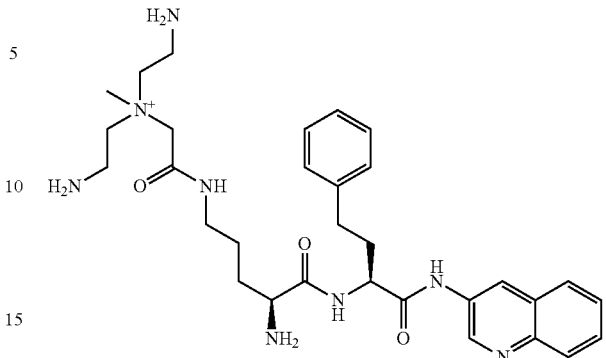
83
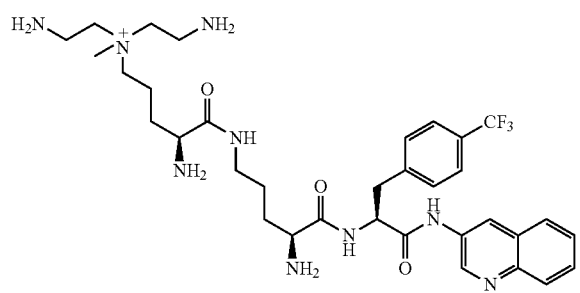
87
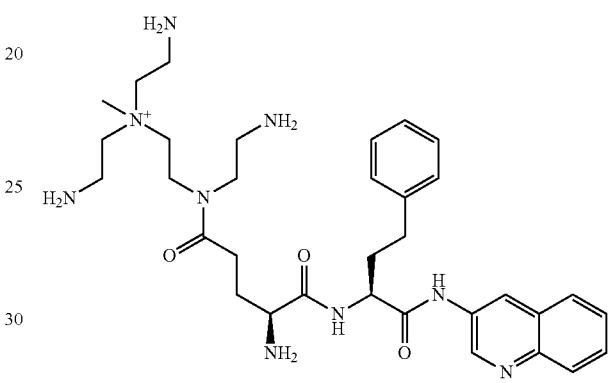
84
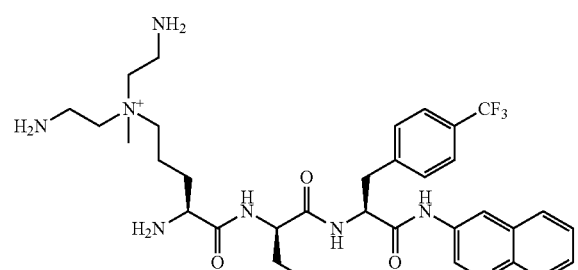
88
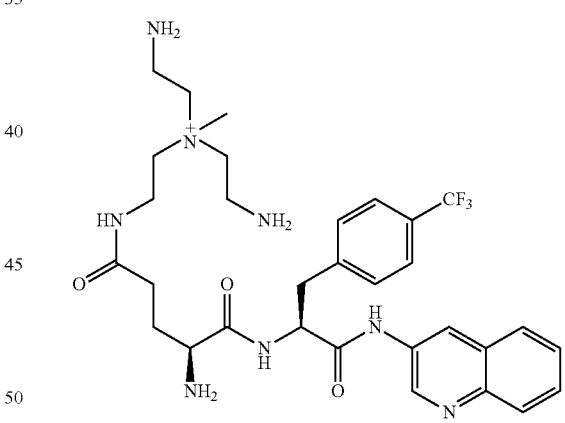
85
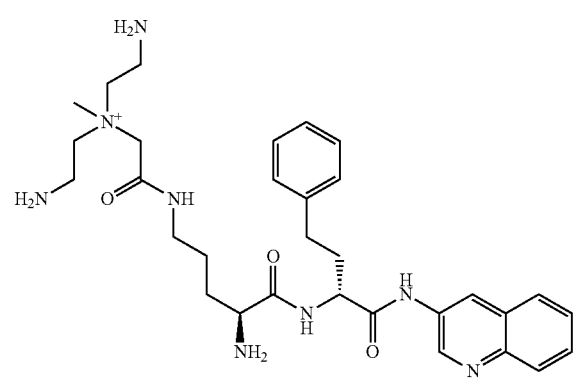
89
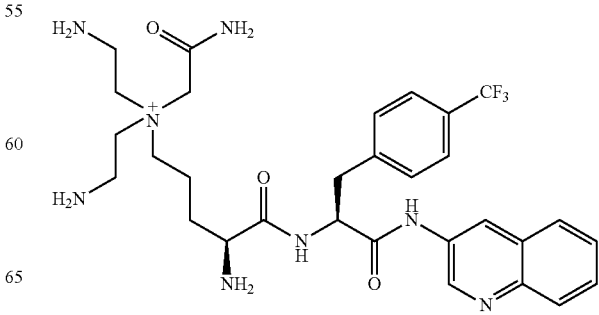

-continued

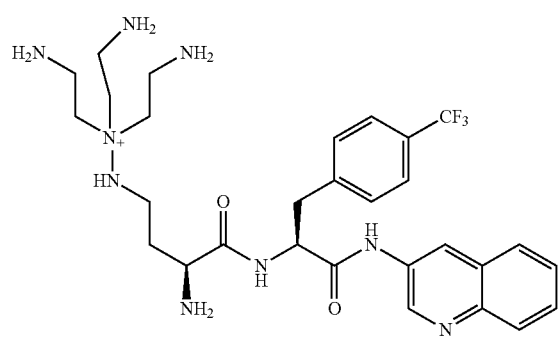
99
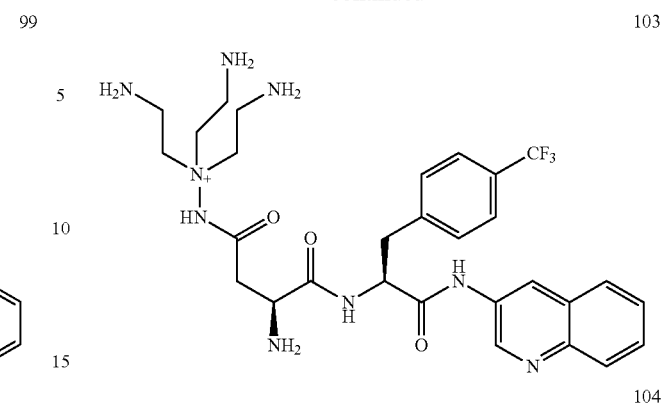
103
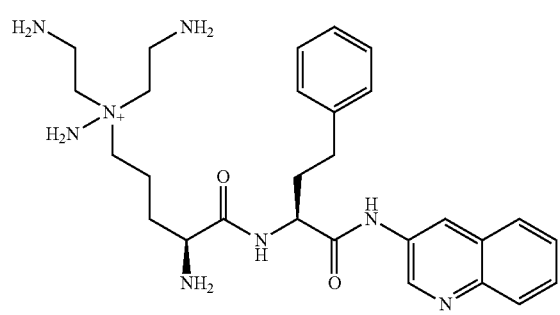
100
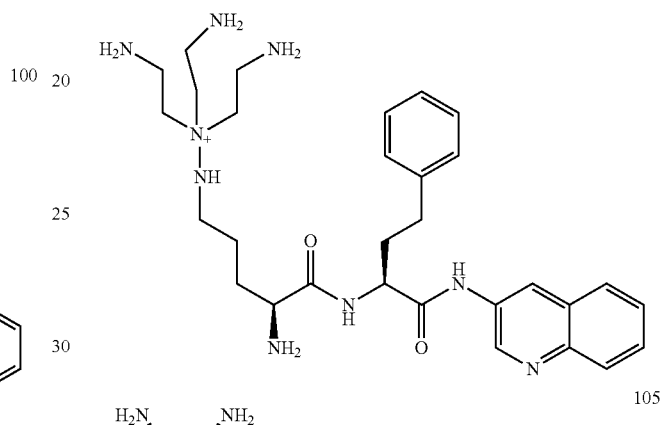
104
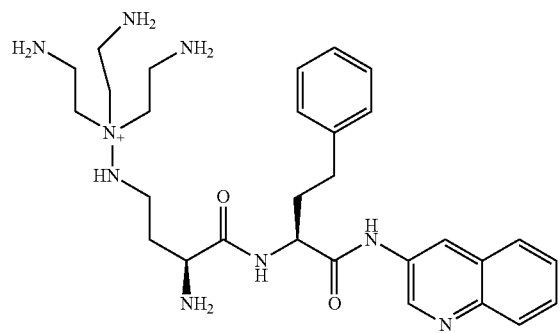
101
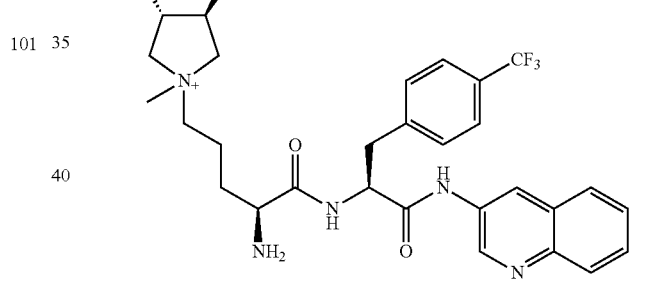
105
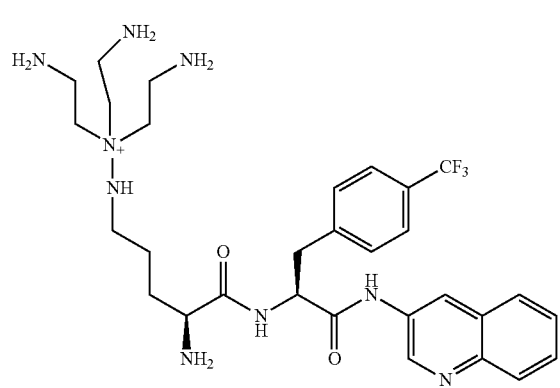
102
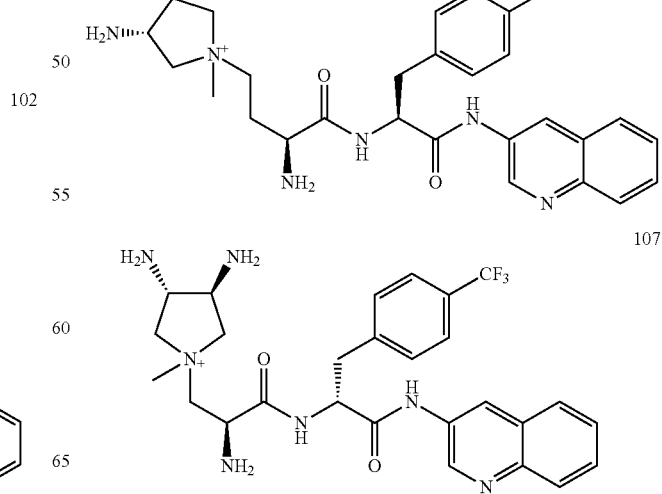
106
107

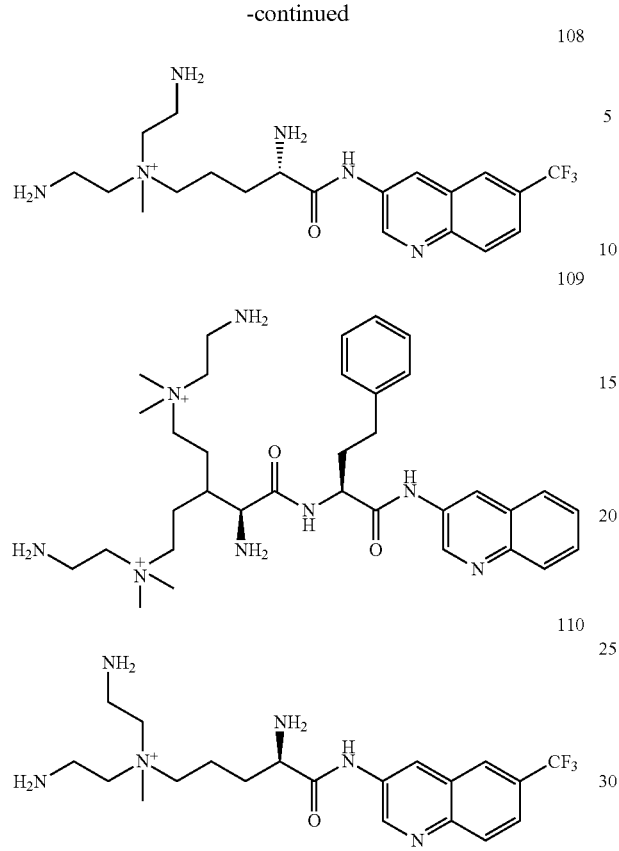
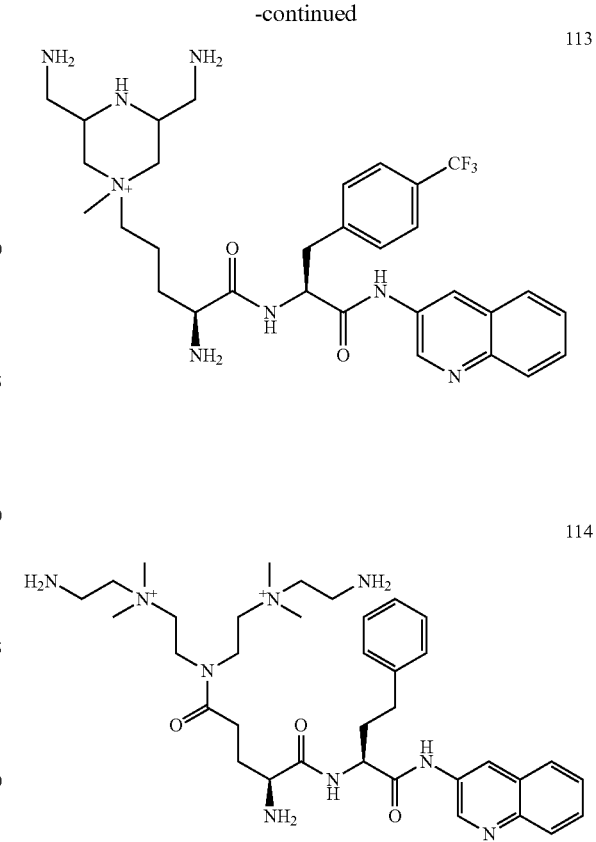
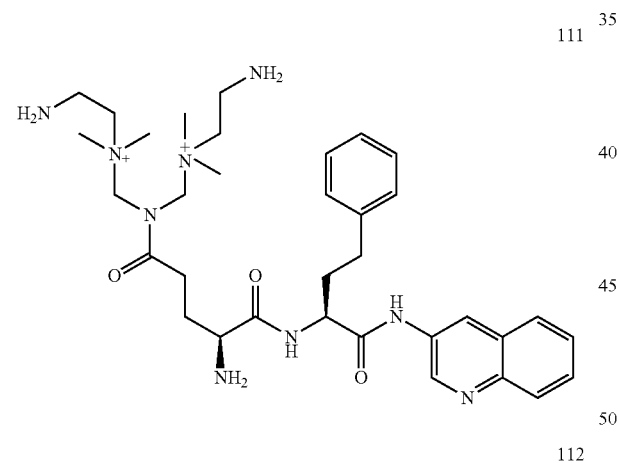
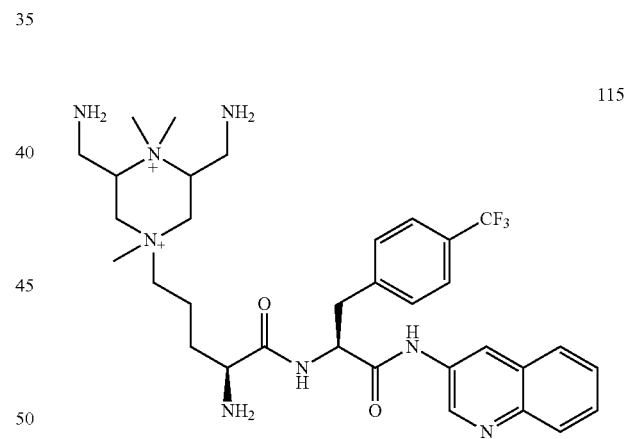
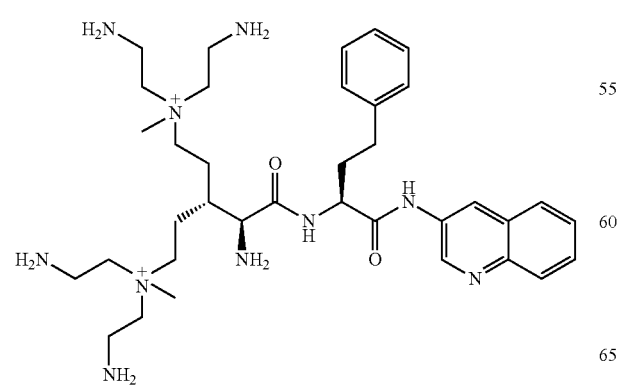
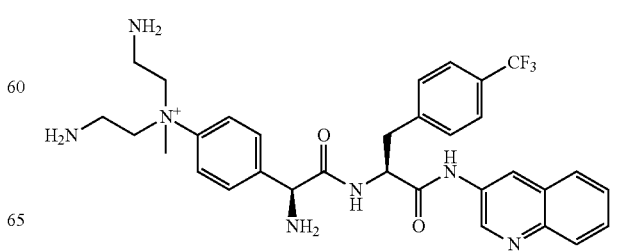

117
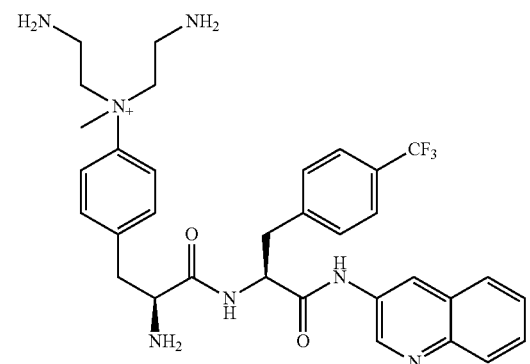
118
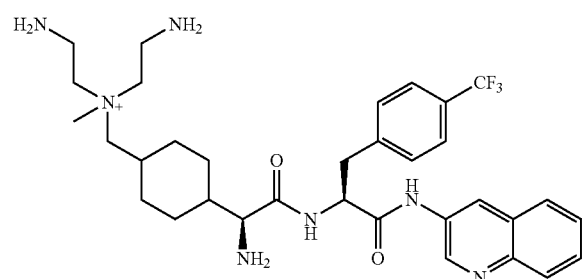
119
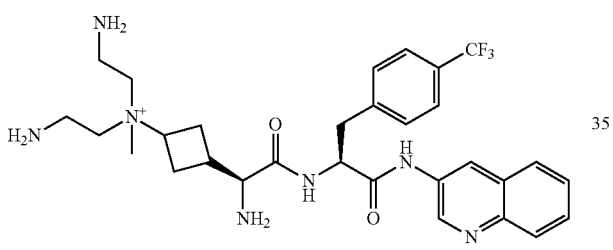
120
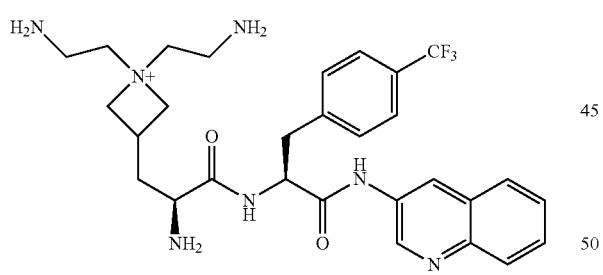
121
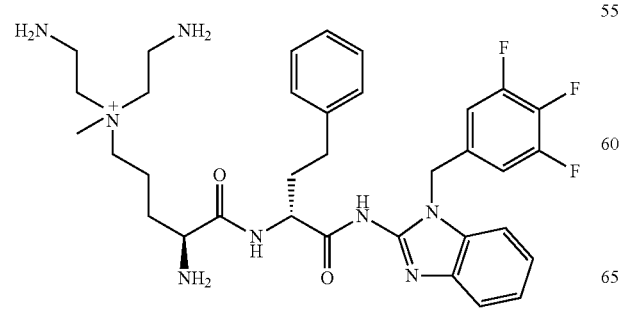
122
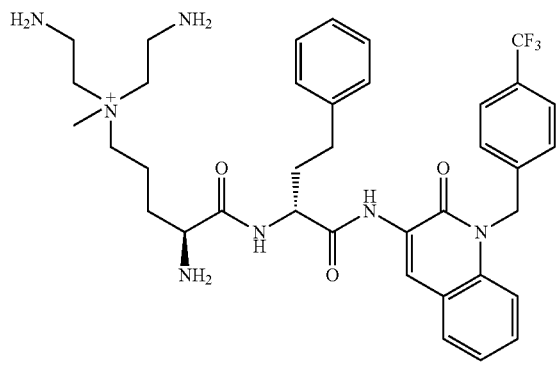
123
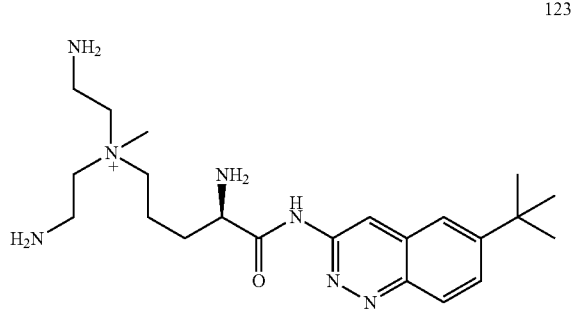
124
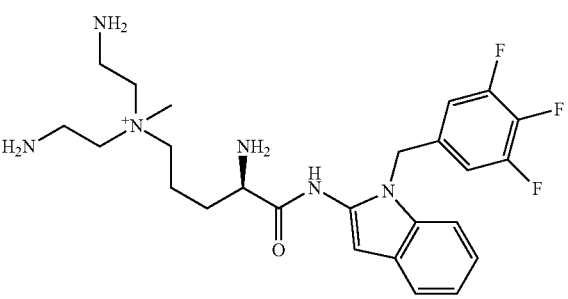
125
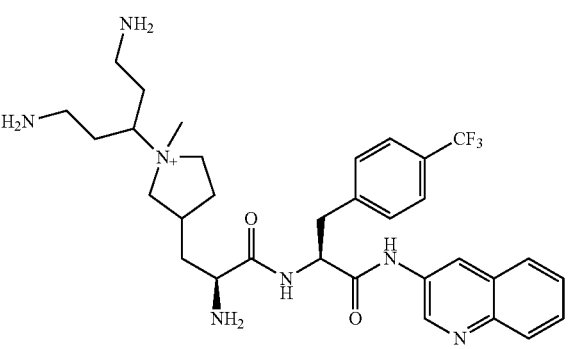

126
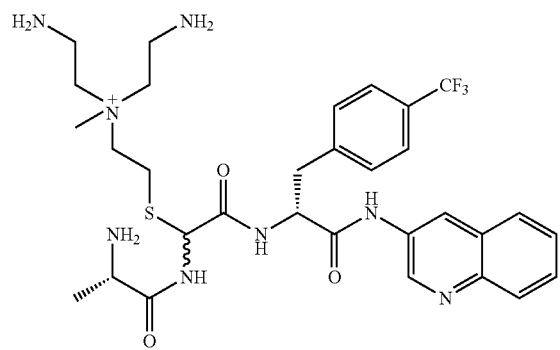
127
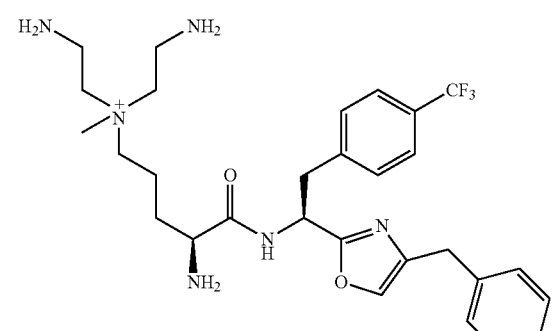
128
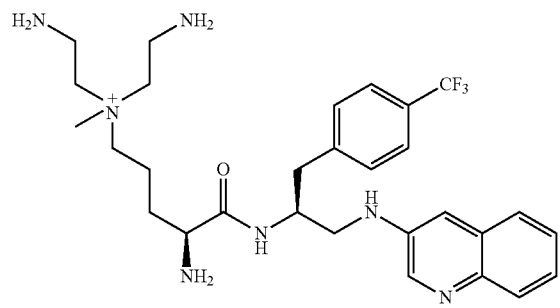
129
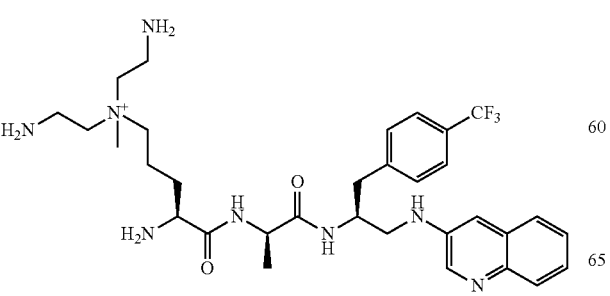
130
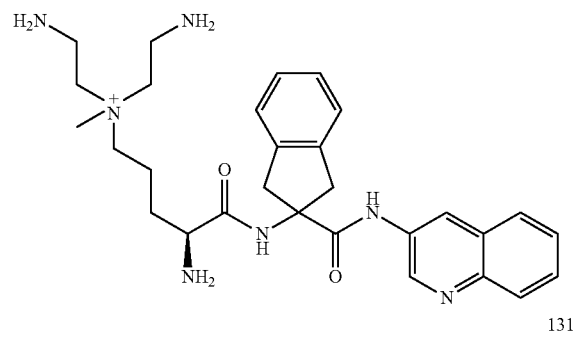
131
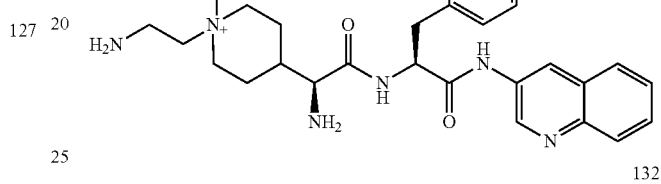
132
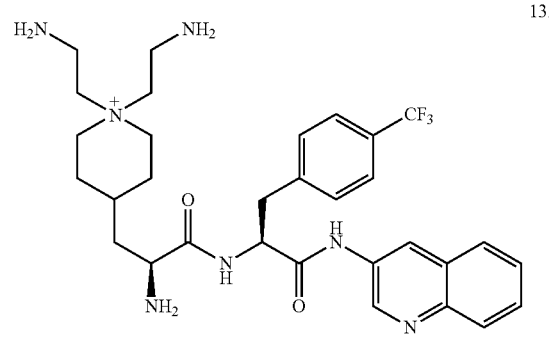
133
134
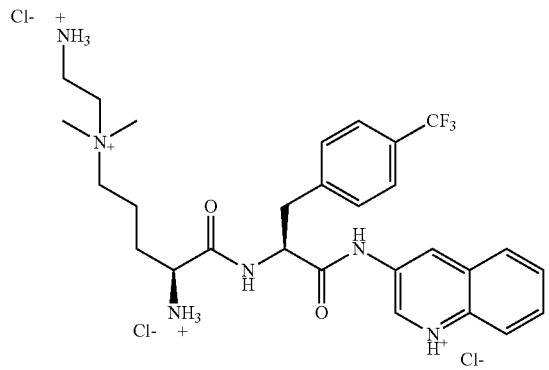

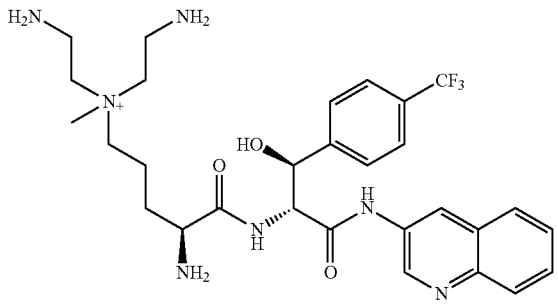

135

Compound Preparation

The starting materials used in preparing the compounds of the invention are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the claimed compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March's Advanced Organic Chemistry: Reactions, Mechanisms, and Structure 6th Ed., John Wiley & Sons (2007), Carey and Sundberg, Advanced Organic Chemistry 5th Ed., Springer (2007) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts Protecting Groups in Organic Synthesis, 4th Ed., John Wiley & Sons (2006).

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

[1]H nuclear magnetic resonance spectra (NMR) were measured in the indicated solvents on either a Bruker NMR spectrometer (Avance™ DRX500, 500 MHz for 1H) or Varian NMR spectrometer (Mercury 400BB, 400 MHz for 1H). Peak positions are expressed in parts per million (ppm) downfield from tetramethylsilane. The peak multiplicities are denoted as follows, s, singlet; d, doublet; t, triplet; m, multiplet.

The following abbreviations have the indicated meanings:
Allyl=CH2=CH2-CH2-
brine=saturated aqueous sodium chloride
CDMT=2-chloro-4,6-dimethoxy-1,3,5-triazine
DCM=dichloromethane
DIBAL=diisobutylaluminum hydride
DIPEA=diisopropylamine
$Boc_2O$=di-tert-butyldicarbonate
DMAP=4-(dimethylamino)-pyridine
DMF=N,N-dimethylformamide
DMSO=dimethylsulfoxide
DMT-MM=4-(4,6-dimethoxy-1,3,5-triazin-2-yl)-4-methylmorpholinium chloride
ESIMS=electron spray mass spectrometry
EtOAc=ethyl acetate
EtONa=sodium ethoxide
EtOH=ethyl alcohol
HATU=2-(1H-7-azabenzotriazol-1-yl)-1,1,3,3-tetramethyl uronium hexafluorophosphate methanaminium
r.t.=room temperature
TBTU=O-(benzotriazol-1-yl)-N,N,N',N'-tetramethyluronium tetrafluoroborate
TEA=triethylamine
TFA=trifluoroacetic acid
THF=tetrahydrofuran
p-TsOH=para-toluenesulfonic acid
TLC=thin layer chromatography
TMS=trimethylsilyl
n-Bu=normal butyl Synthesis of 3-[(2R)-2-[(4S)-1-N-(2-azaniumyl-ethyl)-4-formamido-1-N,1-N-dimethylbutane-1,4-bis(aminium)]-3-[4-(trifluoromethyl)phenyl]propanamido]quinolin-1-ium tetrachloride (3) is depicted below in scheme 1 and example 1
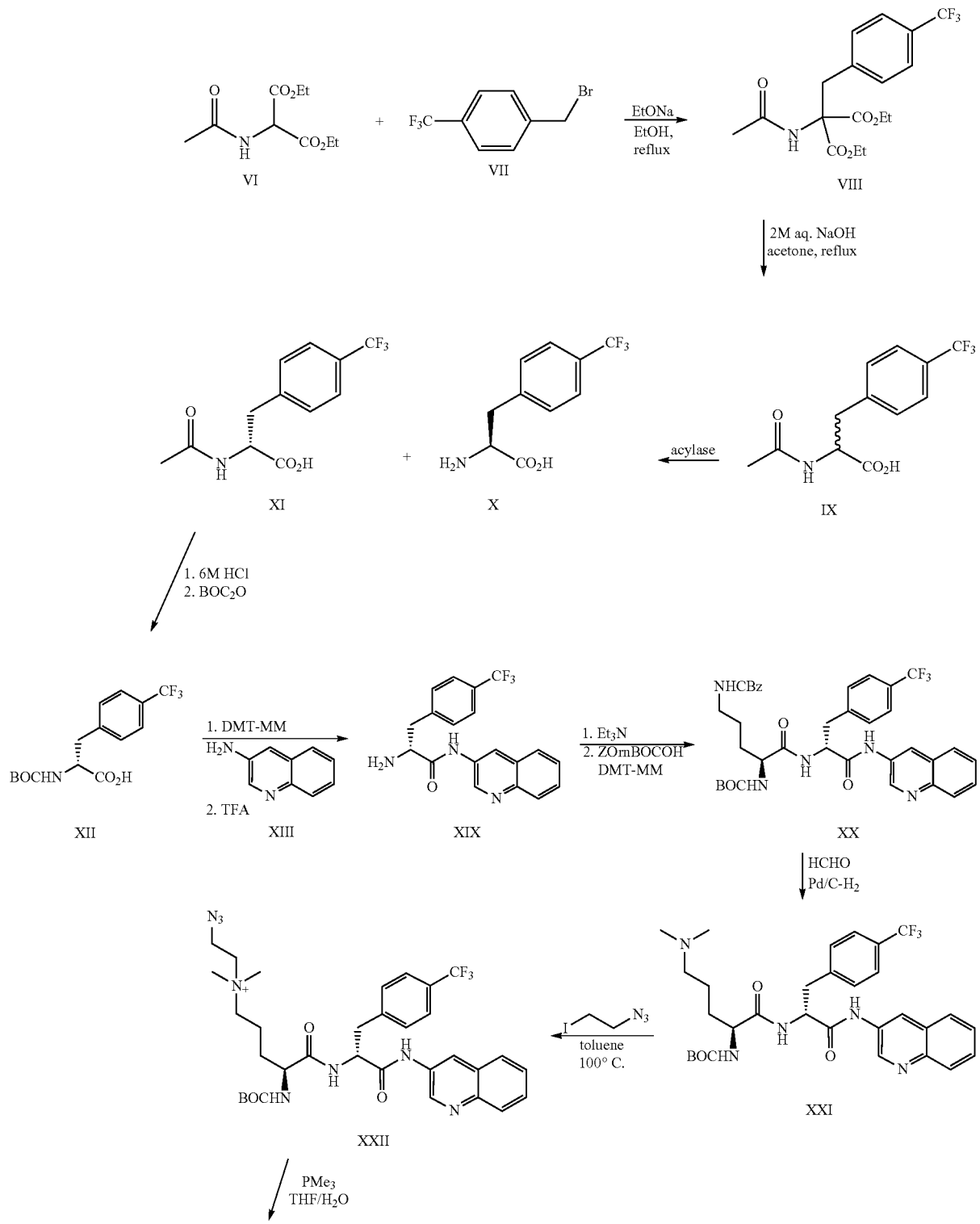
Scheme 1

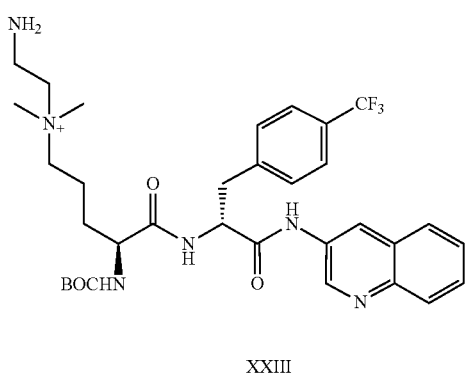

XXIII

-continued

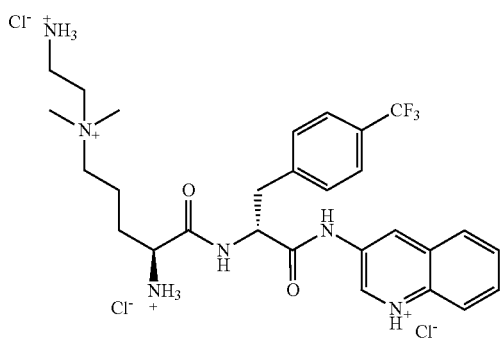

3

Example 1

Step 1

To a solution of sodium metal (2.9 g; 0.125 mol) in absolute ethanol (500 mL) was added diethyl acetamidomalonate VI (27.2 g, 0.125 mol) followed by 4-(trifluoromethyl)benzyl bromide VII (29.9 g, 0.125 mol). The reaction mixture was stirred at reflux overnight, during which time substantial amount of sodium bromide precipitated. The reaction mixture was concentrated to ca. 30% of its initial volume under reduced pressure and poured into cold water (400 mL). The precipitate was filtered and washed with water (3×250 mL), hexanes (3×150 mL) and then air dried to yield compound VIII as a white solid used directly for the next step.

Step 2

To a solution of 1,3-diethyl 2-acetamido-2-{[4-(trifluoromethyl)phenyl]methyl}propanedioate VIII (theoretical 0.125 mole) in acetone (400 mL) was added aq. 2 M NaOH (400 mL). The mixture was refluxed overnight before the solvent was removed under reduced pressure. The residue was taken up in water, washed with hexane (3×), acidify to pH=1 and filtered to produce the product as a white solid IX (25.8 g, 93.7 mmol, 75% yield after two steps).

Step 3

To a solution of 2-acetamido-3-[4-(trifluoromethyl)phenyl]propanoic acid IX (30 g, 109 mol) in 1 M NaOH (50 mL) and water (1 L). The pH was adjusted to 7.6-7.8 before adding $CoCl_2$ (300 mg, 2.3 mmol) and Acylase I (3 g) (from *Aspergilus melleus*). The reaction was stirred in r.t. under argon for 2 days at which time Marfey's test was performed and additional enzyme (1 g) was added and stirred for another day. The mixture was acidified with 2 M HCl to pH=1 and extracted with ethyl acetate (3×) (the aqueous phase containing the L-enantiomer X was saved). The combined organic extracts were washed 2 M HCl (3×), brine (3×) and dried over $MgSO_4$. The solvent was removed under reduced pressure and the residue was recrystallized from EtOAc/hexane. N-acetyl derivative of D-aminoacid XI was obtained with 98% of optical purity (10.2 g, 37 mmol, 68% yield).

Step 4

(2R)-2-acetamido-3-[4-(trifluoromethyl)phenyl]propanoic acid XI was refluxed in 6 M HCl overnight to remove the acetyl group followed by standard Boc protection to yield the BOC protected amino acid XII (10 g, 30 mmol, 81% yield).

Step 5

To a solution of (2R)-2-{[(tert-butoxy)carbonyl]amino}-3-[4-(trifluoromethyl)phenyl]propanoic acid XII (0.93 g, 2.79 mmol) and 3-aminoquinoline XIII (0.45 g, 3.10 mmol) in ethyl acetate (30 mL) was added DMT-MM (1.0 g, 3.63 mmol). After being stirred at r.t. overnight, the reaction was washed with water, 1 N HCl, aq. sat. $NaHCO_3$, water and dried over $Na_2SO_4$. The solvent was removed under reduced pressure to afford tert-butyl N-[(1R)-1-[(quinolin-3-yl)carbamoyl]-2-[4-(trifluoromethyl)phenyl]ethyl]carbamate (1.19 g, 2.59 mmol, 93% yield). $^1$H NMR (DMSO-$d_6$) 1.31 (s, 9H), 2.95-3.15 (m, 1H), 3.22-3.27 (m, 1H), 4.46-4.52 (m, 1H), 7.36 (d, J=8 Hz, 1H), 7.62-7.68 (m, 4H), 7.67 (t, J=8 Hz, 1H), 7.83 (t, J=8 Hz, 1H), 8.13 (t, J=7 Hz, 2H), 8.99 (d, J=2 Hz, 1H), 9.24 (d, J=2 Hz, 1H), 11.18 (s, 1H); ESIMS found for $C_{24}H_{24}N_3O_3F_3$ m/z 460 (M+H).

Step 6

N-[(1R)-1-[(quinolin-3-yl)carbamoyl]-2-[4-(trifluoromethyl)phenyl]ethyl]carbamate (1.19 g, 2.60 mmol) in trifluoroacetic acid (10 mL) and was stirred at r.t. for 1 h. The solvent was removed under reduced pressure before treating with DCM (2×20 mL) and evaporated. Crude XIX was obtained as the trifluoroacetate before suspending in EtOAc (20 mL) and treating with TEA (0.72 mL, 5.2 mmol) while the mixture became homogeneous. This solution was used in the next step.

Step 7

To a solution of (2S)-5-{[(benzyloxy)carbonyl]amino}-2-{[(tert-butoxy) carbonyl]amino}pentanoic acid (952 mg, 2.60 mmol) and DMT-MM (746 mg, 2.7 mmol) in ethyl acetate (20 mL) was added a solution of XIX from the previous step. After stirring at r.t. overnight, the mixture was treated with water, aq. Sat. $NaHCO_3$, water and dried over $Na_2SO_4$. The solvent was removed under reduced pressure and the residue was purified on a silica gel column (1:2 hexane:EtOAc to 100% EtOAc) to produce the protected dipeptide XX (1.7 g, 2.4 mmol, 92% yield). $^1$H NMR (DMSO-$d_6$) 1.15-1.33 (m, 4H), 1.33 (s, 9H), 2.40-2.45 (m, 2H), 2.82-2.99 (m, 1H), 2.95-3.01 (m, 1H), 3.89-3.97 (m, 1H), 4.80-4.86 (m, 1H), 5.01 (s, 2H), 6.95 (d, J=7 Hz, 1H), 7.18 (t, J=5 Hz, 1H), 7.28-7.36 (m, 4H), 7.35-7.38 (m, 2H)

7.57-7.69 (m, 5H), 7.93 (dd, J=15 Hz, J=8 Hz, 2H) 8.49 (d, J=8 Hz, 1H), 8.70 (d, J=2 Hz, 1H), 8.97 (d, J=2 Hz, 1H), 10.43 (s, 1H); ESIMS found for $C_{37}H_{40}N_5O_6F_3$ m/z 708 (M+H).

Step 8

To a solution of tert-butyl N-[(1S)-4-{[(benzyloxy)carbonyl]amino}-1-{[(1R)-1-[(quinolin-3-yl)carbamoyl]-2-[4-(trifluoromethyl)phenyl]ethyl]carbamoyl}butyl]carbamate XX (640 mg, 0.90 mmol) and formaldehyde (36% solution in water, 1.5 mL) in methanol (80 mL) was added 10% Pd/C catalyst (200 mg). The mixture was stirred under an atmosphere of hydrogen at r.t. overnight. The mixture was then filtered through Celite and evaporated to dryness. The residue was purified by column chromatography on silica gel (10:1 EtOAc:MeOH to 1:1 EtOAc:MeOH) to obtain the dipeptide XXI (350 mg, 0.58 mmol, 65% yield). $^1$H NMR (DMSO-$d_6$) 1.15-1.33 (m, 4H), 1.33 (s, 9H), 1.98-2.01 (m, 2H), 2.00 (s, 6H), 2.77-2.79 (m, 1H), 3.00-3.03 (m, 1H), 3.78-3.83 (m, 1H), 4.75-4.78 (m, 1H), 7.01 (d, J=7 Hz, 1H), 7.41-7.45 (m, 1H) 7.53-7.68 (m, 5H), 7.95 (dd, J=16 Hz, J=8 Hz, 2H) 8.72 (d, J=2 Hz, 1H), 8.80 (d, J=8 Hz, 1H), 9.01 (d, J=2 Hz, 1H), 10.64 (s, 1H); ESIMS found for $C_{31}H_{38}N_5O_4F_3$ m/z 602 (M+H).

Step 9

To a solution of tert-butyl N-[(1S)-4-(dimethylamino)-1-{[(1R)-1-[(quinolin-3-yl)carbamoyl]-2-[4-(trifluoromethyl)phenyl]ethyl]carbamoyl}butyl]carbamate XXI (230 mg, 0.38 mmol) in toluene (20 mL) was added 1-azido-2-iodoethane (0.4 mL) followed by heated at 100° C. for 2 days. The solvent was removed under reduced pressure and the residue was then purified on a silica gel column (100% MeOH to 10:1 MeOH: NH$_4$OH) to produce the ammonium salt XXII (130 mg 0.19 mmol, 50% yield). $^1$H NMR (DMSO-$d_6$) 1.34 (s, 9H), 1.46-1.53 (m, 2H), 1.62-1.72 (m, 2H), 3.01 (s, 6H), 3.45-3.50 (m, 2H), 3.85-3.87 (m, 2H), 3.95-4.05 (m, 1H), 4.63 (brs, 1H), 7.53-7.68 (m, 6H), 7.84-7.95 (m, 2H), 8.72 (s, 1H), 9.14 (s, 1H), 9.39 (s, 1H), 11.35 (s, 1H); ESIMS found for $C_{33}H_{42}N_8O_4F_3$ m/z 671 (M+).

Step 10

To a solution of tert-butyl N-[(1S)-4-[(2-azidoethyl)dimethylazaniumyl]-1-{[(1R)-1-[(quinolin-3-yl)carbamoyl]-2-[4-(trifluoromethyl)phenyl]ethyl]carbamoyl}butyl]carbamate XXII (390 mg, 0.58 mmol) in the mixture of THF (15 mL) and water (1 mL) was added Me$_3$P/THF (1 M solution, 0.60 ml, 0.60 mmol). The mixture was stirred overnight before evaporating to dryness. Crude XXIII was used in the next step without purification. ESIMS found for $C_{33}H_{44}N_6O_4F_3$ m/z 645 (M+).

Step 11 tert-butyl N-[(1S)-4-[(2-aminoethyl)dimethylazaniumyl]-1-{[(1R)-1-[(quinoline-3-yl)carbamoyl]-2-[4-(trifluoromethyl)phenyl]ethyl]carbamoyl}butyl]carbamate XXIII (crude from step 7 c.a. 0.58 mmol) was treated with HCl/EtOAc (5 M solution, 8 mL) at r.t. overnight. The solvent was evaporated, treated with diethyl ether and the resulting solid was filtered. The crude solid was then purified on a silica gel column (2:1 MeOH:NH$_4$OH) to afford the final product 3 as a hydrochloride salt (170 mg, 0.26 mmol, 45% yield). $^1$H NMR (DMSO-$d_6$) 1.50-1.59 (m, 2H), 1.72-1.82 (m, 2H), 3.11 (s, 3H), 3.13 (s, 3H), 3.00-3.20 (m, 4H), 3.40-3.45 (m, 2H), 3.61-3.65 (m, 2H), 3.95-4.05 (m, 1H), 4.93-4.98 (m, 1H), 7.81-7.64 (m, 7H), 8.05 (t, J=11 Hz, 2H), 8.45 (brs, 3H), 8.67 (brs, 3H), 8.85 (d, J=2 Hz, 1H), 9.20 (d, J=2 Hz, 1H), 9.39 (s, 1H), 9.40 (d, J=8 Hz, 1H), 11.32 (s, 1H); ESIMS found for $C_{28}H_{36}N_6O_2F_3$ m/z 545 (M+).

The following compounds are prepared in accordance with the procedure described in the above example 1.

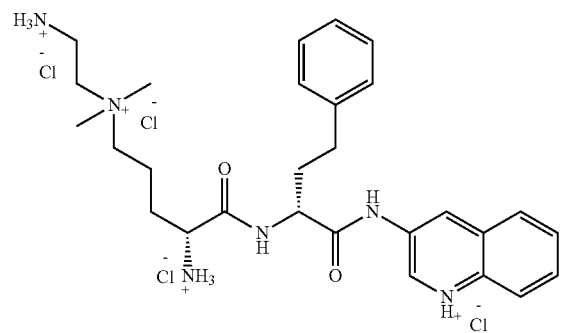

3-[(2R)-2-[(4R)-1-N-(2-azaniumylethyl)-4-formamido-1-N,1-N-dimethylbutane-1,4-bis(aminium)]-4-phenylbutanamido]quinolin-1-ium tetrachloride 1

ESIMS found for $C_{28}H_{39}N_6O_2$ m/z 491 (M+).

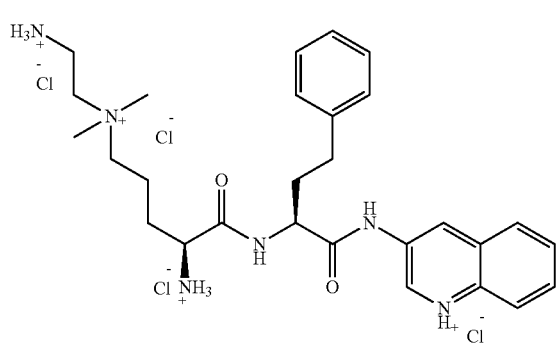

3-[(2S)-2-[(4S)-1-N-(2-azaniumylethyl)-4-formamido-1-N,1-N-dimethylbutane-1,4-bis(aminium)]-4-phenylbutanamido]quinolin-1-ium tetrachloride 2

$^1$H NMR (DMSO-$d_6$) 1.89-1.78 (m, 2H), 2.21-1.96 (m, 4H), 2.76-2.65 (m, 1H), 2.93-2.83 (m, 1H), 3.16 (s, 3H), 3.18 (s, 3H), 3.38-3.31 (m, 2H), 3.51-3.41 (m, 1H), 3.77-3.57 (m, 3H), 4.12 (brs, 1H), 4.58 (brs, 1H), 7.15-7.11 (m, 1H), 7.26-7.20 (m, 2H), 7.31-7.27 (m, 2H), 7.70 (dd, J=8 Hz, J=8 Hz, 1H), 7.80 (dd, J=8 Hz, J=8 Hz, 1H), 8.11 (dd, J=8 Hz, J=8 Hz, 2H), 8.55 (brs, 3H), 8.71 (brs, 3H), 8.95 (brs, 1H), 9.28 (brs, 1H), 9.56 (d, J=6 Hz, 1H), 11.59 (brs, 1H); ESIMS found for $C_{28}H_{39}N_6O_2$ m/z 491 (M+).

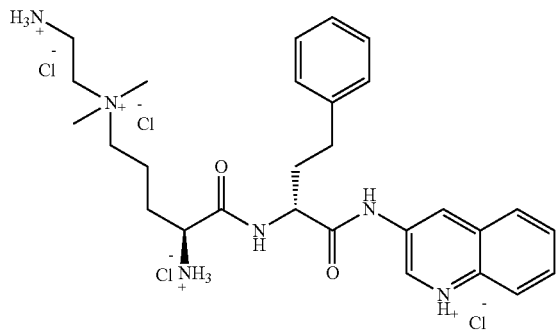

3-[(2S)-2-[(4R)-1-N-(2-azaniumylethyl)-4-forma-mido-1-N,1-N-dimethylbutane-1,4-bis(aminium)]-4-phenylbutanamido]quinolin-1-ium tetrachloride 4

$^1$H NMR (CD$_3$OD) 1.89-2.16 (m, 4H), 2.21-2.35 (m, 2H), 2.75-2.95 (m, 2H), 3.26 (s, 6H), 3.53-3.58 (m, 2H), 3.60-3.65 (m, 2H), 3.74-3.79 (m, 2H), 4.20 (dd, J=4 Hz, J=7 Hz, 1H), 4.63 (dd, J=5 Hz, J=9 Hz, 1H), 7.13-7.18 (m, 1H), 7.24-7.31 (m, 4H), 7.88-7.92 (m, 1H), 8.00-8.05 (m, 1H), 8.15 (d, J=9 Hz, 1H), 8.21 (d, J=8 Hz, 1H), 9.09 (d, J=2 Hz, 1H), 9.48 (d, J=2 Hz, 1H); ESIMS found for C$_{28}$H$_{39}$N$_6$O$_2$ m/z 491 (M+).

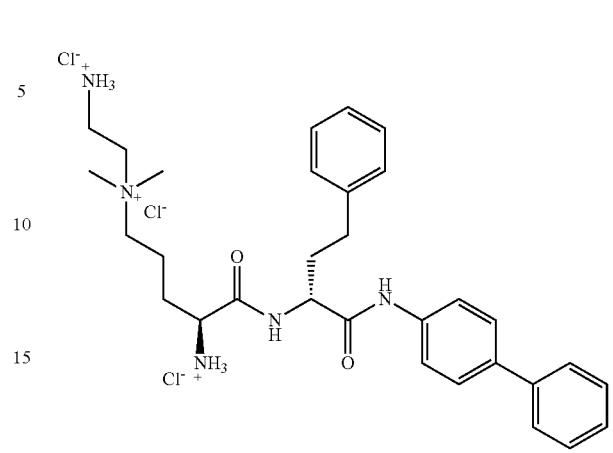

[(4S)-4-azaniumyl-4-{[(1R)-3-phenyl-1-[(4-phe-nylphenyl)carbamoyl]propyl]carbamoyl}butyl](2-azaniumylethyl)dimethylazanium trichloride 6

$^1$H NMR (DMSO-d$_6$) 1.75-2.16 (m, 6H), 2.56-2.87 (m, 4H), 3.11 (s, 6H), 3.43-3.67 (m, 4H), 3.93-4.08 (m, 1H), 4.46-4.63 (m, 1H), 7.12-7.36 (m, 6H), 7.36-7.49 (m, 2H), 7.63 (d, J=8 Hz, 4H), 7.74 (d, J=9 Hz, 2H), 8.47 (brs, 6H), 9.2 (d, J=9 Hz, 1H), 10.39 (s, 1H); ESIMS found for C$_{31}$H$_{42}$N$_5$O$_2$ m/z 516 (M+).

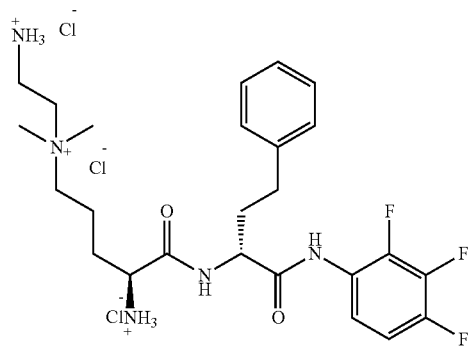

[(4S)-4-azaniumyl-4-{[(1R)-3-phenyl-1-[(2,3,4-trif-luorophenyl) carbamoyl]propyl]carbamoyl}butyl](2-azaniumylethyl)dimethylazanium trichloride 5

$^1$H NMR (DMSO-d$_6$) 1.90-2.10 (m, 8H), 2.60-2.70 (m, 2H), 3.13 (s, 6H), 3.51 ((t, J=6 Hz, 2H), 3.62 (t, J=6 Hz, 2H), 4.02 (brs, 1H), 4.57-4.60 (m, 1H), 7.18-7.33 (m, 7H), 7.42-7.47 (m, 1H), 8.54 (brs, 3H), 8.64 (brs, 3H), 9.31 (d, J=7.5 Hz, 1H), 10.26 (s, 1H); ESIMS found for C$_{25}$H$_{35}$N$_5$O$_2$F$_3$ m/z 494 (M+).

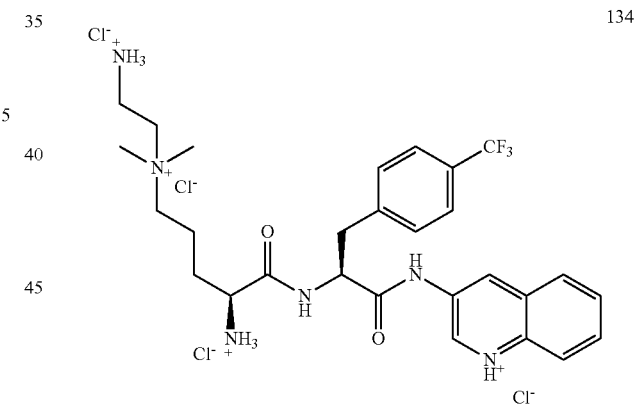

3-[(2S)-2-[(4S)-1-N-(2-azaniumylethyl)-4-forma-mido-1-N,1-N-dimethylbutane-1,4-bis(aminium)]-3-[4-(trifluoromethyl)phenyl]propanamido]quinolin-1-ium tetrachloride 134

$^1$H NMR (DMSO-d$_6$) 1.77-1.83 (m, 2H), 1.92-2.07 (m, 2H), 3.15 (s, 3H), 3.18 (s, 3H), 3.32-3.36 (m, 4H), 3.41-3.47 (m, 1H, 3.56-3.60 (m, 1H), 3.64 (t, J=7 Hz, 2H) 3.92-3.98 (m, 1H), 4.82-4.87 (m, 1H), 7.64 (d, J=8 Hz, 2H), 7.69 (dd, J=8 Hz, J=8 Hz, 1H), 7.78 (dd, J=8 Hz, J=8 Hz, 1H), 7.80 (d, J=8 Hz, 2H), 8.08 (d, J=8 Hz, 1H), 8.09 (d, J=8 Hz, 1H), 8.42 (brs, 3H), 8.67 (brs, 3H), 8.90 (s, 1H), 9.26 (s, 1H), 9.45 (d, J=8 Hz, 1H), 11.77 (s, 1H); $^{19}$F NMR (DMSO-d$_6$) −60.10 (s, 3F); ESIMS found for C$_{29}$H$_{37}$F$_3$N$_5$O$_2$ m/z 545.5 (M+).

Synthesis of 3-[(2S)-2-[(4S)-1-N,1-N-bis(2-azaniumylethyl)-4-formamido-1-N-methylbutane-1,4-bis(aminium)]-4-cyclohexylbutanamido]quinolin-1-ium pentachloride (38) is depicted below in scheme 2 and example 2
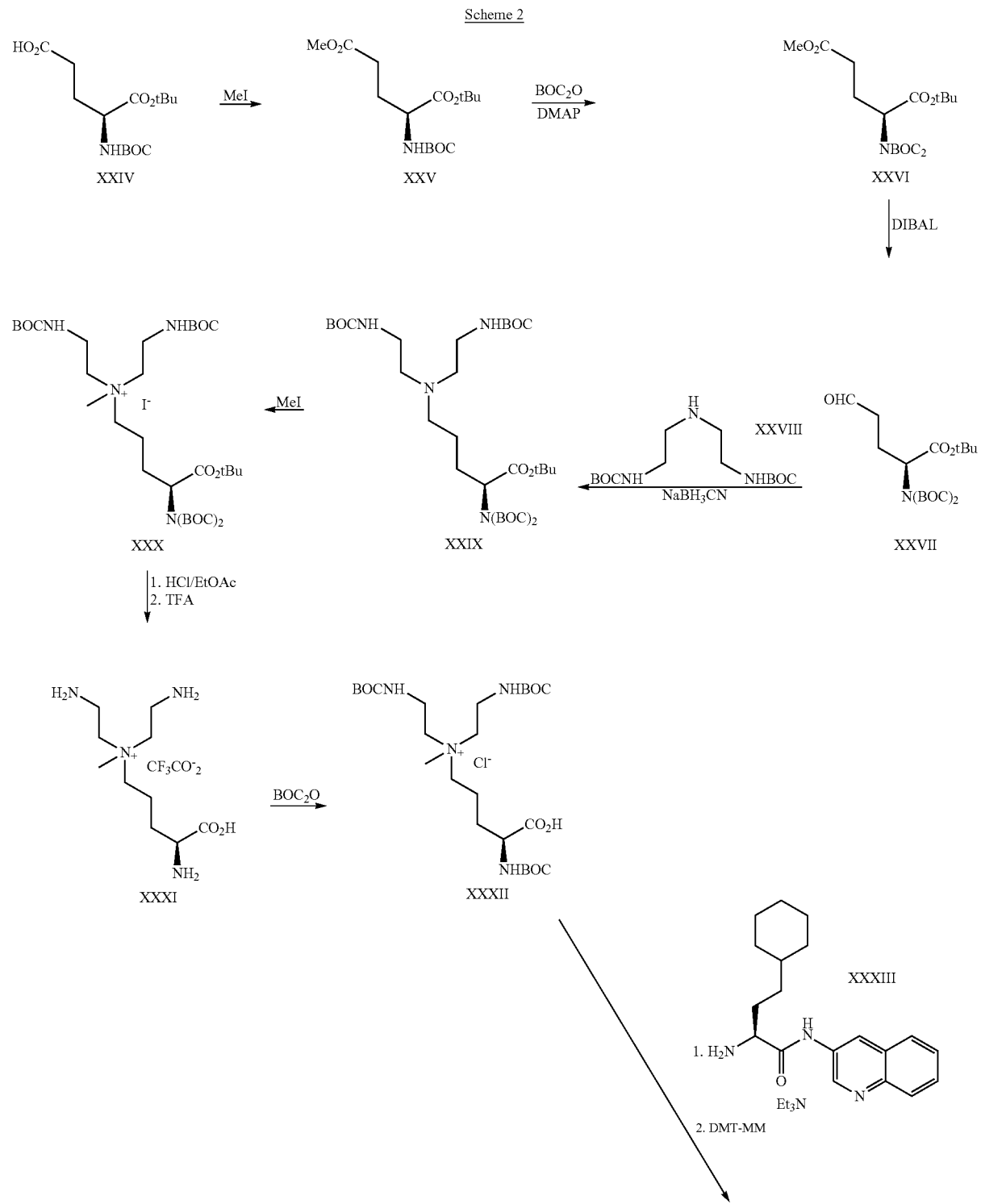

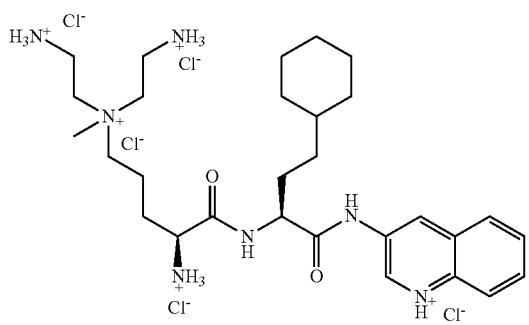

38

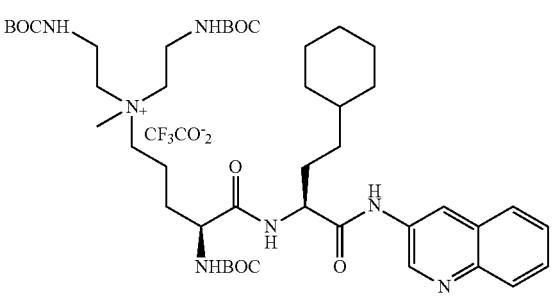

XXXIV

Example 2

Step 1

To a solution of Boc-glutamic acid tert-butyl ester XXIV (50 g, 164.8 mmol) and $K_2CO_3$ (34.2 g, 247.2 mmol) in DMF (250 mL) was added MeI (10.8 ml, 173.1 mmol) dropwise. The reaction mixture was stirred at r.t. for 2 h before adding ethyl acetate (mL). Organic layer was washed 10% $Na_2S_2O_3$ (3×) and dried over $MgSO_4$. The solvent was removed under reduced pressure and the crude product was crystallized from hexane to give the product XXV as a white solid (50.7 g, 159.8 mmol, 95% yield). $^1$H NMR ($CDCl_3$) 1.44 (s, 9H), 1.46 (s, 9H), 1.86-1.96 (m, 11H), 2.08-2.20 (m, 1H), 2.32-2.46 (m, 2H), 3.46 (m, 2H), 3.68 (s, 3H), 4.17-4.21 (m, 1H); ESIMS found for $C_{15}H_{27}NO_6$ m/z 318 (M+H).

Step 2

To a solution of 1-tert-butyl 5-methyl (2S)-2-{[(tert-butoxy)carbonyl]amino}pentanedioate XXV (50.7 g, 159.8 mmol), TEA (26.6 mL, 191.7 mmol) and DMAP (19.5 g, 159.8 mmol) in MeCN (480 mL) was added di-tert-butyl dicarbonate (69.7 g, 319.5 mmol). The reaction mixture was stirred at r.t. overnight before adding additional TEA (11.1 mL, 79.0 mmol), DMAP (9.8 g, 79.9 mmol) and $Boc_2O$ (34.8 g, 159.8 mmol) and stirring for another 2 days. The solvent was removed under reduced pressure and residue was purified on a silica gel column (1:100→1:50→1:30 EtOAc:hexane) to give pure product XXVI as colorless oil. (50.0 g, 119.8 mmol, 75% yield). $^1$H NMR ($CDCl_3$) 1.44 (s, 9H), 1.49 (s, 18H), 2.15 (ddd, J=3 Hz, J=8 Hz, J=19 Hz, 1H), 2.33-2.46 (m, 3H), 3.66 (s, 3H), 4.75 (m, 1H); ESIMS found for $C_{20}H_{35}NO_8$ m/z 857 (2M+23).

Step 3

To a solution of 1-tert-butyl 5-methyl (2S)-2-{bis[(tert-butoxy)carbonyl]amino}pentanedioate XXVI (50.0 g, 119.8 mmol) in dry ethyl ether (120 mL) at −78° C. under Ar was added a solution of DIBAL in toluene (65.0 mL, 65.0 mmol). The reaction mixture was stirred 1.5-2.5 hours at −78° C. The mixture was treated with MeOH (240 mL) and allowed to warm to r.t. The suspension was filtered through Celite and washed with methanol. The solvent was removed under reduced pressure and the residue was purified on a silica gel column (1:20 EtOAc:hexane) to give pure product XXVII as colorless oil. (37.1 g, 95.8 mmol, 80% yield). $^1$H NMR ($CDCl_3$) 1.44 (s, 9H), 1.47 (s, 18H), 2.07-2.15 (m, 1H), 2.37- 2.56 (m, 3H), 4.70 (dd, J=4 Hz, J=9 Hz, 1H), 9.73 (s, 1H); ESIMS found for $C_{19}H_{33}NO_7$ m/z 410 (M+23).

Step 4

To a solution of tert-butyl N-{2-[(2-{[(tert-butoxy)carbonyl]amino}ethyl)amino]ethyl}carbamate XXVIII (prepared according to the literature, Org. Lett., 2000, 2(14), 2117-2120) (1.46 g, 4.81 mmol) in DCM (40 mL) cooled to 0° C. was added acetic acid (1.4 mL, 24 mmol) followed by tert-butyl (2S)-2-{bis[(tert-butoxy)carbonyl]amino}-5-oxopentanoate XXVII (1.7 g, 4.40 mmol). The mixture was stirred at 0° C. for 1 h before adding $NaBH_3CN$ (0.45 g, 7.21 mmol) and stirred at r.t. overnight. The mixture was treated with water, brine and dried over $Na_2SO_4$. The solvent was removed under reduced pressure and the residue was then purified on a silica gel column (3:1 hexane:EtOAc→100% EtOAc) to produce compound XXIX as a yellow oil (2.36 g, 3.50 mmol, 73% yield). $^1$H NMR (DMSO-$d_6$) 1.36 (s, 36H), 1.44 (s, 9H), 1.25-1.80 (m, 6H), 2.41 (brs, 4H), 2.84 (brs, 4H), 4.61 (dd, J=10 Hz, J=5 Hz, 1H), 6.16 (brs 2H); ESIMS found for $C_{33}H_{62}N_4O_{10}$ m/z 675 (M+H).

Step 5

To a solution of tert-butyl (2S)-5-[bis(2-{[(tert-butoxy)carbonyl]amino}ethyl)amino]-2-{bis[(tert-butoxy)carbonyl]amino}pentanoate XXIX (1.68 g, 2.5 mmol) was added excess MeI (20 mL) and then allowed to stir at r.t. for 5 days. The mixture was evaporated to dryness and the residue was then purified on a silica gel column (5:1 EtOAc: MeOH) to produce compound XXX as a yellow oil (0.72 g, 1.0 mmol, 38% yield). $^1$H NMR (DMSO-$d_6$) 1.38 (s, 36H), 1.45 (s, 9H), 1.25-1.80 (m, 6H), 3.03 (s, 3H), 3.30-3.40 (m, 8H), 4.67 (dd, J=8 Hz, J=5 Hz, 1H), 7.17 (brs 2H); ESIMS found for $C_{34}H_{65}N_4O_{10}$ m/z 689 (M+).

Step 6

To a solution of [(4S)-4-{bis[(tert-butoxy)carbonyl]amino}-5-(tert-butoxy)-5-oxopentyl]bis(2-{[(tert-butoxy)carbonyl]amino}ethyl)methylazanium iodide XXX (0.72 g, 1.0 mmol) was added 5 M HCl/EtOAc (10 mL) and then allowed to stir at r.t. for 2 h. The solvent was removed under reduced pressure and then treated with diethyl ether. The solid was filtered and dried and without further purification, treated with TFA (10 mL) at r.t. overnight. The TFA was removed under reduced pressure to yield the product XXXI as a white solid (0.48 g, 90% yield)

Step 7

To a solution of [(4S)-4-amino-4-carboxybutyl]bis(2-aminoethyl)methylazanium 2,2,2-trifluoroacetate salt XXXI in a mixture of (1:2 water:dioxane) (10 mL) cooled to 0° C. was added dropwise a solution of BOC$_2$O (0.72 mg, 3.3 mmol) in a mixture of (1:2 water:dioxane) (10 mL) and 1 N NaOH so that the pH=9 throughout the process. After the addition was complete, the mixture was stirred overnight at r.t. The solvent was removed under reduced pressure, water was added (50 mL) and washed with diethyl ether. The aqueous phase was acidified with 1N HCl until pH=2.5 and then extracted with ethyl acetate, dried over Na$_2$SO$_4$, filtered and concentrated to dryness was then purified on a silica gel column (10:1 EtOAc:MeOH→100% methanol) to afford compound XXXII as a white solid (0.32 g, 53% yield). ESIMS found for C$_{25}$H$_{49}$N$_4$O$_8$ m/z 533 (M+).

Step 8

To a solution of (2S)-2-amino-4-cyclohexyl-N-(quinolin-3-yl)butanamide XXXIII (prepared according to Example 1) (270 mg, 0.5 mmol) in DCM (5 mL) was added TEA (0.14 mL, 1.0 mmol). This solution was then added to a mixture of [(4S)-4-{[(tert-butoxy)carbonyl]amino}-4-carboxybutyl]bis(2-{[(tert-butoxy)carbonyl]amino}ethyl)methylazanium chloride XXXII (200 mg, 0.35 mmol) and DMT-MM (150 mg, 0.5 mmol) in DCM (5 mL). The reaction was stirred at r.t. for 40 h before being washed with water, dried over Na$_2$SO$_4$ and concentrated to dryness. The crude product was then purified on a silica gel column (100% EtOAc→10:1 EtOAc:MeOH→10:1 MeOH:NH$_3$) to yield the protected dipeptide XXXIV (150 mg, 0.16 mmol, 33%). $^1$H NMR (DMSO-d$_6$) 0.85-0.95 (m, 2H), 1.10-1.25 (m, 10H), 1.34 (s, 9H), 1.37 (s, 9H), 1.20-1.90 (m, 9H), 1.70 (s, 9H), 3.16 (s, 3H), 3.70-3.86 (m, 8H), 4.05-4.16 (m, 1H), 4.30-4.35 (m, 1H), 6.68 (brs, 2H), 7.28-7.54 (m, 2H), 7.50-7.60 (m, 2H), 8.69 (d, J=2 Hz, 1H), 9.09 (s, 1H), 11.21 (s, 1H); ESIMS found for C$_{44}$H$_{72}$N$_7$O$_8$ m/z 826 (M+).

Step 9

To a solution of tert-butyl N-(2-{[(4S)-4-{[(tert-butoxy)carbonyl]amino}-4-{[(1S)-3-cyclohexyl-1-[(quinolin-3-yl)carbamoyl]propyl]carbamoyl}butyl](2-{[(tert-butoxy)carbonyl]amino}ethyl)methylazaniumyl]ethyl)carbamate XXXIV (180 mg, 0.20 mmol) was treated with HCl/EtOAc (5 M solution, 8 mL) at r.t. overnight. The solvent was evaporated, treated with diethyl ether and the resulting solid was filtered to afford the final product 38 as a hydrochloride salt (100 mg, 0.14 mmol, 70% yield). $^1$H NMR (DMSO-d$_6$) 0.85-0.95 (m, 2H), 1.10-1.25 (m, 10H), 1.20-1.90 (m, 9H), 3.30 (s, 3H), 3.28-3.33 (m, 4H), 3.71-3.75 (m, 4H), 4.02-4.05 (m, 1H), 4.46-4.48 (m, 1H), 6.68 (brs, 2H), 7.55-7.68 (m, 2H), 7.95-7.98 (m, 2H), 8.47 (brs, 3H), 8.69 (brs, 3H), 8.70 (s, 1H), 9.04 (s, 1H), 9.18 (d, J=7 Hz, 1H), 10.95 (s, 1H); ESIMS found for C$_{29}$H$_{48}$N$_7$O$_2$ m/z 526 (M+).

The following compounds are prepared in accordance with the procedure described in the above example 2.

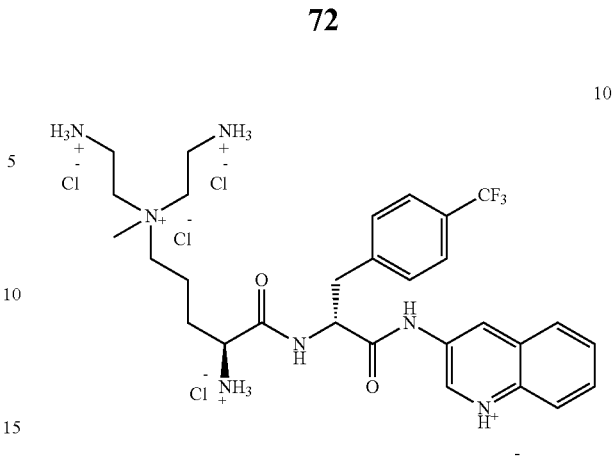

3-[(2R)-2-[(4S)-1-N,1-N-bis(2-azaniumylethyl)-4-formamido-1-N-methylbutane-1,4-bis(aminium)]-3-[4-(trifluoromethyl)phenyl]propanamido]quinolin-1-ium pentachloride 10

$^1$H NMR (DMSO-d$_6$) 1.50-1.78 (m, 2H), 1.85-2.05 (m, 2H), 3.23 (s, 3H), 3.28-3.48 (m, 6H), 3.54-3.80 (m, 6H), 4.83-5.00 (m, 1H), 7.67 (s, 4H), 7.71-7.89 (m, 2H), 8.11 (dd, J=8 Hz, J=8 Hz, 2H), 8.50 (brs, 3H), 8.75 (brs, 6H), 8.99 (s, 1H), 9.33 (s, 1H), 9.43 (d, J=8 Hz, 1H), 11.51 (s, 1H); $^{19}$F NMR (DMSO-d$_6$) −59.69 (s, 3F); ESIMS found for C$_{29}$H$_{39}$F$_3$N$_7$O$_2$ m/z 574 (M+).

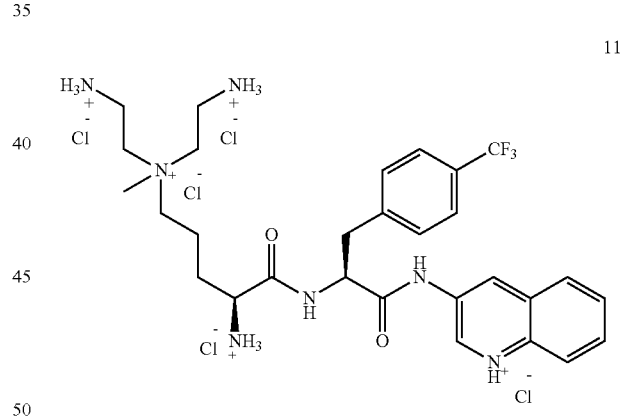

3-[(2R)-2-[(4R)-1-N,1-N-bis(2-azaniumylethyl)-4-formamido-1-N-methylbutane-1,4-bis(aminium)]-3-[4-(trifluoromethyl)phenyl]propanamido]quinolin-1-ium pentachloride 11

$^1$H NMR (DMSO-d$_6$) 1.80-1.88 (m, 2H), 2.04 (brs, 1H), 2.14 (brs, 1H), 3.19 (d, J=11 Hz, 2H), 3.3 (s, 3H), 3.38 (brs 4H), 3.71 (brs, 6H), 3.90-3.97 (m, 1H), 4.81-4.89 (m, 1H), 7.62 (s, 1H), 7.63 (s, 1H), 7.70-7.75 (m, 1H), 7.81-7.89 (m, 3H), 8.17 (dd, J=8 Hz, J=8 Hz, 2H), 8.44 (brs, 3H), 8.71 (brs, 6H), 9.04 (s, 1H), 9.38 (s, 1H), 9.46 (d, J=7 Hz, 1H), 12.05 (s, 1H); $^{19}$F NMR (DMSO-d$_6$) −60.09 (s, 3F); ESIMS found for C$_{29}$H$_{39}$F$_3$N$_7$O$_2$ m/z 574 (M+).

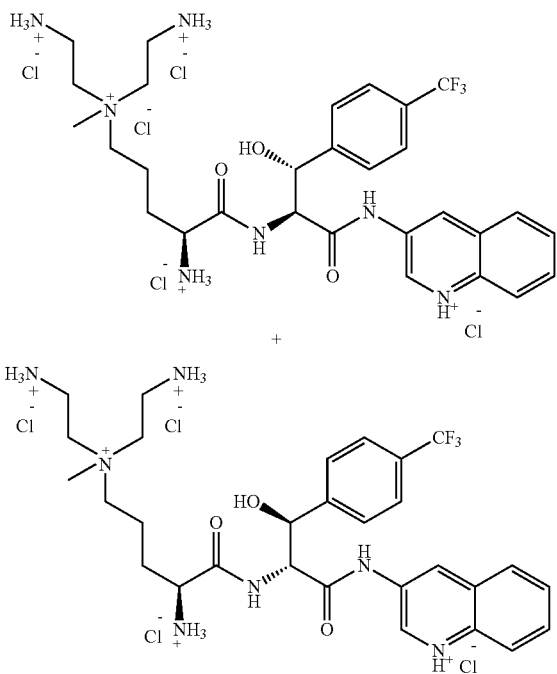

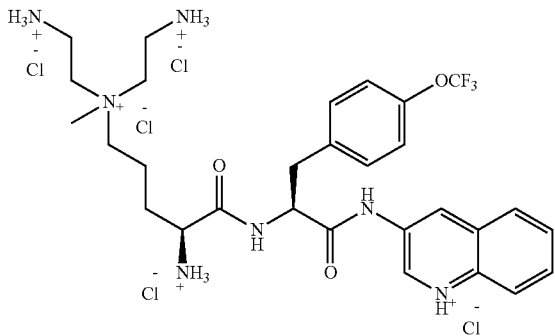

Mixture of 3-[(2S,3R)-2-[(4S)-1-N,1-N-bis(2-azaniumylethyl)-4-formamido-1-N-methylbutane-1,4-bis(aminium)]-3-hydroxy-3-[4-(trifluoromethyl)phenyl]propanamido]quinolin-1-ium pentachloride 15a and 3-[(2R,3S)-2-[(4S)-1-N,1-N-bis(2-azaniumylethyl)-4-formamido-1-N-methylbutane-1,4-bis(aminium)]-3-hydroxy-3-[4-(trifluoromethyl)phenyl]propanamido]quinolin-1-ium pentachloride 15b $^1$H NMR (DMSO-d$_6$) 1.65-1.41 (m, 2H), 1.75-2.04 (m, 4H), [3.32 (s, 1$^{st}$ diastereoisomer); 3.22 (s, 2$^{nd}$ diastereoisomer), 3H], 3.34-3.45 (m, 4H), 3.67-3.76 (m, 4H), 4.00-4.08 (m, 1H), 4.91 (ddd, J=47 Hz, J=9 Hz, J=4 Hz, 1H), 5.47 (dd, J=34 Hz, J=3 Hz), 7.62-7.76 (m, 1H), 7.69-7.75 (m, 3H), 7.79 (d, J=8 Hz, 2H), 7.89 (d, J=8 Hz, 1H), 7.98 (d, J=8 Hz, 1H), 8.34-8.47 (m, 3H), 8.57-8.72 (m, 6H), 8.74 (s, 1H), 9.11 (d, J=10 Hz, 1H), 9.13 (s, 1H), [11.42 (s, 1$^{st}$ diastereoisomer); 11.15 (s, 2$^{nd}$ diastereoisomer), 1H]; $^{19}$F NMR (DMSO-d$_6$) –59.95 (s, 3F, 1$^{st}$ diastereoisomer), –60.09 (s, 3F, 2$^{nd}$ diastereoisomer); ESIMS found for C$_{29}$H$_{39}$F$_3$N$_7$O$_3$ m/z 590 (M+).

3-[(2S)-2-[(4S)-1-N,1-N-bis(2-azaniumylethyl)-4-formamido-1-N-methylbutane-1,4-bis(aminium)]-3-[4-(trifluoromethoxy)phenyl]propanamido]quinolin-1-ium pentachloride 21

$^1$H NMR (DMSO-d$_6$) 1.75-1.90 (brs, 2H) 1.96-2.22 (d, J=47 Hz, 2H), 3.08-3.18 (t, J=13 Hz 1H), 3.20-3.45 (m, 8H), 3.90-4.00 (brs, 1H), 4.72-4.84 (brs, 1H), 7.24-7.32 (d, J=8 Hz, 2H), 7.65-7.88 (m, 4H), 8.05-8.15 (brs, 2H), 8.39-8.49 (s, 3H), 8.60-8.75 (brs, 6H), 8.88-8.95 (s, 1H), 9.23-9.29 (s, 1H), 9.41-9.46 (d, J=6 Hz 1H), 11.69-11.77 (brs, 1H); $^{19}$F NMR (DMSO-d$_6$)-56.09 (s, 3F); ESIMS found for C$_{29}$H$_{38}$F$_3$N$_7$O$_3$ m/z 590 (M+).

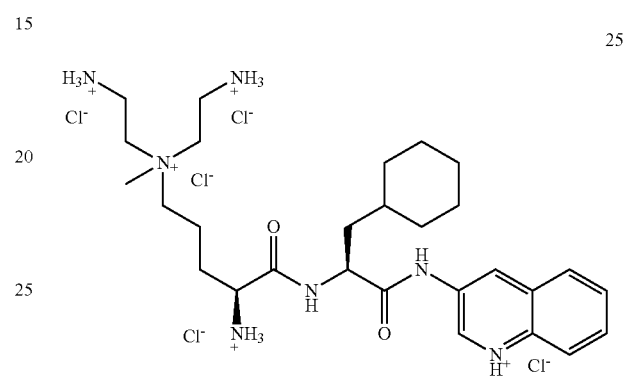

3-[(2S)-2-[(4S)-1-N,1-N-bis(2-azaniumylethyl)-4-formamido-1-N-methylbutane-1,4-bis(aminium)]-3-cyclohexylpropanamido]quinolin-1-ium pentachloride 25

$^1$H NMR (DMSO-d$_6$) 0.89-1.03 (m, 2H), 1.12-1.25 (m, 2H), 1.48-1.58 (m, 1H), 1.59-1.88 (m, 9H), 1.97-2.16 (m, 2H), 3.29 (s, 3H), 3.33-3.47 (m, 5H), 3.55-3.64 (m, 1H), 3.65-3.78 (m, 5H), 4.01-4.09 (m, 1H), 4.54-4.61 (m, 1H), 7.68 (dd, J=8 Hz, J=8 Hz, 1H), 7.77 (dd, J=8 Hz, J=8 Hz, 1H), 8.05-8.13 (m, 2H), 8.51 (brs, 3H), 8.69 (brs, 6H), 8.88 (s, 1H), 9.21 (brs, 2H), 11.21 (s, 1H); ESIMS found for C$_{28}$H$_{46}$N$_7$O$_2$ m/z 512 (M+).

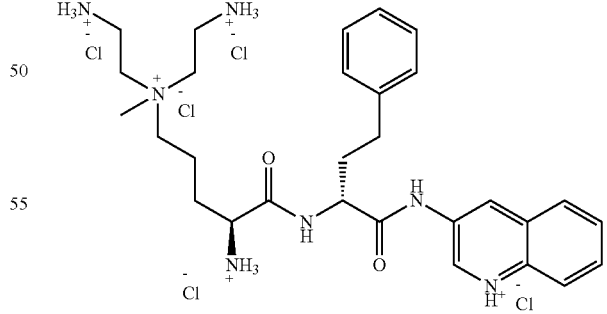

3-[(2R)-2-[(4S)-1-N,1-N-bis(2-azaniumylethyl)-4-formamido-1-N-methylbutane-1,4-bis(aminium)]-4-phenylbutanamido]quinolin-1-ium pentachloride 27

$^1$H NMR (DMSO-d$_6$) 1.85-2.20 (m, 6H), 2.65-2.83 (m, 2H), 3.24 (s, 3H), 3.36-3.42 (m, 4H), 3.61-3.80 (m, 6H), 4.11

(brs, 1H), 4.49-4.56 (m, 1H), 7.12 (brs, 1H), 7.21-7.28 (m, 4H), 7.78 (dd, J=8 Hz, J=8 Hz, 1H), 7.90 (dd, J=8 Hz, J=8 Hz, 1H), 8.18 (d, J=8 Hz, 1H), 8.24 (d, J=7 Hz, 1H), 8.65 (brs, 3H), 8.77 (brs, 6H), 9.20 (s, 1H), 9.48 (s, 1H), 9.49 (s, 1H), 11.49 (s, 1H); ESIMS found for $C_{29}H_{42}N_7O_2$ m/z 521 (M+).

8.22 (d, J=10 Hz, 1H), 8.48 (brs, 3H), 8.51-8.71 (m, 7H), 8.75 (d, J=8 Hz, 2H), 9.28 (d, J=7 Hz, 1H), 11.05 (s, 1H); $^{19}$F NMR (DMSO-$d_6$)-60.11 (s, 3F); ESIMS found for $C_{29}H_{39}F_3N_7O_2$ m/z 575 (M+).

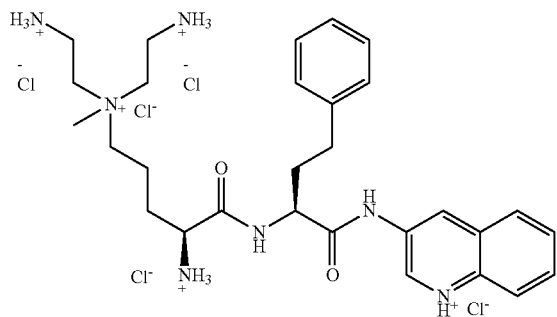

3-[(2S)-2-[(4S)-1-N,1-N-bis(2-azaniumylethyl)-4-formamido-1-N-methylbutane-1,4-bis(aminium)]-4-phenylbutanamido]quinolin-1-ium pentachloride 29

$^1$H NMR (DMSO-$d_6$) 1.79-1.89 (m, 2H), 1.99-2.19 (m, 2H), 2.65-2.74 (m, 1H), 2.84-2.94 (m, 1H), 3.29 (s, 3H), 3.38 (brs, 4H), 3.65-3.73 (m, 5H), 3.74-3.85 (m, 1H), 4.09-4.18 (m, 1H), 4.52-4.60 (m, 1H), 7.10-7.18 (m, 1H), 7.21-7.26 (m, 2H), 7.27-7.32 (m, 2H), 7.60-7.67 (m, 1H), 7.73 (dd, J=7 Hz, J=7 Hz, 1H), 8.01-8.07 (m, 2H), 8.51 (brs, 3H), 8.64 (brs, 6H), 8.83 (s, 1H), 9.16 (s, 1H), 9.51 (d, 1H), 11.30 (s, 1H); ESIMS found for $C_{29}H_{42}N_7O_2$ m/z 520 (M+).

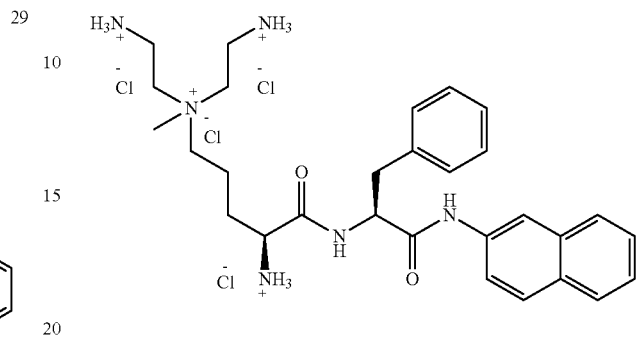

[(4S)-4-azaniumyl-4-{[(1S)-1-[(naphthalen-2-yl)carbamoyl]-2-phenylethyl]carbamoyl}butyl]bis(2-azaniumylethyl)methylazanium tetrachloride 57

$^1$H NMR (DMSO-$d_6$) 1.94 (brs, 2H), 2.02-2.20 (m, 2H), 3.15-3.24 (m, 2H), 3.28 (s, 3H), 3.43 (brs, 4H), 3.66 (brs, 2H), 3.74-3.89 (m, 4H), 4.04 (brs, 1H), 4.79 (brs, 1H), 7.14-7.33 (m, 3H), 7.36-7.51 (m, 2H), 7.59-7.71 (m, 1H), 7.76-7.89 (m, 3H), 8.19 (brs, 1H), 8.61 (brs, 9H), 9.14 (brs, 1H), 10.37 (brs, 1H); ESIMS found for $C_{29}H_{41}N_6O_2$ m/z 505 (M+).

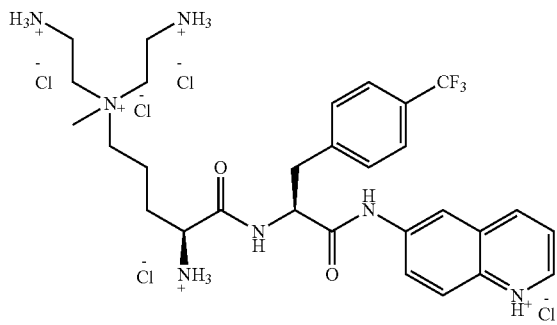

6-[(2S)-2-[(4S)-1-N,1-N-bis(2-azaniumylethyl)-4-formamido-1-N-methylbutane-1,4-bis(aminium)]-3-[4-(trifluoromethyl)phenyl]propanamido]quinolin-1-ium pentachloride 47

$^1$H NMR (DMSO-$d_6$) 1.88-1.98 (m, 2H), 2.03-2.20 (m, 2H), 3.23-3.27 (m, 2H), 3.29 (s, 3H), 3.60-3.72 (m, 6H), 3.77-3.88 (m, 4H), 4.00-4.07 (m, 1H), 4.83-4.89 (m, 1H), 7.58 (d, J=8 Hz, 2H), 7.68-7.76 (m, 3H), 8.14 (d, J=8 Hz, 1H),

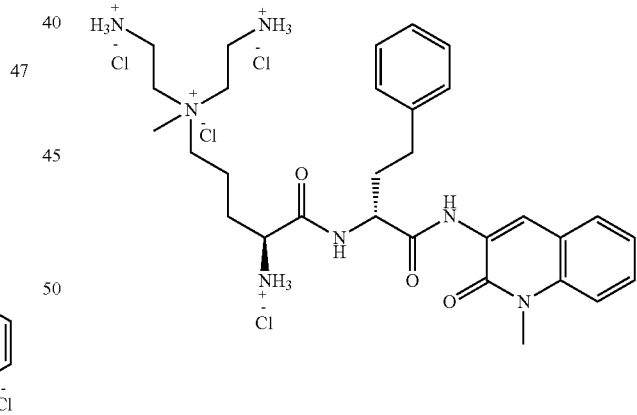

[(4S)-4-azaniumyl-4-{[(1R)-1-[(1-methyl-2-oxo-1,2-dihydroquinolin-3-yl)carbamoyl]-3-phenylpropyl]carbamoyl}butyl]bis(2-azaniumylethyl)methylazanium tetrachloride 59

$^1$H NMR (DMSO-$d_6$) 1.85-1.90 (m, 1H), 1.96-2.10 (m, 5H), 2.5-2.8 (m, 4 H), 3.24 (s, 3H), 3.39-3.42 (m, 4H), 3.69-3.74 (m, 4H), 3.74 (s, 3H), 4.03-4.09 (m, 1H), 4.65-4.68 (m, 1H), 7.13 (brs, 3H), 7.18-7.30 (m, 6H), 7.38 (brs, 3H), 7.55 (d, J=4 Hz, 2H), 8.62 (s, 1H), 8.65 (brs, 3H), 9.41 (d, J=7 Hz, 1H), 9.66 (s, 1H); ESIMS found for $C_{30}H_{44}N_7O_3$ m/z 550 (M+).

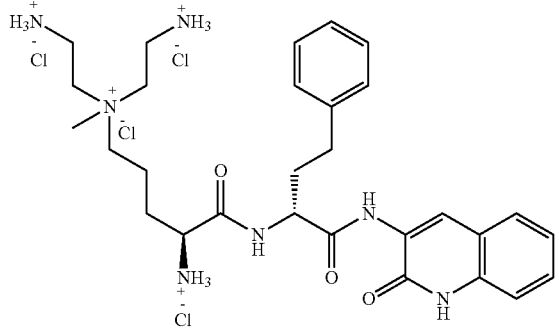

[(4S)-4-azaniumyl-4-{[(1R)-1-[(2-oxo-1,2-dihydro-quinolin-3-yl)carbamoyl]-3-phenylpropyl]carbamoyl}butyl]bis(2-azaniumylethyl)methylazanium tetrachloride 61

$^1$H NMR (DMSO-d$_6$) 1.85-1.90 (m, 1H), 1.99-2.15 (m, 5H), 2.5-2.75 (m, 4 H), 3.25 (s, 3H), 3.38-3.43 (m, 4H), 3.69-3.74 (m, 4H), 3.74 (s, 3H), 4.03-4.09 (m, 1H), 4.65-4.68 (m, 1H), 7.13-7.28 (m, 14H), 7.63 (d, J=4 Hz, 2H), 8.30 (s, 1H), 8.61 (brs, 3H), 9.47 (d, J=7 Hz, 1H), 9.66 (s, 1H); ESIMS found for C$_{29}$H$_{42}$N$_7$O$_3$ m/z 536 (M+).

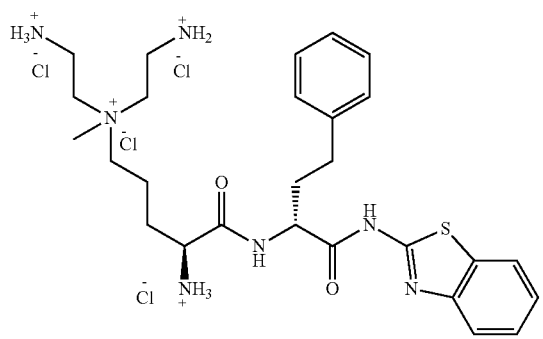

[(4S)-4-azaniumyl-4-{[(1R)-1-[(1,3-benzothiazol-2-yl)carbamoyl]-3-phenylpropyl]carbamoyl}butyl]bis(2-azaniumylethyl)methylazanium tetrachloride 63

$^1$H NMR (DMSO-d$_6$) 1.90-2.90 (m, 10H), 3.24 (s, 3H), 3.30-3.39 (m, 4H), 3.71-3.75 (m, 4H), 4.08-4.12 (m, 1H), 4.60-4.64 (m, 1H), 7.45 (t, J=7 Hz, 1H), 7.76 (d, J=8 Hz, 1H), 7.99 (d, J=8 Hz, 1H), 8.50 (brs, 3H), 8.61 (brs, 6H), 9.43 (d, J=7 Hz, 1H); ESIMS found for C$_{27}$H$_{40}$N$_7$O$_2$S m/z 526 (M+).

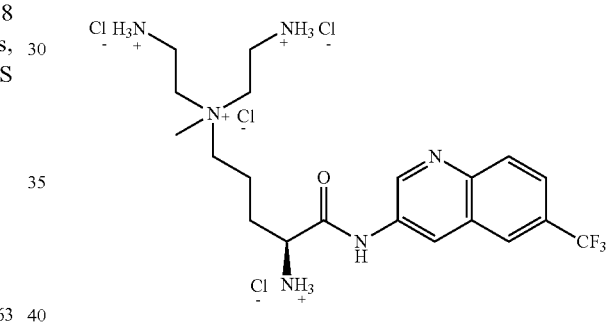

[(4S)-4-azaniumyl-4-{[(1S)-3-phenyl-1-[(2,3,4-trifluorophenyl) carbamoyl]propyl]carbamoyl}butyl]bis(2-azaniumylethyl)methylazanium tetrachloride 67

$^1$H NMR (DMSO-d$_6$) 1.66 (dd, J=6, J=13, 2H), 1.81-1.94 (m, 4H), 2.44-2.52 (m, 1H), 2.65-2.71 (m, 1H), 3.07 (s, 3H), 3.12-3.17, (m, 4H), 3.21-3.34 (m, 2H), 3.37-3.41 (m, 4H), 3.93-3.97 (m, 1H), 4.39 (dd, J=7 Hz, J=14 Hz, 1H), 6.99 (dd, J=7 Hz, J=7 Hz, 1H) 7.06-7.14 (m, 5H), 7.33 (dd, J=6 Hz, J=14 Hz, 1H), 8.36 (brs, 3H), 8.45-8.53 (m, 6H), 9.29 (d, J=8 Hz, 1H), 10.22 (s, 1H); $^{19}$F NMR (DMSO-d$_6$) −159.95 (dd, J=21 Hz, J=21 Hz, 1F), −141.89 (d, J=21 Hz, 1F), −138.96 (d, J=21 Hz, 1F).

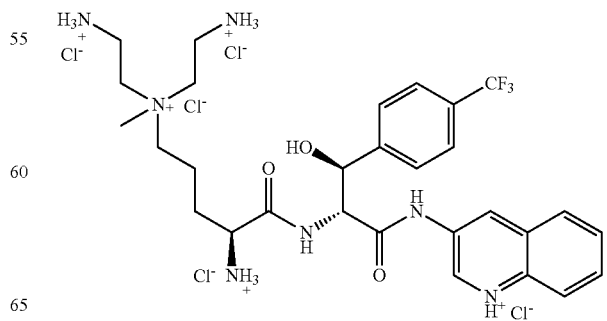

3-[(4S)-1-N,1-N-bis(2-azaniumylethyl)-4-formamido-1-N-methylbutane-1,4-bis(aminium)]-6-(trifluoromethyl)quinolin-1-ium pentachloride 133

$^1$H NMR (DMSO-d$_6$) 1.70-2.10 (m, 6H), 3.27 (s, 3H), 3.40-3.47 (m, 4H), 3.70-3.75 (m, 4H), 4.35-4.39 (m, 1H), 7.45 (d, J=2 Hz, 1H), 7.95 (d, J=8 Hz, 1H), 8.22 (d, J=8 Hz, 1H), 8.59 (brs, 3H), 8.72 (brs, 3H), 8.81 (brs, 3H), 9.05 (d, J=2 Hz, 1H), 9.39 (d, J=2 Hz, 1H), 12.31 (s, 1H); ESIMS found for C$_{20}$H$_{30}$N$_6$OF$_3$ m/z 427 (M+).

3-[(2R,3S)-2-[(4S)-1-N,1-N-bis(2-azaniumylethyl)-4-formamido-1-N-methylbutane-1,4-bis(aminium)]-3-hydroxy-3-[4-(trifluoromethyl)phenyl]propanamido]quinoline-1-ium pentachloride 135

$^1$H NMR (DMSO-$d_6$) 1.35-1.61 (m, 2H), 1.79-2.12 (m, 4H), 3.23 (s, 3H), 3.36 (brs, 4H), 3.68 (brs, 4H), 4.24 (brs, 1H), 4.94 (dd, J=3 Hz, J=9 Hz), 1H), 5.47 (d, J=3 Hz, 1H), 7.63-7.72 (m, 3H), 7.73-7.82 (m, 3H), 8.03 (d, J=8 Hz, 1H), 8.08 (d, J=9 Hz, 1H), 8.40 (brs, 3H), 8.71 (brs, 6H), 8.88 (s, 1H), 9.08 (d, J=10 Hz, 1H), 9.28 (s, 1H), 11.48 (s, 1H); $^{19}$F NMR (DMSO-$d_6$)-59.93 (s, 3F); ESIMS found for $C_{29}H_{39}F_3N_7O_3$ m/z 590 (M+).

Synthesis of 3-[(2R)-2-[(4S)-1-N,1-N-bis(2-azaniumylethyl)-4-formamido-1-N-methylbutane-1,4-bis(aminium)]-4-[4-(trifluoromethyl)phenyl]butanamido]-6-fluoroquinolin-1-ium pentachloride (34) is depicted below in scheme 3 and example 3

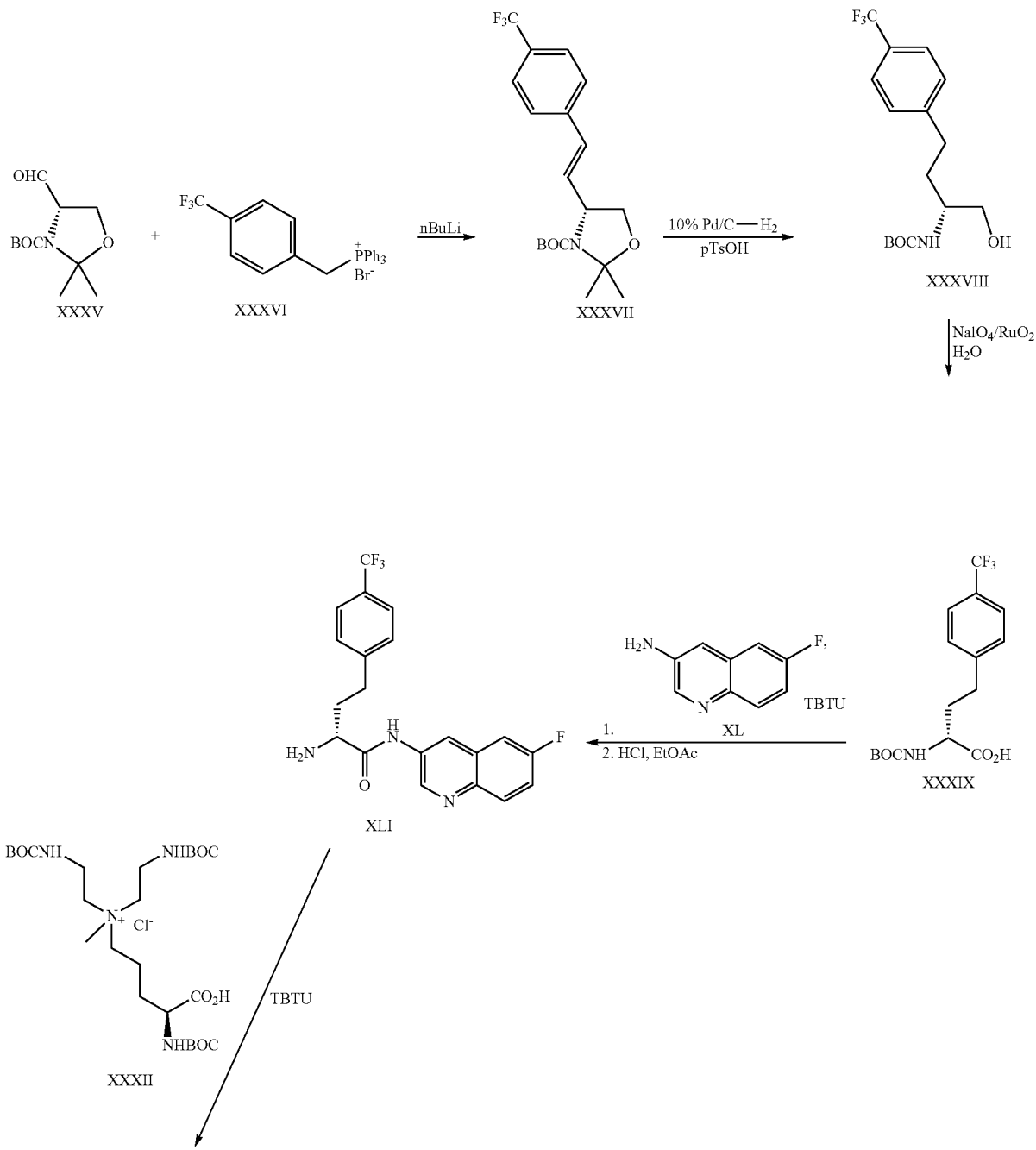

Scheme 3

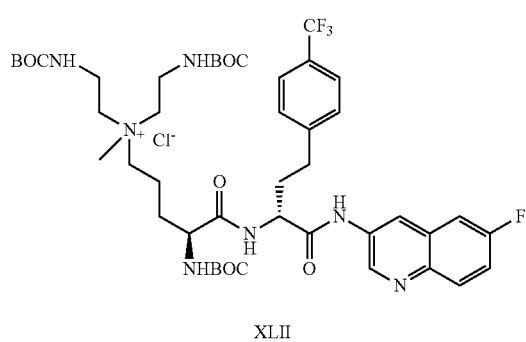

XLII

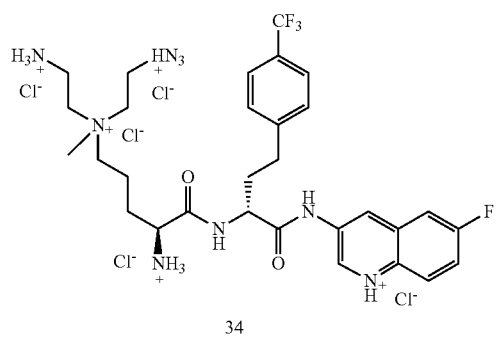

34

Example 3

Step 1

To a solution of triphenyl({[4-(trifluoromethyl)phenyl]methyl})phosphonium bromide XXXIV (80.2 g; 0.16 mol) in THF (640 mL) under argon and cooled to −68° C. was added n-BuLi (100 mL; 0.56 mol; as 2.5 M solution in hexanes). After 10 minutes the reaction mixture was warmed to −40° C. until the precipitate disappeared. The mixture was cooled to −68° C. again and a solution of Garner's aldehyde XXXV (36.7 g; 0.16 mol) (obtained from L-serine) in THF (50 mL) was added dropwise over 25 minutes. The reaction was warmed to r.t. and stirred overnight before quenching with methanol (250 mL) for an additional 30 minutes. The solvent was removed under reduced pressure and the residue was then purified on a silica gel column (20:1 hexane:EtOAc) to give (R,Z-E)-tert-butyl-2,2-dimethyl-4-(4-trifluoromethylstyryl)oxazolidine-3-carboxylate XXXVII as a light-yellow oil (47.3 g, 0.128 mol, 80% yield). ESIMS found for $C_{19}H_{24}F_3NO_3$ m/z 372.4 (M+H).

Step 2

To a solution of the olefin XXXVII (47.2 g; 0.127 mol) in methanol (500 mL) was added 10% Pd/C (4 g) and para-toluenesulfonic acid monohydrate (0.24 g; 1.27 mmol). The suspension was stirred under hydrogen at normal pressure and r.t. overnight. The mixture was filtered through Celite and concentrated under reduced pressure to produce compound XXXVIII as a white solid (41.7 g, 125.1 mmol, 98% yield). ESIMS found for $C_{16}H_{22}F_3NO_3$ m/z 334.3 (M+H).

Step 3

To a solution of tert-butyl (1R)-1-(hydroxymethyl)-3-[4-(trifluoromethyl)phenyl]propylcarbamate XXXVIII (41.3 g; 0.124 mol) in 60% aqueous acetone was added a solid sodium (meta)periodate (266 g; 1.24 mol) followed by ruthenium(II) oxide hydrate (1.65 g; 12.4 mmol). The greenish suspension was stirred for 3 h before adding propan-2-ol (500 mL) and stirring for an additional 30 min to consume excess oxidant. The resulting suspension was filtered through Celite, and the filtrate was concentrated under reduced vacuum to give a brown oil. To the brown foam was added 1 N HCl to pH=1 extracted with EtOAc. The organic layer was washed with brine and dried with $MgSO_4$. The crude residue was then purified on a silica gel column (10:1 hexane:EtOAc) to obtain (2R)-2-[(tert-butoxycarbonyl)amino]-4-[4-(trifluoromethyl)phenyl]butanoic acid XXXIX (18 g; 51.8 mmol, 42% yield). $^1$H NMR (CDCl$_3$) 1.46 (brs, 9H), 1.93-2.30 (m, 2H), 2.68-2.87 (m, 2H), 4.12-4.47 (m, 1H), 5.04-5.23 (m, 1H), 7.30 (d, J=8 Hz, 2H), 7.55 (d, J=8 Hz, 2H); ESIMS found for $C_{16}H_{20}F_3NO_4$ m/z 348.3 (M+H).

Step 4-7

Procedures can be found in examples 1-2. The final compound 34 was isolated as the hydrochloride salt. $^1$H NMR (DMSO-d$_6$) 1.96-2.22 (m, 4H), 2.76-2.82 (m, 1H), 2.85-2.94 (m, 1H), 3.25 (s, 3H), 3.34-3.45 (m, 4H), 3.60-3.74 (m, 6H), 4.05-4.12 (m, 1H), 4.52-4.56 (m, 1H), 7.51 (d, 2H, J=8 Hz), 7.57 (ddd, 1H, J=3 Hz, J=9 Hz), 7.63 (d, 2H, J=8 Hz), 7.78 (dd, 1H, J=2 Hz, J=10 Hz), 8.03 (dd, 1H, J=5 Hz, J=9 Hz), 8.56 (brs, 3H), 8.67 (brs, 6H), 8.74 (s, 1H), 9.08 (s, 1H), 9.45 (d, 1H, J=8 Hz), 10.98 (s, 1H); $^{19}$F NMR (DMSO-d$_6$) −112.29 (s, 1F), −60.08 (s, 3F); ESIMS found for $C_{30}H_{40}F_4N_7O_2$ m/z 606.8 (M+).

The following compound was prepared in accordance with the procedure described in the above example 3.

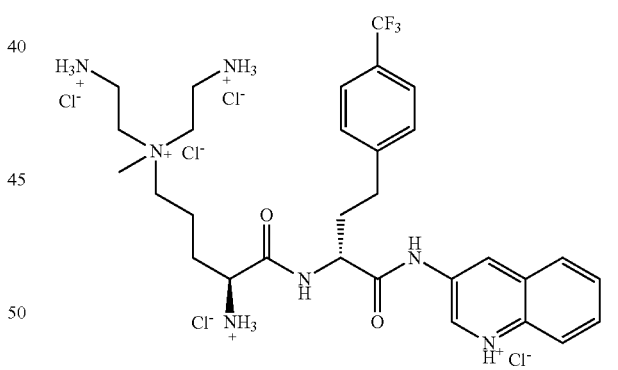

33

3-[(2R)-2-[(4S)-1-N,1-N-bis(2-azaniumylethyl)-4-formamido-1-N-methylbutane-1,4-bis(aminium)]-4-[4-(trifluoromethyl)phenyl]butanamido]quinolin-1-ium pentachloride 33

$^1$H NMR (DMSO-d$_6$) 1.71-2.09 (m, 6H), 2.61-2.76 (m, 2H), 3.09 (s, 3H), 3.18-3.31 (m, 4H), 3.46-3.56 (m, 2H), 3.58-3.68 (m, 4H), 3.95-4.00 (m, 1H), 4.36-4.42 (m, 1H), 7.30-7.34 (m, 2H), 7.38-7.44 (m, 2H), 7.47-7.52 (m, 1H), 7.73 (d, J=8 Hz, 1H), 7.82 (d, J=9 Hz, 1H), 8.40-8.57 (brs, 9H), 8.50 (d, J=3 Hz, 1H), 9.00 (d, J=2 Hz, 1H), 9.17 (d, J=8 Hz, 1H), 10.50 (s, 1H); $^{19}$F NMR (DMSO-d$_6$)-60.06 (s, 3F); ESIMS found for $C_{30}H_{41}F_3N_7O_2$ m/z 588 (M+).

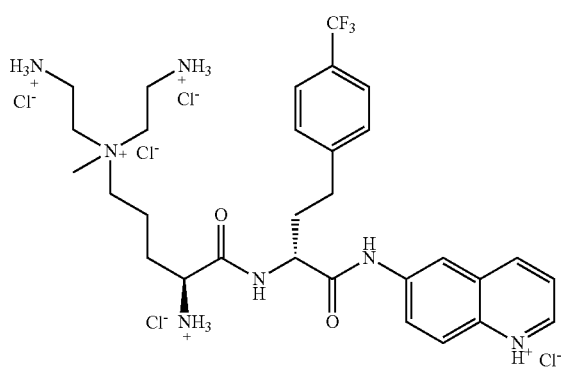

46

6-[(2R)-2-[(4S)-1-N,1-N-bis(2-azaniumylethyl)-4-formamido-1-N-methylbutane-1,4-bis(aminium)]-4-[4-(trifluoromethyl)phenyl]butanamido]quinolin-1-ium pentachloride 46

$^1$H NMR (DMSO-d$_6$) 2.02-2.26 (m, 6H), 2.79-2.94 (m, 2H), 3.28 (s, 3H), 3.39-3.45 (m, 4H), 3.65-3.76 (m, 2H), 3.78-3.88 (m, 4H), 4.11-4.18 (m, 1H), 4.52-4.58 (m, 1H), 7.50 (d, J=8 Hz, 2H), 7.57 (d, J=8 Hz, 2H), 7.68-7.75 (m, 1H), 7.82 (t, J=12 Hz, 1H), 8.19-8.24 (m, 2H), 8.52 (s, 1H), 8.64 (brs, 3H), 8.77 (brs, 6H), 8.92 (s, 1H), 9.38 (d, J=8 Hz, 1H), 10.72 (s, 1H); $^{19}$F NMR (DMSO-d$_6$)-60.10 (s, 3F); ESIMS found for C$_{30}$H$_{41}$F$_3$N$_7$O$_2$ m/z 589.6 (M+).

Synthesis of 3-[(2S)-2-[(4S)-1-N,1-N-bis(2-azaniumylethyl)-4-formamido-1-N-methylbutane-1,4-bis(aminium)]-2-(naphthalen-2-yl)acetamido]quinolin-1-ium pentachloride (26) is depicted below in scheme 4 and example 4

Scheme 4

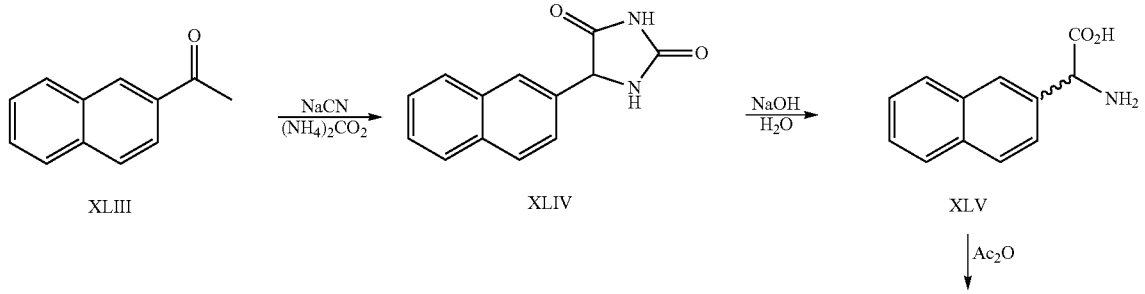

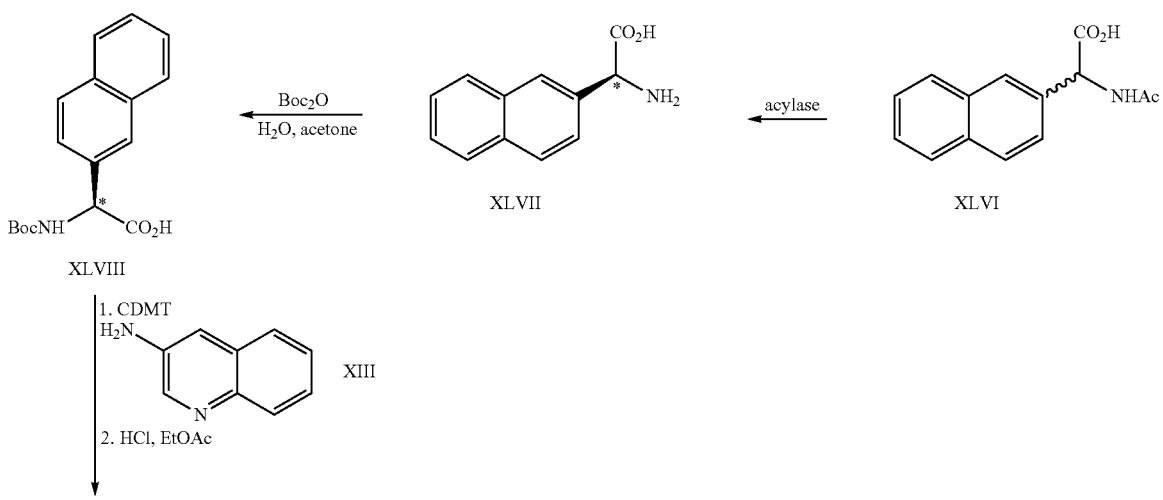

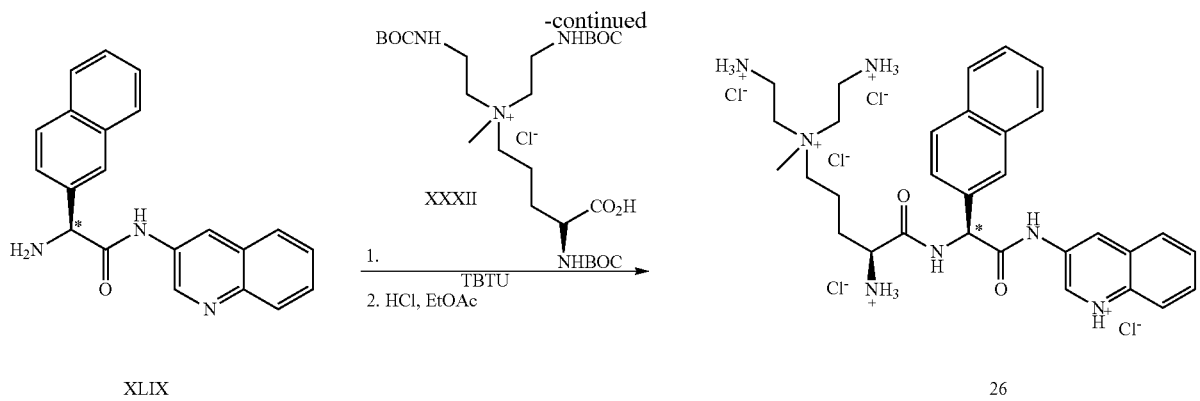

XLIX
*4:1 L:D

26

Example 4

Step 1

To a solution of 2-naphthaldehyde XLIII (25 g, 160.0 mmol) in EtOH (650 mL) was added water (650 mL), KCN (31.3 g, 480 mmol) and $(NH_4)_2CO_3$ (61.5 g, 640 mmol). The mixture was refluxed for 19 h before the EtOH was removed under reduced pressure. The remaining aqueous phase was acidified to pH 1.5 with 6 M HCl. The precipitate was filtered, washed with 1 M HCl and air-dried. The crude product XLIV (31.3 g, 138.4 mmol, 86.5% yield) was directly taken to the next step. ESIMS found for $C_{13}H_{10}N_2O$ m/z 225 (M−H).

Step 2

A solution of 5-(naphthalen-2-yl)imidazolidine-2,4-dione XLIV (31.3 g, 138.4 mmol) in 16% NaOH (700 ml) was refluxed for 2 h before the hot mixture was filtrated. The solution was cooled to r.t., washed EtOAc (2×) and acidified to pH 1.5 with 6 M HCl. The precipitate was filtered, washed with 1 M HCl and dried in electric heater. The product XLV was isolated as a grey solid (20.1 g, 99.9 mmol) and used directly in the next step. ESIMS found for $C_{12}H_{11}NO_2$ m/z 202 (M+H).

Step 3

A suspension of crude 2-amino-2-(naphthalen-2-yl)acetic acid XLV (20.1 g, 99.9 mmol) in water was alkalinized to pH=12 with 2 M NaOH before adding acetic anhydride (28.4 ml, 300 mmol). The mixture was stirred overnight at r.t. The reaction mixture was acidified to pH=2 with 6 M HCl and filtered to produce acetylated product as white crystals XLVI (17.2 g, 70.7 mmol, 70.8% yield) which were used in the next step. ESIMS found for $C_{14}H_{13}NO_3$ m/z 242 (M−H).

Step 4

To a solution of 2-acetamido-2-(naphthalen-2-yl)acetic acid XLVI (5 g, 20.6 mmol) and potassium carbonate (pH=8-9) in water (6 L) heated to 45° C. while sparged by argon. To the suspension was added acylase (1 g) from *Aspergilus melleus* and the mixture was heated at 45° C. for 5 days under argon. The precipitate containing (80% L-isomer and 20% D-isomer) XLVII (2.4 g, 11.7 mmol) was filtered and washed with water and ethyl ether. Filtrate was concentrated and acidified to pH=1 and the acetyl-D-isomer was extracted ethyl acetate. The EtOAc was washed with water, dried over $MgSO_4$ and evaporated to yield a grey solid as a mixture of acetyl-D-isomer and acetyl-L-isomer (2.2 g). ESIMS found for $C_{12}H_{11}NO_2$ m/z 202 (M+H).

Step 5

To a solution of (2S)-2-amino-2-(naphthalen-2-yl)acetic acid (4:1 L:D) XLVII (1.2 g, 5.7 mmol) in water (20 mL) was added $K_2CO_3$ until pH=10 followed by a solution of $Boc_2O$ (1.4 g, 6.3 mmol) in acetone (15 mL). The mixture was stirred at r.t. overnight while maintaining the pH=10 with additions of $K_2CO_3$. The acetone was then removed under vacuum. The remaining aqueous solution was alkalinized to pH=12, washed 2× diethyl ether, acidified with to pH=2, washed DCM (4×), washed with brine and dried over $MgSO_4$. The solvent was removed under reduced pressure to obtain the product as a white solid XLVIII (1.07 g, 3.54 mmol, 62% yield). ESIMS found for $C_{17}H_{19}NO_4$ m/z 300 (M−H).

Step 6

To a solution of CDMT (683 mg, 3.9 mmol) in DCM (20 mL) cooled to 0° C. was added N-methylmorpholine (0.43 ml, 3.9 mmol) and stirred for 10 min. (2S)-2-{[(tert-butoxy)carbonyl]amino}-2-(naphthalen-2-yl)acetic acid XLVIII (1.07 g, 3.54 mmol) was added and the solution stirred for another 40 min. 3-aminoquinoline (562 mg, 3.89 mmol) was then added and the mixture stirred at r.t. overnight. The reaction mixture was washed with 1 M aqueous $K_2CO_3$, 1 M aqueous HCl (2×), brine and dried over anhydrous $MgSO_4$. The solvent was removed under reduced pressure and the product recrystallized from chloroform/hexane to obtain XLVIX as a white solid (1.35 g, 3.15 mmol, 88% yield). ESIMS found for $C_{26}H_{25}N_3O_3$ m/z 428 (M+H).

Step 7-9

Procedures can be found in examples 1-3. The final compound 26 was isolated as the hydrochloride salt. $^1$H NMR (DMSO-$d_6$) 1.81-1.94 (m, 2H), 1.98-2.14 (m, 2H), [3.30 (s, $1^{st}$ diastereoisomer); 3.31 (s, $2^{nd}$ diastereoisomer), 3H), 3.38 (brs, 4H), 3.59-3.63 (m, 4H), 3.67-3.75 (m, 6H), 4.14 (brs, 2H), [5.95 (d, J=7 Hz $1^{st}$ diastereoisomer); 5.99 (d, J=8 Hz $2^{nd}$ diastereoisomer), 1H), 7.49-7.52 (m, 3H), [7.64 (m, $2^{nd}$ diastereoisomer); 7.74-7.81 (m, $1^{st}$ diastereoisomer), 3H], [7.87-7.89 (m, $2^{nd}$ diastereoisomer); 7.90-7.97 (m, $1^{st}$ diastereoisomer), 3H], [8.03-8.07 (m, $2^{nd}$ diastereoisomer); 8.08-8.12 (m, 1st diastereoisomer), 2H], [8.14 (s, 2nd diastereoisomer); 8.18 (s, 1st diastereoisomer), 1H], [8.56 (brs, 1st diastereoisomer); 8.61 (brs, 2nd diastereoisomer), 3H], 8.71 (brs, 6H), [9.28 (s, 1st diastereoisomer); 9.32 (s, 2nd diastereoisomer), 1H], [9.60 (d, J=6 Hz, 1st diastereoisomer), 9.70 (d, J=7 Hz, 2nd diastereoisomer), 1H], [11.80 (s, second diastereoisomer); 11.84 (s, 1st diastereoisomer), 1H]; ESIMS found for $C_{31}H_{40}N_7O_2$ m/z 542 (M+).

Synthesis of 3-[(2R)-2-[(4S)-1-N,1-N-bis(2-azaniumylethyl)-1-N-methyl-4-(N-methylformamido)butane-1,4-bis(aminium)]-3-[4-(trifluoromethyl)phenyl]propanamido]quinolin-1-ium pentachloride (20) is depicted below in scheme 5 and example 5 portions. Methyl iodide (1.12 mL, 18 mmol) was then added and the mixture was stirred at r.t. for 3 days. The mixture was then treated with water before removing the THF under reduced pressure. The aqueous phase was acidified and extracted EtOAc (2×). The combined EtOAc was washed with sodium thiosulfate, dried and evaporated under reduced pressure. The residue was crystallized to produce (2R)-2-[(tert-butoxycarbonyl) (methyl)amino]-3-[4-(trifluoromethyl)phenyl]-propanoic acid L (0.73 g, 2 mmol, 70% yield).

Step 2-5

Procedures can be found in examples 1-4. The final compound 20 was isolated as the hydrochloride salt. $^1$H NMR

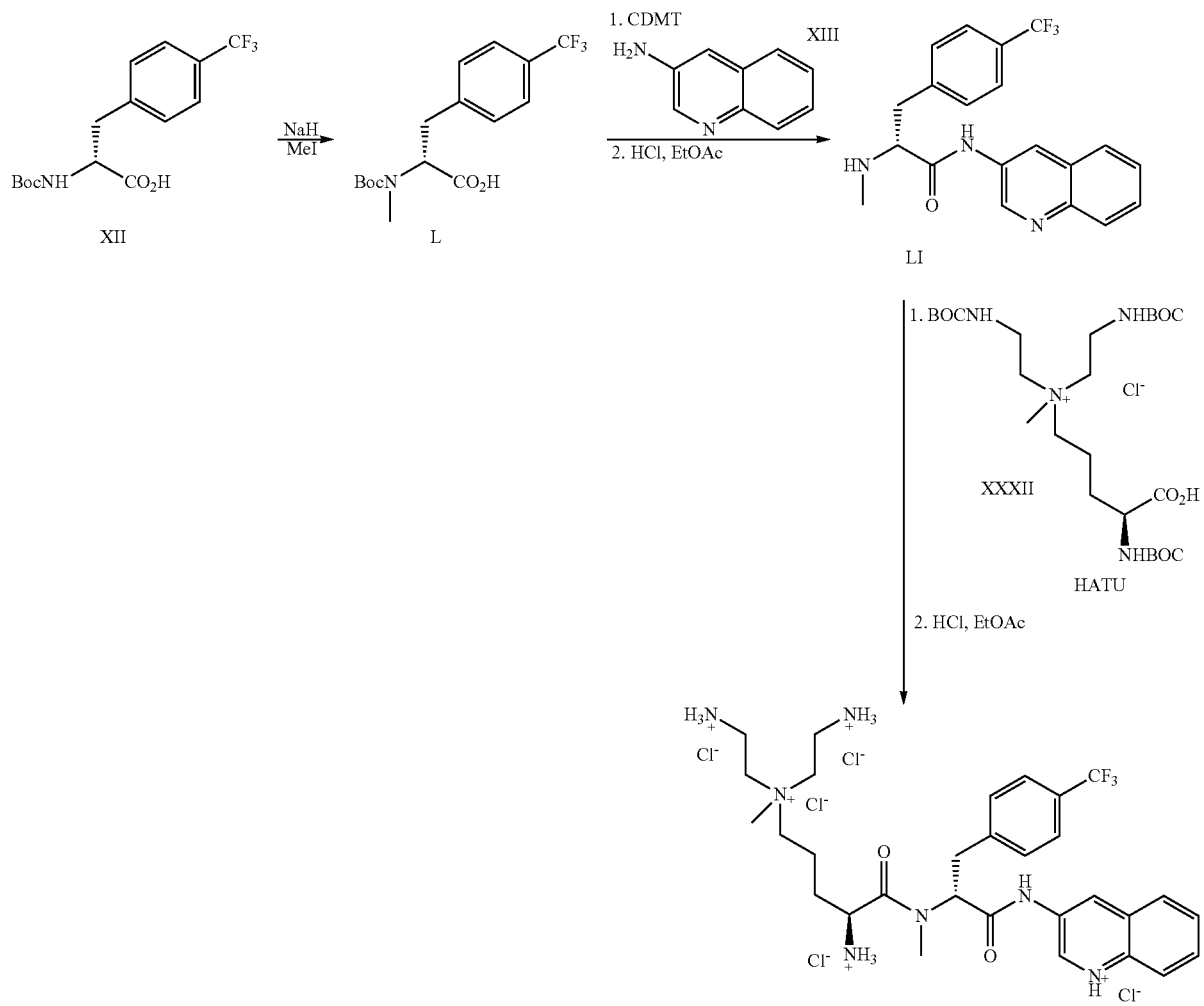

Scheme 5

Example 5

Step 1

To a solution of (2R)-2-[(tert-butoxycarbonyl)amino]-3-[4-(trifluoromethyl)phenyl]propanoic acid XII (1 g, 3 mmol) in dry THF (10 mL) was added sodium hydride (60% suspension in mineral oil) (0.72 g, 18 mmol; 6 eq. of pure NaH) in (DMSO-$d_6$) 1.0 (t, J=7 Hz, 1H); 1.1-1.3 (m, 4H); 1.8-1.9 (m, 2H); 3.01 (s, 3H); 3.1 (s, 3H); 3.13-3.21 (m, 1H); 3.26-3.33 (m, 7H); 4.20-4.27 (m, 1H) 5.43-5.49 (m, 1H); 7.49-7.55 (m, 3H) 7.59-7.63 (m, 3H), 7.83-7.91 (m, 2H) 8.31-8.41 (brs, 3H); 8.47-8.53 (brs, 6H); 8.66 (s, 1H); 9.06 (s, 1H); 10.59 (s, 1H); $^{19}$F NMR (DMSO-$d_6$) −112.29 (s, 1F), −60.53 (s, 3F); ESIMS found for $C_{30}R_{41}F_3N_7O_2$ m/z 588.5 (M+).

Synthesis of 3-[(2R)-2-[(4S)-1-N,1-N-bis(2-azaniumylethyl)-4-formamido-1-N-methylbutane-1,4-bis(aminium)]-4-phenylbutanamido]-1-{[4-(trifluoromethyl)phenyl]methyl}quinolin-1-ium pentachloride (53) is depicted below in scheme 6 and example 6

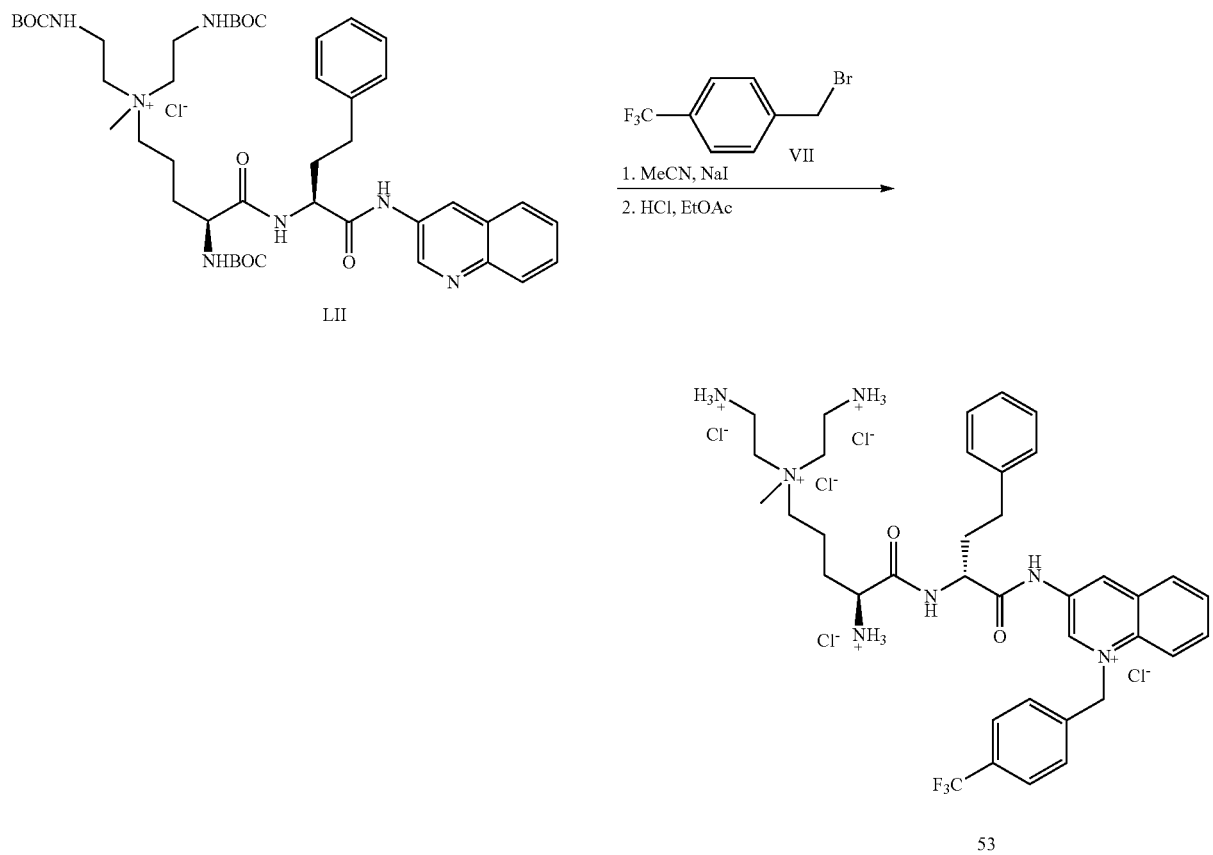

Example 6

To a solution of tert-butyl N-(2-{[(4S)-4-{[(tert-butoxy)carbonyl]amino}-4-{[(1S)-3-phenyl-1-[(quinolin-3-yl)carbamoyl]propyl]carbamoyl}butyl](2-{[(tert-butoxy) carbonyl]amino}ethyl)methylazaniumyl}ethyl)carbamate chloride LII (0.27 g, 0.3 mmol) in acetonitrile was added 4-(trifluoromethyl)benzyl bromide VII (0.52 g, 2.1 mmol) and a catalytic amount of NaI. The mixture was stirred at r.t. for 7-10 days. Acetonitrile was removed under reduced pressure and the residue was treated with 3.5 M HCl in EtOAc. The precipitate was filtered, washed with diethyl ether and purified on preparative HPLC to produce the desired compound 53 (40 mg, 0.05 mmol, 18% yield). $^1$H NMR (DMSO-$d_6$) 1.74-2.00 (m, 3H), 2.02-2.30 (m, 4H), 2.62-3.08 (m, 2H), 3.54-4.06 (m, 9H), 4.09-4.31 (m, 1H), 4.46-4.71 (m, 1H), 6.43-6.68 (m, 2H), 7.06-7.45 (m, 6H), 7.57 (d, J=8 Hz, 2H), 7.76 (d, J=8 Hz, 2H), 7.86-8.13 (m, 2H), 8.27-8.40 (m, 1H), 8.42-8.81 (m, 9H), 9.38-9.45 (m, 1H), 9.57-9.73 (m, 1H), 9.95 (brs, 1H), 11.89 (brs, 1H); $^{19}$F NMR (DMSO-$d_6$)-60.51 (s, 3F); ESIMS found for $C_{37}H_{48}F_3N_7O_2$ m/z 678 (M−H).

The following compound was prepared in accordance with the procedure described in the above example 6.

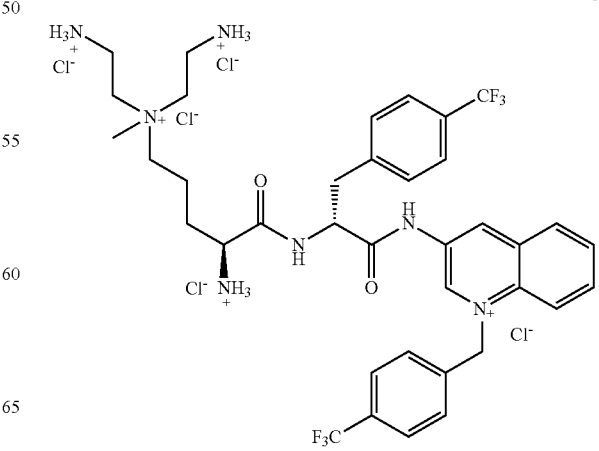

54

3-[(2R)-2-[(4S)-1-N,1-N-bis(2-azaniumylethyl)-4-formamido-1-N-methylbutane-1,4-bis(aminium)]-3-[4-(trifluoromethyl)phenyl]propanamido]-1-{(trifluoromethyl)phenyl]methyl}quinolin-1-ium pentachloride 54

$^1$H NMR (DMSO-d$_6$) 1.56 (brs, 1H), 1.70 (brs, 1H), 1.94 (brs, 2H), 3.00-3.09 (m, 1H), 3.10-3.16 (m, 1H), 3.24 (s, 3H), 3.17 (brs, 6H), 3.40 (brs, 4H), 3.99 (brs, 4H), 4.96 (brs, 4H), 6.55 (s, 2H), 7.60-7.67 (m, 2H), 7.69-7.71 (m, 2H), 7.72-7.82 (m, 4H), 7.92-8.00 (m, 1H), 8.05-8.12 (m, 1H), 8.45 (d, J=9 Hz, 1H), 8.48 (d, J=8 Hz, 1H), 8.54 (brs, 2H), 8.70 (brs, 5H), 9.50 (brs, 1H), 9.54 (d, J=7 Hz, 1H), 10.16 (s, 1H), 12.11 (s, 1H); $^{19}$F NMR (DMSO-d$_6$) −59.93 (s, 3F), −60.54 (s, 3F); ESIMS found for C$_{37}$H$_{45}$F$_6$N$_7$O$_2$ m/z 367 (M/2+1).

Synthesis of 3-{2-[(4S)-1-N,1-N-bis(2-azaniumylethyl)-4-(N-methylformamido)-1-N-(prop-2-en-1-yl)butane-1,4-bis(aminium)]-3-[4-(trifluoromethyl)phenyl]propanamido}quinolin-1-ium pentachloride (92) is depicted below in scheme 7 and example 7

Example 7

Step 1

To a solution of tert-butyl (2S)-5-[bis(2-{[(tert-butoxy)carbonyl]amino}ethyl)amino]-2-{bis[(tert-butoxy)carbonyl]amino}pentanoate XXIX (2 g, 3 mmol) in allyl bromide (2.5 mL, 30 mmol) was added DIPEA (5 mL, 30 mmol) and stirred at r.t. for 8 days. Reaction mixture was concentrated under reduced pressure and the residue was then purified on a silica gel column (100:1→50:1 DCM:MeOH) to give compound LIII as yellow oil. (1.8 g, 2.26 mmol, 75% yield). ESIMS found for C$_{36}$H$_{67}$N$_4$O$_{10}$ m/z 715 (M+).

Step 2-6

Procedures can be found in examples 1-4. The final compound 92 was isolated as the hydrochloride salt. $^1$H NMR (DMSO-d$_6$) 1.40-1.61 (m, 2H), 1.84-2.03 (m, 2H), 3.19 (brs, 6H), 3.40 (brs, 2H), 3.73 (brs, 2H), 4.03-4.04 (m, 2H), 4.62-4.72 (m, 1H), 5.41-5.63 (m, 2H), 5.89-5.96 (m, 1H), 7.44-7.50 (m, 4H), 7.57-7.64 (m, 2H), 7.83-7.91 (m, 2H), 8.21 (s,

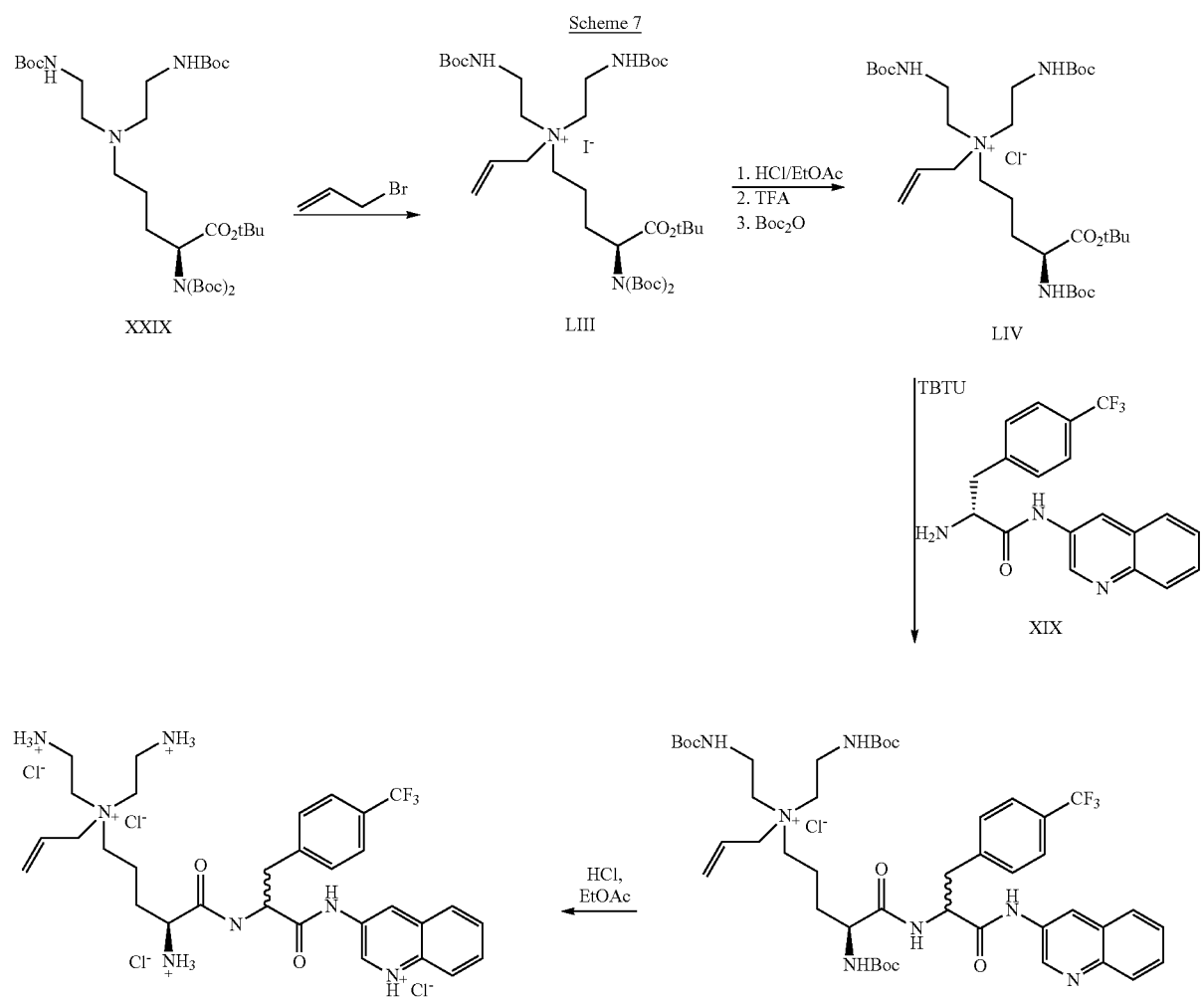

Scheme 7

3H, 2$^{nd}$ diastereoisomer), 8.27 (s, 3H, 1$^{st}$ diastereoisomer), 8.50 (s, 6H), 8.71 (s, 1H, 2$^{nd}$ diastereoisomer), 8.73 (s, 1H, 1$^{st}$ diastereoisomer), 9.07 (d, J=6 Hz, 1H), 9.17 (s, 1H, 2$^{nd}$ diastereoisomer), 9.19 (s, 1H, 1$^{st}$ diastereoisomer), 11.28 (s, 1H, 2$^{nd}$ diastereoisomer), 11.633 (s, 1H, 1$^{st}$ diastereoisomer); $^{19}$F NMR (DMSO-d$_6$)-60.09 (1$^{st}$ diastereoisomer), −59.97 (2$^{nd}$ diastereoisomer); ESIMS found for C$_{31}$H$_{44}$F$_3$N$_7$O$_2$ m/z 601 (M+).

Synthesis of 3-[(2S)-2-[(4S)-1-N-(2-azaniumylethyl)-1-N-{2-[(azaniumylmethanimidoyl)amino]ethyl}-4-formamido-1-N-methylbutane-1,4-bis(aminium)]-3-[4-(trifluoromethyl)phenyl]propanamido]quinolin-1-ium pentachloride (75) is depicted below in scheme 8 and example 8

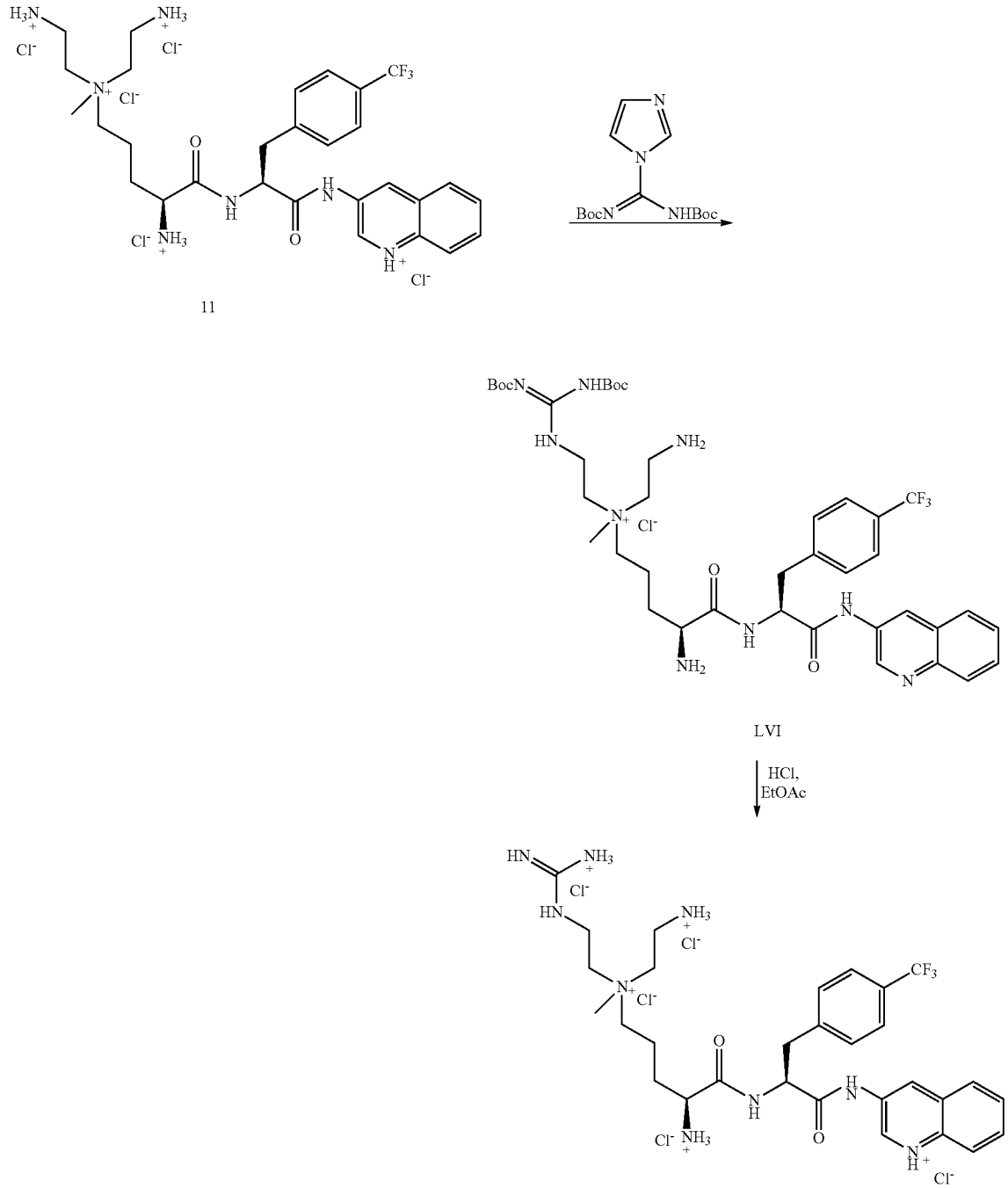

Example 8

Step 1

To a solution of 3-[(2S)-2-[(4S)-4-amino-N,N-bis(2-azaniumylethyl)-4-formamido-N-methylbutan-1-aminium]-3-[4-(trifluoromethyl)phenyl]propanamido]quinolin-1-ium pentachloride 11 (500 mg, 0.66 mmol) in MeOH/THF (5 mL/5 mL) was added Et$_3$N (0.51 mL, 3.64 mmol). To this mixture was added tert-butyl N-[(1Z)-{[(tert-butoxy)carbonyl]imino}(1H-imidazol-1-yl)methyl]carbamate (205 mg, 0.66 mmol) dissolved in MeOH/THF (1.5 mL/1.5 mL) dropwise. The mixture was stirred at r.t. for 15 days removing the solvent under reduced pressure. The residue was purified by preparative HPLC to produce compound LVI as a white solid (188 mg, 0.22 mmol, 33% yield)

Step 2 tert-Butyl N-[(1E)-[(2-{[(4S)-4-amino-4-{[(1S)-1-[(quinoline-3-yl) carbamoyl]-2-[4-(trifluoromethyl)phenyl]ethyl]carbamoyl}butyl](2-aminoethyl)methylazaniumyl}ethyl)amino]({[(tert-butoxy)carbonyl]amino})methylidene]carbamate chloride LVI (188 mg, 0.22 mmol) was treated with HCl (5 mL) (3 M solution in EtOAc) at r.t. for 1 hour. Diethyl ether (5 mL) was then added and the reaction mixture was then filtered. The solid was washed with diethyl ether (30 mL) to give the desired product 75 as a white solid (175 mg, 0.21 mmol, 95% yield). $^1$H NMR (DMSO-d$_6$) 1.88-1.98 (m, 2H), 2.03-2.23 (m, 2H), 3.03-3.09 (m, 1H), 3.25-3.28 (m, 1H), 3.34 (s, 3H), 3.54-3.70 (m, 1H), 3.72-3.85 (m, 4H), 3.89-3.98 (m, 2H), 4.01-4.08 (m, 1H), [4.66 (brs, 2$^{nd}$ diastereoisomer), 4.90 (s, 1$^{st}$ diastereoisomer), 1H], 7.61-7.77 (m, 7H), 7.82-7.87 (m, 4H), 8.10-8.18 (m, 2H), 8.19-8.29 (m, 1H), 8.49 (brs, 3H), 8.78 (brs, 4H), 8.94 (s, 1H), 9.33 (s, 1H), 9.39-9.47 (m, 1H), [11.56 (s, 2$^{nd}$ diastereoisomer); 11.70 (s, 1$^{st}$ diastereoisomer), 1H]; $^{19}$F NMR (DMSO-d$_6$) [−59.98 (s, 2$^{nd}$ diastereoisomer); −60.07 (s, 1$^{st}$ diastereoisomer), 3F]; ESIMS found for C$_{30}$R$_{41}$F$_3$N$_9$O$_2$ m/z 616 (M+).

Synthesis of 3-[(2S)-2-[(4S)—N,N-bis(2-azaniumylethyl)-4-formamido-4-[(1R)-1-formamidoethan-1-aminium]-N-methylbutan-1-aminium]-3-[4-(trifluoromethyl)phenyl]propanamido]quinolin-1-ium pentachloride (44) is depicted below in scheme 9 and example 9

Scheme 9

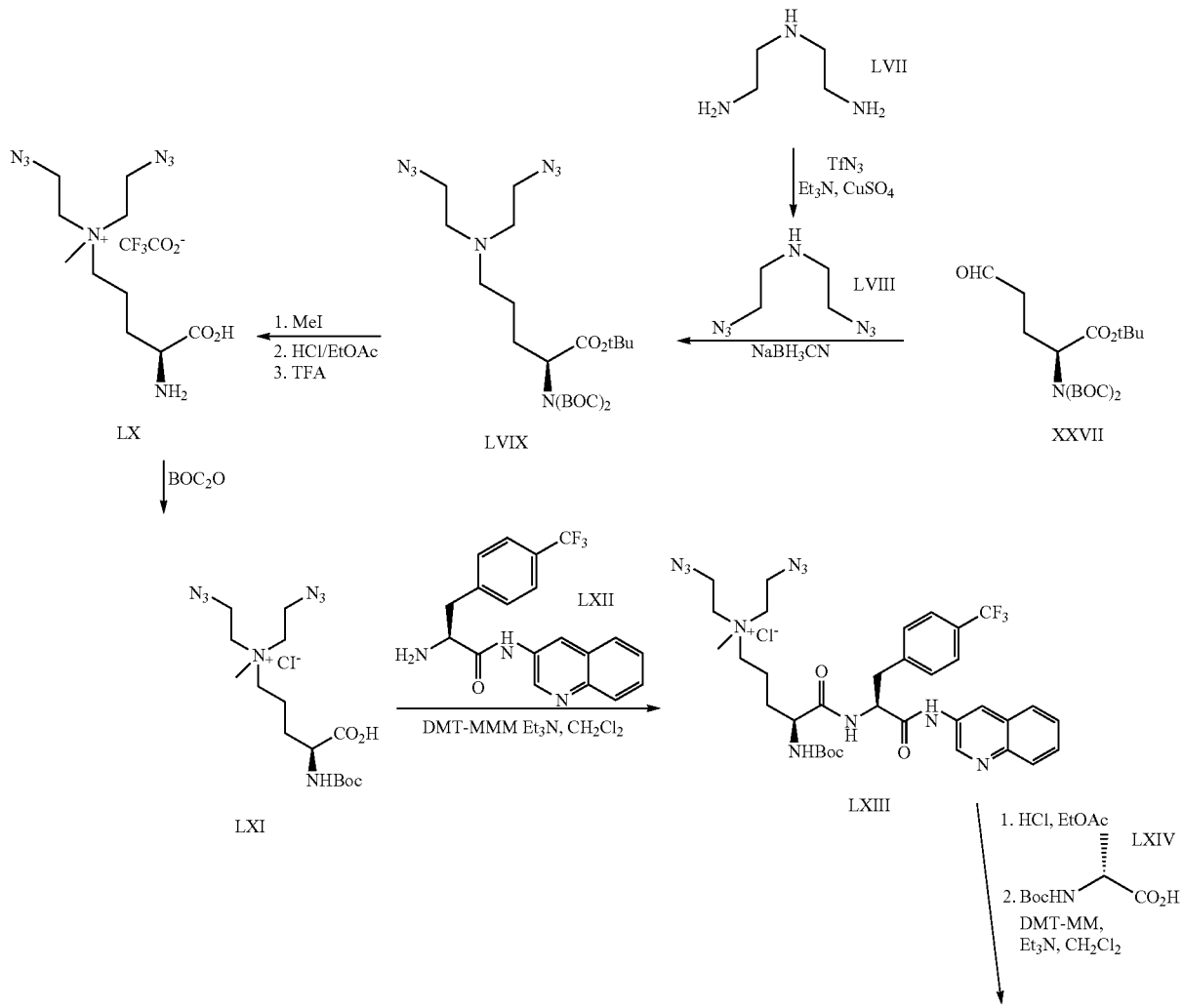

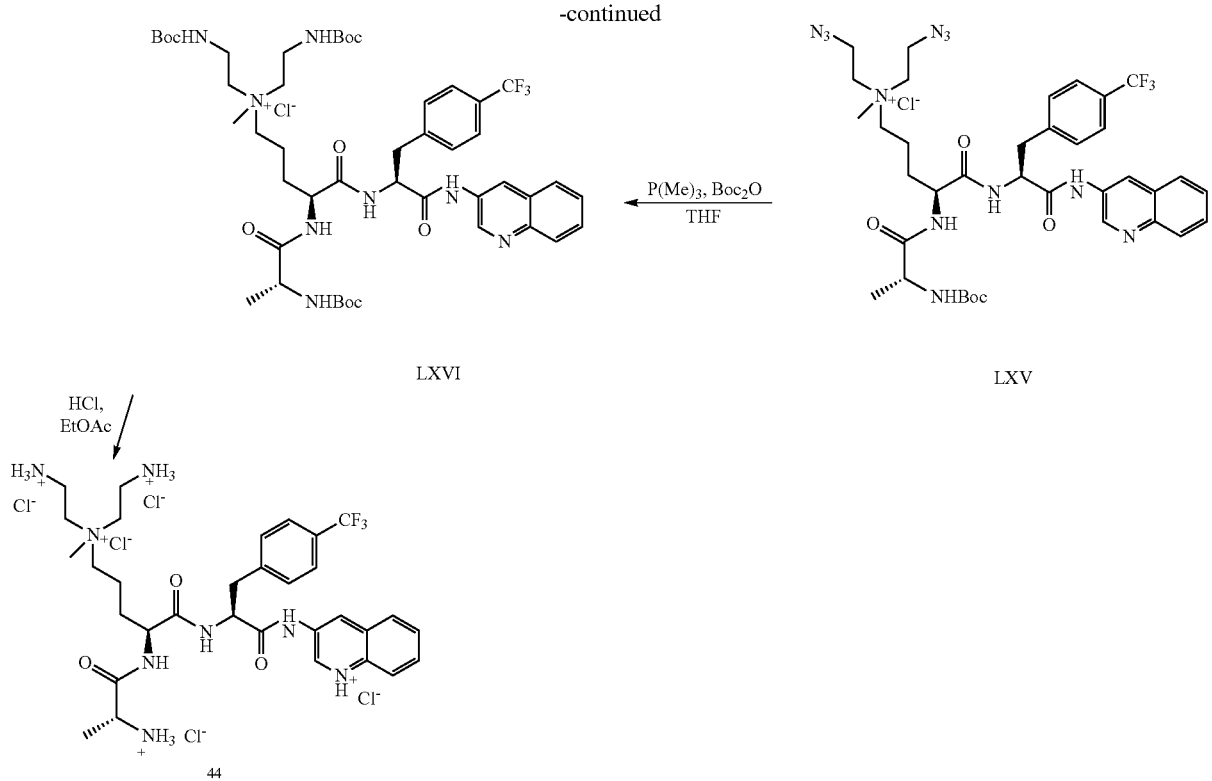

Example 9

Step 1

To a solution of bis(2-aminoethyl)amine LVII (5.0 g, 0.05 mole) in a mixture of water (60 mL) and methanol (160 mL) was added a catalytic amount of $CuSO_4$ (100 mg) and TEA (20.2 g, 0.20 mole). To this mixture was then added dropwise a solution of triflic azide prepared from trifluoromethane-sulfonic anhydride (52.8 g, 0.19 mole) (prepared according to *Tetrahedron Lett.* 1996, 37, 6029). The mixture was stirred at r.t. for 48 h before the solvent was removed under reduced pressure. The residue was then purified on a silica gel column (1:2 hexane:EtOAc→100% EtOAc→1:1 EtOAc:MeOH) to product the bis(2-azidoethyl)amine LVIII (7.60 g, 0.049 mole, 98% yield). $^1$H NMR ($CDCl_3$) 2.84 (t, J=6 Hz, 4H), 3.48 (t, J=6 Hz, 4H); ESIMS found for $C_4H_9N_7$ m/z 156 (M+H).

Step 2-6

Performed according to procedures listed in example 2.

Step 7

To a solution of (2S)-2-amino-N-(quinolin-3-yl)-3-[4-(trifluoromethyl)phenyl]propanamide LXII (1.54 g, 3.6 mmol) in DCM (20 mL) was added TEA (1.0 mL, 7.2 mmol) and stirred until the mixture became homogeneous. This solution was then added to the mixture of compound LXI (2.25 g, 5.5 mmol) and DMT-MM (1.60 mg, 6.0 mmol) in DCM (30 mL). The reaction was stirred at r.t. for 40 h. The solution was washed with water, dried over $Na_2SO_4$ and concentrated under reduced pressure. The residue was then purified on a silica gel column with (100% EtOAc→1:1 EtOAc:MeOH→5:1 MeOH:$NH_3$) to afford compound LXIII (1.16 g, 0.16 mmol, 30% yield). $^1$H NMR (DMSO-$d_6$) 1.34 (s, 9H), 1.39-1.41 (m, 2H), 1.62-1.70 (m, 4H), 3.03 (s, 3H), 3.34-3.39 (m, 2H), 3.51-3.53 (m, 4H), 3.88-3.91 (m, 4H), 4.00-4.04 (m, 1H), 4.70-4.75 (m, 1H), 6.68 (brs, 1H), 7.04 (d, J=8 Hz, 1H), 7.30 (brs, 1H), 7.55-7.66 (m, 6H), 7.88 (d, J=8 Hz, 1H), 7.95 (d, J=8 Hz, 1H), 8.69 (s, 1H), 9.06 (s, 1H); ESIMS found for $C_{34}H_{43}N_{11}O_4F_3$ m/z 726 (M+).

Step 8

Compound LXIII (500 mg, 0.67 mmol) was treated with HCl/AcOEt (5 M solution, 10 mL) at r.t. overnight. The solvent was evaporated, the residue was treated with diethyl ether and the solid was filtered to produce crude product as a hydrochloride salt. The salt was suspended in DCM (10 mL) and treated with TEA (0.2 mL, 1.5 mmol) with stirring until the mixture became homogeneous. This solution was added to the mixture of (2R)-2-{[(tert-butoxy)carbonyl]amino}propanoic acid LXIV (140 mg, 0.7 mmol) and DMT-MM (260 mg, 0.8 mmol) in DCM (10 mL). It was stirred at r.t. for 48 h before the solution was washed with water, dried over $Na_2SO_4$ and concentrated under reduced pressure. The residue was then purified on a silica gel column with (100% EtOAc→1:1 EtOAc:MeOH→5:1 MeOH:$NH_3$) to afford compound LXV (390 mg, 0.45 mmol, 67% yield). $^1$H NMR (DMSO-$d_6$) 1.32 (d, J=7 Hz, 3H), 1.35 (s, 9H), 1.40-1.43 (m, 2H), 1.65-1.70 (m, 4H), 3.08 (s, 3H), 3.36-3.41 (m, 2H), 3.55-3.58 (m, 4H), 3.88-3.95 (m, 4H), 4.03-4.09 (m, 1H), 4.62-4.67 (m, 1H), 4.68-4.76 (m, 1H), 6.69 (brs, 1H), 7.04 (d, J=8 Hz, 1H), 7.31 (brs, 2H), 7.53-7.66 (m, 6H), 7.88 (d, J=8 Hz, 1H), 7.99 (d, J=8 Hz, 1H), 8.69 (s, 1H), 9.09 (s, 1H); ESIMS found for $C_{37}H_{48}N_{12}O_5F_3$ m/z 797 (M+).

Step 9

To a solution of compound LXV (340 mg, 0.43 mmol) in a mixture of THF (50 mL) and water (1 mL) was added PMe$_3$ (1 M solution in THF, 2.0 mL, 1.72 mmol) and Boc$_2$O (380 mg, 1.8 mmol). The mixture was stirred at r.t. overnight before the solvent was removed under reduced pressure. The residue was then purified on a silica gel column (100% EtOAc→5:1 EtOAc:MeOH→5:1 MeOH:NH$_3$) to afford compound LXVI (110 mg, 0.11 mmol, 25% yield). $^1$H NMR (DMSO-d$_6$) 1.33 (d, J=7 Hz, 3H), 1.35 (s, 9H), 1.39 (s, 18H), 1.54-1.62 (m, 2H), 1.66-1.84 (m, 4H), 3.23 (s, 3H), 3.26-3.41 (m, 10H), 3.98-4.01 (m, 1H), 4.32-4.38 (m, 1H), 4.60-4.65 (m, 1H), 6.70 (brs, 1H), 7.27 (brs, 2H), 7.53-7.66 (m, 9H), 7.86 (d, J=8 Hz, 1H), 7.94 (d, J=8 Hz, 1H), 8.72 (s, 1H), 9.12 (s, 1H); ESIMS found for C$_{47}$H$_{68}$N$_8$O$_9$F$_3$ m/z 945 (M+).

Step 10

Compound LXVI (110 mg, 0.11 mmol) was treated with HCl/EtOAc (5 M solution, 8 mL) at r.t. overnight. The solvent was evaporated and the residue was treated with diethyl ether and filtered to yield compound 44 as the hydrochloride salt (70 mg, 0.10 mmol, 93% yield). $^1$H NMR (DMSO-d$_6$) 1.33 (d, J=7 Hz, 3H), 1.22-1.30 (m, 2H), 1.60-1.68 (m, 4H), 3.04 (s, 3H), 3.27-3.31 (m, 2H), 3.35-3.38 (m, 4H), 3.60-3.66 (m, 4H), 3.93-4.01 (m, 1H), 4.38-4.40 (m, 1H), 4.76-4.78 (m, 1H), 7.60-7.67 (m, 6H), 7.97-7.80 (m, 2H), 8.25 (brs, 3H), 8.58 (brs, 3H), 8.68 (s, 1H), 8.84-8.90 (m, 2H), 9.04 (s, 1H), 10.91 (s, 1H); ESIMS found for C$_{32}$H$_{44}$N$_8$O$_3$F$_3$ m/z 645 (M+).

Methods of Treatment

Some embodiments include a method of inhibiting a bacterial efflux pump comprising administering to a subject infected with a bacteria, a compound according to any of the structures described above. Other embodiments include a method of treating or preventing a bacterial infection comprising administering to a subject infected with a bacteria or subject to infection with a bacterial a compound according to any of the structures described above in combination with another anti-bacterial agent.

Microbial Species

The microbial species to be inhibited through the use of efflux pump inhibitors, such as the above-described EPIs, can be from other bacterial groups or species, such as one of the following: *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtherias, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*.

A particularly appropriate example of a microbe appropriate for the use of an efflux pump inhibitor of the preferred embodiments is a pathogenic bacterial species, *Pseudomonas aeruginosa*, which is intrinsically resistant to many of the commonly used antibacterial agents. Exposing this bacterium to an efflux pump inhibitor can significantly slow the export of an antibacterial agent from the interior of the cell or the export of siderophores. Therefore, if another antibacterial agent is administered in conjunction with the efflux pump inhibitor of preferred embodiments, the antibacterial agent, which would otherwise be maintained at a very low intracellular concentration by the export process, can accumulate to a concentration, which will inhibit the growth of the bacterial cells. This growth inhibition can be due to either bacteriostatic or bactericidal activity, depending on the specific antibacterial agent used. While *P. aeruginosa* is an example of an appropriate bacterium, other bacterial and microbial species may contain similar broad substrate pumps, which actively export a variety of antimicrobial agents, and thus can also be appropriate targets.

Antimicrobial Agents

In particular embodiments various antibacterial agents can be used in combination with the efflux pump inhibitors described herein. These include quinolones, tetracyclines, glycopeptides, aminoglycosides, β-lactams, rifamycins, macrolides/ketolides, oxazolidinones, coumermycins, and chloramphenicol. In particular embodiments, an antibiotic of the above classes can be, for example, one of the following.

Beta-Lactam Antibiotics

Beta-lactam antibiotics include, but are not limited to, imipenem, meropenem, biapenem, cefaclor, cefadroxil, cefamandole, cefatrizine, cefazedone, cefazolin, cefixime, cefmenoxime, cefodizime, cefonicid, cefoperazone, cefcranide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefmetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, and LY206763.

Macrolides

Macrolides include, but are not limited to, azithromycin, clarithromycin, erythromycin, oleandomycin, rokitamycin, rosaramicin, roxithromycin, and troleandomycin.

Ketolides

Ketolides include, but are not limited to, telithromycin and cethrimycin.

Quinolones

Quinolones include, but are not limited to, amifloxacin, cinoxacin, ciprofloxacin, enoxacin, fleroxacin, flumequine, lomefloxacin, nalidixic acid, norfloxacin, ofloxacin, levofloxacin, oxolinic acid, pefloxacin, rosoxacin, temafloxacin, tosufloxacin, sparfloxacin, clinafloxacin, moxifloxacin; gemifloxacin; garenofloxacin; PD 131628, PD138312, PD140248, Q-35, AM-1155, NM394, T-3761, rufloxacin, OPC-17116, DU-6859a (see, e.g., Sato, K. et al., 1992, Antimicrob Agents Chemother. 37:1491-98), and DV-7751a (see, e.g., Tanaka, M. et al., 1992, Antimicrob. Agents Chemother. 37:2212-18).

Tetracyclines, Glycylcyclines and Oxazolidinones

Tetracyclines, glycylcyclines, and oxazolidinones include, but are not limited to, chlortetracycline, demeclocycline, doxycycline, lymecycline, methacycline, minocycline, oxytetracycline, tetracycline, tigecycline, linezolide, and eperozolid.

Aminoglycosides

Aminoglycosides include, but are not limited to amikacin, arbekacin, butirosin, dibekacin, fortimicins, gentamicin, kanamycin, meomycin, netilmicin, ribostamycin, sisomicin, spectinomycin, streptomycin, and tobramycin.

Lincosamides

Lincosamides include, but are not limited to, clindamycin and lincomycin.

Efflux pumps export substrate molecules from the cytoplasm in an energy-dependent manner, and the exported substrate molecules can include antibacterial agents. Such efflux pump inhibitors are useful, for example, for treating microbial infections by reducing the export of a co-administered antimicrobial agent or by preventing the export of a compound synthesized by microbes (e.g., bacteria) to allow or improve their growth. While the endogenous substrates of efflux pumps are not yet identified, there are some indications that efflux pumps may be important for bacterial virulence. Thus, also disclosed herein are compositions that include such efflux pump inhibitors and methods for treating microbial infections using those compositions.

In some embodiments, a method is provided for treating a microbial infection in an animal, specifically including in a mammal, by treating an animal suffering from such an infection with an antimicrobial agent and an efflux pump inhibitor, which increase the susceptibility of the microbe for that antimicrobial agent. Such efflux pump inhibitors can be selected from any of the compounds generically or specifically described herein. In this way a microbe involved in the infection can be treated using the antimicrobial agent in smaller quantities, or can be treated with an antimicrobial agent, which is not therapeutically effective when used in the absence of the efflux pump inhibitor. Thus, this method of treatment is especially appropriate for the treatment of infections involving microbial strains that are difficult to treat using an antimicrobial agent alone due to a need for high dosage levels (which can cause undesirable side effects), or due to lack of any clinically effective antimicrobial agents. However, it is also appropriate for treating infections involving microbes that are susceptible to particular antimicrobial agents as a way to reduce the dosage of those particular agents. This can reduce the risk of side effects. It is also appropriate for treating infections involving microbes that are susceptible to particular antimicrobial agents as a way of reducing the frequency of selection of resistant microbes. In particular embodiments the microbe is a bacterium, which may, for example, be from any of the groups or species indicated above.

In some embodiments, a method is provided for prophylactic treatment of a mammal. In this method, an antimicrobial agent and an efflux pump inhibitor is administered to a mammal at risk of a microbial infection, e.g., a bacterial infection. The efflux pump inhibitor can be selected from any of the compounds generically or specifically described herein.

In some embodiments, a method is provided for enhancing the antimicrobial activity of an antimicrobial agent against a microbe, in which such a microbe is contacted with an efflux pump inhibitor, and an antibacterial agent. The efflux pump inhibitor can be selected from any of the compounds generically or specifically described herein. Thus, this method makes an antimicrobial agent more effective against a cell, which expresses an efflux pump when the cell is treated with the combination of an antimicrobial agent and an efflux pump inhibitor. In particular embodiments the microbe is a bacterium or a fungus, such as any of those indicated above; the antibacterial agent can be selected from a number of structural classes of antibiotics including, e.g., beta-lactams, glycopeptides, aminoglycosides, quinolones, oxazolidinones, tetracyclines, rifamycins, coumermycins, macrolides, and chloramphenicol. In particular embodiments an antibiotic of the above classes can be as stated above.

In other embodiments, a method is provided for suppressing growth of a microbe, e.g., a bacterium, expressing an efflux pump, e.g., a non-tetracycline-specific efflux pump. As illustrated by the case where the microbe is a bacterium, the method involves contacting that bacterium with an efflux pump inhibitor, in the presence of a concentration of antibacterial agent below the MIC of the bacterium. The efflux pump inhibitor can be selected from any of the compounds generically or specifically described herein. This method is useful, for example, to prevent or cure contamination of a cell culture by a bacterium possessing an efflux pump. However, it applies to any situation where such growth suppression is desirable.

In some embodiments, any of the compounds generically or specifically described herein may be administered as an efflux pump inhibitor either alone or, more preferably, in conjunction with another therapeutic agent. In some embodiments, any of the compounds generically or specifically described herein may be administered as an efflux pump inhibitor in conjunction with any of the antibacterial agents specifically or generically described herein, as well as with any other antibacterial agent useful against the species of bacterium to be treated, when such bacteria do not utilize an efflux pump resistance mechanism. In some embodiments, the antibacterial agents are administered at their usual recommended dosages. In other embodiments, the antibacterial agents are administered at reduced dosages, as determined by a physician. For all conventional antibacterials on the market, and many in clinical development, dosage ranges and preferred routes of administration are well established, and those dosages and routes can be used in conjunction with the efflux pump inhibitors of the preferred embodiments. Reduced dosages of the antibacterials are contemplated due to the increased efficacy of the antibacterial when combined with an efflux pump inhibitor.

Potential efflux pump inhibitor compounds can be tested for their ability to inhibit multi-drug resistance efflux pumps of various microbes using the methods described herein as well as those known in the art. For example, treatment of P.

*aeruginosa* with a test compound allows obtaining one or more of the following biological effects:

1) *P. aeruginosa* strains will become susceptible to antibiotics that could not be used for treatment of pseudomonad infections, or become more susceptible to antibiotics, which do inhibit pseudomonal growth.

2) *P. aeruginosa* strains will become more susceptible to antibiotics currently used for treatment of pseudomonad infections.

3) Inhibition of the pump will result in a decreased frequency of resistance development to antibiotic, which is a substrate of the pump.

Obtaining even one of these effects provides a potential therapeutic treatment for infections by this bacterium. Also, similar pumps are found in other microorganisms. Some or all of the above effects can also be obtained with those microbes, and they are therefore also appropriate targets for detecting or using efflux pump inhibitors.

Administration

The efflux pump inhibitors are administered at a therapeutically effective dosage, e.g., a dosage sufficient to provide treatment for the disease states previously described. While human dosage levels have yet to be optimized for the compounds of the preferred embodiments, generally, a daily dose for most of the inhibitors described herein is from about 0.05 mg/kg or less to about 100 mg/kg or more of body weight, preferably from about 0.10 mg/kg to 10.0 mg/kg of body weight, and most preferably from about 0.15 mg/kg to 1.0 mg/kg of body weight. Thus, for administration to a 70 kg person, the dosage range would be about 3.5 mg per day or less to about 7000 mg per day or more, preferably from about 7.0 mg per day to 700.0 mg per day, and most preferably from about 10.0 mg per day to 100.0 mg per day. The amount of active compound administered will, of course, be dependent on the subject and disease state being treated, the severity of the affliction, the manner and schedule of administration and the judgment of the prescribing physician; for example, a likely dose range for oral administration can be from about 70 mg per day to 700 mg per day, whereas for intravenous administration a likely dose range can be from about 700 mg per day to 7000 mg per day, the active agents being selected for longer or shorter plasma half-lives, respectively. Screening techniques described herein for the compounds of preferred embodiments can be used with other efflux pump inhibitors described herein to establish the efficacy of those inhibitors in comparison to reference compounds, and the dosage of the inhibitor can thus be adjusted to achieve an equipotent dose to the dosages of reference compound.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administration are customary in treating the indications that are the subject of the preferred embodiments.

Pharmaceutically acceptable compositions include solid, semi-solid, liquid and aerosol dosage forms, such as, e.g., tablets, capsules, powders, liquids, suspensions, suppositories, aerosols or the like. The compounds can also be administered in sustained or controlled release dosage forms, including depot injections, osmotic pumps, pills, transdermal (including electrotransport) patches, and the like, for prolonged and/or timed, pulsed administration at a predetermined rate. Preferably, the compositions are provided in unit dosage forms suitable for single administration of a precise dose.

The compounds can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical formulation will contain about 0.005% to 95%, preferably about 0.5% to 50% by weight of a compound of the preferred embodiments. Actual methods of preparing such dosage forms are known, or will be apparent, to those skilled in this art; for example, see Remington's Pharmaceutical Sciences, Mack Publishing Company, Easton, Pa.

In addition, the compounds can be co-administered with, and the pharmaceutical compositions can include, other medicinal agents, pharmaceutical agents, adjuvants, and the like. Suitable additional active agents include, for example, antimicrobial agents as described above. When used, other active agents may be administered before, concurrently, or after administration of an efflux pump inhibitor of the preferred embodiments. In some embodiments, an efflux pump inhibitor is co-administered with one or more other antimicrobial agents. By "co-administer" it is meant that the efflux pump inhibitors are administered to a patient such that the present compounds as well as the co-administered compound may be found in the patient's bloodstream at the same time, regardless of when the compounds are actually administered, including simultaneously. In one advantageous embodiment, the pharmacokinetics of the efflux pump inhibitors and the co-administered antimicrobial agent are substantially the same.

Thus, in the preferred embodiments, an efflux pump inhibitor compound as set forth herein can be administered through a first route of administration, and the antimicrobial agent can be administered through a second route. Thus, for example, an efflux pump inhibitor can be administered via a pulmonary route, e.g., through a nebulizer, atomizer, mister, aerosol, dry powder inhaler, or other suitable device or technique, and the antimicrobial can be administered via the same or a different route, e.g., orally, parenterally, intramuscularly, intraperitoneally, intratracheally, intravenously, subcutaneously, transdermally, or as a rectal or vaginal suppository. The blood levels of drugs are affected by the route of administration. Thus, in one preferred embodiment, when the efflux pump inhibitor is administered by a first route, and the antibiotic or antimicrobial through a second route, the dosages or dosage forms are adjusted, as appropriate, to match the pharmcokinetic profiles of each drug. This may also be done when both drugs are administered by the same route. In either event, conventional techniques, including controlled release formulations, timing of administration, use of pumps and depots, and/or use of biodegradable or bioerodible carriers can be used to match the pharmacokinetics of the two active moieties.

In one preferred embodiment, the compositions will take the form of a unit dosage form such as a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule. Unit dosage forms in which the two active ingredients (inhibitor and antimicrobial) are physically separated are also contemplated; e.g., capsules with granules of each drug; two-layer tablets; two-compartment gel caps, etc.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid, which will be subsequently diluted to the above percentages. In some embodiments, the composition will comprise 0.2-2% of the active agent in solution.

Efflux pump inhibitors (EPIs) as described herein, including any of the compounds generically or specifically described herein, can also be administered to the respiratory tract as an aerosol. For the purposes of delivery to the respiratory tract, any of the inhaler designs known in the art may be used. In some embodiments, a metered dose inhaler (MDI) is used. A typical MDI for use with the EPIs described herein comprises the EPI compound suspended or dissolved in a pressurized liquid propellant, with or without other excipients. When the MDI inhaler is activated, a metered amount of the propellant is released and rapidly evaporates due to the sudden reduction in pressure. The process causes an aerosol cloud of drug particles to be released that can be inhaled by the patient.

Solid compositions can be provided in various different types of dosage forms, depending on the physicochemical properties of the drug, the desired dissolution rate, cost considerations, and other criteria. In one of the embodiments, the solid composition is a single unit. This implies that one unit dose of the drug is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In a preferred embodiment, the solid composition is a highly porous lyophilized form. Such lyophilizates, sometimes also called wafers or lyophilized tablets, are particularly useful for their rapid disintegration, which also enables the rapid dissolution of the active compound.

On the other hand, for some applications the solid composition may also be formed as a multiple unit dosage form as defined above. Examples of multiple units are powders, granules, microparticles, pellets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution.

Another type of multiparticulate system which is also capable of achieving rapid drug dissolution is that of powders, granules, or pellets from water-soluble excipients which are coated with the drug, so that the drug is located at the outer surface of the individual particles. In this type of system, the water-soluble low molecular weight excipient is useful for preparing the cores of such coated particles, which can be subsequently coated with a coating composition comprising the drug and, preferably, one or more additional excipients, such as a binder, a pore former, a saccharide, a sugar alcohol, a film-forming polymer, a plasticizer, or other excipients used in pharmaceutical coating compositions.

For purposes of co-administration of an EPI as described herein and another anti-bacterial compound, the EPI can be administered by the same route as the other anti-bacterial compound, either simultaneously or sequentially. In some embodiments, the EPI and other anti-bacterial compound or compounds are both administered intravenously (i.v.), either mixed in a fixed drug formulation or present in separate formulations. In other embodiments, the EPI and other anti-bacterial compound or compounds are both administered orally, either in the same fixed formulation or in separate formulations. In still other embodiments, the EPI and other anti-bacterial compound or compounds are both administered intramuscularly (i.m.), again either mixed in a fixed drug formulation or present in separate formulations.

In some embodiments, the EPI and other anti-bacterial compound to be co-administered are administered by separate routes. For example, the EPI may be administered by inhalation while the other anti-bacterial compound is administered i.v., i.m., or orally. Any other possible combination of separate route administration is also contemplated.

The preferred embodiments also include any of the novel compounds disclosed herein per se, as well as any of the efflux pump inhibitors disclosed herein in unit dosage forms combined with or for coadministration with an antimicrobial, as well as methods of treating an animate or inanimate subject or object with those efflux pump inhibitors, preferably in combination with an antimicrobial. Metered dose inhalers or other delivery devices containing both an efflux pump inhibitor as described herein as well as an antimicrobial are also preferred embodiments

EXAMPLES

EPI activity was recorded as concentration of an EPI compound that is necessary to increase susceptibility to levofloxacin of the strain of *P. aeruginosa*, PAM1723, overexpressing the MexAB-OprM efflux pump eight-fold. The levofloxacin potentiating activity of the test compounds was assessed by the checkerboard assay (Antimicrobial Combinations, Antibiotics in Laboratory Medicine, Ed. Victor Lorian, M.D., Fourth edition, 1996, pp 333-338, which is incorporated herein by reference in its entirety) using a broth microdilution method performed as recommended by the NCCLS (National Committee for Clinical Laboratory Standards (NCCLS), 1997, Methods for Dilution of Antimicrobial Susceptibility Tests for Bacteria That Grow Aerobically, Fourth Edition; Approved Standard. NCCLS Document M7-A4, Vol 17 No. 2, which is incorporated herein by reference in its entirety). In this assay, multiple dilutions of two drugs, namely an EPI and levofloxacin, were tested, alone and in combination, at concentrations equal to, above and below their respective minimal inhibitory concentrations (MICs). All EPI compounds were readily soluble in water and stock solutions were prepared at a final concentration of 10 mg/ml. Stock solutions were further diluted, according to the needs of the particular assay, in Mueller Hinton Broth (MHB). Stock solution was stored at −80° C.

The checkerboard assay was performed in microtiter plates. Levofloxacin was diluted in the x-axis, each column containing a single concentration of levofloxacin. EPIs were diluted in the y-axis, each row containing a single concentration of an EPI. The result of these manipulations was that each well of the microtiter plate contained a unique combination of concentrations of the two agents. The assay was performed in MHB with a final bacterial inoculum of 5.times.105 CFU/ml (from an early-log phase culture). Microtiter plates were incubated during 20 h at 35° C. and were read using a microtiterplate reader (Molecular Devices) at 650 nm as well as visual observation using a microtiter plate-reading mirror. The MIC (here referred to as MPC; see infra) was defined as the lowest concentration of antibiotics, within the combination, at which the visible growth of the organism was completely inhibited.

Example 1

Potentiation of In Vitro Antibacterial Activity of Levofloxacin Against *P. aeuruiginosa* Strain PAM1723 Overexpressing MexAB-OprM by Efflux Pump Quaternary Ammonium Polyamine Efflux Pump Inhibitors

TABLE 1

| Compound | MPC$_8$ (μg/mL) | MPC$_{32}$ (μg/mL) |
|---|---|---|
| 1 | 2.5 | 10 |
| 2 | 5 | 10 |
| 4 | 2.5 | 5 |
| 5 | 5 | >10 |
| 6 | 1.25 | 1.25 |
| 10 | 0.156 | 0.156 |
| 11 | 0.156 | 0.312 |
| 15 | 0.312 | 0.625 |
| 21 | 0.156 | 0.156 |
| 25 | 0.312 | 0.625 |
| 26 | 0.312 | 0.625 |
| 27 | 0.156 | 0.312 |
| 29 | 0.312 | 0.625 |
| 33 | 0.156 | 0.156 |
| 34 | 0.312 | 0.312 |
| 38 | 1.25 | 1.25 |
| 44 | 0.625 | 1.25 |
| 46 | 0.312 | 0.625 |
| 47 | 0.156 | 0.312 |
| 53 | 2.5 | 5 |
| 54 | 0.312 | >10 |
| 57 | 0.625 | 1.25 |
| 59 | >10 | >10 |
| 61 | 10 | >10 |
| 63 | 2.5 | >10 |
| 67 | >10 | >10 |
| 75 | >10 | >10 |
| 92 | 0.312 | 0.625 |
| 134 | 2.5 | >10 |

In the experiment depicted in Table 1, potentiating activities of selected inhibitors are reported as Minimum Potentiating Concentration MPC$_8$ values (or MPC$_{32}$) which correspond to the lowest concentration of the inhibitor required to achieve antibacterial activity in combination with the concentration of levofloxacin equal to ⅛ (or 1/32) of the levofloxacin concentration required to achieve the same antibacterial effect alone (MIC of levofloxacin).

Example 2

Pharmacokinetics of Quaternary Ammonium Polyamine Efflux Pump Inhibitors in Rats after IV Infusion

TABLE 2

| Compound | Dose (mg/kg) | Clearance$^a$ (L/h/kg) | C$_{max}$ (μg/mL) |
|---|---|---|---|
| 4 | 10 | 1.29 | 13.4 |
| 5 | 20 | 1.23 | 19.6 |
| 10 | 10 | 0.31 | 30.6 |
| 11 | 10 | 2.87 | 7.3 |
| 25 | 10 | 1.00 | 13.0 |
| 27 | 20 | 0.35 | 54.6 |
| 29 | 10 | 0.85 | 25.6 |
| 33 | 20 | 1.00 | 63.0 |
| 44 | 20 | 0.65 | 40.2 |
| 92 | 20 | 1.59 | 18.3 |

$^a$free drug clearance

In the experiment depicted in Table 2, rat serum pharmacokinetics of compounds selected inhibitor compounds was evaluated after 1.5-hour IV infusion of 1.5 ml solution of corresponding efflux pump inhibitor in 0.9% saline. Depending on the concentration used the total infused dose was 10 or 20 mg/kg. A two-compartment model was used to fit the data and calculate PK parameters. Compounds 10, 27 and 44 had the best serum PK profiles. Compound 10 in addition to the displaying lowest free drug clearance showed one of the best efflux pump inhibitory activities.

Although the invention has been described with reference to embodiments and examples, it should be understood that numerous and various modifications can be made without departing from the spirit of the invention. Accordingly, the invention is limited only by the following claims.

What is claimed is:

1. A compound having the structure of formula I:

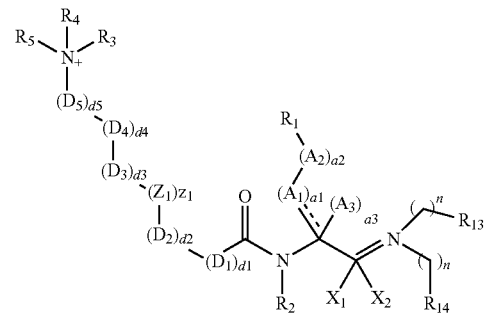

or a pharmaceutically acceptable salt or pro-drug thereof wherein;

each bond represented by a dashed and solid line represents a bond selected from the group consisting of a single bond and a double bond;

each R$_1$ is independently selected from C$_3$-C$_6$ carbocyclyl, aryl and heteroaryl, each optionally substituted with up to 3 substituents independently selected from the group consisting of halo, $C_1$-$C_6$ alkyl, carbocyclyl, —$(CH_2)_n$aryl, —$OR_2$, —$OR_{14}$, —$S(R_2)_2$, —$SO_2NHR_{14}$, —$(CH_2)_n$SH, —$CF_3$, —$OCF_3$, —$N(R_2)_2$, —$NO_2$, —CN, —$CO_2$alkyl, and —$CO_2$aryl;

each $R_2$ is independently selected from H and $C_1$-$C_6$ alkyl;

$R_3$ is —$(CH_2)_n CHR_6 R_7$;

each $R_4$ is independently selected from —$(CH_2)_m R_9$, allyl, —$(CH_2)_n CO_2H$—, —$(CH_2)_n CONH_2$ and —$(CH_2)_n CHR_6 R_7$;

each $R_5$ is independently selected from —$(CH_2)_m R_9$, —$NHR_2$, and —$(CH_2)_n CHR_6 R_7$;

each $R_6$ is independently selected from H and —$(CH_2)_m NH_2$;

each $R_7$ is independently selected from —$(CH_2)_m NHR_8$, —$(CH_2)_m NHC(=NH)NH_2$, and —$(CH_2)_m NHC(R_2)=NH$;

each $R_8$ is independently selected from H, $C_1$-$C_6$ alkyl, Alanine, Arginine, Aspartic acid, and Cysteine;

each $R_9$ is independently selected from H, $C_1$-$C_6$ alkyl, SH and OH;

$R_{13}$ is H, with the proviso that $R_{13}$ is directly attached to the nitrogen;

$R_{14}$ is quinolin, optionally substituted with up to 3 substituents independently selected from the group consisting of a halide, alkyl, carbocyclyl, —$(CH_2)_n R_1$, —$OR_2$, —$OR_1$, =O, —$S(R_2)_2$, —$SO_2NHR_1$, —$(CH_2)_n SH$, —$CF_3$, —$OCF_3$, —$N(R_2)_2$, —$NO_2$, —CN, —(C=X)$R_1$, —(C=X)$R_2$, —$CO_2$alkyl, and —$CO_2$aryl, with the proviso that $R_{14}$ is directly attached to the nitrogen;

$A_1$ is —$(CH_2)_m$— or —$[C(R_2R_9)]_m$—;

$A_2$ is —$O(CH_2)_n$—;

$A_3$ is H or $A_3$ is —$CH_2$— bonded to $R_1$ to form a ring;

a1, a2, and a3 are independently equal to 0 or 1;

$D_1$ is selected from —CH($NHR_8$)— and —CH($R_2$)—;

$D_2$, $D_3$, and $D_4$ are independently selected from the group consisting of —$(CH_2)_m$—, —CH($R_2$)—, —CH($NHR_8$)—, —N($R_6$)—, —S—, —C(=O)—, and —$SO_2$—, $D_5$ is —$(CH_2)_m$—, d1, d2, d3, d4 and d5 are independently equal to 0 or 1;

$Z_1$ is an aryl or carbocyclyl;

z1 is 0 or 1;

if z1 is 0 then at least two of d1, d2, d3, d4 and d5 are equal to 1;

if z1 is 1 then at least one of d1, d2, d3, d4 and d5 is equal to 1;

$X_1$ and $X_2$ are each hydrogen or taken together are =O, or $X_1$ is absent and $X_2$ is —O— bonded to $R_{14}$ to form a 5- or 6-membered heteroaryl, wherein when $X_1$ is absent, the bond to nitrogen represented by a dashed and solid line is a double bond;

each X is independently O or S;

each n is independently an integer from 0 to 4; and each m is independently an integer from 1 to 3.

2. The compound of claim 1 wherein $R_1$ is $C_{3-6}$ carbocyclyl.

3. The compound of claim 1 wherein $R_1$ is selected from cyclopentyl and cyclohexyl.

4. The compound of claim 1 wherein $R_1$ is selected from aryl and heteroaryl.

5. The compound of claim 1 wherein $R_1$ is aryl optionally substituted with up to 3 substituents independently selected from the group consisting of halo, $C_{1-6}$ alkyl, $OR_2$, $CF_3$, $OCF_3$, and CN.

6. The compound of claim 1 wherein $R_2$ is selected from H and $C_1$-$C_2$ alkyl.

7. The compound of claim 1 wherein $R_2$ is selected from H and Me.

8. The compound of claim 1 wherein $R_2$ is H.

9. The compound of claim 1 wherein $R_3$ is —$(CH_2)_n CHR_6 R_7$ wherein $R_6$ is H, $R_7$ is —$(CH_2)_m NHR_8$, $R_8$ is H, n is 0 to 2, and m is 1 or 2.

10. The compound of claim 1 wherein $R_3$ is —$(CH_2)_n CHR_6 R_7$ wherein $R_6$ is H, $R_7$ is —$(CH_2)_m NHC(=NH)NH_2$, n is 0 to 2, and m is 1 to 2.

11. The compound of claim 1 wherein $R_3$ is —$(CH_2)_n CHR_6 R_7$ wherein $R_6$ is H, $R_7$ is $(CH_2)_m NHC(R_2)=NH$, $R_2$ is H, Me, or Et, n is 0 to 2, and m is 1 or 2.

12. The compound of claim 1 wherein $R_3$ is —$(CH_2)_n CHR_6 R_7$ wherein $R_6$ is —$(CH_2)_m NH_2$, $R_7$ is —$(CH_2)_m NHR_8$, $R_8$ is H, n is 0 to 2, and m is 1 or 2.

13. The compound of claim 1 wherein $R_4$ is selected from allyl and —$(CH_2)_m R_9$ wherein $R_9$ is selected from H or Me and m is 1 or 2.

14. The compound of claim 1 wherein $R_4$ is —$(CH_2)_m R_9$ wherein $R_9$ is selected from SH or OH and m is 1 or 2.

15. The compound of claim 1 wherein $R_4$ is selected from —$(CH_2)_n CO_2H$— and —$(CH_2)$—$CONH_2$ wherein n is 1 or 2.

16. The compound of claim 1 wherein $R_4$ is —$(CH_2)_n CHR_6 R_7$ wherein $R_6$ is H, $R_7$ is —$(CH_2)_m NHR_8$, $R_8$ is H, n is 0 to 2, and m is 1 or 2.

17. The compound of claim 1 wherein $R_4$ is —$(CH_2)_n CHR_6 R_7$ wherein $R_6$ is H, $R_7$ is —$(CH_2)_m NHC(=NH)NH_2$, n is 0 to 2, and m is 1 or 2.

18. The compound of claim 1 wherein $R_4$ is —$(CH_2)_n CHR_6 R_7$ wherein $R_6$ is H, $R_7$ is $(CH_2)_m NHC(R_2)=NH$, $R_2$ is selected from H, Me or Et, n is 0 to 2, and m is 1 or 2.

19. The compound of claim 1 wherein $R_4$ is —$(CH_2)_n CHR_6 R_7$ wherein $R_6$ is —$(CH_2)_m NH_2$, $R_7$ is —$(CH_2)_m NHR_8$, $R_8$ is H, n is 0 to 2, and m is 1 or 2.

20. The compound of claim 1 wherein $R_5$ is selected from allyl and —$(CH_2)_m R_9$ wherein $R_9$ is selected from H and Me and m is 1 or 2.

21. The compound of claim 1 wherein $R_5$ is —$(CH_2)_m R_9$ wherein $R_9$ is selected from SH and OH and m=1 or 2.

22. The compound of claim 1 wherein $R_5$ is —$NHR_2$ wherein $R_2$ is H.

23. The compound of claim 1 wherein $R_5$ is —$NHR_2$ wherein $R_2$ is selected from Me and Et.

24. The compound of claim 1 wherein $R_5$ is —$(CH_2)_n CHR_6 R_7$ wherein $R_6$ is H, $R_7$ is —$(CH_2)_m NHR_8$, $R_8$ is H, n is 0 to 2, and m is 1 or 2.

25. The compound of claim 1 wherein $R_5$ is —$(CH_2)_n CHR_6 R_7$ wherein $R_6$ is H, $R_7$ is —$(CH_2)_m NHC(=NH)NH_2$, n is 0 to 2, and m is 1 or 2.

26. The compound of claim 1 wherein $R_5$ is —$(CH_2)_n CHR_6 R_7$ wherein $R_6$ is H, $R_7$ is $(CH_2)_m NHC(R_2)=NH$, $R_2$ is selected from H, Me and Et, n is 0 to 2, and m is 1 or 2.

27. The compound of claim 1 wherein $R_5$ is —$(CH_2)_n CHR_6 R_7$ wherein $R_6$ is —$(CH_2)_m NH_2$, $R_7$ is —$(CH_2)_m NHR_8$, $R_8$ is H, n is 0 to 2, and m is 1 or 2.

28. The compound of claim 1 wherein $R_5$ is —$(CH_2)_n CHR_6 R_7$ wherein $R_6$ is —$(CH_2)_m NH_2$, $R_7$ is —$(CH_2)_m NHR_8$, $R_8$ is selected from Alanine, Arginine, and Aspartic acid, n=0-2 and m=1 or 2.

29. The compound of claim 1, wherein $R_{14}$ is quinolin, optionally substituted with up to 3 substituents independently selected from the group consisting of a halo, alkyl, carbocyclyl, —$(CH_2)_n R_1$, —$OR_2$, —$OR_1$, —$S(R_2)_2$, —$SO_2NHR_1$, —$CF_3$, —$OCF_3$, and —CN.

30. The compound of claim 1 wherein $A_1$ is —$(CH_2)_m$ wherein m is 1 or 2; $A_3$ is H; a1 is 1; and a2 is 0.

31. The compound of claim 1 wherein $A_1$ is $—(CH_2)_m—$ wherein m is 1 or 2; $A_2$ is selected from $—O(CH_2)_n—$ wherein n is 0; $A_3$ is H; and a1 and a2 are equal to 1.

32. The compound of claim 1 wherein $A_1$ is selected from $—[C(R_2R_8)]_m—$ wherein m is 1 or 2, $R_2$ is H, and $R_8$ is selected from H, SH or OH with the proviso that at least one $R_8$ be SH or OH; $A_3$ is H; a1 is 1; and a2 is 0.

33. The compound of claim 1 wherein $A_1$ is $—(CH_2)_m—$ wherein m is 1 or 2; a1 is 1; a2 is 0; $A_3$ is $—CH_2—$ bonded to $R_1$ to form a ring; and $R_1$ is aryl optionally substituted with up to 2 substituents independently selected from the group consisting of halo, alkyl, OMe, $CF_3$, $OCF_3$, and CN.

34. The compound of claim 1 wherein $D_1$ is $—CH(NHR_8)—$ wherein $R_8$ is H; $D_2$ is $—(CH_2)_m—$; d1 and d2 are equal to 1; and z1, d3, d4 and d5 are equal to 0.

35. The compound of claim 1 wherein $D_1$ is $—CH(NHR_8)—$ wherein $R_8$ is H; $D_2$ is $—CH(R_2)—$ wherein $R_2$ is selected from Me and Et; $D_3$ is $—(CH_2)_m—$; d1, d2 and d3 are equal to 1; and z1, d4 and d5 are equal to 0.

36. The compound of claim 1 wherein $D_1$ is $—CH(NHR_8)—$ wherein $R_8$ is H; $D_2$ is $—(CH_2)_m—$ wherein m is 1 or 2; $D_3$ is selected from $—S—$, $—S(=O)—$ and $—SO_2—$; $D_4$ is $—(CH_2)_m—$ wherein m is 1 or 2; d1, d2, d3, and d4 are equal to 1; and z1 and d5 are equal to 0.

37. The compound of claim 1 wherein $D_1$ is $—CH(NHR_8)—$ wherein $R_8$ is H; $D_2$ is $—(CH_2)_m—$; $D_3$ is $—C(=O)—$; $D_4$ is $—N(R_6)—$ wherein $R_6$ is H; $D_5$ is $—(CH_2)_m—$; d1, d2, d3, d4 and d5 are equal to 1; and z1 is equal to 0.

38. The compound of claim 1 wherein $D_1$ is $—CH(NHR_8)—$ wherein $R_8$ is H; $D_2$ is $—(CH_2)_m—$; $D_3$ is $—C(=O)—$; $D_4$ is $—N(R_6)—$ wherein $R_6$ is $—(CH_2)_mNH_2$ wherein m is 1 to 3; $D_5$ is $—(CH_2)_m—$; d1, d2, d3, d4 and d5 are equal to 1; and z1 is equal to 0.

39. The compound of claim 1 wherein $D_1$ is $—CH(NHR_8)—$ wherein $R_8$ is H; $D_2$ is $—(CH_2)_m—$; $D_3$ is $—N(R_6)—$ wherein $R_6$ is H; $D_4$ is $—C(=O)—$; $D_5$ is $—(CH_2)_m—$; d1, d2, d3, d4 and d5 are equal to 1; and z1 is equal to 0.

40. The compound of claim 1 wherein $D_1$ is $—CH(R_2)—$ wherein $R_2$ is selected from H, Me and Et; $D_2$ is $—N(R_6)—$ wherein $R_6$ is H; $D_3$ is $—C(=O)—$; $D_4$ is $—CH(NHR_8)—$ wherein $R_8$ is H; $D_5$ is $—(CH_2)_m—$; d1, d2, d3, d4 and d5 are equal to 1; and z1 is equal to 0.

41. The compound of claim 1 wherein $D_1$ is $—CH(NHR_8)—$ wherein $R_8$ is H; $D_2$ is $—(CH_2)_m—$; $D_3$ is $—N(R_6)—$ wherein $R_6$ is H; d1, d2 and d3 are equal to 1; and z1, d4 and d5 are equal to 0.

42. The compound of claim 1 wherein $D_1$ is $—CH(NHR_8)—$ wherein $R_8$ is H; $D_2$ is $—(CH_2)_m—$; $D_3$ is $—C(=O)—$; $D_4$ is $—N(R_6)—$ wherein $R_6$ is H; d1, d2, d3 and d4 are equal to 1; and z1, d5 are equal to 0.

43. The compound of claim 1 wherein $D_1$ is $—CH(NHR_8)—$ wherein $R_8$ is selected from Alanine, Arginine, Aspartic acid, and Cysteine; $D_2$ is $—(CH_2)_m—$; d1 and d2 are equal to 1; and z1, d3, d4 and d5 are equal to 0.

44. The compound of claim 1 wherein $D_1$ is $—CH(NHR_8)—$ wherein $R_8$ is H; $D_2$ is $—(CH_2)_m—$; $Z_1$ is an aryl; z1, d1 and d2 are equal to 1; and d3, d4 and d5 are equal to 0.

45. The compound of claim 1 wherein $D_1$ is $—CH(NHR_8)—$ wherein $R_8$ is H; $Z_1$ is an aryl; z1 and d1 are equal to 1; and d2, d3, d4 and d5 are equal to 0.

46. The compound of claim 1 wherein $D_1$ is $—CH(NHR_8)—$ wherein $R_8$ is H; $Z_1$ is an aryl; $D_3$ is $—(CH_2)_m—$; z1, d1 and d3 are equal to 1; and d2, d4 and d5 are equal to 0.

47. The compound of claim 1 wherein $D_1$ is $—CH(NHR_8)—$ wherein $R_8$ is H; $D_2$ is $—(CH_2)_m—$; $Z_1$ is a carbocyclyl; z1, d1 and d2 are equal to 1; and d3, d4 and d5 are equal to 0.

48. The compound of claim 1 wherein $D_1$ is $—CH(NHR_8)—$ wherein $R_8$ is H; $Z_1$ is a carbocyclyl; z1 and d1 are equal to 1; and d2, d3, d4 and d5 are equal to 0.

49. The compound of claim 1 wherein $D_1$ is $—CH(NHR_8)—$ wherein $R_8$ is H; $Z_1$ is a carbocyclyl; $D_3$ is $—(CH_2)_m—$; z1, d1 and d3 are equal to 1; and d2, d4 and d5 are equal to 0.

50. The compound of claim 1 wherein $X_1$ together with $X_2$ is O.

51. The compound of claim 1 wherein $X_1$ and $X_2$ are each H.

52. The compound of claim 1, wherein $A_3$ is $—CH_2—$ bonded to $R_1$ to form a ring and a2 is 0.

53. The compound of claim 1, wherein the combined length of $D_2$, $D_3$, $D_4$ and $D_5$ is not more than 10 atoms.

54. The compound of claim 1, wherein $Z_1$ is attached to the rest of the compound by way of attachment points on two different atoms of $Z_1$.

55. The compound of claim 1, wherein the compound is selected from the group consisting of:

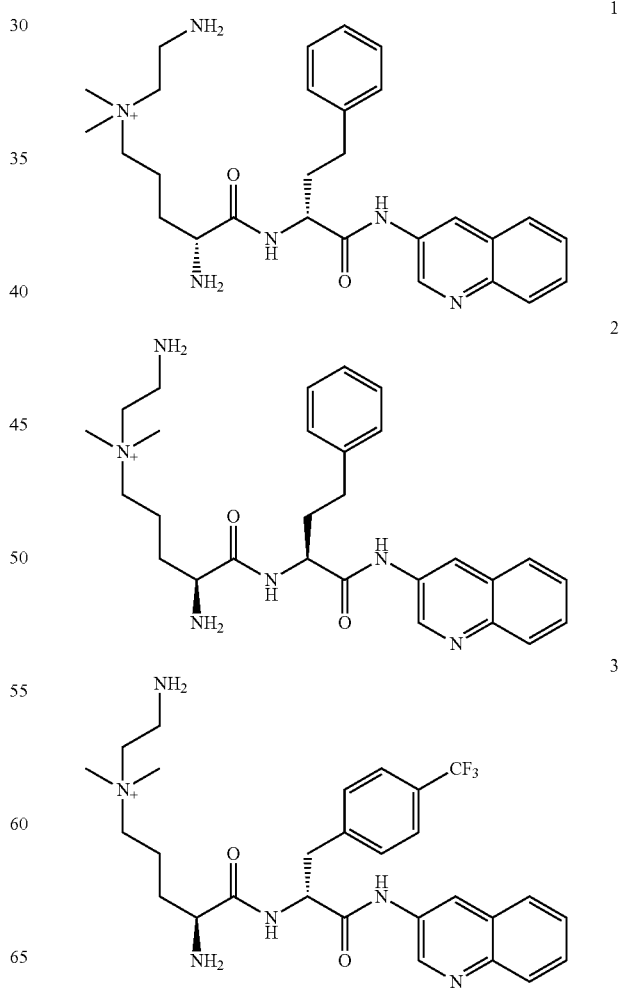

4
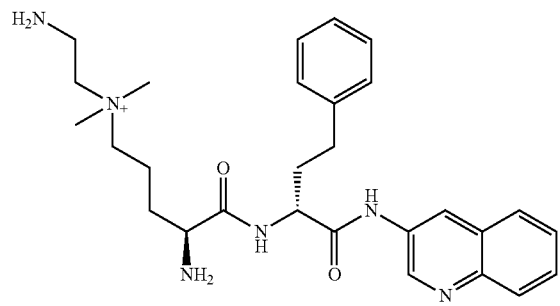
7
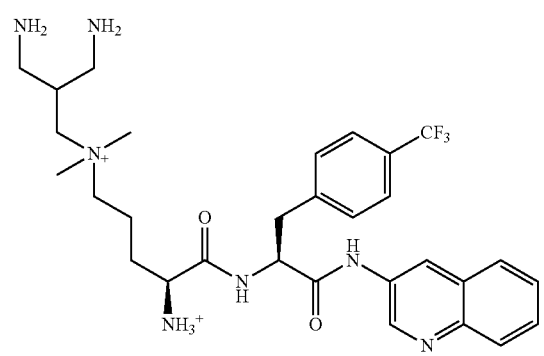
8
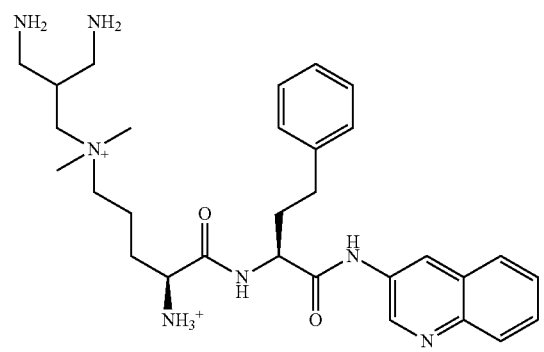
9
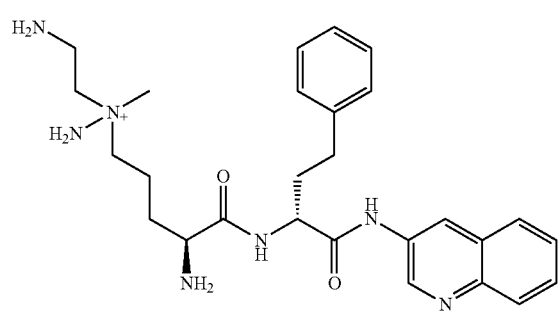
10
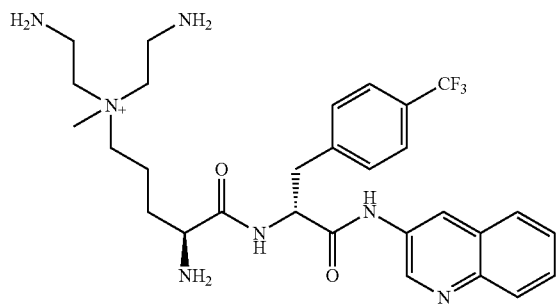
11
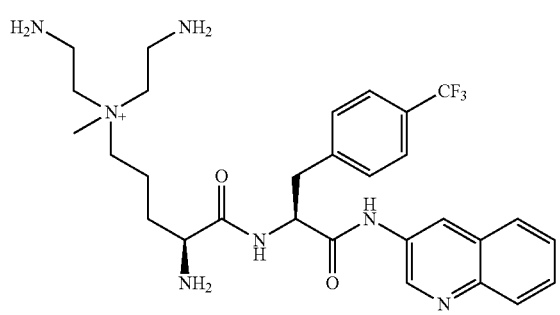
12
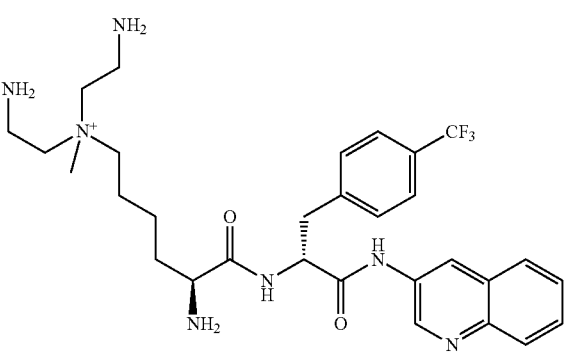
13
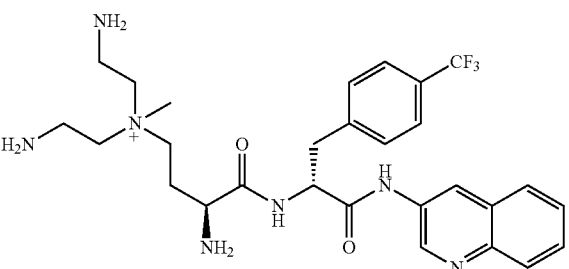
14
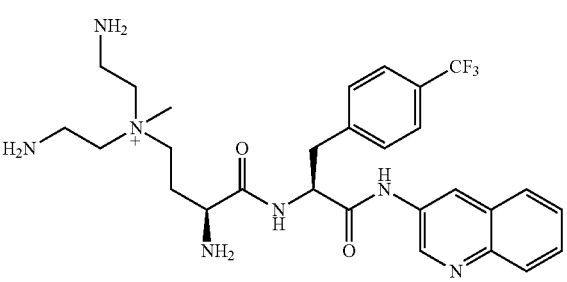

115
-continued
15
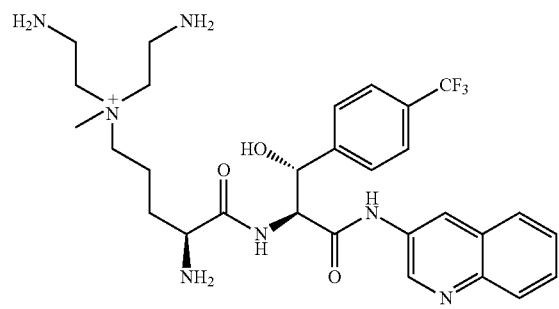
16
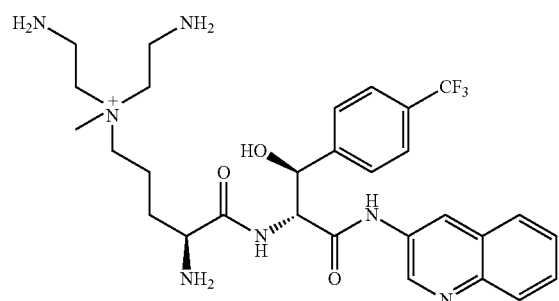
17
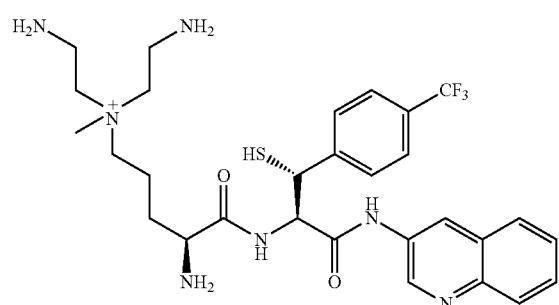
18
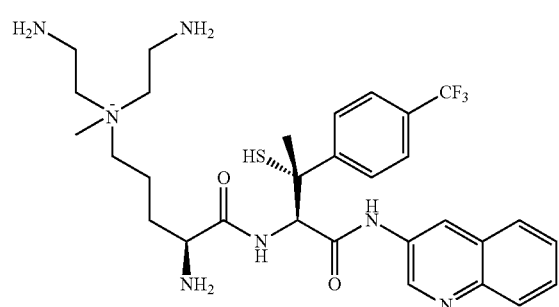
19
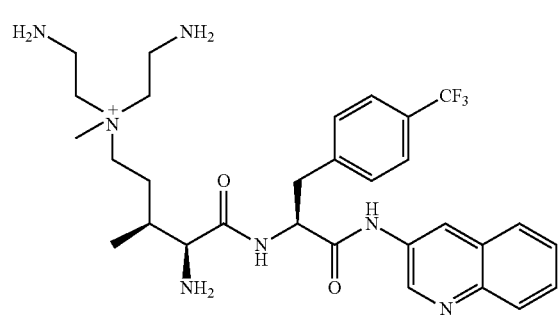
116
-continued
20
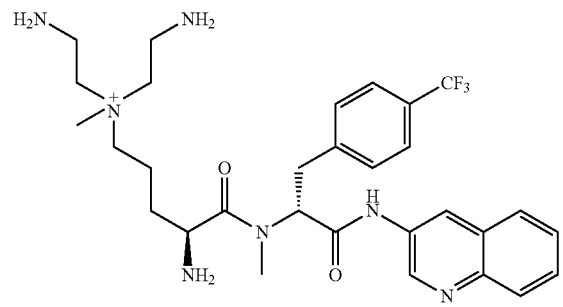
21
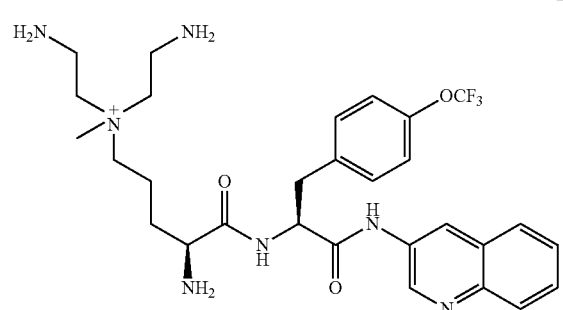
22
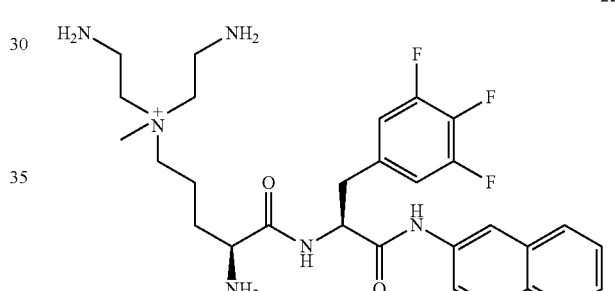
23
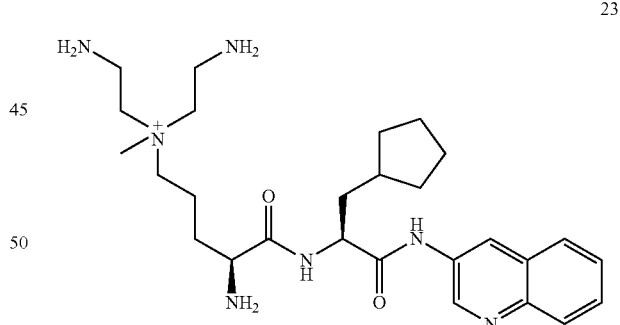
24
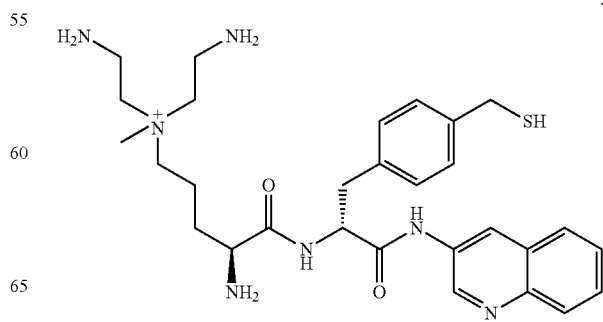

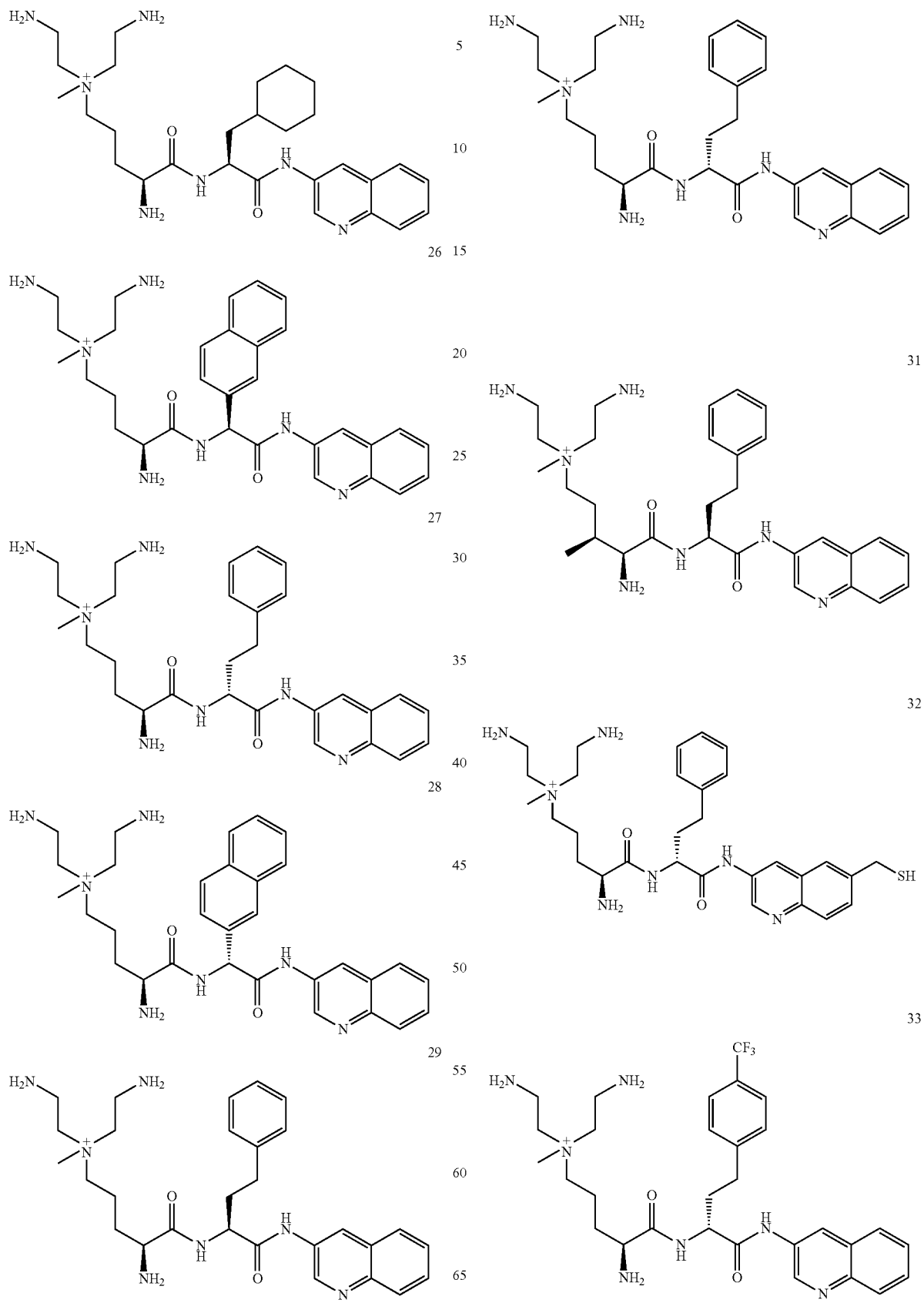

34
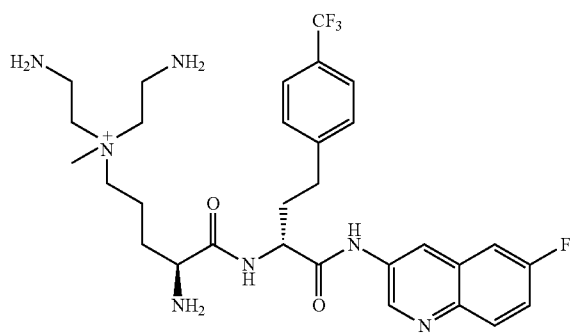
35
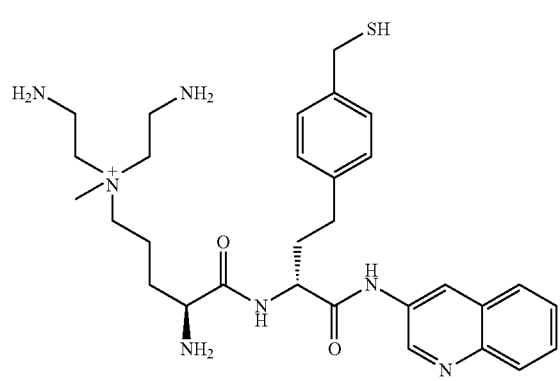
36
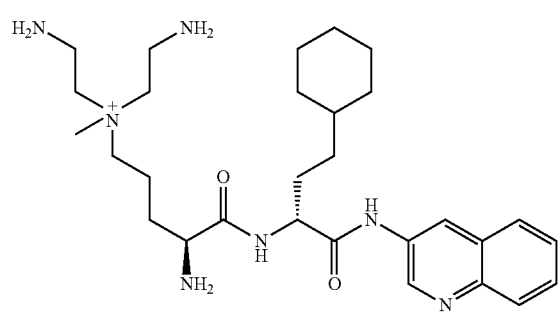
37
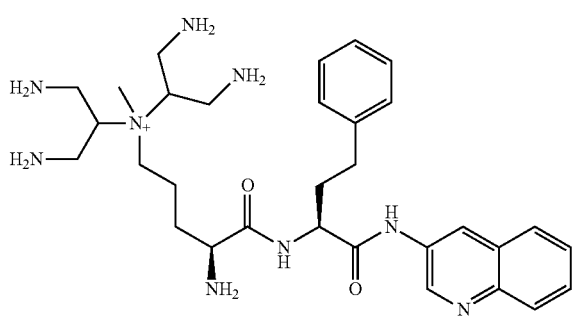
38
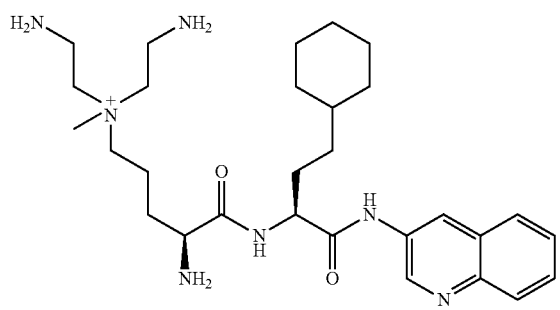
39
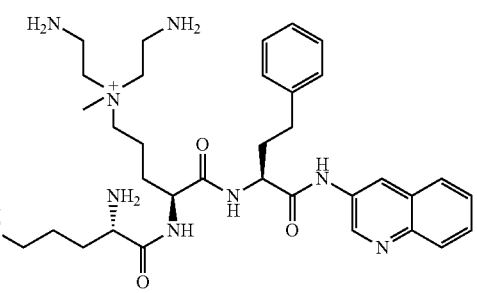
40
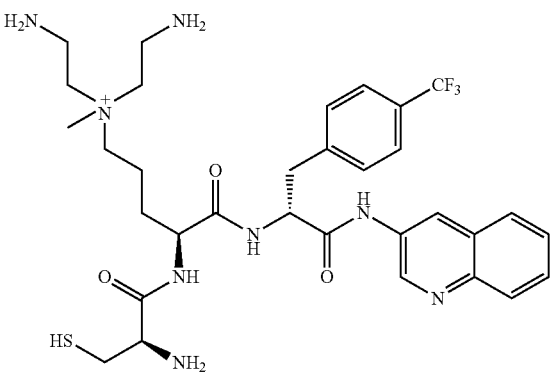
41

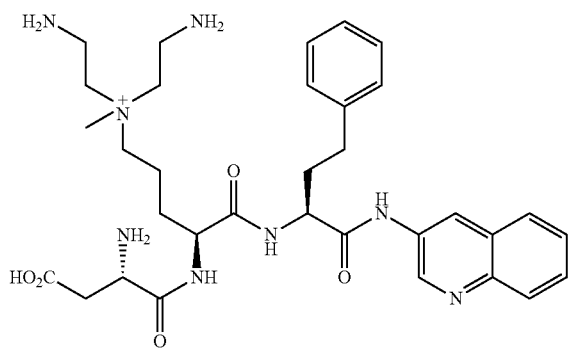
42
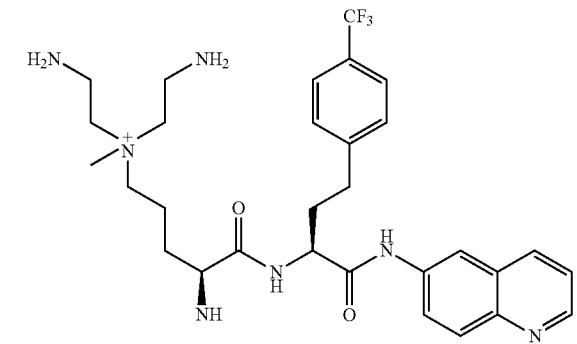
46
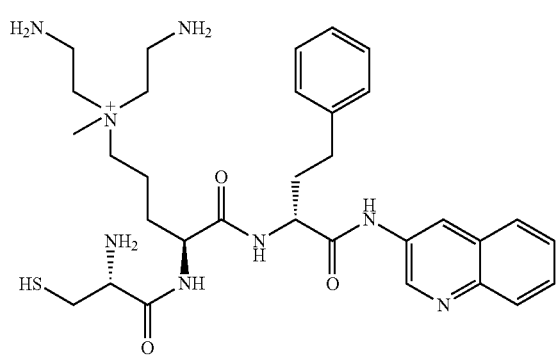
43
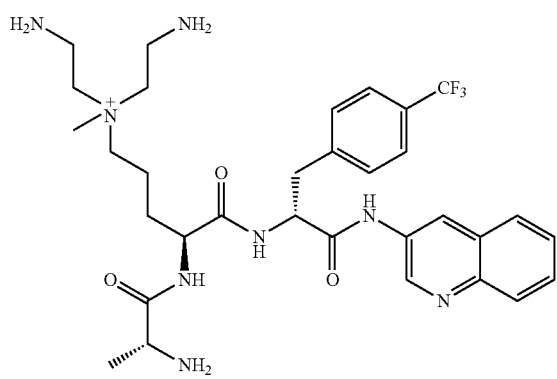
44
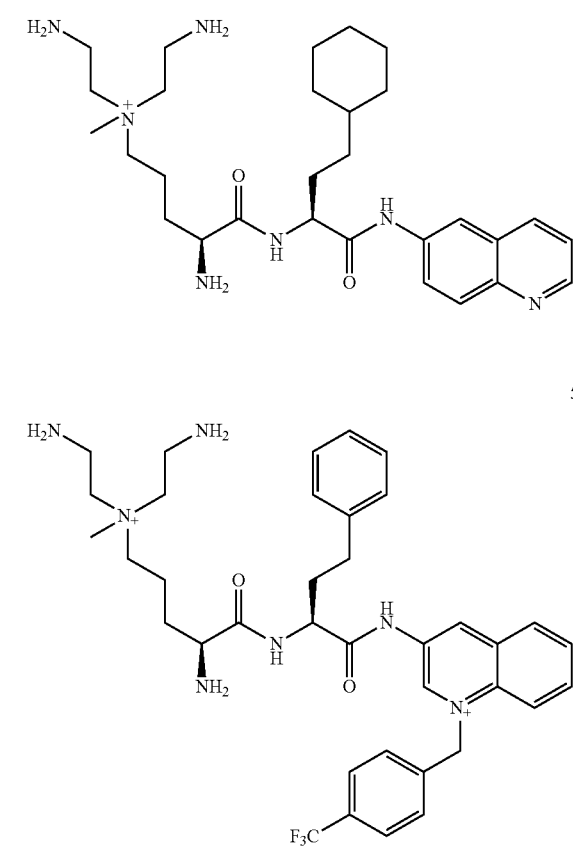
45

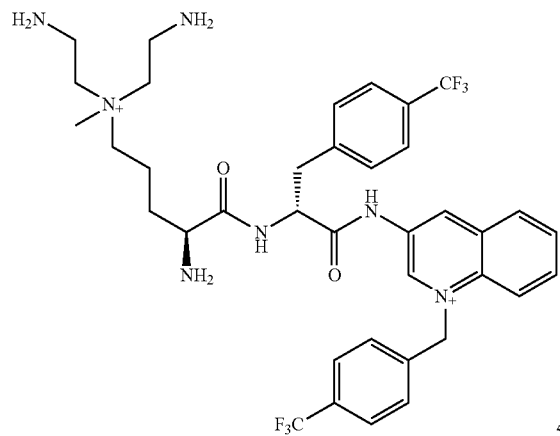
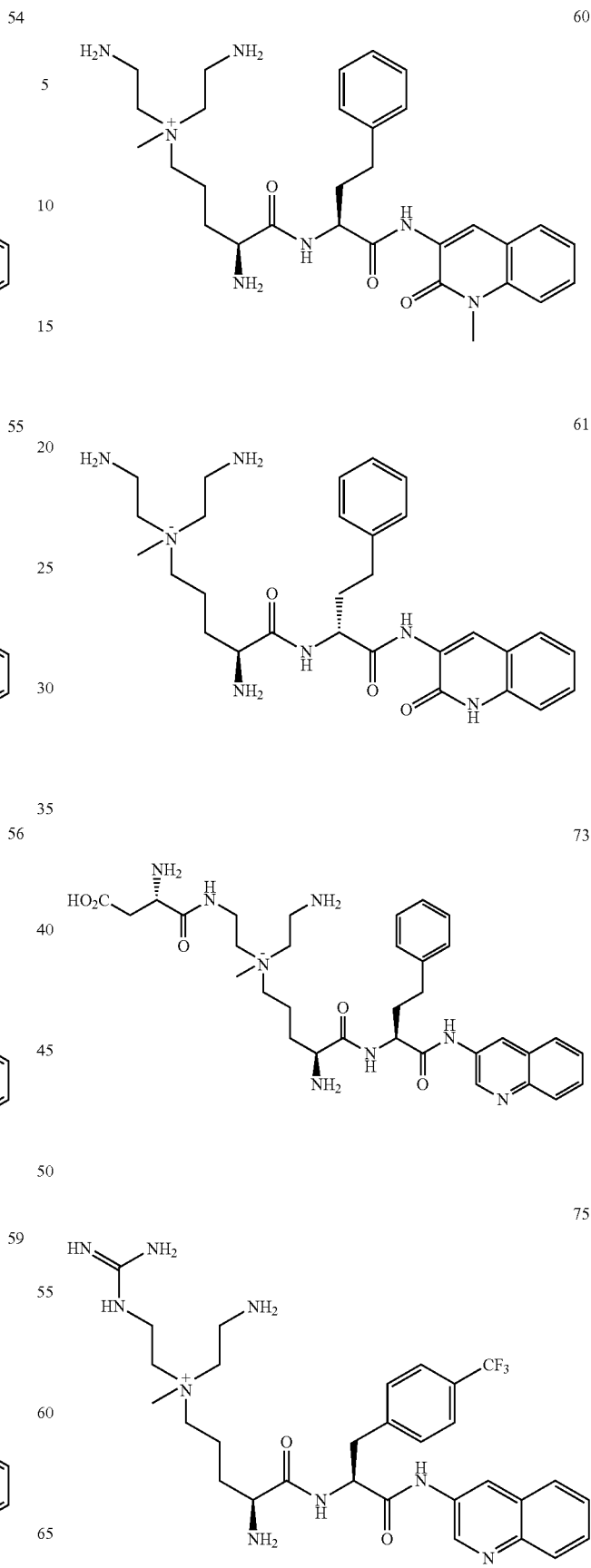

76
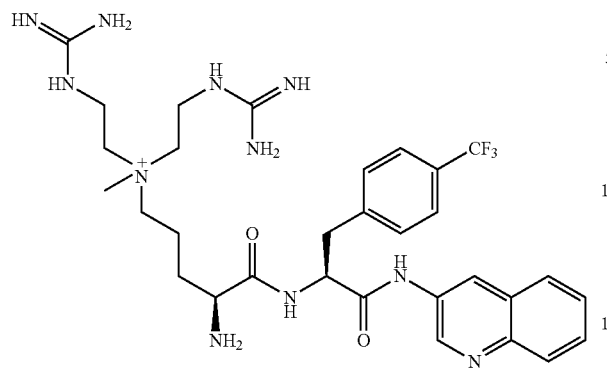
80
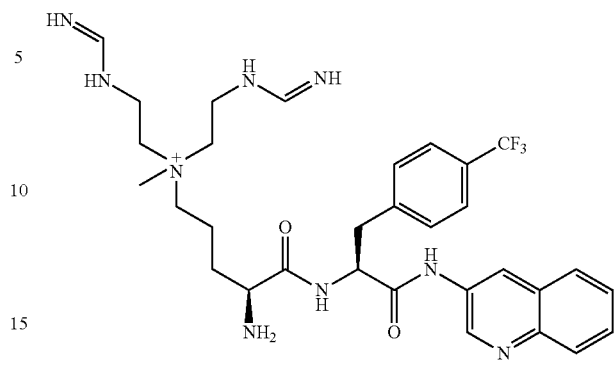
77
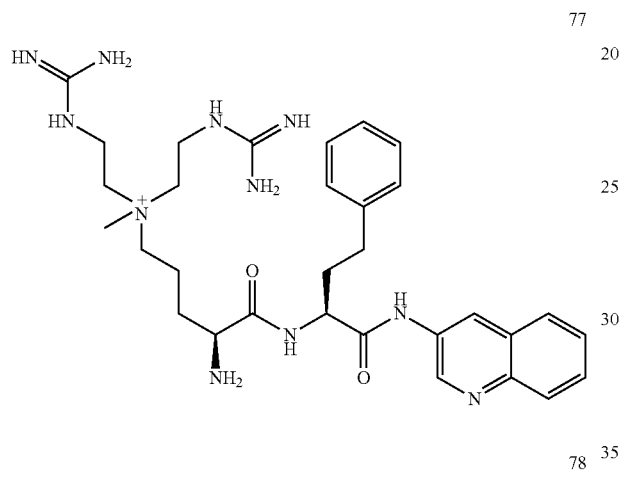
81
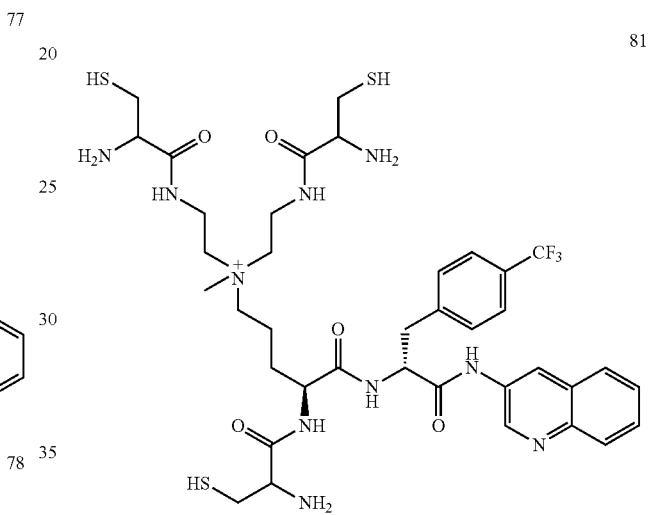
78
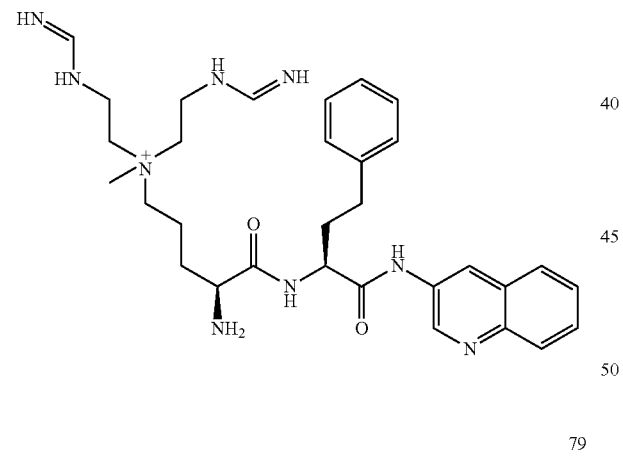
82
79
83
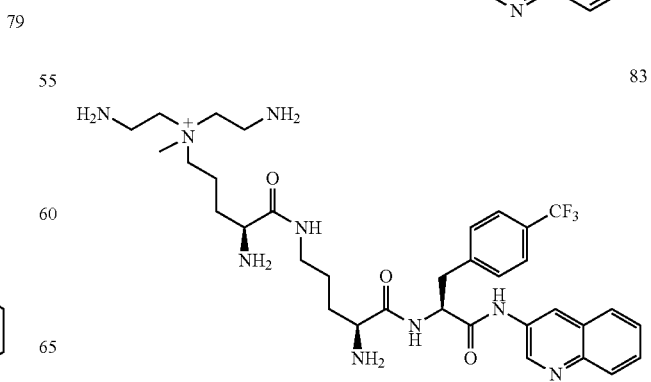

127
84
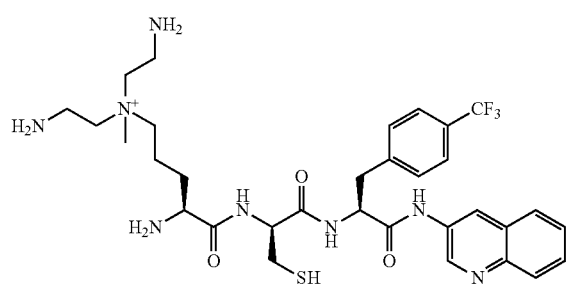
85
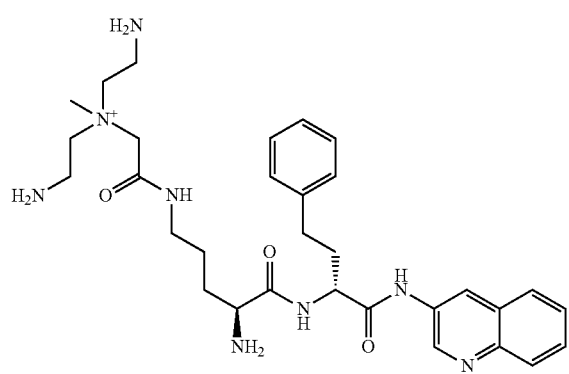
86
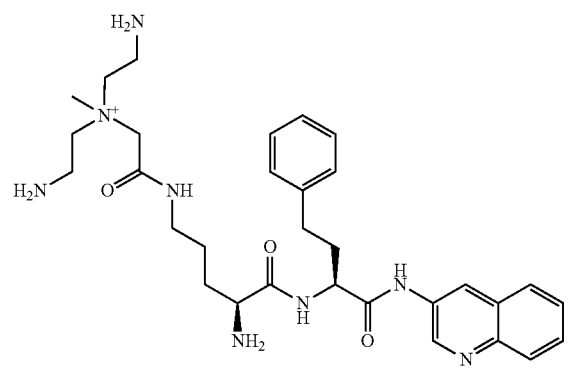
87
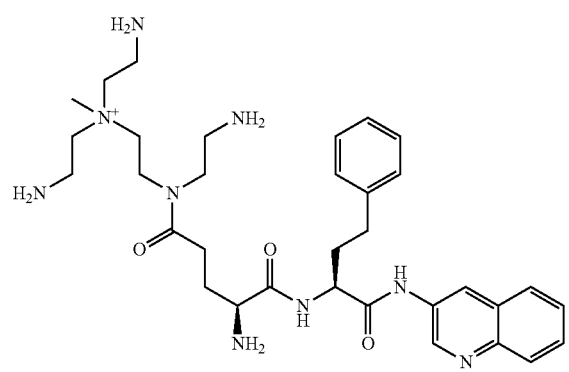
128
88
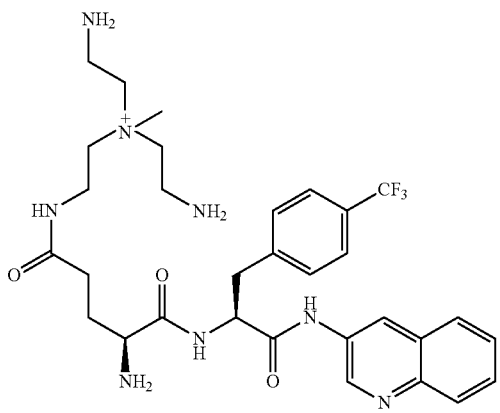
89
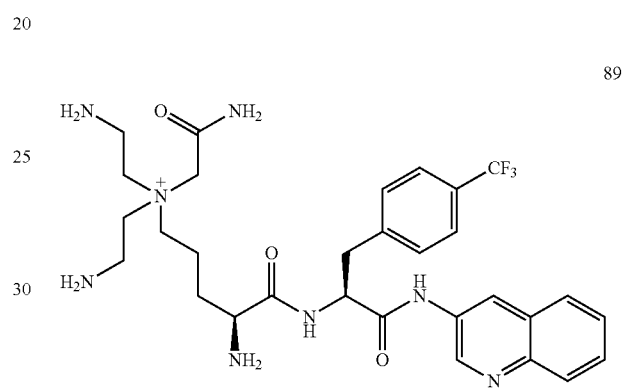
90
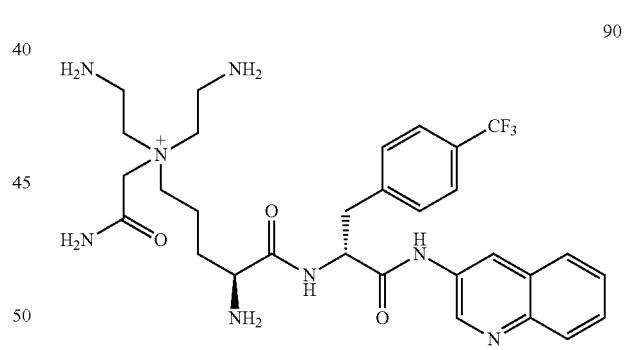
91

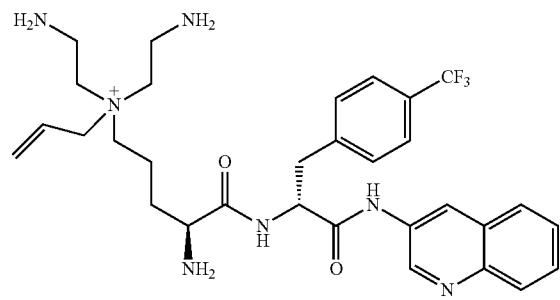
92
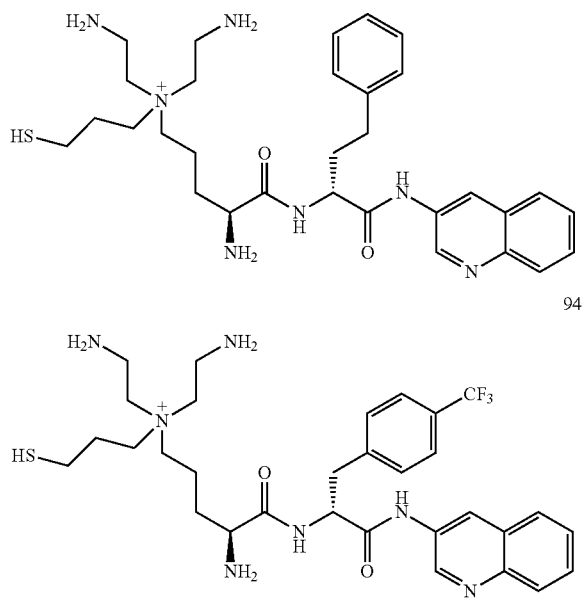
93
94
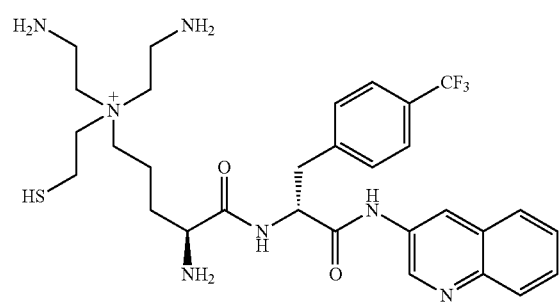
95
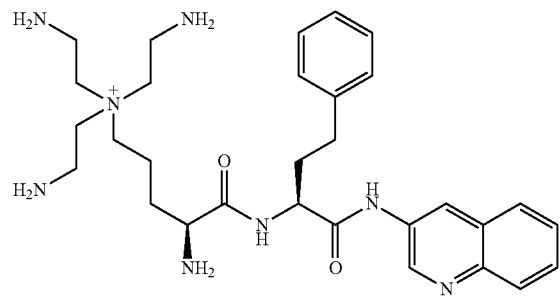
96
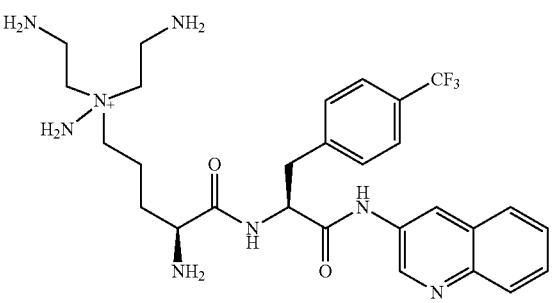
97
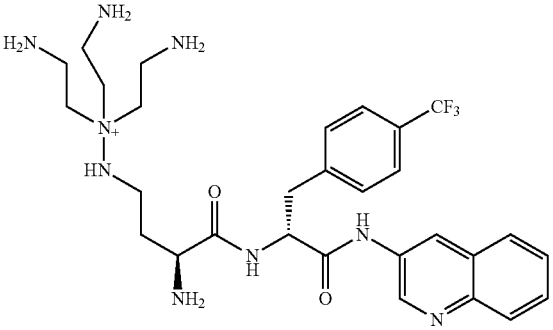
98
99
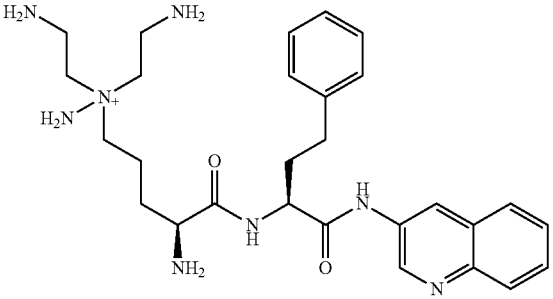
100

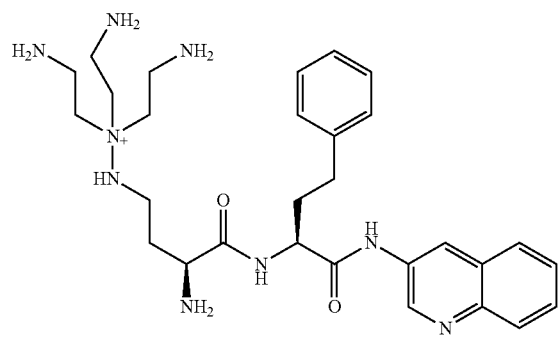
101
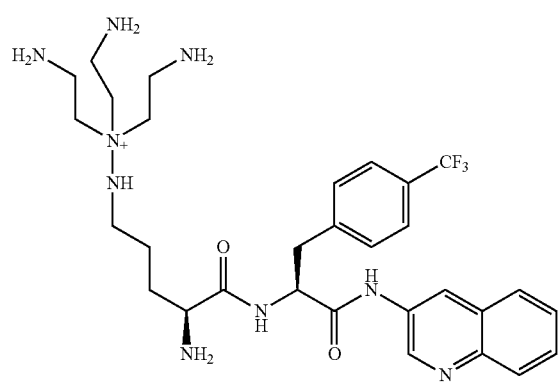
102
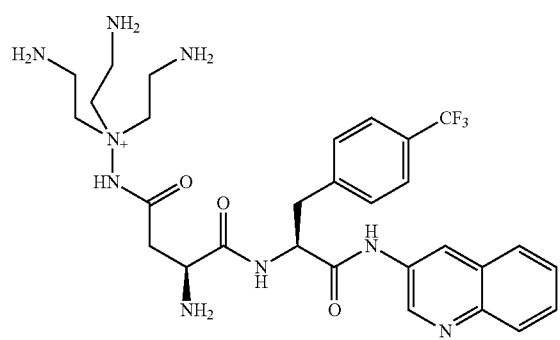
103
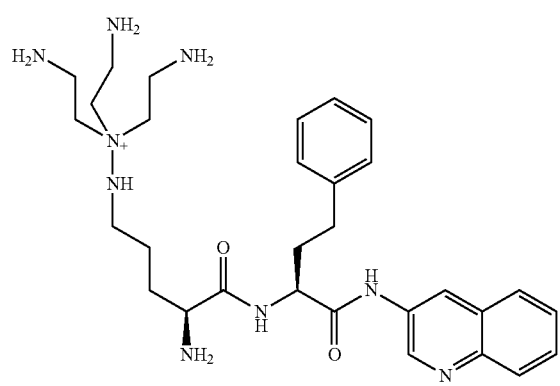
104
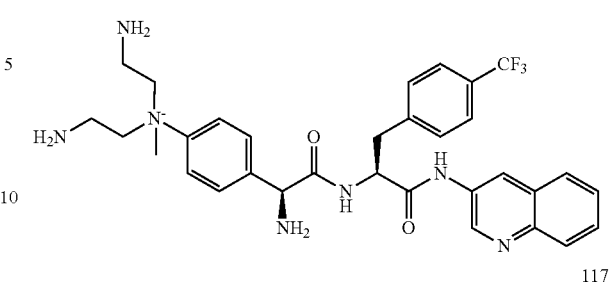
116
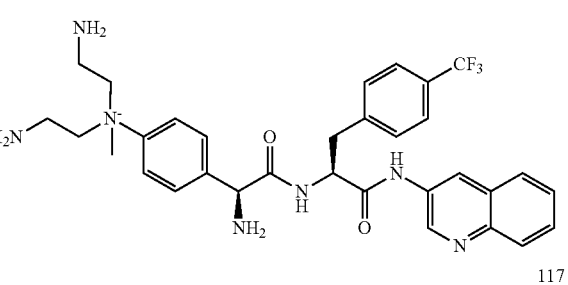
117
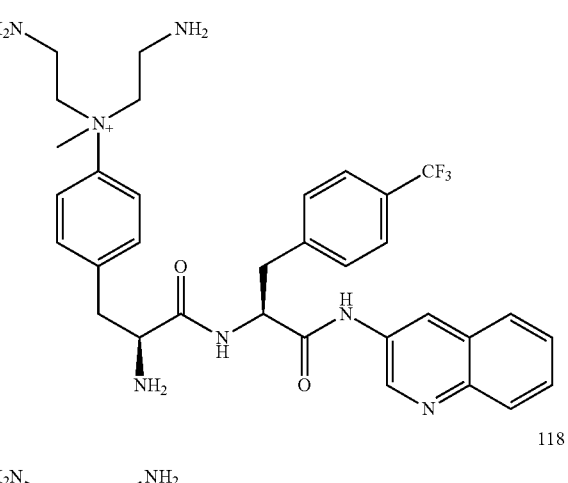
118
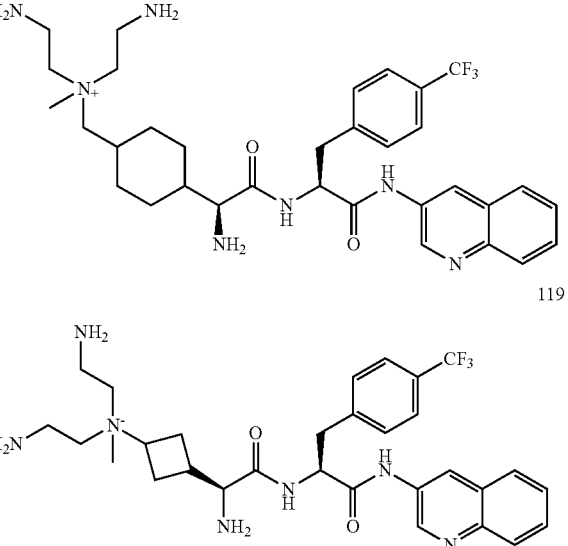
119
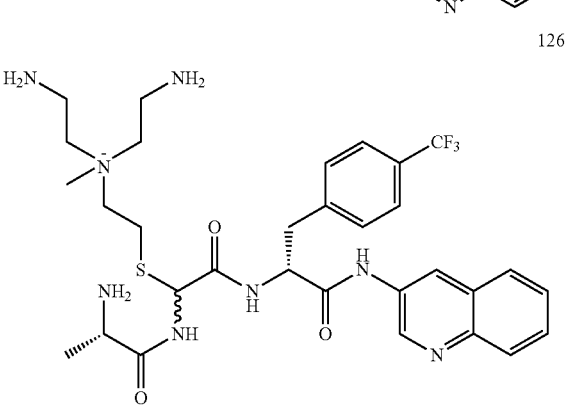
126

-continued
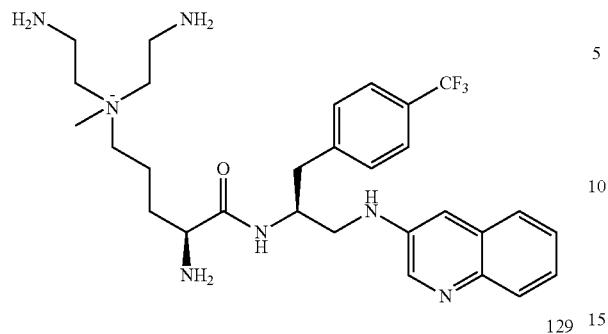
128
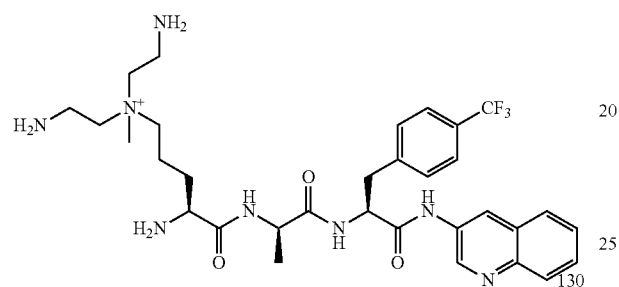
129
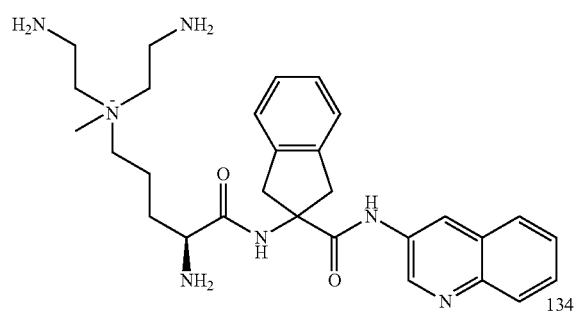
134
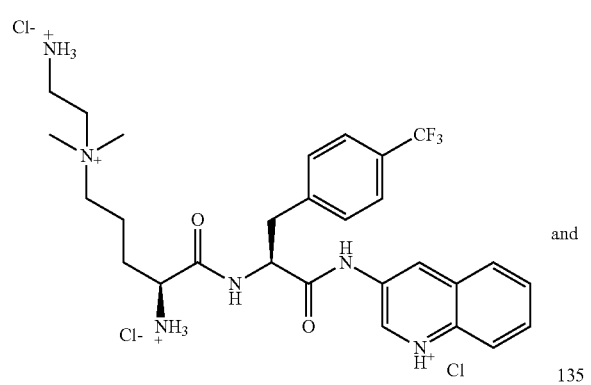
and
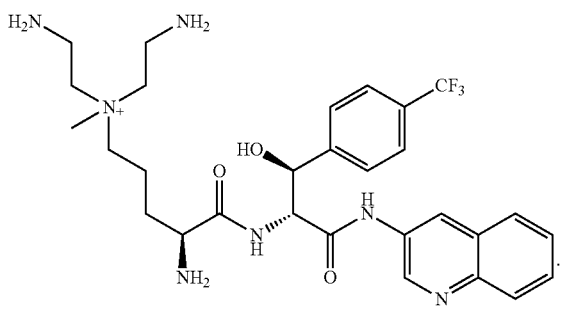
56. The compound of claim 1, wherein the compound is selected from the group consisting of:
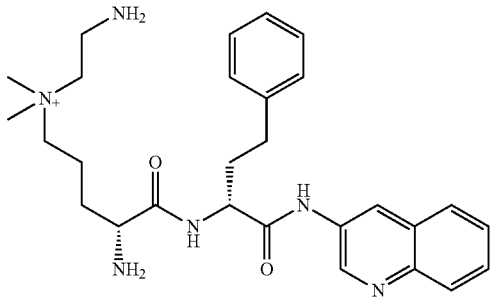
1
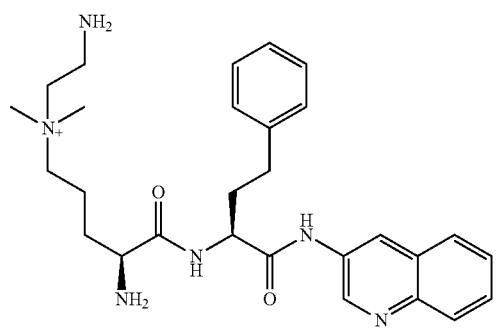
2
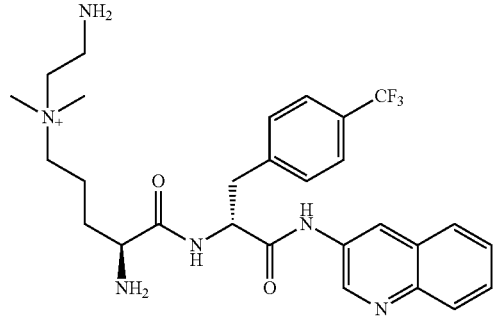
3
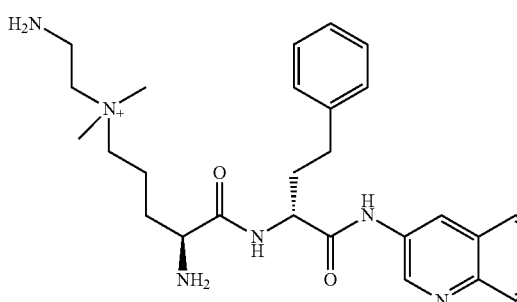
4
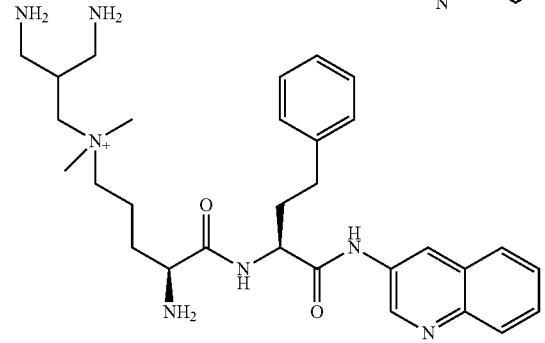
8

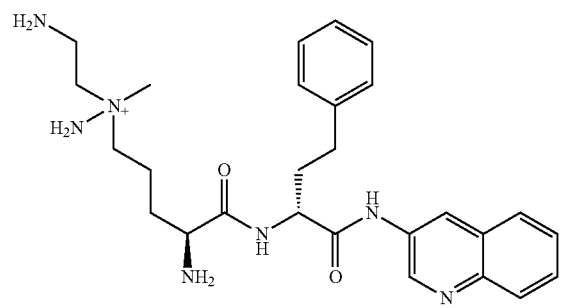
9
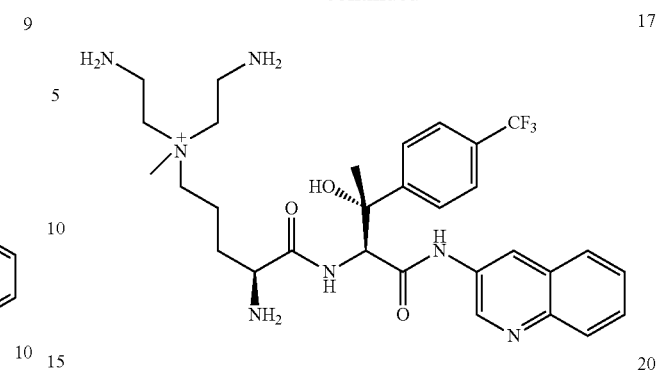
17
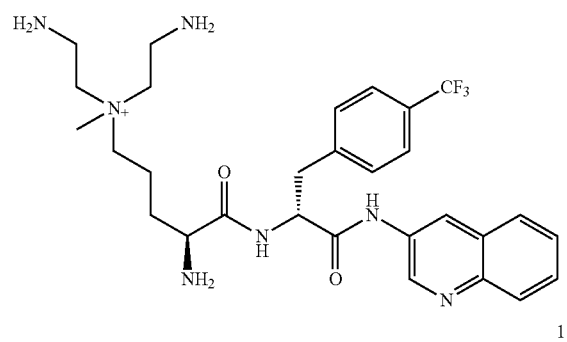
10
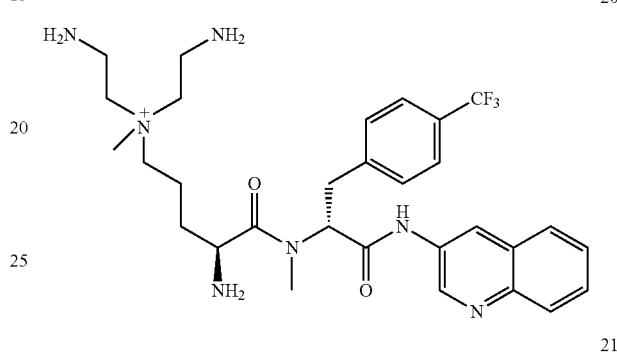
20
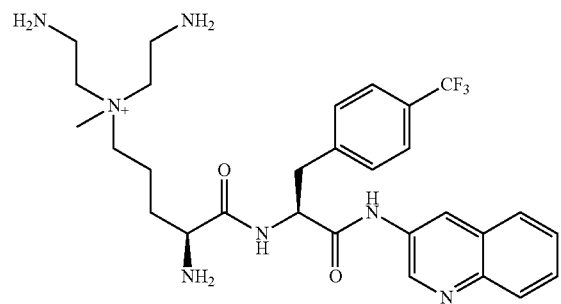
11
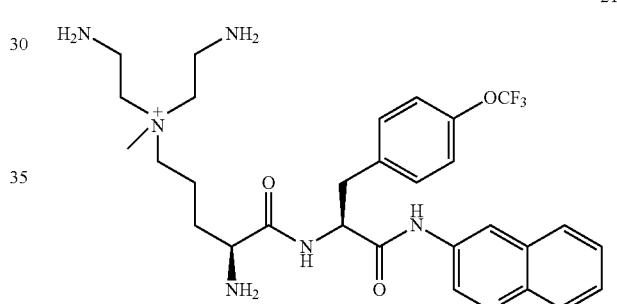
21
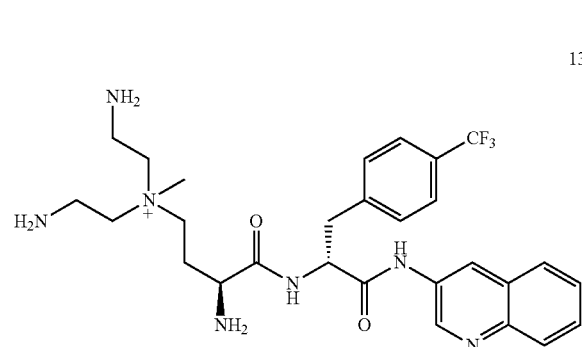
13
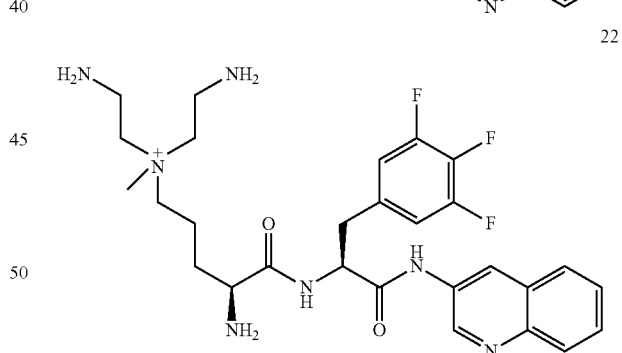
22
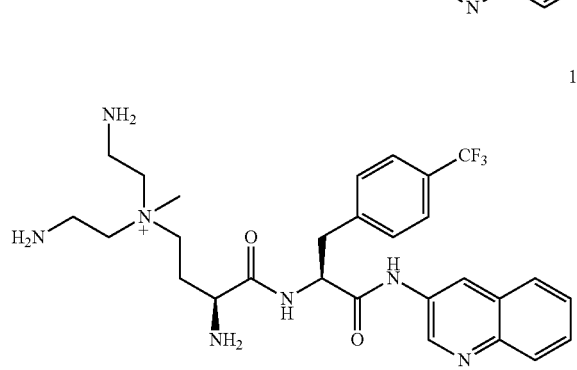
14
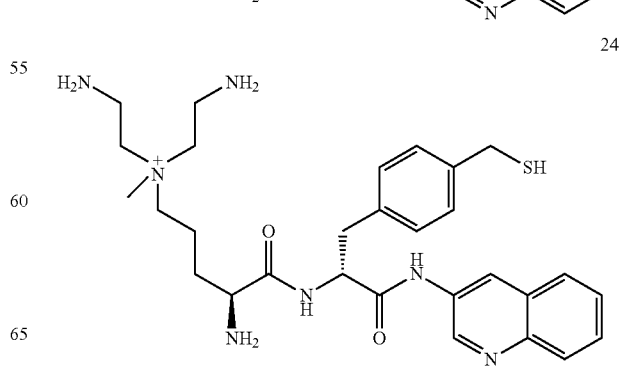
24

137
-continued
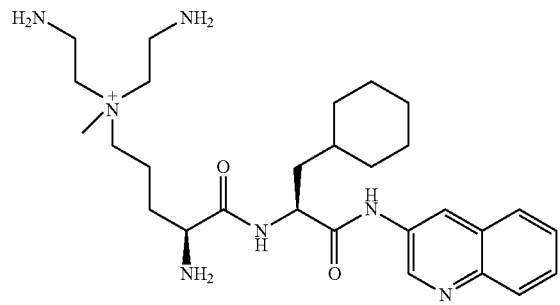
27
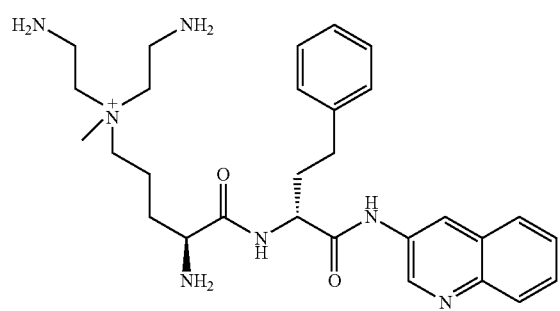
29
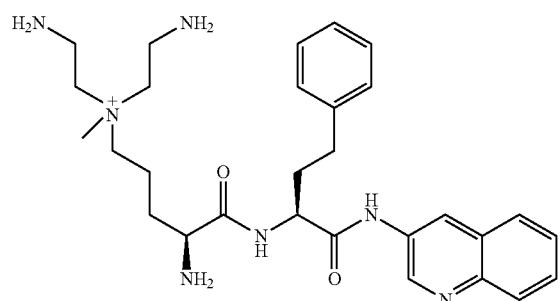
30
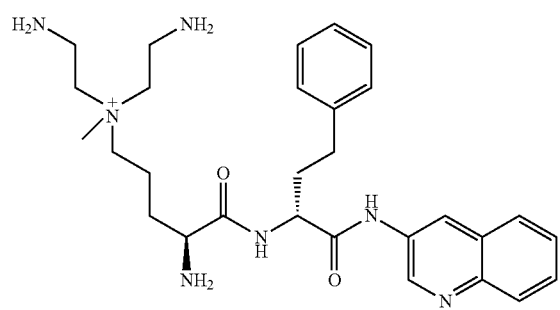
32
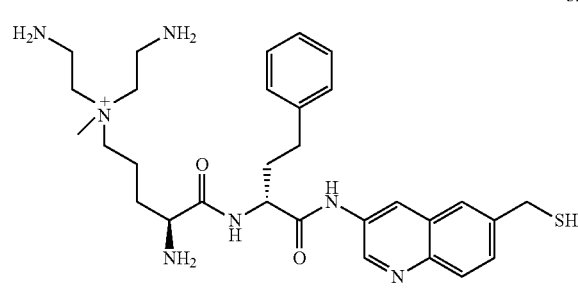
138
-continued
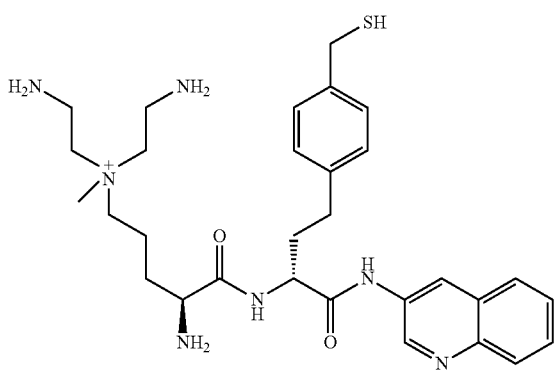
35
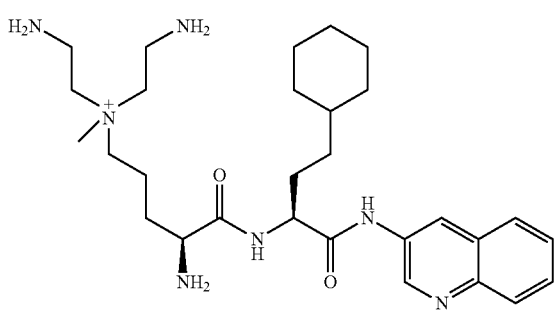
38
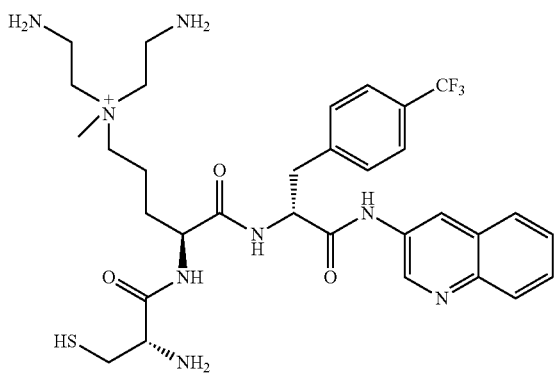
40
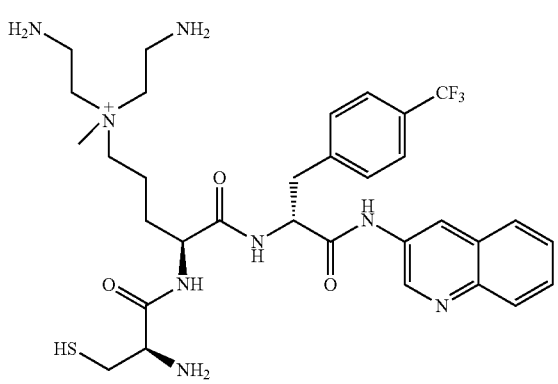
41

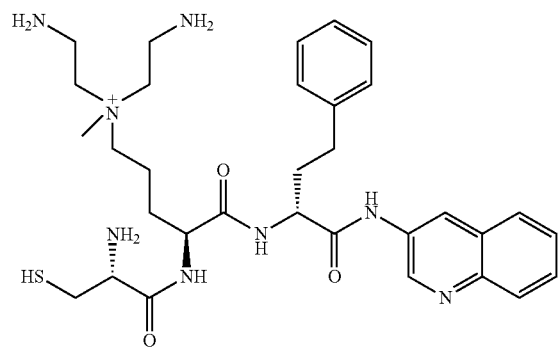
43
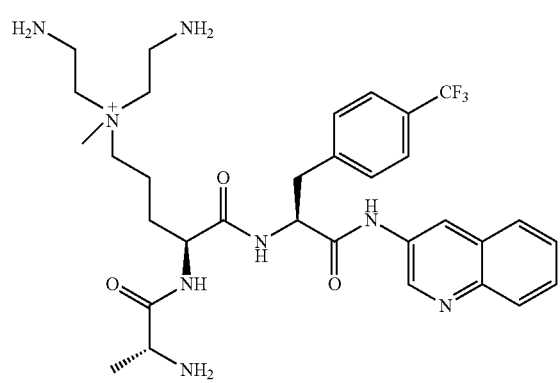
44
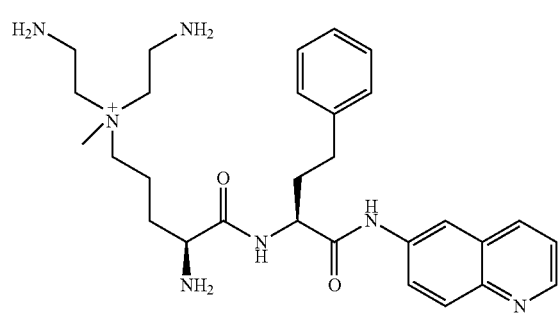
45
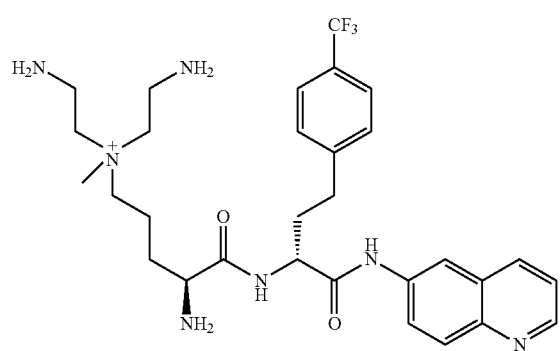
46
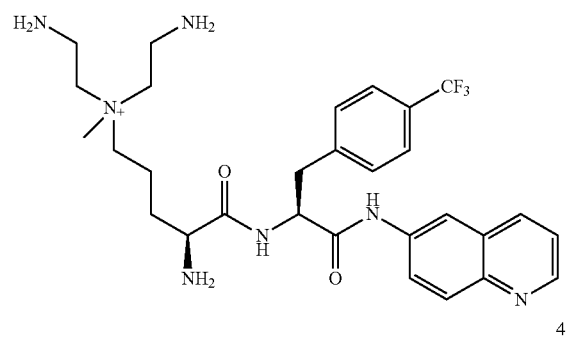
47
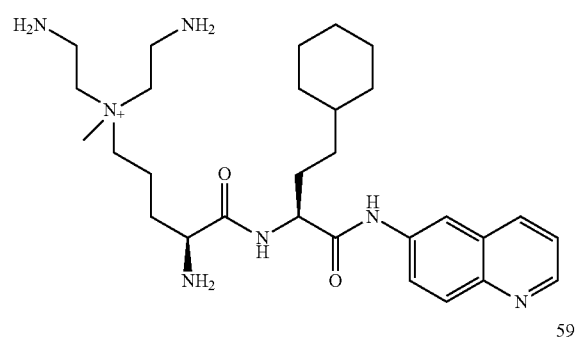
48
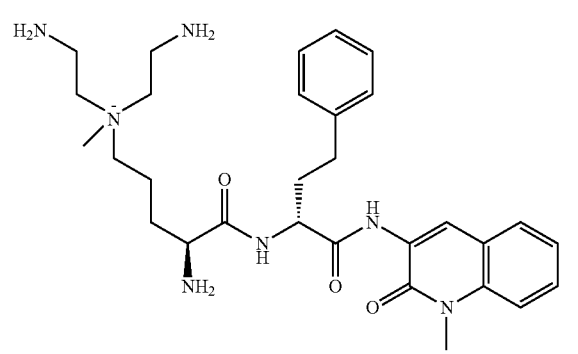
59
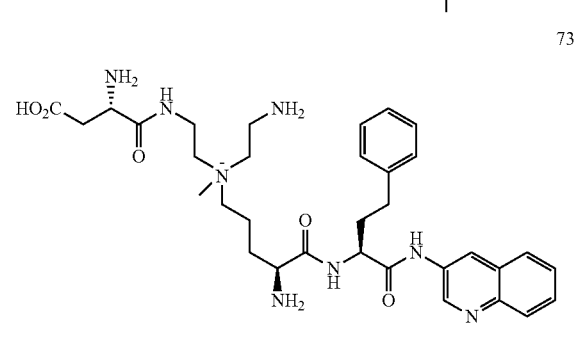
73
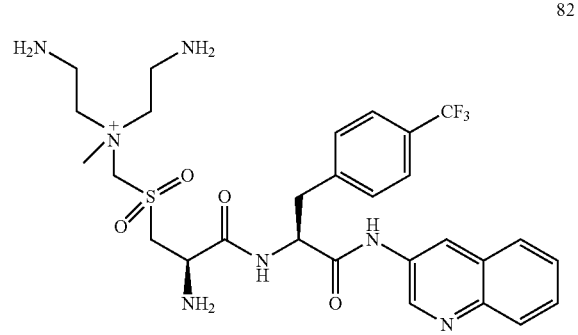
82

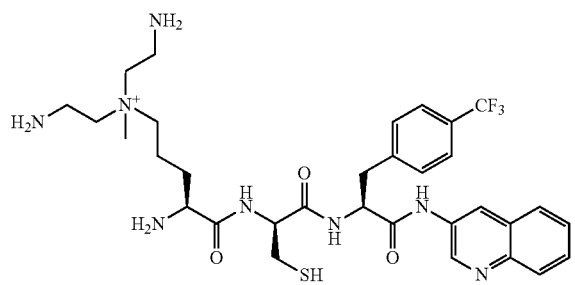
84
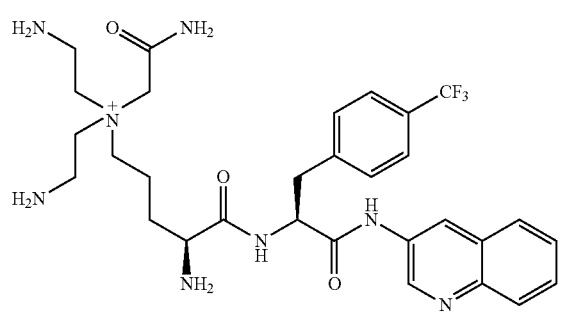
89
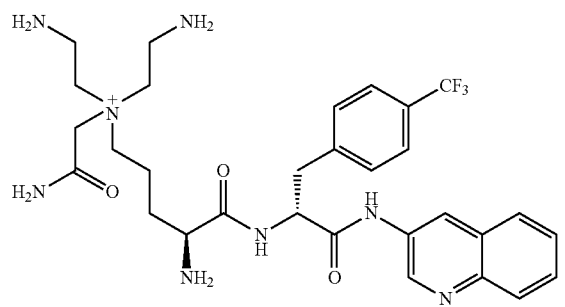
90
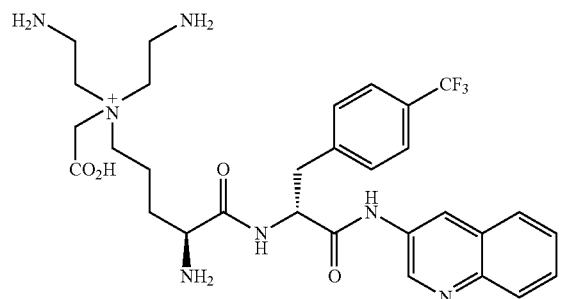
91
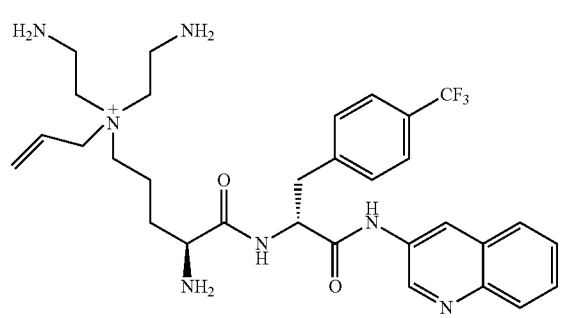
92
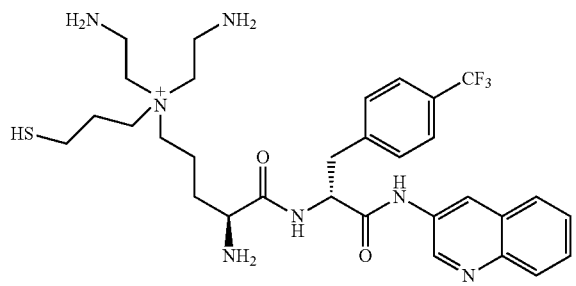
94
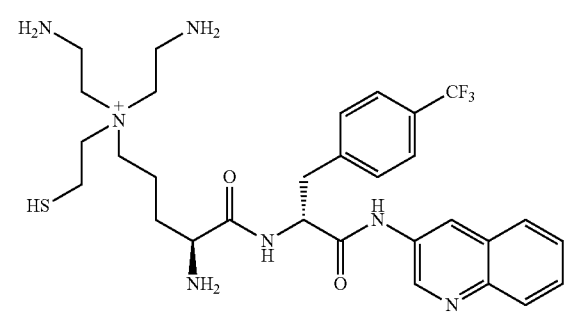
95
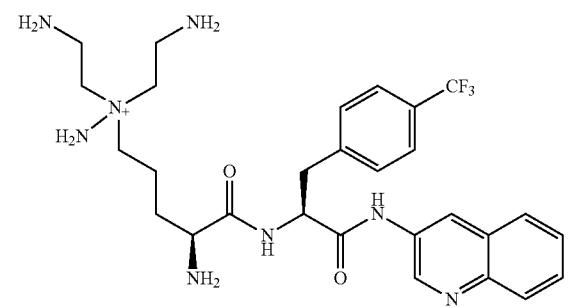
97
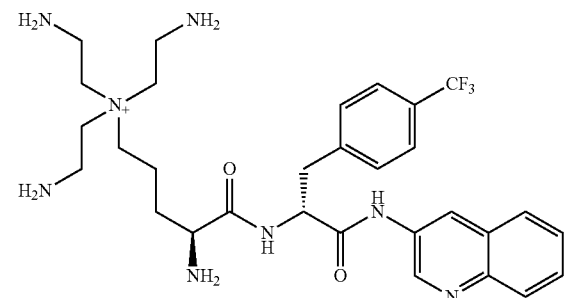
98
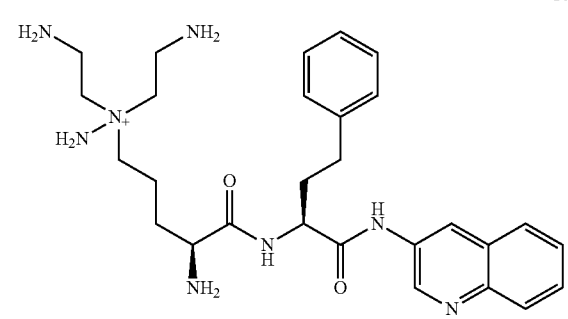
100

-continued
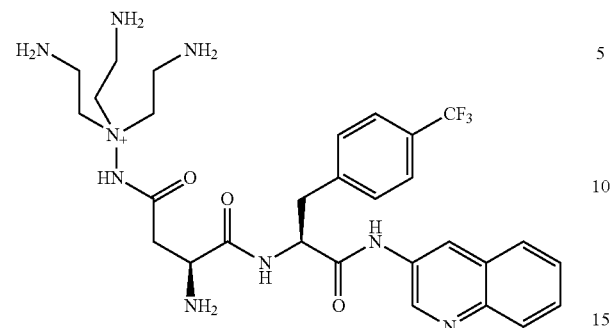
103
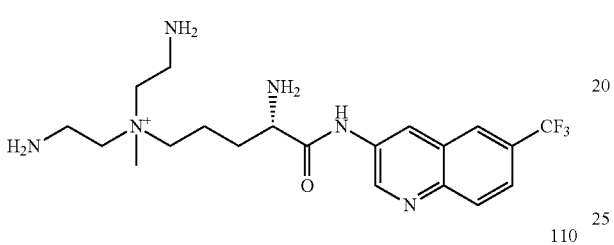
108
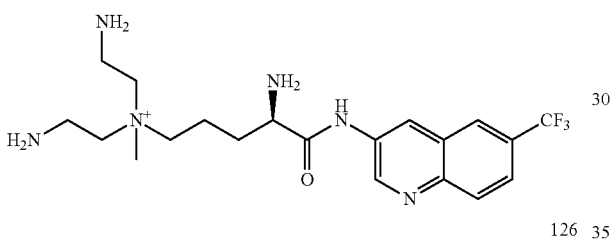
110
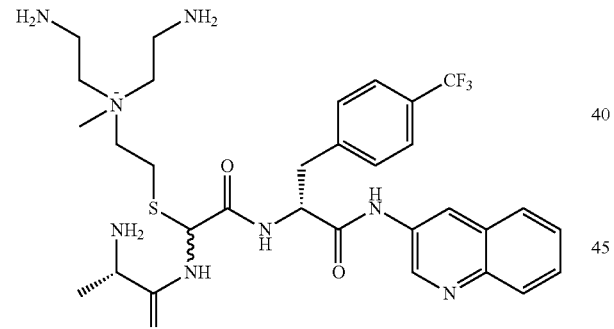
126
and
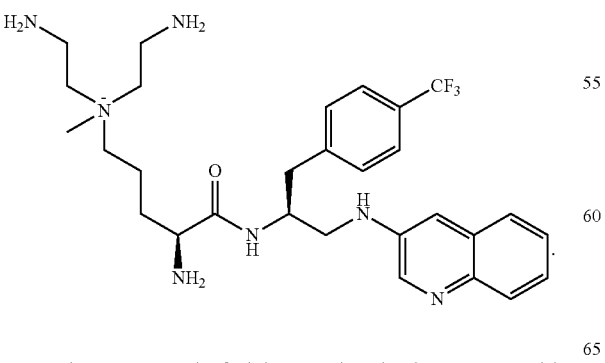
128
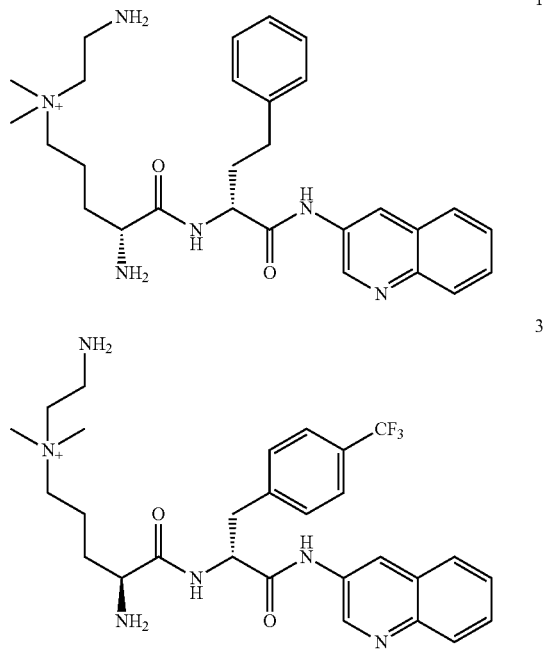
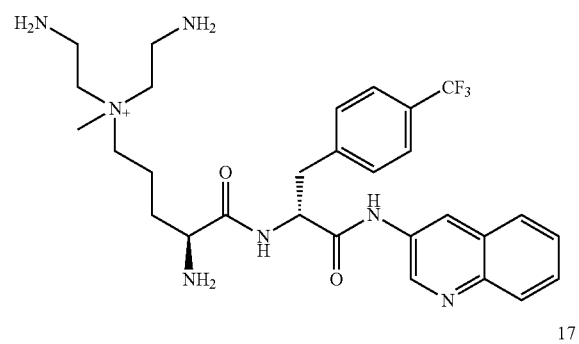
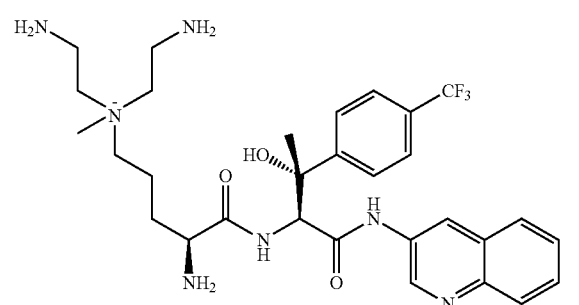
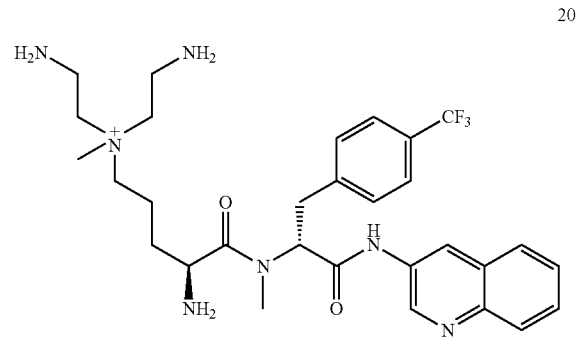
57. The compound of claim 1, wherein the compound is selected from the group consisting of:

145
-continued
24
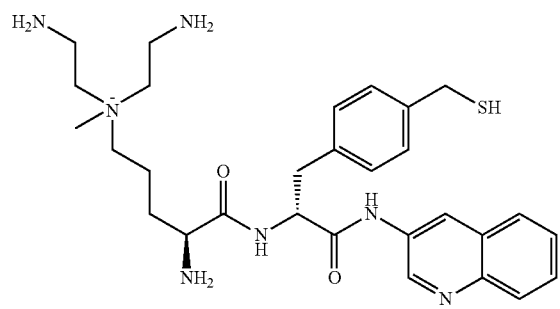
30
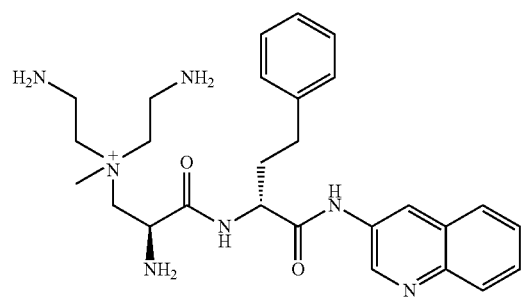
32
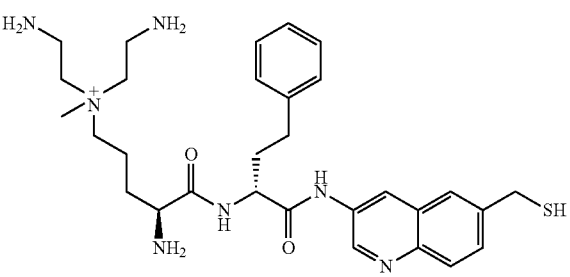
40
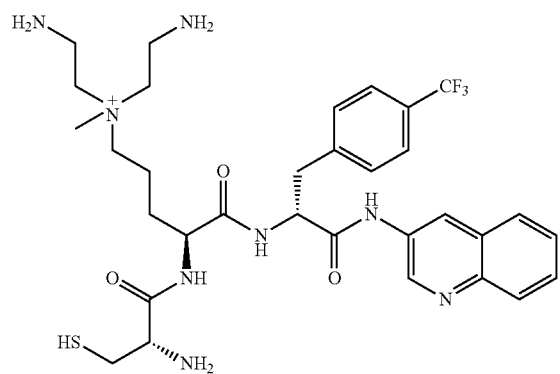
146
-continued
44
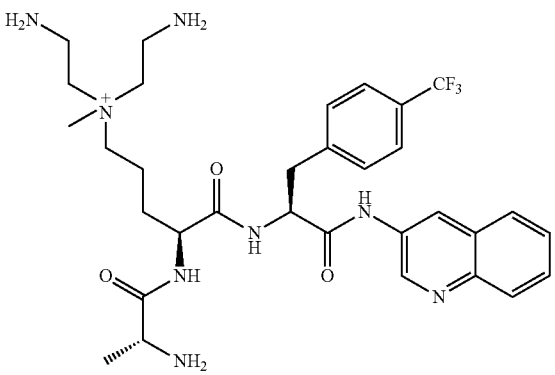
73
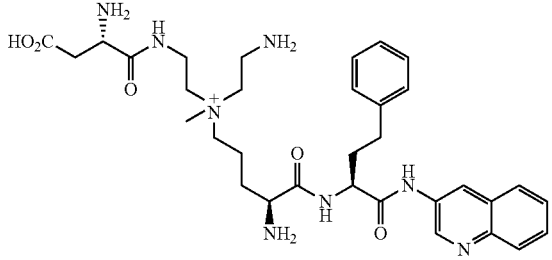
82
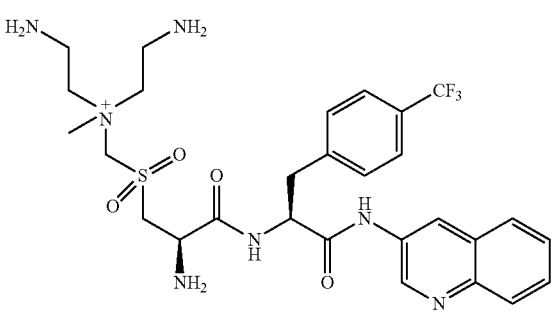
84
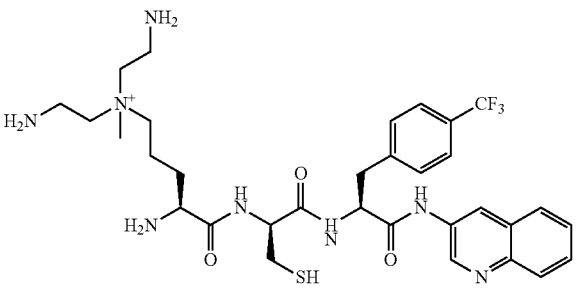
90
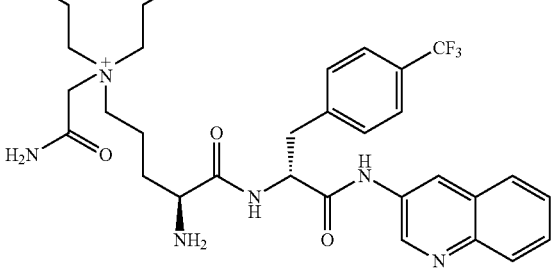

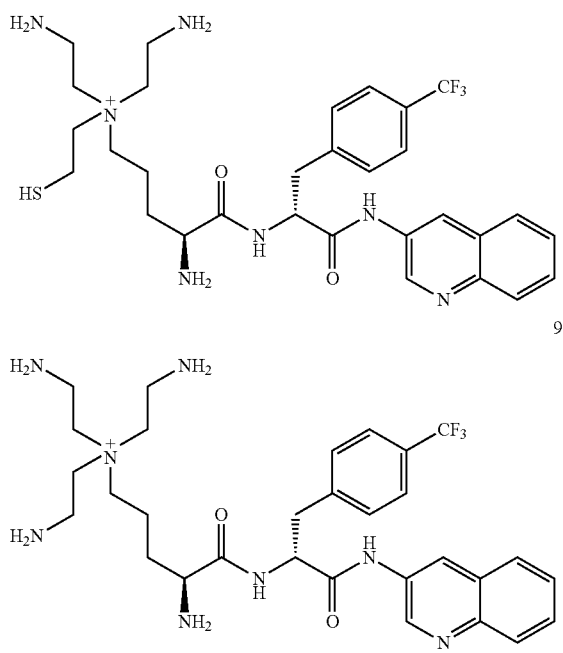
and
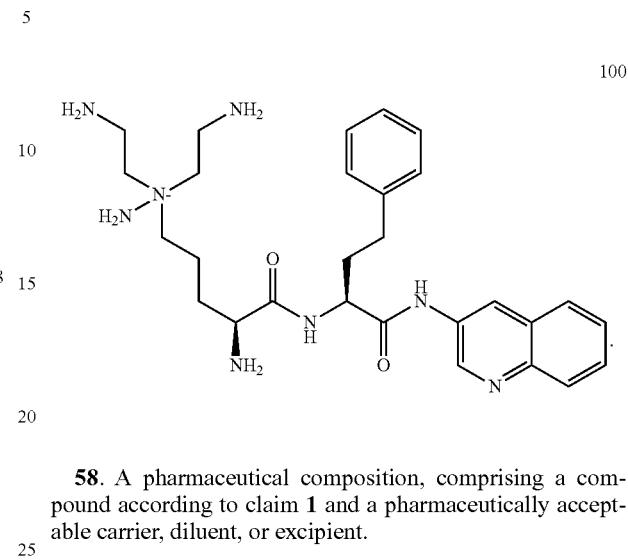
58. A pharmaceutical composition, comprising a compound according to claim 1 and a pharmaceutically acceptable carrier, diluent, or excipient.
* * * * *